US009045470B2

(12) United States Patent
Wu et al.

(10) Patent No.: US 9,045,470 B2
(45) Date of Patent: Jun. 2, 2015

(54) COMPOUNDS AND COMPOSITIONS AS TLR ACTIVITY MODULATORS

(75) Inventors: Tom Yao Hsiang Wu, San Diego, CA (US); Yongkai Li, San Diego, CA (US); Alex Cortez, San Diego, CA (US); Kathy Yue, Riverside, CA (US); Xiaoyue Zhang, San Diego, CA (US); Manmohan Singh, Lexington, MA (US); David Skibinski, Siena (IT)

(73) Assignee: IRM LLC, Hamilton (BM)

( * ) Notice: Subject to any disclaimer, the term of this patent is extended or adjusted under 35 U.S.C. 154(b) by 724 days.

(21) Appl. No.: 12/874,153

(22) Filed: Sep. 1, 2010

(65) Prior Publication Data

US 2011/0053893 A1     Mar. 3, 2011

Related U.S. Application Data

(60) Provisional application No. 61/239,217, filed on Sep. 2, 2009.

(51) Int. Cl.
| | |
|---|---|
| *A01N 61/00* | (2006.01) |
| *A61K 31/00* | (2006.01) |
| *A01N 57/00* | (2006.01) |
| *A61K 31/675* | (2006.01) |
| *C07D 471/04* | (2006.01) |

(52) U.S. Cl.
CPC .................................. *C07D 471/04* (2013.01)

(58) Field of Classification Search
USPC ....................................................... 514/1, 81
See application file for complete search history.

(56) References Cited

U.S. PATENT DOCUMENTS 5,741,909 A     4/1998    Gerster et al.

FOREIGN PATENT DOCUMENTS

| WO | WO2004111051 | 12/2004 |
| WO | WO 2007109813 | 9/2007 |
| WO | WO 2009/111337 * | 9/2009 |
| WO | WO2009111337 | 9/2009 |
| WO | WO 2010/144734 * | 12/2010 |
| WO | WO2010144734 | 12/2010 |

OTHER PUBLICATIONS

Giannini, et al., "Enhanced humoral and memory B cellular immunity using HPV 16/18 L1 VLP vaccine formulated with the MPL/aluminium salt combination (AS04) compared to aluminium salt only", Vaccine, 2006, pp. 5937-5949, vol. 24, Issues 33-34, Elsevier Science Ltd., US.

Romanenko, et al., "Fluorinated Phosphonates: Synthesis and Biomedical Application", Chem. Rev., 2006, pp. 3868-3935, vol. 106, American Chemical Society, US.

Hem, et al., "Relationship between physical and chemical properties of aluminum-containing adjuvants and immunopotentiation", Expert Rev. Vaccines, 2007, pp. 685-698, vol. 6, Issue 5, Future Drugs, Ltd., United Kingdom.

Hansen, et al., "Relationship between the strength of antigen adsorption to an aluminium-containing adjuvant and the immune response", Vaccine, 2007, vol. 25, pp. 6618-6624, Elsevier Science Ltd., US.

Pichichero, "Improving vaccine delivery using novel adjuvant systems", Human Vaccines, Jul./Aug. 2008, vol. 4, Issue 4, pp. 262-270, Landes Bioscience, US.

Zhao, et al., "Surface Phosphophilicity of Aluminum-Containing Adjuvants Probed by Their Efficiency for Catalyzing the P-O Bond Cleavage with Chromogenic and Fluorogenic Substrates", Analytical Biochemistry, 2001, vol. 295, pp. 76-81, Academic Press, US.

Morefield, G.L., et al., Effect of phosphorylation of ovalbumin on adsorption by aluminum-containing adjuvants and elution upon exposure to interstitial fluid. Vaccine, 2005. 23(12): p. 1502-6.

Iyer, S., Hogenesch, H, and Hem, S.L., Effect of the degree of phosphate substitution in aluminum hydroxide adjuvant on the adsorption of phosphorylated proteins. Pharm Dev Technol, 2003. 8(1): p. 81-6.

Didierlaurent, A.M., et al., AS04, an aluminum salt-and TLR4 agonist-based adjuvant system, induces a transient localized innate immune response leading to enhanced adaptive immunity. The Journal of Immunology, 2009. 183(10): p. 6186.

Matheis, W., A. Zott and M. Schwanig, The role of the adsorption process for production and control combined adsorbed vaccines. Vaccine, 2001. 20(1-2): p. 67-73.

Rinella, J.V., et al., Effect of anions on model aluminum-adjuvant-containing vaccines. Journal of Colloid and Interface Science, 1995. 172(172): p. 121-130.

* cited by examiner

*Primary Examiner* — Marcos Sznaidman
(74) *Attorney, Agent, or Firm* — The Genomics Institute of the Novartis Research Foundation; Daniel E. Raymond

(57) ABSTRACT

The invention provides a novel class of compounds, immunogenic compositions and pharmaceutical compositions comprising such compounds and methods of using such compounds to treat or prevent diseases or disorders associated with Toll-Like Receptors 7. In one aspect, the compounds are useful as adjuvants for enhancing the effectiveness of a vaccine.

7 Claims, 2 Drawing Sheets

COMPOUNDS AND COMPOSITIONS AS TLR ACTIVITY MODULATORS

CROSS-REFERENCE TO RELATED APPLICATIONS

This application claims the benefit of priority under 35 U.S.C. §119(e) to U.S. Provisional Patent Application No. 61/239,217, filed Sep. 2, 2009, the disclosure which is incorporated herein by reference in its entirety and for all purposes.

STATEMENT OF GOVERNMENT SUPPORT

This invention was made in part with Government support under DTRA Grant No. HDTRA1-07-9-0001 awarded by the Department of Defense. The Government has certain rights in the invention.

FIELD OF THE INVENTION

The invention relates to modulators of Toll-Like Receptors (TLRs), and methods of using such compounds.

BACKGROUND OF THE INVENTION

Early detection of specific classes of pathogens is accomplished by the innate immune system with the help of pattern recognition receptors (PRRs). The detected pathogens include viruses, bacteria, protozoa and fungi, and each constitutively expresses a set of class-specific, mutation-resistant molecules called pathogen-associated molecular patterns (PAMPs). These molecular markers may be composed of proteins, carbohydrates, lipids, nucleic acids or combinations thereof, and may be located internally or externally. Examples of PAMPs include bacterial carbohydrates (lipopolysaccharide or LPS, mannose), nucleic acids (bacterial or viral DNA or RNA), peptidoglycans and lipotechoic acids (from Gram positive bacteria), N-formylmethionine, lipoproteins and fungal glucans.

Pattern recognition receptors have evolved to take advantage of three PAMP qualities. First, constitutive expression allows the host to detect the pathogen regardless of its life cycle stage. Second, the PAMPs are class specific, which allows the host to distinguish between pathogens and thereby tailor its response. Third, mutation resistance allows the host to recognize the pathogen regardless of its particular strain.

Pattern recognition receptors are involved in more than just recognition of pathogens via their PAMPs. Once bound, pattern recognition receptors tend to cluster, recruit other extracellular and intracellular proteins to the complex, and initiate signaling cascades that ultimately impact transcription. Additionally, pattern recognition receptors are involved in activation of complement, coagulation, phagocytosis, inflammation, and apoptosis functions in response to pathogen detection.

Pattern recognition receptors (PRRs) may be divided into endocytic PRRs or signaling PRRs. The signaling PRRs include the large families of membrane-bound Toll-like receptors (TLRs) and cytoplasmic NOD-like receptors, while the endocytic PRRs promote the attachment, engulfment and destruction of microorganisms by phagocytes without relaying an intracellular signal, are found on all phagocytes and mediate removal of apoptotic cells. In addition, endocytic PRRs recognize carbohydrates and include mannose receptors of macrophages, glucan receptors present on all phagocytes and scavenger receptors that recognize charged ligands.

SUMMARY OF THE INVENTION

Provided herein are compounds and pharmaceutical compositions thereof, which are agonists of toll-like receptor 7 (TLR7). Such TLR7 agonists are immune potentiators that bind to aluminum-containing adjuvants, such as, by way of example only, aluminum hydroxide, aluminum oxyhydroxide and aluminum hydroxyphosphate. Thus, also provided herein are immunogenic compositions that contain an antigen and a TLR7 agonist provided herein that bind to aluminum-containing adjuvants. When such immunogenic compositions are administered to a subject in need thereof, such TLR7 agonists enhance the immune response to the immunogenic composition.

In one aspect provided herein such compounds, and the pharmaceutically acceptable salts, pharmaceutically acceptable solvates (e.g. hydrates), the N-oxide derivatives, prodrug derivatives, protected derivatives, individual isomers and mixture of isomers thereof, have a structure according to Formula (I):

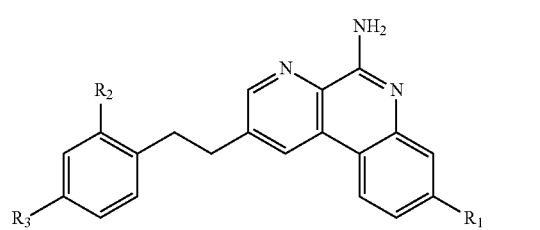

Formula (I)

wherein:
$R^1$ is H, $C_1$-$C_6$alkyl, —$C(R^5)_2$OH, -$L^1R^5$, -$L^1R^6$, -$L^2R^5$, -$L^2R^6$, —$OL^2R^5$, or —$OL^2R^6$;
$L^1$ is —C(O)— or —O—;
$L^2$ is $C_1$-$C_6$alkylene, $C_2$-$C_6$alkenylene, arylene, heteroarylene or —$((CR^4R^4)_pO)_q(CH_2)_p$—, wherein the $C_1$-$C_6$alkylene and $C_2$-$C_6$alkenylene of $L^2$ are optionally substituted with 1 to 4 fluoro groups;
each $L^3$ is independently selected from $C_1$-$C_6$alkylene and —$((CR^4R^4)_pO)_q(CH_2)_p$—, wherein the $C_1$-$C_6$alkylene of $L^3$ is optionally substituted with 1 to 4 fluoro groups;
$L^4$ is arylene or heteroarylene;
$R^2$ is H or $C_1$-$C_6$alkyl;
$R^3$ is selected from $C_1$-$C_4$alkyl, -$L^3R^5$, -$L^1R^5$, -$L^3R^7$, -$L^3L^4L^3R^7$, -$L^3L^4R^5$, -$L^3L^4L^3R^5$, —$OL^3R^5$, —$OL^3R^7$, —$OL^3L^4R^7$, —$OL^3L^4L^3R^7$, —$OR^8$, —$OL^3L^4R^5$, —$OL^3L^4L^3R^5$ and —$C(R^5)_2$OH;
each $R^4$ is independently selected from H and fluoro;
$R^5$ is —$P(O)(OR^9)_2$,
$R^6$ is —$CF_2P(O)(OR^9)_2$ or —$C(O)OR^{10}$;
$R^7$ is —$CF_2P(O)(OR^9)_2$ or —$C(O)OR^{10}$;
$R^8$ is H or $C_1$-$C_4$alkyl;
each $R^9$ is independently selected from H and $C_1$-$C_6$alkyl;
$R^{10}$ is H or $C_1$-$C_4$alkyl;
each p is independently selected from 1, 2, 3, 4, 5 and 6, and q is 1, 2, 3 or 4;
with the proviso that when $R^3$ is $C_1$-$C_4$ alkyl or —$OR^8$, $R^1$ is —$C(R^5)_2$OH, -$L^1R^5$, -$L^1R^6$, -$L^2R^5$, -$L^2R^6$, —$OL^2R^5$, or —$OL^2R^6$, wherein $R^6$ is —$CF_2P(O)(OR^9)_2$ and $R^7$ is —$CF_2P(O)(OR^9)_2$.

In certain embodiments of the compounds of Formula (I), $R^1$ is $C_1$-$C_6$ alkyl, in other embodiments $R^1$ is a methyl. In certain embodiments, $R^1$ is H. In other embodiments, $R^1$ is —$C(R^5)_2OH$, -$L^1R^5$, -$L^1R^6$, -$L^2R^5$, -$L^2R^6$, —$OL^2R^5$, or —$OL^2R^6$.

In certain embodiments of the compounds of Formula (I), when $R^1$—$C(R^5)_2OH$, -$L^1R^5$, -$L^1R^6$, -$L^2R^5$, -$L^2R^6$, —$OL^2R^5$, or —$OL^2R^6$, then $R^3$ is —$OR^8$ or $C_1$-$C_6$ alkyl. In certain embodiments, $R^1$ is —$C(R^5)_2OH$, -$L^1R^5$, -$L^1R^6$, -$L^2R^5$, -$L^2R^6$, —$OL^2R^5$, or —$OL^2R^6$, and $R^3$ is —OMe.

In some embodiments of the compounds of Formula (I), $R^3$ is $C_1$-$C_6$alkyl. In certain embodiments, $R^2$ is methyl.

In some embodiments of the compounds of Formula (I), $R^3$ is selected from $C_1$-$C_4$ alkyl, -$L^3R^5$, -$L^1R^5$, -$L^3R^7$, -$L^3L^4L^3R^7$, -$L^3L^4R^5$, and -$L^3L^4L^3R^5$. In alternative embodiments, $R^3$ is selected from —$OL^3R^5$, —$OL^3R^7$, —$OL^3L^4R^7$, —$OL^3L^4L^3R^7$, —$OR^8$, —$OL^3L^4R^5$, —$OL^3L^4L^3R^5$ and —$C(R^5)_2OH$. In certain embodiments, $R^3$ is —$OL^3R^5$, wherein —$OL^3R^5$ is a group of the formula —$O(CH_2)_{1-5}P(O)(OR)_2$. In other embodiments, $R^3$ is —$OL^3R^5$, wherein —$OL^3R^5$ is a group of the formula —$O(CH_2)_{1-5}CF_2P(O)(OR)_2$.

In some embodiments, $R^3$ is selected from $C_1$-$C_4$alkyl, -$L^3R^5$, -$L^1R^5$, -$L^3R^7$, -$L^3L^4L^3R^7$, -$L^3L^4R^5$, -$L^3L^4L^3R^5$, —$OL^3R^5$, —$OL^3R^7$, —$OL^3L^4R^7$, —$OL^3L^4L^3R^7$, —$OR^8$, —$OL^3L^4R^5$, and —$OL^3L^4L^3R^5$.

Where more than one $R^9$ is present, as in compounds comprising a —$P(O)(OR^9)_2$ moiety, the $R^9$ groups are the same or are different. In certain embodiments of such compounds of Formula (I), $R^9$ is H at each occurrence. In other embodiments, at least one $R^9$ is H and the other $R^9$ is $C_1$-$C_6$alkyl. In other embodiments, at least one $R^9$ is H and the other $R^9$ is methyl. In other embodiments, at least one $R^9$ is H and the other $R^9$ is ethyl. In other embodiments of such compounds of Formula (I), each $R^9$ is $C_1$-$C_6$alkyl and in certain embodiments, $R^9$ is methyl or ethyl, or a combination thereof.

In certain embodiments of the compounds of Formula (I), $L^2$ and/or $L^3$ is a group of the formula —$((CR^4R^4)_pO)_q(CH_2)_p$—, and in certain embodiments, this group is of the formula —$(CH_2CH_2O)_{1-3}(CH_2)_{1-3}$—.

In certain embodiments of the compounds of Formula (I), $L^2$ is $C_1$-$C_6$ alkylene, while in other embodiments $L^2$ is $C_1$-$C_6$ alkylene substituted with one to four fluoro groups. In certain embodiments of such compounds of Formula (I), $L^2$ is of the formula $(CH_2)_{0-5}CF_2$, wherein the fluoro-substituted carbon is not directly attached to the phenyl ring of Formula I. In certain embodiments of the compounds of Formula (I), $L^2$ is $C_2$-$C_6$ alkenylene, while in other embodiments $L^2$ is $C_2$-$C_6$ alkenylene substituted with one to four fluoro groups.

In certain embodiments of the compounds of Formula (I), $L^3$ is $C_1$-$C_6$ alkylene while in other embodiments $L^3$ is $C_1$-$C_6$ alkylene substituted with one to four fluoro groups. In certain embodiments of such compounds of Formula (I), $L^3$ is of the formula $(CH_2)_{0-5}CF_2$, wherein the fluoro-substituted carbon is not directly attached to the phenyl ring of Formula I.

In certain embodiments of the compounds of Formula (I), $L^2$ is arylene or heteroarylene. In some of these embodiments, $L^2$ is phenylene, such as 1,3-disubstituted phenylene or 1,4-disubstituted phenylene.

In certain embodiments of such compounds of Formula (I), $R^1$ is $C_1$-$C_6$alkyl; $R^2$ is $C_1$-$C_6$alkyl; $R^3$ is —$OL^3R^5$ or —$OL^3R^7$; $R^5$ is —$P(O)(OR^9)_2$; $R^7$ is —$CF_2P(O)(OR^9)_2$, and $L^3$ is $C_1$-$C_6$alkylene.

In certain embodiments of such compounds of Formula (I), $R^1$ is $C_1$-$C_6$alkyl; $R^2$ is $C_1$-$C_6$alkyl; $R^3$ is —$OL^3R^5$ or —$OL^3R^7$; $R^5$ is —$P(O)(OR^9)_2$; $R^7$ is —$CF_2P(O)(OR^9)_2$; $L^3$ is —$((CR^4R^4)_pO)_q(CH_2)_p$—; $R^4$ is H; q is 1 or 2, and p is 2.

In certain embodiments of such compounds of Formula (I), $R^1$ is -$L^2R^6$; $R^2$ is $C_1$-$C_6$alkyl; $R^3$ is —$OL^3R^5$ or —$OL^3R^7$; $R^5$ is —$P(O)(OR^9)_2$; $R^6$ is —$C(O)OR^{10}$; $R^7$ is —$CF_2P(O)(OR^9)_2$; $L^2$ is $C_1$-$C_6$alkylene, and $L^3$ is $C_1$-$C_6$alkylene.

In certain embodiments of such compounds of Formula (I), $R^1$ is -$L^2R^6$; $R^2$ is $C_1$-$C_6$alkyl; $R^3$ is —$OL^3R^5$ or —$OL^3R^7$; $R^5$ is —$P(O)(OR^9)_2$; $R^6$ is —$C(O)OR^{10}$; $R^7$ is —$CF_2P(O)(OR^9)_2$; $L^2$ is $C_1$-$C_6$alkylene; $L^3$ is —$((CR^4R^4)_pO)_q(CH_2)_p$—; $R^4$ is H; q is 1 or 2, and p is 2.

In certain embodiments of such compounds of Formula (I), $R^1$ is —$C(R^5)_2OH$, -$L^1R^5$, -$L^2R^5$ or -$L^1R^6$; $R^2$ is $C_1$-$C_6$alkyl; $R^3$ is —$OR^8$; $R^8$ is $C_1$-$C_6$alkyl; $R^5$ is —$P(O)(OR^9)_2$; $R^6$ is —$CF_2P(O)(OR^9)_2$; $L^1$ is —$C(O)$—, and $L^2$ is $C_1$-$C_6$alkylene or $C_2$-$C_6$alkenylene, each optionally substituted with 1 to 4 fluoro groups.

In certain embodiments of such compounds of Formula (I), $R^1$ is $C_1$-$C_6$alkyl; $R^2$ is $C_1$-$C_6$alkyl; $R^3$ is —$OL^3L^4R^5$—$OL^3L^4L^3R^5$, or —$OL^3L^4L^3R^7$; $R^5$ is —$P(O)(OR^9)_2$; $R^7$ is —$CF_2P(O)(OR^9)_2$; each $L^3$ is independently a $C_1$-$C_6$alkylene, and $L^4$ is phenylene.

In certain embodiments of such compounds of Formula (I), $R^1$ is $C_1$-$C_6$alkyl; $R^2$ is $C_1$-$C_6$alkyl; $R^3$ is —$C(R^5)_2OH$ or -$L^1R^5$; $R^5$ is —$P(O)(OR^9)_2$, and $L^1$ is —$C(O)$— or —$O$—.

In certain embodiments, of such compounds of Formula (I), and the pharmaceutically acceptable salts, pharmaceutically acceptable solvates (e.g. hydrates), the N-oxide derivatives, prodrug derivatives, protected derivatives, individual isomers and mixture of isomers thereof,

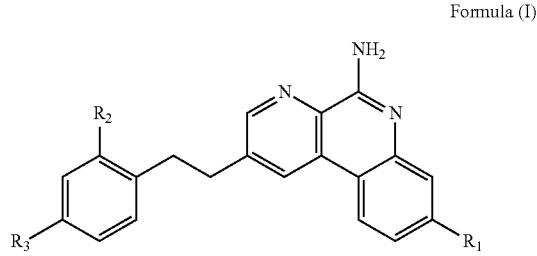

Formula (I)

$R^1$ is $C_1$-$C_4$alkyl, —$C(R^5)_2OH$, -$L^1R^5$, -$L^2R^5$, -$L^2R^6$, —$OL^2R^5$, or —$OL^2R^6$;

$L^1$ is —$C(O)$— or —$O$—;

$L^2$ is $C_1$-$C_6$alkylene, $C_2$-$C_6$alkenylene, arylene, heteroarylene or —$((CR^4R^4)_pO)_q(CH_2)_p$—, wherein the $C_1$-$C_6$alkylene and $C_2$-$C_6$alkenylene of $L^2$ are optionally substituted with 1 to 4 fluoro groups;

each $L^3$ is independently selected from $C_1$-$C_6$alkylene and —$((CR^4R^4)_pO)_q(CH_2)_p$—, wherein the $C_1$-$C_6$alkylene of $L^3$ is optionally substituted with 1 to 4 fluoro groups;

$L^4$ is arylene or heteroarylene;

$R^2$ is H or $C_1$-$C_4$alkyl;

$R^3$ is selected from $C_1$-$C_4$alkyl, -$L^3R^5$, -$L^1R^5$, -$L^3R^7$, -$L^3L^4L^3R^7$, -$L^3L^4R^5$, -$L^3L^4L^3R^5$, —$OL^3R^5$, —$OL^3R^7$, —$OL^3L^4R^7$, —$OL^3L^4L^3R^7$, —$OR^8$, —$OL^3L^4R^5$, —$OL^3L^4L^3R^5$ and —$C(R^5)_2OH$;

each $R^4$ is independently selected from H and fluoro;

$R^5$ is —$P(O)(OH)_2$, $R^6$ is —$CF_2P(O)(OH)_2$ or —$C(O)OH$;

$R^7$ is —$CF_2P(O)(OH)_2$ or —$C(O)OH$;

$R^8$ is H or $C_1$-$C_4$alkyl;

each p is independently selected from 1, 2, 3, 4, 5 and 6;

q is 1, 2, 3 or 4, with the proviso that when $R^3$ is —$OR^8$, $R^1$ is —$C(R^5)_2OH$, -$L^1R^5$, -$L^1R^6$, -$L^2R^5$, -$L^2R^6$, —$OL^2R^5$, or —$OL^2R^6$, wherein $R^6$ is —$CF_2P(O)(OH)_2$ and $R^7$ is —$CF_2P(O)(OH)_2$.

In certain embodiments of such compounds of Formula (I), $R^1$ is $C_1$-$C_6$alkyl; $R^2$ is $C_1$-$C_6$alkyl; $R^3$ is —$OL^3R^5$ or —$OL^3R^7$; $R^5$ is —$P(O)(OH)_2$; $R^7$ is —$CF_2P(O)(OH)_2$, and $L^3$ is $C_1$-$C_6$alkylene.

In certain embodiments of such compounds of Formula (I), $R^1$ is $C_1$-$C_6$alkyl; $R^2$ is $C_1$-$C_6$alkyl; $R^3$ is —$OL^3R^5$ or —$OL^3R^7$; $R^5$ is —$P(O)(OH)_2$; $R^7$ is —$CF_2P(O)(OH)_2$; $L^3$ is —$((CR^4R^4)_pO)_q(CH_2)_p$—; $R^4$ is H; q is 1 or 2, and p is 2.

In certain embodiments of such compounds of Formula (I), $R^1$ is -$L^2R^6$; $R^2$ is $C_1$-$C_6$alkyl; $R^3$ is —$OL^3R^5$ or —$OL^3R^7$; $R^5$ is —$P(O)(OH)_2$; $R^6$ is —$C(O)OH$; $R^7$ is —$CF_2P(O)(OH)_2$; $L^2$ is $C_1$-$C_6$alkylene, and $L^3$ is $C_1$-$C_6$alkylene.

In certain embodiments of such compounds of Formula (I), $R^1$ is -$L^2R^6$; $R^2$ is $C_1$-$C_6$alkyl; $R^3$ is —$OL^3R^5$ or —$OL^3R^7$; $R^5$ is —$P(O)(OH)_2$; $R^6$ is —$C(O)OH$; $R^7$ is —$CF_2P(O)(OH)_2$; $L^2$ is $C_1$-$C_6$alkylene; $L^3$ is -$((CR^4R^4)_pO)_q(CH_2)_p$—; $R^4$ is H; q is 1 or 2, and p is 2.

In certain embodiments of such compounds of Formula (I), $R^1$ is —$C(R^5)_2OH$, -$L^1R^5$, -$L^2R^5$ or -$L^1R^6$; $R^2$ is $C_1$-$C_6$alkyl; $R^3$ is —$OR^8$; $R^8$ is $C_1$-$C_6$alkyl; $R^5$ is —$P(O)(OH)_2$; $R^6$ is —$CF_2P(O)(OH)_2$; $L^1$ is —$C(O)$—, and $L^2$ is $C_1$-$C_6$alkylene or $C_2$-$C_6$alkenylene, each optionally substituted with 1 to 4 fluoro groups.

In certain embodiments of such compounds of Formula (I), $R^1$ is $C_1$-$C_6$alkyl; $R^2$ is $C_1$-$C_6$alkyl; $R^3$ is —$OL^3L^4R^5$—$OL^3L^4L^3R^5$, or —$OL^3L^4L^3R^7$; $R^5$ is —$P(O)(OH)_2$; $R^7$ is —$CF_2P(O)(OH)_2$; each $L^3$ is independently a $C_1$-$C_6$alkylene, and $L^4$ is phenylene.

In certain embodiments of such compounds of Formula (I), $R^1$ is $C_1$-$C_6$alkyl; $R^2$ is $C_1$-$C_6$alkyl; $R^3$ is —$C(R^5)_2OH$ or -$L^1R^5$; $R^5$ is —$P(O)(OR^9)_2$, and $L^1$ is —$C(O)$— or —$O$—.

In certain embodiments of the aforementioned compounds of Formula (I), $R^8$ is methyl. In certain embodiments of the aforementioned compounds of Formula (I), $R^1$ is methyl. In certain embodiments of the aforementioned compounds of Formula (I), $R^2$ is methyl.

In certain embodiments of the compounds of Formula (I) is selected from: 4-(4-(2-(5-amino-8-methylbenzo[f][1,7]naphthyridin-2-yl)ethyl)-3-methylphenoxy)-1,1-difluorobutylphosphonic acid; 3-(5-amino-2-(4-(4,4-difluoro-4-phosphonobutoxy)-2-methylphenethyl)benzo[f][1,7]naphthyridin-8-yl)propanoic acid; 3-(5-amino-2-(4-(2-(3,3-difluoro-3-phosphonopropoxy)ethoxy)-2-methylphenethyl)benzo[f][1,7]naphthyridin-8-yl)propanoic acid; 3-(5-amino-2-(2-methyl-4-(2-(2-(2-phosphonoethoxy)ethoxy)ethoxy)phenethyl)benzo[f][1,7]naphthyridin-8-yl)propanoic acid; 4-(2-(5-amino-8-methylbenzo[f][1,7]naphthyridin-2-yl)ethyl)-3-methylphenyl dihydrogen phosphate; (4-(2-(5-amino-8-methylbenzo[f][1,7]naphthyridin-2-yl)ethyl)-3-methylphenoxy)methylphosphonic acid; 5-(4-(2-(5-amino-8-methylbenzo[f][1,7]naphthyridin-2-yl)ethyl)-3-methylphenoxy)-1,1-difluoropentylphosphonic acid; 4-(4-(2-(5-amino-8-methylbenzo[f][1,7]naphthyridin-2-yl)ethyl)-3-methylphenoxy)-1,1-difluorobutylphosphonic acid; 3-(2-(4-(2-(5-amino-8-methylbenzo[f][1,7]naphthyridin-2-yl)ethyl)-3-methylphenoxy)ethoxy)-1,1-difluoropropylphosphonic acid; 2-(4-((4-(2-(5-amino-8-methylbenzo[f][1,7]naphthyridin-2-yl)ethyl)-3-methylphenoxy)methyl)phenyl)-1,1-difluoroethylphosphonic acid; 2-(5-amino-2-(4-methoxy-2-methylphenethyl)benzo[f][1,7]naphthyridin-8-yl)-1,1-difluoro-2-oxoethylphosphonic acid; (E)-2-(5-amino-2-(4-methoxy-2-methylphenethyl)benzo[f][1,7]naphthyridin-8-yl)vinylphosphonic acid; 2-(5-amino-2-(4-methoxy-2-methylphenethyl)benzo[f][1,7]naphthyridin-8-yl)ethylphosphonic acid; (E)-2-(5-amino-2-(4-methoxy-2-methylphenethyl)benzo[f][1,7]naphthyridin-8-yl)-1-fluorovinylphosphonic acid; 3-((4-(2-(5-amino-8-methylbenzo[f][1,7]naphthyridin-2-yl)ethyl)-3-methylphenoxy)methyl)phenylphosphonic acid; 5-amino-2-(4-methoxy-2-methylphenethyl)benzo[f][1,7]naphthyridine-8-carbonylphosphonic acid; 3-(5-amino-2-(2-methyl-4-(3-phosphonopropoxy)phenethyl)benzo[f][1,7]naphthyridin-8-yl)propanoic acid; 3-(5-amino-2-(4-(2-(2-(3,3-difluoro-3-phosphonopropoxy)ethoxy)ethoxy)-2-methylphenethyl)benzo[f][1,7]naphthyridin-8-yl)propanoic acid; 3-(5-amino-2-(2-methyl-4-(2-(2-phosphonoethoxy)ethoxy)phenethyl)benzo[f][1,7]naphthyridin-8-yl)propanoic acid; 2-(4-(2-(5-amino-8-methylbenzo[f][1,7]naphthyridin-2-yl)ethyl)-3-methylphenoxy)ethylphosphonic acid; 6-(4-(2-(5-amino-8-methylbenzo[f][1,7]naphthyridin-2-yl)ethyl)-3-methylphenoxy)hexylphosphonic acid; 6-(4-(2-(5-amino-8-methylbenzo[f][1,7]naphthyridin-2-yl)ethyl)-3-methylphenoxy)-1,1-difluorohexylphosphonic acid; 4-((4-(2-(5-amino-8-methylbenzo[f][1,7]naphthyridin-2-yl)ethyl)-3-methylphenoxy)methyl)benzylphosphonic acid; 2-(2-(2-(4-(2-(5-amino-8-methylbenzo[f][1,7]naphthyridin-2-yl)ethyl)-3-methylphenoxy)ethoxy)ethoxy)ethylphosphonic acid; 3-[5-amino-2-(2-{4-[2-(3,3-difluoro-3-phosphonopropoxy)ethoxy]-2-methylphenyl}ethyl)benzo[f]1,7-naphthyridin-8-yl]propanoic acid; {5-[4-(2-{5-amino-8-methylbenzo[f]1,7-naphthyridin-2-yl}ethyl)-3-methylphenoxy]pentyl}phosphonic acid, and {4-[4-(2-{5-amino-8-methylbenzo[f]1,7-naphthyridin-2-yl}ethyl)-3-methylphenoxy]butyl}phosphonic acid. Each of these compounds individually comprises a preferred embodiment of the compounds, compositions, and methods described herein.

Another aspect provided herein, is methods of using compounds of Formula (I), and pharmaceutical compositions comprising such compounds.

Another aspect provided herein are pharmaceutical compositions that include a therapeutically effective amount of a compound of Formula (I), and a pharmaceutically acceptable carrier. In certain embodiments of such pharmaceutical compositions, the pharmaceutical composition is formulated for intravenous administration, intravitrial administration, intramuscular administration, oral administration, rectal administration inhalation, nasal administration, topical administration, ophthalmic administration or otic administration. In other embodiments, the pharmaceutical compositions are in the form of a tablet, a pill, a capsule, a liquid, an inhalant, a nasal spray solution, a suppository, a solution, an emulsion, an ointment, eye drop or ear drop. In other embodiments, such pharmaceutical compositions further include one or more additional therapeutic agents.

Another aspect provided herein are pharmaceutical compositions that include a therapeutically effective amount of a compound of Formula (I), an aluminum-containing adjuvant, an antigen and a pharmaceutically acceptable carrier. In such pharmaceutical compositions the compound of Formula (I) is present in an amount sufficient to produce an immunostimulatory effect when administered. In certain embodiments of such pharmaceutical compositions, the pharmaceutical composition is formulated for intravenous administration, intravitrial administration or intramuscular administration. In such compositions the aluminum-containing adjuvant is selected from aluminum hydroxide, aluminum oxyhydroxide and aluminum hydroxyphosphate. In certain embodiments of such compositions, the aluminum-containing adjuvant is aluminum oxyhydroxide or aluminum hydroxide.

Another aspect provided herein is a pharmaceutical composition that includes a therapeutically effective amount of a compound of Formula (I) bound to an aluminum-containing adjuvant and a pharmaceutically acceptable carrier. In certain embodiments, such a composition is a dried down solid. In certain embodiments, such a composition is a lyophilized solid. In such compositions the aluminum-containing adjuvant is selected from aluminum hydroxide, aluminum oxyhydroxide and aluminum hydroxyphosphate. In certain embodiments of such compositions, the aluminum-containing adjuvant is aluminum oxyhydroxide or aluminum hydroxide.

Another aspect provided herein are immunogenic compositions comprising a compound of Formula (I), an aluminum-containing adjuvant and an antigen. In certain embodiments, the compound of Formula (I) is present in an amount effective to elicit, induce or enhance an immune response to the antigen in a subject to whom the composition is administered. In such immunogenic compositions the compound of Formula (I) is present in an amount sufficient to produce an immunostimulatory effect when administered. In such immunogenic compositions the aluminum-containing adjuvant is selected from aluminum hydroxide, aluminum oxyhydroxide and aluminum hydroxyphosphate. In certain embodiments of such immunogenic compositions, the aluminum-containing adjuvant is aluminum oxyhydroxide or aluminum hydroxide. In certain embodiments of such immunogenic compositions, the antigen is a bacterial antigen. In other embodiments of such immunogenic compositions, the antigen is a viral antigen or a fungal antigen. In certain embodiments of such immunogenic compositions, the antigen is a polypeptide. In certain embodiments such immunogenic compositions further comprise an additional adjuvant. In certain embodiments, such an immunogenic composition is a dried down solid. In certain embodiments, such an immunogenic composition is a lyophilized solid.

In certain embodiments, compounds of the invention are not bisphosphonates.

Another aspect provided herein is a method for enhancing the effectiveness of an immunogenic composition, wherein the immunogenic composition comprises an aluminum-containing adjuvant, and the method comprises adding an effective amount of a compound of Formula (I) to the immunogenic composition. In such methods the aluminum-containing adjuvant is selected from aluminum hydroxide, aluminum oxyhydroxide and aluminum hydroxyphosphate. In certain embodiments of such methods, the aluminum-containing adjuvant is aluminum oxyhydroxide or aluminum hydroxide.

Another aspect provided herein are methods for eliciting or inducing an immune response in a vertebrate subject comprising administering to the vertebrate subject an effective amount of an immunogenic composition of the invention. In some embodiments, the present invention provides methods for eliciting or inducing a cytotoxic-T lymphocyte (CTL) response in a vertebrate subject comprising administering to the vertebrate subject an effective amount of an immunogenic composition of the invention. In other embodiments, the present invention provides methods of eliciting or inducing an antibody-mediated immune response in a vertebrate subject comprising administering to the vertebrate subject an effective amount of an immunogenic composition of the invention.

Another aspect provided herein are methods of making immunogenic compositions described herein.

Another aspect provided herein are vaccine compositions that comprise an immunogenic composition of the invention.

Another aspect provided herein are medicaments for treating a patient with a disease or disorder associated with TLR7 receptor activity, and such medicaments include a therapeutically effective amount of a compound of Formula (I) wherein the compound of Formula (I) is a TLR7 receptor agonist.

Another aspect provided herein is the use of a compound of Formula (I) in the manufacture of a medicament for treating a disease or disorder in a patient where modulation of a TLR7 receptor is implicated.

Another aspect provided herein includes methods for activating a TLR7 receptor, wherein the method includes administering to a system or a subject in need thereof, a therapeutically effective amount of a compound of Formula (I), or pharmaceutically acceptable salts or pharmaceutical compositions thereof, thereby activating the TLR receptor. In such methods, the compound of Formula (I) is a TLR7 receptor agonist. In certain embodiments of such methods, the methods include administering the compound to a cell or tissue system or to a human or animal subject.

Another aspect provided herein includes methods for treating a disease or disorder where modulation of TLR7 receptor is implicated, wherein the method includes administering to a system or subject in need of such treatment an effective amount of a compound of Formula (I), or pharmaceutically acceptable salts or pharmaceutical compositions thereof, thereby treating the disease or disorder. In such methods, the compound of Formula (I) is a TLR7 receptor agonist. In certain embodiments of such methods, the methods include administering the compound to a cell or tissue system or to a human or animal subject.

In certain embodiments of such methods, the disease or condition is an infectious disease, an inflammatory disease, a respiratory disease, a dermatological disease or an autoimmune disease. In certain embodiments of such methods, the disease or condition is asthma, chronic obstructive pulmonary disease (COPD), adult respiratory distress syndrome (ARDS), ulcerative colitis, Crohns disease, bronchitis, dermatitis, actinic keratosis, basal cell carcinoma, allergic rhinitis, psoriasis, scleroderma, urticaria, rheumatoid arthritis, multiple sclerosis, cancer, breast cancer, HIV or lupus.

Another aspect provided herein includes methods for treating a cell-proliferative disease, comprising administering to a system or subject in need of such treatment an effective amount of a compound of Formula (I), or pharmaceutically acceptable salts or pharmaceutical compositions thereof; wherein the cell-proliferative disease is lymphoma, osteosarcoma, melanoma, or a tumor of breast, renal, prostate, colorectal, thyroid, ovarian, pancreatic, neuronal, lung, uterine or gastrointestinal tumor.

Another aspect provided herein are pharmaceutical composition that include a compound of Formula (I), an antigen and a pharmaceutically acceptable carrier, wherein such pharmaceutical compositions are immunogenic compositions, and the compound is an immune potentiator and is present in an amount effective to enhance an immune response to the antigen, in a subject receiving the composition. In certain embodiments, such pharmaceutical compositions, further includes one or more immunoregulatory agents. In certain embodiments, the one or more immunoregulatory agents include one or more adjuvants. In certain embodiments, such adjuvants are selected from adjuvants that are a mineral-containing composition, an oil emulsion, a saponin formulation, a virosome, a virus-like particle, a bacterial derivative, a microbial derivative, a human immunomodulator, a bioadhesive, a mucoadhesive, a microparticle, a liposome, a polyoxyethylene ether formulation, a polyoxyethylene ester formulation, a polyphosphazene, a muramyl peptide, or an imidazoquinolone compound. In certain embodiments, the adjuvant is an oil emulsion. In certain embodiments the immunogenic compositions are useful as vaccines, and the compound is present in an amount sufficient to produce an immunostimulatory effect upon administration.

Another aspect provided herein is compound for use in a method of medical treatment, wherein the method of medical treatment is for treating a disease associated with TLR7 receptor activity, wherein the disease is selected from an infectious disease, an inflammatory disease, a respiratory disease, a dermatological disease or an autoimmune disease, and wherein the compound is a compound of Formula (I) of claim 1. In certain embodiments of such methods, the disease or condition is asthma, chronic obstructive pulmonary disease (COPD), adult respiratory distress syndrome (ARDS), ulcerative colitis, Crohns disease, bronchitis, dermatitis, actinic keratosis, basal cell carcinoma, allergic rhinitis, psoriasis, scleroderma, urticaria, rheumatoid arthritis, multiple sclerosis, cancer, breast cancer, HIV or lupus.

DETAILED DESCRIPTION OF THE INVENTION

Definitions

Figure 1:
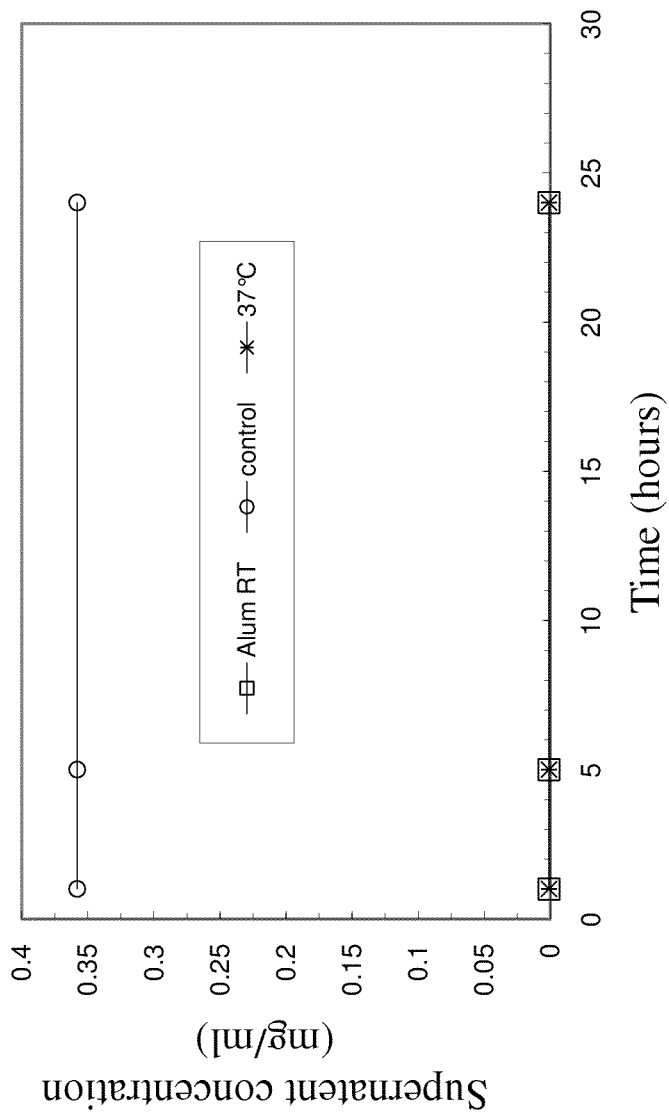
FIG. 1 shows the concentration of compound 1 in the supernatant with and without the addition of aluminum hydroxide. The concentration was obtained via HPLC analysis.

The terms "alkenyl" or "alkene," as used herein, refers to a partially unsaturated branched or straight chain hydrocarbon having at least one carbon-carbon double bond. Atoms oriented about the double bond are in either the cis (Z) or trans (E) conformation. In certain embodiments such alkenyl or alkene group are optionally substituted. As used herein, the terms "$C_2$-$C_3$alkenyl", "$C_2$-$C_4$alkenyl", "$C_2$-$C_5$alkenyl", "$C_2$-$C_6$alkenyl", "$C_2$-$C_7$alkenyl", and "$C_2$-$C_8$alkenyl" refer to an alkenyl group containing at least 2, and at most 3, 4, 5, 6, 7 or 8 carbon atoms, respectively. If not otherwise specified, an alkenyl group generally is a $C_2$-$C_6$ alkenyl. Non-limiting examples of alkenyl groups, as used herein, include ethenyl, propenyl, butenyl, pentenyl, hexenyl, heptenyl, octenyl, nonenyl, decenyl and the like.

The term "alkenylene," as used herein, refers to a partially unsaturated branched or straight chain divalent hydrocarbon radical derived from an alkenyl group. In certain embodiments such alkenylene group are optionally substituted. As used herein, the terms "$C_2$-$C_3$alkenylene", "$C_2$-$C_4$alkenylene", "$C_2$-$C_5$alkenylene", "$C_2$-$C_6$alkenylene", "$C_2$-$C_7$alkenylene", and "$C_2$-$C_8$alkenylene" refer to an alkenylene group containing at least 2, and at most 3, 4, 5, 6, 7 or 8 carbon atoms respectively. If not otherwise specified, an alkenylene group generally is a $C_2$-$C_6$ alkenylene. Non-limiting examples of alkenylene groups as used herein include, ethenylene, propenylene, butenylene, pentenylene, hexenylene, heptenylene, octenylene, nonenylene, decenylene and the like.

The term "alkyl," as used herein, refers to a saturated branched or straight chain hydrocarbon. In certain embodiments such alkyl groups are optionally substituted. As used herein, the terms "$C_1$-$C_3$alkyl", "$C_1$-$C_4$alkyl", "$C_1$-$C_5$alkyl", "$C_1$-$C_6$alkyl", "$C_1$-$C_7$alkyl" and "$C_1$-$C_8$alkyl" refer to an alkyl group containing at least 1, and at most 3, 4, 5, 6, 7 or 8 carbon atoms, respectively. If not otherwise specified, an alkyl group generally is a $C_1$-$C_6$ alkyl. Non-limiting examples of alkyl groups as used herein include methyl, ethyl, n-propyl, isopropyl, n-butyl, isobutyl, sec-butyl, t-butyl, n-pentyl, isopentyl, hexyl, heptyl, octyl, nonyl, decyl and the like.

The term "alkylene," as used herein, refers to a saturated branched or straight chain divalent hydrocarbon radical derived from an alkyl group. In certain embodiments such alkylene groups are optionally substituted. As used herein, the terms "$C_1$-$C_3$alkylene", "$C_1$-$C_4$alkylene", "$C_1$-$C_5$alkylene", "$C_1$-$C_6$alkylene", "$C_1$-$C_7$alkylene" and "$C_1$-$C_8$alkylene" refer to an alkylene group containing at least 1, and at most 3, 4, 5, 6, 7 or 8 carbon atoms respectively. If not otherwise specified, an alkylene group generally is a $C_1$-$C_6$ alkylene. Non-limiting examples of alkylene groups as used herein include, methylene, ethylene, n-propylene, isopropylene, n-butylene, isobutylene, sec-butylene, t-butylene, n-pentylene, isopentylene, hexylene and the like.

The term "alkoxy," as used herein, refers to the group —$OR_a$, where $R_a$ is an alkyl group as defined herein. An alkoxy group can be optionally substituted. As used herein, the terms "$C_1$-$C_3$alkoxy", "$C_1$-$C_4$alkoxy", "$C_1$-$C_5$alkoxy", "$C_1$-$C_6$alkoxy", "$C_1$-$C_7$alkoxy" and "$C_1$-$C_8$alkoxy" refer to an alkoxy group wherein the alkyl moiety contains at least 1, and at most 3, 4, 5, 6, 7 or 8, carbon atoms. Non-limiting examples of alkoxy groups, as used herein, include methoxy, ethoxy, n-propoxy, isopropoxy, n-butyloxy, t-butyloxy, pentyloxy, hexyloxy, heptyloxy, octyloxy, nonyloxy, decyloxy and the like.

The term "aryl," as used herein, refers to monocyclic, bicyclic, and tricyclic ring systems having a total of five to fourteen ring members, wherein at least one ring in the system is aromatic and wherein each ring in the system contains 3 to 7 ring members. In certain embodiments such aryl groups are optionally substituted. Non-limiting examples of an aryl group, as used herein, include phenyl, naphthyl, fluorenyl, indenyl, azulenyl, anthracenyl and the like. As an optional alternative, the term "aryl" can instead refer to monocyclic or fused bicyclic ring systems having a total of six, ten or fourteen carbon atom ring members, optionally substituted with one or more substituents; non-limiting examples of such aryl groups include phenyl and naphthyl.

The term "arylene," as used herein means a divalent radical derived from an aryl group. In certain embodiments such arylene groups are optionally substituted.

The term "halogen," as used herein, refers to fluorine (F), chlorine (Cl), bromine (Br), or iodine (I).

The term "halo," as used herein, refers to the halogen radicals: fluoro (—F), chloro (—Cl), bromo (—Br), and iodo (—I).

The terms "haloalkyl" or "halo-substituted alkyl," as used herein, refers to an alkyl group as defined herein, substituted with one or more halogen groups, wherein the halogen groups are the same or different. A haloalkyl group can be optionally substituted. Non-limiting examples of such branched or straight chained haloalkyl groups, as used herein, include methyl, ethyl, propyl, isopropyl, isobutyl and n-butyl substituted with one or more halogen groups, wherein the halogen groups are the same or different, including, but not limited to, trifluoromethyl, pentafluoroethyl, and the like.

The terms "haloalkenyl" or "halo-substituted alkenyl," as used herein, refers to an alkenyl group as defined herein, substituted with one or more halogen groups, wherein the halogen groups are the same or different. A haloalkenyl group can be optionally substituted. Non-limiting examples of such branched or straight chained haloalkenyl groups, as used herein, include ethenyl, propenyl, butenyl, pentenyl, hexenyl, heptenyl, octenyl, nonenyl, decenyl and the like substituted with one or more halogen groups, wherein the halogen groups are the same or different.

The term "heteroaryl," as used herein, refers to monocyclic, bicyclic, and tricyclic ring systems having a total of five to fourteen ring members, wherein at least one ring in the system is aromatic, at least one ring in the system contains one or more heteroatoms selected from nitrogen, oxygen and sulfur, and wherein each ring in the system contains 3 to 7 ring members. In certain embodiments such heteroaryl groups are optionally substituted. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl, triazolyl and tetrazolyl. As an optional alternative, the term "heteroaryl" can instead refer to monocyclic or fused bicyclic ring systems having a total of 5, 6, 9 or 10 ring members, wherein at least one ring member is a heteroatom selected from nitrogen, oxygen and sulfur, optionally substituted with one or more substituents e.g. benzofuranyl, benzofurazanyl, benzoxazolyl, benzopyranyl, benzthiazolyl, benzothienyl, benzazepinyl, benzimidazolyl, benzothiopyranyl, benzo[b]furyl, benzo[b]thienyl, cinnolinyl, furazanyl, furyl, imidazolyl, indolyl, indolizinyl, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, thiazolyl, thiadiazolyl, thienyl, triazinyl, triazolyl and tetrazolyl.

The term "heteroarylene," as used herein means a divalent radical derived from a heteroaryl group. In certain embodiments such heteroarylene groups are optionally substituted.

The term "heteroatom," as used herein, refers to one or more of oxygen, sulfur, nitrogen, phosphorus, or silicon.

The term "hydroxyl," as used herein, refers to the group —OH.

The term "hydroxyalkyl," as used herein refers to an alkyl group as defined herein substituted with one or more hydroxyl group. Non-limiting examples of branched or straight chained "$C_1$-$C_6$ hydroxyalkyl groups as used herein include methyl, ethyl, propyl, isopropyl, isobutyl and n-butyl groups substituted with one or more hydroxyl groups.

The term "optionally substituted," as used herein, means that the referenced group may or may not be substituted with one or more additional group(s) individually and independently selected from alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof. Non-limiting examples of optional substituents include, halo, —CN, =O, =N—OH, =N—OR, =N—R, —OR, —C(O)R, —C(O)OR, —OC(O)R, —OC(O)OR, —C(O)NHR, —C(O)NR$_2$, —OC(O)NHR, —OC(O)NR$_2$, —SR—, —S(O)R, —S(O)$_2$R, —NHR, —N(R)$_2$, —NHC(O)R, —NRC(O)R, —NHC(O)OR, —NRC(O)OR, S(O)$_2$NHR, —S(O)$_2$N(R)$_2$, —NHS(O)$_2$NR$_2$, —NRS(O)$_2$NR$_2$, —NHS(O)$_2$R, —NRS(O)$_2$R, $C_1$-$C_8$alkyl, $C_1$-$C_8$alkoxy, aryl, heteroaryl, cycloalkyl, heterocycloalkyl, halo-substituted $C_1$-$C_8$alkyl, and halo-substituted $C_1$-$C_8$alkoxy, where each R is independently selected from H, halo, $C_1$-$C_8$alkyl, $C_1$-$C_8$alkoxy, aryl, heteroaryl, cycloalkyl, heterocycloalkyl, halo-substituted $C_1$-$C_8$alkyl, and halo-substituted $C_1$-$C_8$alkoxy. The placement and number of such substituent groups is done in accordance with the well-understood valence limitations of each group, for example =O is a suitable substituent for an alkyl group but not for an aryl group.

The term "solvate," as used herein, refers to a complex of variable stoichiometry formed by a solute (by way of example, a compound of Formula (I), or a salt thereof, as described herein) and a solvent. Non-limiting examples of a solvent are water, acetone, methanol, ethanol and acetic acid.

The term "acceptable" with respect to a formulation, composition or ingredient, as used herein, means having no persistent detrimental effect on the general health of the subject being treated.

The term "administration" or "administering" of the subject compound means providing a compound of Formula (I), a pharmaceutically acceptable salt, a pharmaceutically acceptable solvate, or prodrug thereof to a subject in need of treatment.

The term "antigen" refers to a molecule containing one or more epitopes (e.g., linear, conformational or both) that elicit an immunological response. The term may be used interchangeably with the term "immunogen." By "elicit" is meant to induce, promote, enhance or modulate an immune response or immune reaction. In some instances, the immune response or immune reaction is a humoral and/or cellular response. An antigen may induce, promote, enhance or modulate an immune response or immune reaction in cells in vitro and/or in vivo in a subject and/or ex vivo in a subject's cells or tissues. Such immune response or reaction may include, but is not limited to, eliciting the formation of antibodies in a subject, or generating a specific population of lymphocytes reactive with the antigen. Antigens are typically macromolecules (e.g., proteins, polysaccharides, polynucleotides) that are foreign to the host.

The term "antigen", as used herein, also denotes subunit antigens (i.e., antigens which are separate and discrete from a whole organism with which the antigen is associated in nature), as well as killed, attenuated or inactivated bacteria, viruses, parasites, parasites or other pathogens or tumor cells, including extracellular domains of cell surface receptors and intracellular portions containing T-cell epitopes. Antibodies such as anti-idiotype antibodies, or fragments thereof, and synthetic peptide mimotopes, which can mimic an antigen or antigenic determinant, are also encompassed by the definition of antigen as used herein. Similarly, an oligonucleotide or polynucleotide that expresses an immunogenic protein, antigen or antigenic determinant in vivo, such as in gene therapy or nucleic acid immunization applications, is also encompassed by the definition of antigen herein.

The term "epitope" refers to that portion of given species (e.g., an antigenic molecule or antigenic complex) that determines its immunological specificity. An epitope is within the scope of the present definition of antigen. Commonly, an epitope is a polypeptide or polysaccharide in a naturally occurring antigen. In artificial antigens, it can be a low molecular weight substance such as an arsanilic acid derivative. Normally, a B-cell epitope will include at least about 5 amino acids but can be as small as 3-4 amino acids. A T-cell epitope, such as a CTL epitope, will typically include at least about 7-9 amino acids, and a helper T-cell epitope will typically include at least about 12-20 amino acids.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

The term "carrier," as used herein, refers to chemical compounds or agents that facilitate the incorporation of a compound described herein into cells or tissues.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "dermatological disorder," as used herein refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, actinic keratosis, basal cell carcinoma and urticaria.

The term "diluent," as used herein, refers to chemical compounds that are used to dilute a compound described herein prior to delivery. Diluents can also be used to stabilize compounds described herein.

The terms "effective amount" or "therapeutically effective amount," as used herein, refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "excipient" refers to any essentially accessory substance that may be present in the finished dosage form. For example, the term "excipient" includes vehicles, binders, disontegrants, fillers (diluents), lubricants, suspending/dispersing agents, and the like.

The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis.

The term "iatrogenic," as used herein, means a condition, disorder, or disease created or worsened by medical or surgical therapy.

The term "immunologically effective amount," as used herein, means that the administration of a sufficient amount to an individual, either in a single dose or as part of a series, that is effective for treatment or prevention of an immunological disease or disorder. This amount varies depending upon the health and physical condition of the individual to be treated, age, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

An "immunological response" or "immune response" to an antigen or composition, as used herein, refers to the development in a subject of a humoral and/or cellular immune response to the antigen or composition.

Immune responses include innate and adaptive immune responses. Innate immune responses are fast-acting responses that provide a first line of defense for the immune system. In contrast, adaptive immunity uses selection and clonal expansion of immune cells having somatically rearranged receptor genes (e.g., T- and B-cell receptors) that recognize antigens from a given pathogen or disorder (e.g., a tumor), thereby providing specificity and immunological memory. Innate immune responses, among their many effects, lead to a rapid burst of inflammatory cytokines and activation of antigen-presenting cells (APCs) such as macrophages and dendritic cells. To distinguish pathogens from self-components, the innate immune system uses a variety of relatively invariable receptors that detect signatures from pathogens, known as pathogen-associated molecular patterns, or PAMPs. The addition of microbial components to experimental vaccines is known to lead to the development of robust and durable adaptive immune responses. The mechanism behind this potentiation of the immune responses has been reported to involve pattern-recognition receptors (PRRs), which are differentially expressed on a variety of immune cells, including neutrophils, macrophages, dendritic cells, natural killer cells, B cells and some nonimmune cells such as epithelial and endothelial cells. Engagement of PRRs leads to the activation of some of these cells and their secretion of cytokines and chemokines, as well as maturation and migration of other cells. In tandem, this creates an inflammatory environment that leads to the establishment of the adaptive immune response. PRRs include nonphagocytic receptors, such as Toll-like receptors (TLRs) and nucleotide-binding oligomerization domain (NOD) proteins, and receptors that induce phagocytosis, such as scavenger receptors, mannose receptors and β-glucan receptors. Dendritic cells are recognized as some of the most important cell types for initiating the priming of naive $CD4^+$ helper T ($T_H$) cells and for inducing $CD8^+$ T cell differentiation into killer cells. TLR signaling has been reported to play an important role in determining the quality of these helper T cell responses, for instance, with the nature of the TLR signal determining the specific type of $T_H$ response that is observed (e.g., $T_H1$ versus $T_H2$ response). A combination of antibody (humoral) and cellular immunity are produced as part of a $T_H1$-type response, whereas a $T_H2$-type response is predominantly an antibody response.

A "humoral immune response" refers to an immune response mediated by antibody molecules, while a "cellular immune response" refers to an immune response mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, non-specific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition such as an as an immunogenic composition or a vaccine that elicits a cellular immune response may thus serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen or composition to stimulate a cell-mediated immunological response may be determined by a number of assays known in the art, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al. (1993) J. Immunol. 151:4189-4199; Doe et al. (1994) Eur. J. Immunol. 24:2369-2376. Thus, an immunological response as used herein may be one which stimulates the production of CTLs and/or the production or activation of helper T-cells. The antigen of interest may also elicit an antibody-mediated immune response. Hence, an immunological response may include, for example, one or more of the following effects among others: the production of antibodies by, for example, B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

The immunogenic compositions of the invention display "enhanced immunogenicity" for a given antigen when they possess a greater capacity to elicit an immune response than the immune response elicited by an equivalent amount of the antigen in a differing composition (e.g., wherein the antigen is administered as a soluble protein). Thus, a composition may display "enhanced immunogenicity," for example, because the composition generates a stronger immune response, or because a lower dose or fewer doses of antigen is necessary to achieve an immune response in the subject to which it is administered. Such enhanced immunogenicity can be determined, for example, by administering the compositions of the invention, and antigen controls, to animals and comparing assay results of the two.

The term "inflammatory disorders," as used herein, refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporal arthritis); joints (arthritis: crystalline, osteo-, psoriatic, reactive, rheumatoid, Reiter's); gastrointestinal tract (Disease); skin (dermatitis); or multiple organs and tissues (systemic lupus erythematosus).

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist or an antagonist.

The terms "ocular disease" or "ophthalmic disease," as used herein, refer to diseases which affect the eye or eyes and potentially the surrounding tissues as well. Ocular or ophthalmic diseases include, but are not limited to, conjunctivitis, retinitis, scleritis, uveitis, allergic conjunctivitis, vernal conjunctivitis, papillary conjunctivitis and cytomegalovirus (CMV) retinitis.

The term "oligonucleotide", as used herein, refers to a polynucleotide having in the range of 5 to 100 nucleotides, typically 5 to 30 nucleotides in size.

The term "pharmaceutically acceptable," as used herein, refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

The term "pharmaceutically acceptable salt," as used herein, refers to a formulation of a compound that does not cause significant irritation to an organism to which it is administered and does not abrogate the biological activity and properties of the compounds described herein.

The terms "combination" or "pharmaceutical combination," as used herein mean a product that results from the mixing or combining of more than one active ingredient and includes both fixed and non-fixed combinations of the active ingredients. The term "fixed combination" means that the active ingredients, by way of example, a compound of Formula (I) and an additional therapeutic agent, are both administered to a patient simultaneously in the form of a single entity or dosage. The term "non-fixed combination" means that the active ingredients, by way of example, a compound of Formula (I) and an additional therapeutic agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The terms "composition" or "pharmaceutical composition," as used herein, refers to a mixture of at least one compound, such as the compounds of Formula (I) provided herein, with at least one and optionally more than one other pharmaceutically acceptable chemical components, such as carriers, stabilizers, diluents, dispersing agents, suspending agents, thickening agents, and/or excipients.

By "physiological pH" or a "pH in the physiological range" is meant a pH in the range of approximately 7.2 to 8.0 inclusive, more typically in the range of approximately 7.2 to 7.6 inclusive.

The term "prodrug," as used herein, refers to an agent that is converted into the parent drug in vivo. A non-limiting example of a prodrug of the compounds described herein is a compound described herein administered as an ester which is then metabolically hydrolyzed to a carboxylic acid, the active entity, once inside the cell. A further example of a prodrug is a short peptide bonded to an acid group where the peptide is metabolized to reveal the active moiety.

The terms "polynucleotide" and "nucleic acid" are used interchangeably, and refer to a single- or double-stranded polymer of deoxyribonucleotide or ribonucleotide bases. Single-stranded polynucleotides include coding strands and antisense strands. Polynucleotides include RNA and DNA, and may be isolated from natural sources, synthesized in vitro, or prepared from a combination of natural and synthetic molecules. Examples of polynucleotides include, but are not limited to, genes, cDNAs, mRNAs, self-replicating RNA molecules, self-replicating DNA molecules, genomic DNA sequences, genomic RNA sequences, oligonucleotides. Self-replicating RNA molecules and self-replicating DNA molecules are able to self amplify when introduced into a host cell.

A polynucleotide can be linear or non-linear (e.g., comprising circular, branched, etc. elements). The terms "polynucleotide" and "nucleic acid" encompass modified variants (e.g., sequences with a deletion, addition and/or substitution). Modified variants may be deliberate, such as through site-directed mutagenesis, or may be accidental, such as through natural mutations.

A polynucleotide can be composed of monomers that are naturally-occurring nucleotides (such as DNA and RNA), or analogs of naturally-occurring nucleotides, or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Polynucleotide monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The terms "polynucleotide" and "nucleic acid" also include so-called "peptide nucleic acids", which comprise naturally-occurring or modified nucleic acid bases attached to a polyamide backbone.

The term "polynucleotide-containing species", as used herein, refers to a molecule, at least a portion of which is a polynucleotide.

The terms "polypeptide", "protein" and "peptide", as used herein, refer to any polymer formed from multiple amino acids, regardless of length or posttranslational modification (e.g., phosphorylation or glycosylation), associated, at least in part, by covalent bonding (e.g., "protein" as used herein refers both to linear polymers (chains) of amino acids associated by peptide bonds as well as proteins exhibiting secondary, tertiary, or quaternary structure, which can include other forms of intramolecular and intermolecular association, such as hydrogen and van der Waals bonds, within or between peptide chain(s)). Examples of polypeptides include, but are not limited to, proteins, peptides, oligopeptides, dimers, multimers, variants, and the like. In some embodiments, the polypeptide can be unmodified such that it lacks modifications such as phosphorylation and glycosylation. A polypeptide can contain part or all of a single naturally-occurring polypeptide, or can be a fusion or chimeric polypeptide containing amino acid sequences from two or more naturally-occurring polypeptides.

The term "polypeptide-containing species" refers to a molecule, at least a potion of which is a polypeptide. Examples include polypeptides, glycoproteins, metalloproteins, lipoproteins, saccharide antigens conjugated to carrier proteins, and so forth.

The term "respiratory disease," as used herein, refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "subject" or "patient," as used herein, encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like. Frequently the subject is a human, and may be a human who has been diagnosed as in need of treatment for a disease or disorder disclosed herein.

The term "TLR7 modulator," as used herein, refers to a compound which modulates a TLR7 receptor.

The term "TLR7 disease" or a "disease or disorder associated with TLR7 activity," as used herein, refers to any disease state associated with a toll-like receptor. Such diseases or disorders include, but are not limited to, infectious diseases, inflammatory diseases, respiratory diseases and autoimmune diseases, such as, by way of example only, asthma, chronic obstructive pulmonary disease (COPD), adult respiratory distress syndrome (ARDs), Crohns disease, bronchitis, dermatitis, allergic rhinitis, psoriasis, scleroderma, urticaria, rheumatoid arthritis, multiple sclerosis, cancer, HIV and lupus.

The term "therapeutically effective amount," as used herein, refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The terms "treat," "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

The term "vector construct" generally refers to any assembly that is capable of directing the expression of a nucleic acid sequence(s) or gene(s) of interest. A "DNA vector construct" refers to a DNA molecule that is capable of directing the expression of a nucleic acid sequence(s) or gene(s) of interest. One specific type of DNA vector construct is a plasmid, which is a circular episomal DNA molecule capable of autonomous replication within a host cell. Typically, a plasmid is a circular double stranded DNA loop into which additional DNA segments can be ligated. pCMV is one specific plasmid that is well known in the art. Other DNA vector constructs are known, which are based on RNA viruses. These DNA vector constructs typically comprise a promoter that functions in a eukaryotic cell, 5' of a cDNA sequence for which the transcription product is an RNA vector construct (e.g., an alphavirus RNA vector replicon), and a 3' termination region. Other examples of vector constructs include RNA vector constructs (e.g., alphavirus vector constructs) and the like. As used herein, "RNA vector construct", "RNA vector replicon" and "replicon" refer to an RNA molecule that is capable of directing its own amplification or self-replication in vivo, typically within a target cell. The RNA vector construct is used directly, without the requirement for introduction of DNA into a cell and transport to the nucleus where transcription would occur. By using the RNA vector for direct delivery into the cytoplasm of the host cell, autonomous replication and translation of the heterologous nucleic acid sequence occurs efficiently.

The compound names provided herein were obtained using ChemDraw Ultra 10.0 (CambridgeSoft®) or JChem version 5.2.2 (ChemAxon).

Other objects, features and advantages of the methods, compositions and combinations described herein will become apparent from the following detailed description. It should be understood, however, that the detailed description and the specific examples, while indicating specific embodiments, are given by way of illustration only.

Description Of The Preferred Embodiments

Provided herein are compounds and pharmaceutical compositions thereof, which are agonists of toll-like receptor-7 (TLR7). Also provided herein are compounds, pharmaceutical compositions and methods for the treatment of diseases and/or disorders associated with TLR7 activity.

The TLR7 agonists provided herein are compounds having the structure of Formula (I), and pharmaceutically acceptable salts, pharmaceutically acceptable solvates (e.g. hydrates), the N-oxide derivatives, prodrug derivatives, protected derivatives, individual isomers and mixture of isomers thereof:

Formula (I)

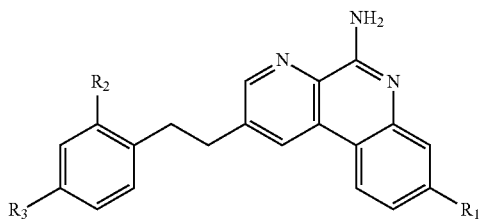

wherein:
$R^1$ is H, $C_1$-$C_6$alkyl, —$C(R^5)_2$OH, -$L^1R^5$, -$L^1R^6$, -$L^2R^5$, -$L^2R^6$, —$OL^2R^5$, or —$OL^2R^6$;
$L^1$ is —C(O)— or —O—;
$L^2$ is $C_1$-$C_6$alkylene, $C_2$-$C_6$alkenylene, arylene, heteroarylene or —$((CR^4R^4)_pO)_q(CH_2)_p$—, wherein the $C_1$-$C_6$alkylene and $C_2$-$C_6$alkenylene of $L^2$ are optionally substituted with 1 to 4 fluoro groups;
each $L^3$ is independently selected from $C_1$-$C_6$alkylene and —$((CR^4R^4)_pO)_q(CH_2)_p$—, wherein the $C_1$-$C_6$alkylene of $L^3$ is optionally substituted with 1 to 4 fluoro groups;
$L^4$ is arylene or heteroarylene;
$R^2$ is H or $C_1$-$C_6$alkyl;
$R^3$ is selected from $C_1$-$C_4$alkyl, -$L^3R^5$, -$L^1R^5$, -$L^3R^7$, -$L^3L^4L^3R^7$, -$L^3L^4R^5$, -$L^3L^4L^3R^5$, —$OL^3R^5$, —$OL^3R^7$, —$OL^3L^4R^7$, —$OL^3L^4L^3R^7$, —$OR^8$, —$OL^3L^4R^5$, —$OL^3L^4L^3R^5$ and —$C(R^5)_2$OH;
each $R^4$ is independently selected from H and fluoro;
$R^5$ is —$P(O)(OR^9)_2$,
$R^6$ is —$CF_2P(O)(OR^9)_2$ or —$C(O)OR^{10}$;
$R^7$ is —$CF_2P(O)(OR^9)_2$ or —$C(O)OR^{10}$;
$R^8$ is H or $C_1$-$C_4$alkyl;
each $R^9$ is independently selected from H and $C_1$-$C_6$alkyl;
$R^{10}$ is H or $C_1$-$C_4$alkyl;
each p is independently selected from 1, 2, 3, 4, 5 and 6, and q is 1, 2, 3 or 4;
with the proviso that when $R^3$ is $C_1$-$C_4$ alkyl or —$OR^8$, $R^1$ is —$C(R^5)_2$OH, -$L^1R^5$, -$L^1R^6$, -$L^2R^5$, -$L^2R^6$, —$OL^2R^5$, or —$OL^2R^6$, wherein $R^6$ is —$CF_2P(O)(OR^9)_2$ and $R^7$ is —$CF_2P(O)(OR^9)_2$ In certain embodiments of the compounds of Formula (I), $R^1$ is $C_1$-$C_6$ alkyl, in other embodiments $R^1$ is a methyl. In certain embodiments, $R^1$ is H. In other embodiments, $R^1$ is —$C(R^5)_2$OH, -$L^1R^5$, -$L^1R^6$, -$L^2R^5$, -$L^2R^6$, —$OL^2R^5$, or —$OL^2R^6$.

In certain embodiments of the compounds of Formula (I), when $R^1$—$C(R^5)_2$OH, -$L^1R^5$, -$L^1R^6$, -$L^2R^5$, -$L^2R^6$, —$OL^2R^5$, or —$OL^2R^6$, then $R^3$ is —$OR^8$ or $C_1$-$C_6$ alkyl. In certain embodiments, $R^1$ is —$C(R^5)_2$OH, -$L^1R^5$, -$L^1R^6$, -$L^2R^5$, -$L^2R^6$, —$OL^2R^5$, or —$OL^2R^6$, and $R^3$ is —OMe.

In some embodiments of the compounds of Formula (I), $R^2$ is $C_1$-$C_6$alkyl. In certain embodiments, $R^2$ is methyl.

In some embodiments of the compounds of Formula (I), $R^3$ is selected from $C_1$-$C_4$ alkyl, -$L^3R^5$, -$L^1R^5$, -$L^3R^7$, -$L^3L^4L^3R^7$, -$L^3L^4R^5$, and -$L^3L^4L^3R^5$. In alternative embodiments, $R^3$ is selected from —$OL^3R^5$, —$OL^3R^7$, —$OL^3L^4R^7$, —$OL^3L^4L^3R^7$, —$OR^8$, —$OL^3L^4R^5$, —$OL^3L^4L^3R^5$ and —$C(R^5)_2$OH. In certain embodiments, $R^3$ is —$OL^3R^5$, wherein —$OL^3R^5$ is a group of the formula —$O(CH_2)_{1-5}$P(O)$(OR)_2$. In other embodiments, $R^3$ is —$OL^3R^5$, wherein —$OL^3R^5$ is a group of the formula —$O(CH_2)_{1-5}CF_2P(O)(OR)_2$.

In some embodiments, $R^3$ is selected from $C_1$-$C_4$alkyl, -$L^3R^5$, -$L^3R^7$, -$L^3L^4L^3R^7$, -$L^3L^4R^5$, -$L^3L^4L^3R^5$, —$OL^3R^5$, —$OL^3R^7$, —$OL^3L^4R^7$, —$OL^3L^4L^3R^7$, —$OR^8$, —$OL^3L^4R^5$, and —$OL^3L^4L^3R^5$.

Where more than one $R^9$ is present, as in compounds comprising a —$P(O)(OR^9)_2$ moiety, the $R^9$ groups are the same or are different. In certain embodiments of such compounds of Formula (I), $R^9$ is H at each occurrence. In other embodiments, at least one $R^9$ is H and the other $R^9$ is $C_1$-$C_6$alkyl. In other embodiments, at least one $R^9$ is H and the other $R^9$ is methyl. In other embodiments, at least one $R^9$ is H and the other $R^9$ is ethyl. In other embodiments of such compounds of Formula (I), each $R^9$ is $C_1$-$C_6$alkyl and in certain embodiments, $R^9$ is methyl or ethyl, or a combination thereof.

In certain embodiments of the compounds of Formula (I), $L^2$ and/or $L^3$ is a group of the formula —$((CR^4R^4)_pO)_q(CH_2)_p$—, and in certain embodiments, this group is of the formula —$(CH_2CH_2O)_{1-3}(CH_2)_{1-3}$—.

In certain embodiments of the compounds of Formula (I), $L^2$ is $C_1$-$C_6$ alkylene, while in other embodiments $L^2$ is $C_1$-$C_6$ alkylene substituted with one to four fluoro groups. In certain embodiments of such compounds of Formula (I), $L^2$ is of the formula $(CH_2)_{0-5}CF_2$, wherein the fluoro-substituted carbon is not directly attached to the phenyl ring of Formula I. In certain embodiments of the compounds of Formula (I), $L^2$ is $C_2$-$C_6$ alkenylene, while in other embodiments $L^2$ is $C_2$-$C_6$ alkenylene substituted with one to four fluoro groups.

In certain embodiments of the compounds of Formula (I), $L^3$ is $C_1$-$C_6$ alkylene while in other embodiments $L^3$ is $C_1$-$C_6$ alkylene substituted with one to four fluoro groups. In certain embodiments of such compounds of Formula (I), $L^3$ is of the formula $(CH_2)_{0-5}CF_2$, wherein the fluoro-substituted carbon is not directly attached to the phenyl ring of Formula I.

In certain embodiments of the compounds of Formula (I), $L^2$ is arylene or heteroarylene. In some of these embodiments, $L^2$ is phenylene, such as 1,3-disubstituted phenylene or 1,4-disubstituted phenylene.

In certain embodiments of such compounds of Formula (I), $R^1$ is $C_1$-$C_6$alkyl; $R^2$ is $C_1$-$C_6$alkyl; $R^3$ is —$OL^3R^5$ or —$OL^3R^7$; $R^5$ is —$P(O)(OR^9)_2$; $R^7$ is —$CF_2P(O)(OR^9)_2$, and $L^3$ is $C_1$-$C_6$alkylene.

In certain embodiments of such compounds of Formula (I), $R^1$ is $C_1$-$C_6$alkyl; $R^2$ is $C_1$-$C_6$alkyl; $R^3$ is —$OL^3R^5$ or —$OL^3R^7$; $R^5$ is —$P(O)(OR^9)_2$; $R^7$ is —$CF_2P(O)(OR^9)_2$; $L^3$ is —$((CR^4R^4)_pO)_q(CH_2)_p$—; $R^4$ is H; q is 1 or 2, and p is 2.

In certain embodiments of such compounds of Formula (I), $R^1$ is -$L^2R^6$; $R^2$ is $C_1$-$C_6$alkyl; $R^3$ is —$OL^3R^5$ or —$OL^3R^7$; $R^5$ is —$P(O)(OR^9)_2$; $R^6$ is —$C(O)OR^{10}$; $R^7$ is —$CF_2P(O)(OR^9)_2$; $L^2$ is $C_1$-$C_6$alkylene, and $L^3$ is $C_1$-$C_6$alkylene.

In certain embodiments of such compounds of Formula (I), $R^1$ is -$L^2R^6$; $R^2$ is $C_1$-$C_6$alkyl; $R^3$ is —$OL^3R^5$ or —$OL^3R^7$; $R^5$ is —$P(O)(OR^9)_2$; $R^6$ is —$C(O)OR^{10}$; $R^7$ is —$CF_2P(O)(OR^9)_2$; $L^2$ is $C_1$-$C_6$alkylene; $L^3$ is -$((CR^4R^4)_pO)_q(CH_2)_p$—; $R^4$ is H; q is 1 or 2, and p is 2.

In certain embodiments of such compounds of Formula (I), $R^1$ is —$C(R^5)_2OH$, -$L^1R^5$, -$L^2R^5$ or -$L^1R^6$; $R^2$ is $C_1$-$C_6$alkyl; $R^3$ is —$OR^8$; $R^8$ is $C_1$-$C_6$alkyl; $R^5$ is —$P(O)(OR^9)_2$; $R^6$ is —$CF_2P(O)(OR^9)_2$; $L^1$ is —$C(O)$—, and $L^2$ is $C_1$-$C_6$alkylene or $C_2$-$C_6$alkenylene, each optionally substituted with 1 to 4 fluoro groups.

In certain embodiments of such compounds of Formula (I), $R^1$ is $C_1$-$C_6$alkyl; $R^2$ is $C_1$-$C_6$alkyl; $R^3$ is —$OL^3L^4R^5$—$OL^3L^4L^3R^5$, or —$OL^3L^4L^3R^7$; $R^5$ is —$P(O)(OR^9)_2$; $R^7$ is —$CF_2P(O)(OR^9)_2$; each $L^3$ is independently a $C_1$-$C_6$alkylene, and $L^4$ is phenylene.

In certain embodiments of such compounds of Formula (I), $R^1$ is $C_1$-$C_6$alkyl; $R^2$ is $C_1$-$C_6$alkyl; $R^3$ is —$C(R^5)_2OH$ or -$L^1R^5$; $R^5$ is —$P(O)(OR^9)_2$, and $L^1$ is —$C(O)$— or —$O$—.

In certain embodiments, of such compounds of Formula (I), and pharmaceutically acceptable salts, pharmaceutically acceptable solvates (e.g. hydrates), the N-oxide derivatives, prodrug derivatives, protected derivatives, individual isomers and mixture of isomers thereof:

Formula (I)

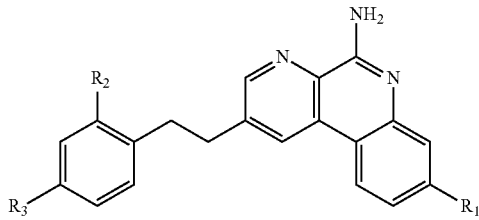

$R^1$ is $C_1$-$C_4$alkyl, —$C(R^5)_2OH$, -$L^1R^5$, -$L^2R^5$, -$L^2R^6$, —$OL^2R^5$, or —$OL^2R^6$;
$L^1$ is —$C(O)$— or —$O$—;
$L^2$ is $C_1$-$C_6$alkylene, $C_2$-$C_6$alkenylene, arylene, heteroarylene or $((CR^4R^4)_pO)_q(CH_2)_p$—, wherein the $C_1$-$C_6$alkylene and $C_2$-$C_6$alkenylene of $L^2$ are optionally substituted with 1 to 4 fluoro groups;
each $L^3$ is independently selected from $C_1$-$C_6$alkylene and —$((CR^4R^4)_pO)_q(CH_2)_p$—, wherein the $C_1$-$C_6$alkylene of $L^3$ is optionally substituted with 1 to 4 fluoro groups;
$L^4$ is arylene or heteroarylene;
$R^2$ is H or $C_1$-$C_4$alkyl;
$R^3$ is selected from $C_1$-$C_4$alkyl, -$L^3R^5$, -$L^1R^5$, -$L^3R^7$, -$L^3L^4L^3R^7$, -$L^3L^4R^5$, -$L^3L^4L^3R^5$, —$OL^3R^5$, —$OL^3R^7$, —$OL^3L^4R^7$, —$OL^3L^4L^3R^7$, —$OR^8$, —$OL^3L^4R^5$, —$OL^3L^4L^3R^5$ and —$C(R^5)_2OH$;
each $R^4$ is independently selected from H and fluoro;
$R^5$ is —$P(O)(OH)_2$,
$R^6$ is —$CF_2P(O)(OH)_2$ or —$C(O)OH$;
$R^7$ is —$CF_2P(O)(OH)_2$ or —$C(O)OH$;
$R^8$ is H or $C_1$-$C_4$alkyl;
each p is independently selected from 1, 2, 3, 4, 5 and 6, and q is 1, 2, 3 or 4,
with the proviso that when $R^3$ is —$OR^8$, $R^1$ is —$C(R^5)_2OH$, -$L^1R^5$, $L^1R^6$, $L^2R^5$, $L^2R^6$,$OL^2R^5$, or —$OL^2R^6$, wherein $R^6$ is —$CF_2P(O)(OH)_2$ and $R^7$ is —$CF_2P(O)(OH)_2$.

In certain embodiments of such compounds of Formula (I), $R^1$ is $C_1$-$C_6$alkyl; $R^2$ is $C_1$-$C_6$alkyl; $R^3$ is —$OL^3R^5$ or —$OL^3R^7$; $R^5$ is —$P(O)(OH)_2$; $R^7$ is —$CF_2P(O)(OH)_2$, and $L^3$ is $C_1$-$C_6$alkylene.

In certain embodiments of such compounds of Formula (I), $R^1$ is $C_1$-$C_6$alkyl; $R^2$ is $C_1$-$C_6$alkyl; $R^3$ is —$OL^3R^5$ or —$OL^3R^7$; $R^5$ is —$P(O)(OH)_2$; $R^7$ is —$CF_2P(O)(OH)_2$; $L^3$ is —$((CR^4R^4)_pO)_q(CH_2)_p$—; $R^4$ is H; q is 1 or 2, and p is 2.

In certain embodiments of such compounds of Formula (I), $R^1$ is -$L^2R^6$; $R^2$ is $C_1$-$C_6$alkyl; $R^3$ is —$OL^3R^5$ or —$OL^3R^7$; $R^5$ is —$P(O)(OH)_2$; $R^6$ is —$C(O)OH$; $R^7$ is —$CF_2P(O)(OH)_2$; $L^2$ is $C_1$-$C_6$alkylene, and $L^3$ is $C_1$-$C_6$alkylene.

In certain embodiments of such compounds of Formula (I), $R^1$ is -$L^2R^6$; $R^2$ is $C_1$-$C_6$alkyl; $R^3$ is —$OL^3R^5$ or —$OL^3R^7$; $R^5$ is —$P(O)(OH)_2$; $R^6$ is —$C(O)OH$; $R^7$ is —$CF_2P(O)(OH)_2$; $L^2$ is $C_1$-$C_6$alkylene; $L^3$ is —$((CR^4R^4)_pO)_q(CH_2)_p$—; $R^4$ is H; q is 1 or 2, and p is 2.

In certain embodiments of such compounds of Formula (I), $R^1$ is —$C(R^5)_2OH$, -$L^1R^5$, -$L^2R^5$ or -$L^1R^6$; $R^2$ is $C_1$-$C_6$alkyl; $R^3$ is —$OR^8$; $R^8$ is $C_1$-$C_6$alkyl; $R^5$ is —$P(O)(OH)_2$; $R^6$ is —$CF_2P(O)(OH)_2$; $L^1$ is —$C(O)$—, and $L^2$ is $C_1$-$C_6$alkylene or $C_2$-$C_6$alkenylene, each optionally substituted with 1 to 4 fluoro groups.

In certain embodiments of such compounds of Formula (I), $R^1$ is $C_1$-$C_6$alkyl; $R^2$ is $C_1$-$C_6$alkyl; $R^3$ is —$OL^3L^4R^5$—$OL^3L^4L^3R^5$, or —$OL^3L^4L^3R^7$; $R^5$ is —$P(O)(OH)_2$; $R^7$ is —$CF_2P(O)(OH)_2$; each $L^3$ is independently a $C_1$-$C_6$alkylene, and $L^4$ is phenylene.

In certain embodiments of such compounds of Formula (I), $R^1$ is $C_1$-$C_6$alkyl; $R^2$ is $C_1$-$C_6$alkyl; $R^3$ is —$C(R^5)_2OH$ or -$L^1R^5$; $R^5$ is —$P(O)(OR^9)_2$, and $L^1$ is —$C(O)$— or —$O$—.

In certain embodiments of the aformentioned compounds of Formula (I), $R^8$ is methyl. In certain embodiments of the aformentioned compounds of Formula (I), $R^1$ is methyl. In certain embodiments of the aformentioned compounds of Formula (I), $R^2$ is methyl.

In other embodiments of compounds of Formula (I),
$R^5$ is —$P(O)(O^-X^+)_2$ or —$P(O)(O^-)_2X^{2+}$;
$R^6$ is —$CF_2P(O)(O^-X^+)_2$, —$CF_2P(O)(O^-)_2X^{2+}$ or —$C(O)O^-X^+$, and
$R^7$ is —$CF_2P(O)(O^-X^+)_2$, —$CF_2P(O)(O^-)_2X^{2+}$ or —$C(O)O^-X^+$, wherein X⁺ and X²⁺ are pharmaceutically acceptable cations. In certain embodiments, such pharmaceutically acceptable cations are selected from sodium, potassium, calcium, zinc, and magnesium.

In certain embodiments of compounds of Formula (I),
$R^5$ is —$PO_3^-X^{3+}$;
$R^6$ is —$CF_2PO_3^-X^{3+}$, and
$R^7$ is —$CF_2PO_3^-X^{3+}$,
wherein $X^{3+}$ is $Al^{3+}$.

Aluminum-containing adjuvants, such as aluminum hydroxide, aluminum oxyhydroxide and aluminum hydroxyphosphate, are used in vaccines to bind antigens. A discussion of aluminum-containing adjuvants and their uses in vaccines is given in *Expert Rev. Vaccines,* 46(5), 2007, 685-698 and *Vaccines,* 25, 2007, 6618-6624, the disclosures of which are herein incorporated by references in their entirety.

Compounds of Formula (I) provided herein are TLR7 agonists that bind to aluminum-containing adjuvants, such as, by way of example only, aluminum hydroxide, aluminum oxyhydroxide and aluminum hydroxyphosphate. In certain embodiments, such compounds of Formula (I) have a phosphate, a phosphonic acid, a phosphonate, a fluorinated phosphonic acid or a fluorinated phosphonate group. While in other embodiments, such compounds of Formula (I) have a phosphate, a phosphonic acid, a phosphonate, a fluorinated phosphonic acid or fluorinated phosphonate group, and one or more additional ionizable groups selected from a carboxylic acid and sulphate.

In certain embodiments compounds of Formula (I) provided herein are combined with an antigen, an aluminum-containing adjuvant, and optionally a carrier, pharmaceutically acceptable excipient, to provide an immunogenic composition. In other embodiments, such immunogenic composition comprise a compound of Formula (I) and an antigen, wherein the antigen includes, but is not limited to, a bacterial antigen, a viral antigen, a fungal antigen, a tumor antigen, or an antigen associated with an STD, Alzheimer's, respiratory disorders, autoimmune disorders such as, by way of example only, rheumatoid arthritis or lupus, pediatric disorders and obesity, and wherein the amount of the compound is an amount effective to enhance an immune response to the antigen in a subject to whom the composition is administered. Suitable antigens for use in such immunogenic compositions are described herein.

In certain embodiments, such immunogenic compositions include a bacterial antigen of a strain of *Neisseria meningitides,* such as serogroup A, C, W135, Y and/or B. Specific antigens for use in these compositions are described herein. In other embodiments, such immunogenic compositions, and others provided herein, are used as vaccines; their use in the treatment of disorders associated with the antigen included in the composition is described herein.

The compounds of Formula (I), pharmaceutically acceptable salts, solvates, N-oxides, prodrugs and isomers thereof, and pharmaceutical compositions provided herein also includes all suitable isotopic variations of such compounds, and pharmaceutically acceptable salts, solvates, N-oxides, prodrugs and isomers thereof, and pharmaceutical compositions. An isotopic variation of a compound provided herein or a pharmaceutically acceptable salt thereof is defined as one in which at least one atom is replaced by an atom having the same atomic number but an atomic mass different from the atomic mass usually found in nature. Examples of isotopes that may be incorporated into the compounds provided herein and pharmaceutically acceptable salts thereof include but are not limited to isotopes of hydrogen, carbon, nitrogen and oxygen such as $^2H$, $^3H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations of the compounds provided herein and pharmaceutically acceptable salts thereof, for example, those in which a radioactive isotope such as $^3H$ or $^{14}C$ is incorporated, are useful in drug and/or substrate tissue distribution studies. In particular examples, $^3H$ and $^{14}C$ isotopes may be used for their ease of preparation and detectability. In other examples, substitution with isotopes such as $^2H$ may afford certain therapeutic advantages resulting from greater metabolic stability, such as increased in vivo half-life or reduced dosage requirements. Isotopic variations of the compounds, and pharmaceutically acceptable salts, solvates, N-oxides, prodrugs and isomers thereof, and pharmaceutical compositions provided herein are prepared by conventional procedures using appropriate isotopic variations of suitable reagents.

Processes for Making Compounds of Formula (I)

General procedures for preparing compounds of Formula (I) are described in the Examples, infra. In the reactions described, reactive functional groups, for example hydroxy, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry," John Wiley and Sons, 1991).

In certain embodiments, the compounds of Formula (I) provided herein are prepared as a pharmaceutically acceptable acid addition salt by reacting the free base form of the compound of Formula (I) with a pharmaceutically acceptable organic acid or inorganic acid. In other embodiments, a pharmaceutically acceptable base addition salt of compounds of Formula (I) provided herein is prepared by reacting the free acid form of the compound of Formula (I) with a pharmaceutically acceptable organic base or inorganic base. Alternatively, the salt forms of the compounds of Formula (I) provided herein are prepared using salts of the starting materials or intermediates. In certain embodiments, the compounds of Formula (I) provided herein are in the form of other salts including, but not limited to, oxalates and trifluoroacetates. In certain embodiments, hemisalts of acids and bases are formed, for example, hemisulphate and hemicalcium salts.

Such pharmaceutically acceptable acid addition salts of compounds of Formula (I) include, but are not limited to, a hydrobromide, hydrochloride, sulfate, nitrate, succinate, maleate, formate, acetate, adipate, besylatye, bicarbonate/carbonate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate), hexanoate salt, bisulphate/sulphate, borate, camsylate, cyclamate, edisylate, esylate, gluceptate, gluconate, glucuronate, hexafluorophosphate, hibenzate, hydrochloride/chloride, hydrobromide/bromide, hydroiodide/iodide, isethionate, lactate, malate, malonate, mesylate, methylsulphate, naphthylate, 2-napsylate, nicotinate, orotate, oxalate, palmitate, pamoate, phosphate/hydrogen phosphate/dihydrogen phosphate, pyroglutamate, saccharate, stearate, tannate, tosylate, trifluoroacetate and xinofoate salts.

The organic acid or inorganic acids used to form certain pharmaceutically acceptable acid addition salts of compounds of Formula (I) include, but are not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid.

Such pharmaceutically acceptable base addition salt of a compound of Formula (I) include, but are not limited to, aluminium, arginine, benzathine, calcium, choline, diethylamine, diolamine, glycine, lysine, magnesium, meglumine, olamine, potassium, sodium, tromethamine and zinc salts.

In certain embodiments, the free acid or free base forms of the compounds of Formula (I) provided herein are prepared from the corresponding base addition salt or acid addition salt from, respectively. For example a compound Formula (I) in an acid addition salt form is converted to the corresponding free base by treating with a suitable base (by way of example only, an ammonium hydroxide solution, a sodium hydroxide, and the like). For example, a compound of Formula (I) in a base addition salt form is converted to the corresponding free acid by treating with a suitable acid (by way of example only, hydrochloric acid).

In certain embodiments, compounds of Formula (I) in unoxidized form are prepared from N-oxides of compounds Formula (I) by treating with a reducing agent (by way of example only, sulfur, sulfur dioxide, triphenyl phosphine, lithium borohydride, sodium borohydride, phosphorus trichloride, tribromide, or the like) in a suitable inert organic solvent (by way of example only, acetonitrile, ethanol, aqueous dioxane, or the like) at 0 to 80° C.

In certain embodiments, prodrug derivatives of compounds Formula (I) are prepared using methods known to those of ordinary skill in the art (e.g., for further details see Saulnier et al., (1994), Bioorganic and Medicinal Chemistry Letters, Vol. 4, p. 1985). For example, appropriate prodrugs are prepared by reacting a non-derivatized compound of Formula (I) with a suitable carbamylating agent (by way of example only, 1,1-acyloxyalkylcarbanochloridate, para-nitrophenyl carbonate, or the like).

In certain embodiments, compounds of Formula (I) are prepared as protected derivatives using methods known to those of ordinary skill in the art. A detailed description of the techniques applicable to the creation of protecting groups and their removal can be found in T. W. Greene, "Protecting Groups in Organic Chemistry," 3$^{rd}$ edition, John Wiley and Sons, Inc., 1999.

In certain embodiments, compounds of Formula (I) are prepared or formed, as solvates (e.g., hydrates). In certain embodiments, hydrates of compounds of Formula (I) are prepared by recrystallization from an aqueous/organic solvent mixture, using organic solvents such as dioxin, tetrahydrofuran or methanol.

In certain embodiments, compounds of Formula (I) are prepared as their individual stereoisomers. In other embodiments, the compounds of Formula (I) provided herein are prepared as their individual stereoisomers by reacting a racemic mixture of the compound with an optically active resolving agent to form a pair of diastereoisomeric compounds, separating the diastereomers and recovering the optically pure enantiomers. In certain embodiments, resolution of enantiomers is carried out using covalent diastereomeric derivatives of the compounds of Formula (I), or by using dissociable complexes (e.g., crystalline diastereomeric salts). Diastereomers have distinct physical properties (e.g., melting points, boiling points, solubility, reactivity, etc.) and are readily separated by taking advantage of these dissimilarities. In certain embodiments, the diastereomers are separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981.

Compounds of Formula (I) are made by processes described herein and as illustrated in the Examples. In certain embodiments, compounds of Formula (I) are made by:

(a) optionally converting a compound of Formula (I) into a pharmaceutically acceptable salt;

(c) optionally converting a salt form of a compound of Formula (I) to a non-salt form;

(d) optionally converting an unoxidized form of a compound of Formula (I) into a pharmaceutically acceptable N-oxide;

(e) optionally converting an N-oxide form of a compound of Formula (I) to its unoxidized form;

(f) optionally resolving an individual isomer of a compound of Formula (I) from a mixture of isomers;

(g) optionally converting a non-derivatized compound of Formula (I) into a pharmaceutically acceptable prodrug derivative; and (h) optionally converting a prodrug derivative of a compound of Formula (I) to its non-derivatized form.

Non-limiting examples of synthetic schemes used to make compounds of Formula (I) provided herein are illustrated in reaction schemes (I)-(XI).

Scheme (I) illustrates the synthesis of benzonaphthyridines (I-3) by coupling 2-(tert-butoxycarbonyl-amino)phenylboronic acids (I-1) with 3-halopicolinonitrile derivatives (I-2) in the presence of a palladium catalyst. By way of example only, the halo moiety of the 3-halopicolinonitrile derivatives is bromo or chloro. The $R_A$ and $R_B$ groups on benzonaphthyridines (I-3) are as described herein for substituents of Formula (I) at the respective positions, or $R_A$ and $R_B$ are groups that are further modified to obtain the respective substituents of Formula (I), as described herein.

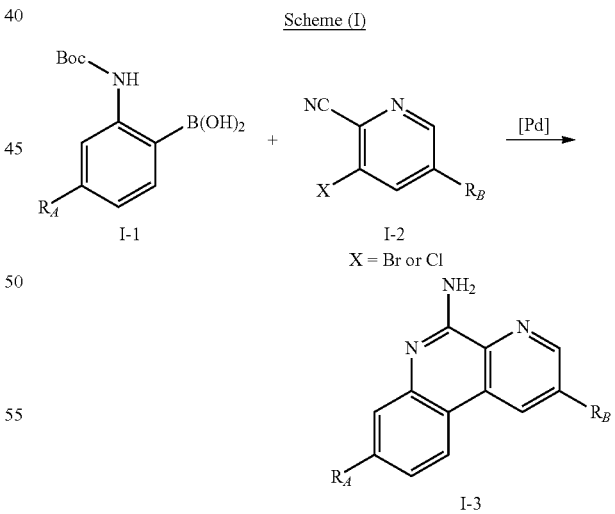

Scheme (I)

In certain embodiments, the phenyl boronic acids used in the synthesis of compounds of Formula (I) were synthesized according to scheme (II). In scheme (II) aniline (II-1) is Boc-protected under basic conditions to give (II-2), and then converted into the boronic acids (I-1) through ortho-lithiation and reaction with trimethyl borate followed by aqueous workup.

Scheme (II)

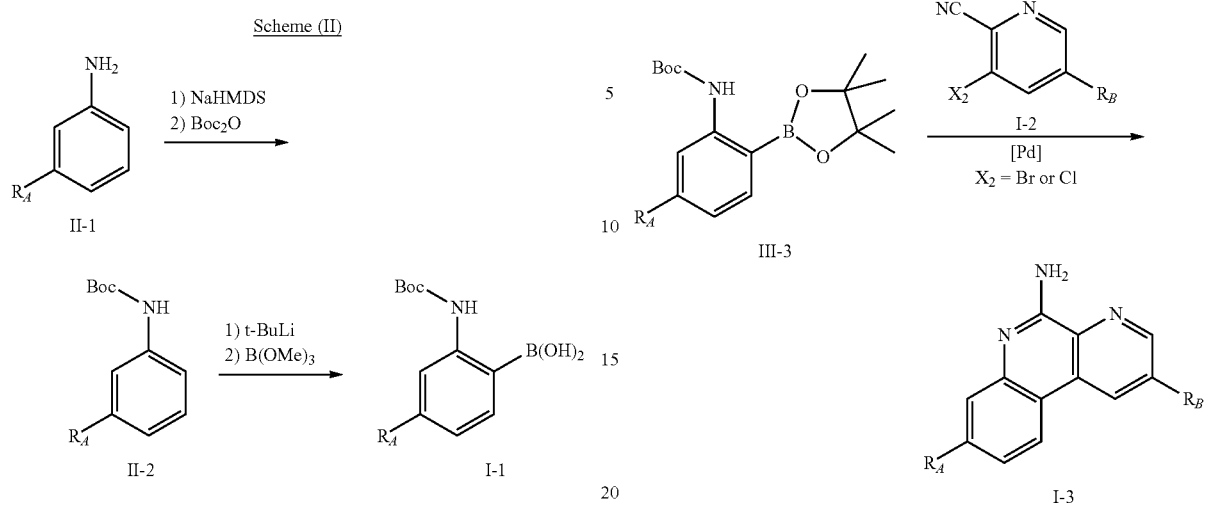

Boric acids (I-1) are used as in scheme (I) and reacted cyanopyridines (I-2) to afford benzonaphthyridines (I-3).

In certain embodiments, boronic acid equivalents including, but not limited to, boronate esters were used in the synthesis of compounds of Formula (I). Scheme (III) illustrates the synthesis of such boronate esters (III-3), which were used as boronic acid equivalents in the synthesis of benzonaphthyridines (I-3). In scheme (III) 2-haloanilines (III-1) were Boc-protected under basic conditions to give (III-2), which were then converted into the boronate esters (III-3) using palladium-mediated catalysis. These boronate esters (III-3) were used as in scheme (I) and reacted with cyanopyridines (I-2) to afford substituted or unsubsubstituted benzonaphthyridines (I-3).

In certain embodiments, 2-bromoanilines used as in scheme (III) were synthesized from their corresponding nitrobenzene compounds as illustrated below:

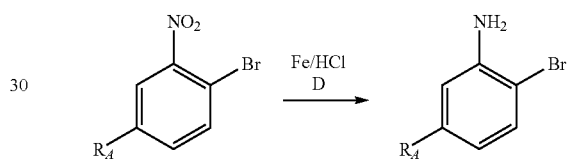

In other embodiments, compounds of Formula (I) were synthesized using the methodologies described in scheme (IV).

Scheme (III)

Scheme (IV)

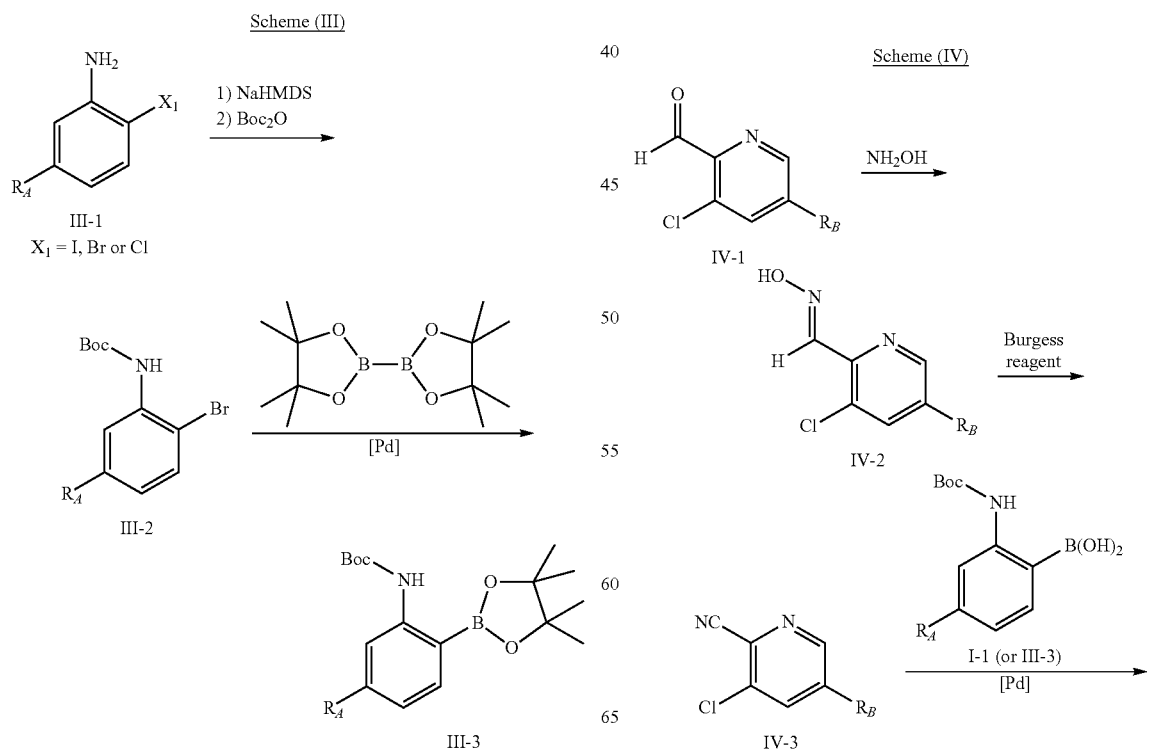

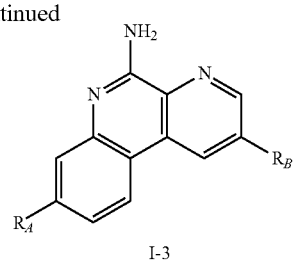

In scheme (IV), 3-chlorobenzaldehyde (IV-1) is first converted to the corresponding hydroxylamine (IV-2), which is then used to make the corresponding nitrile (IV-3). Using palladium-mediated conditions, as in scheme (I), derivatives of nitrile (IV-3) are coupled with boronic acids (I1) (or boronate esters (III-3) to give the benzonaphthyridine (I-3).

In other embodiments, certain compounds of Formula (I) having carbon-linked substituents, including benzonaphthyridines with various carbon-linked substituents at the 2-position, were prepared using the synthetic route shown in scheme (V).

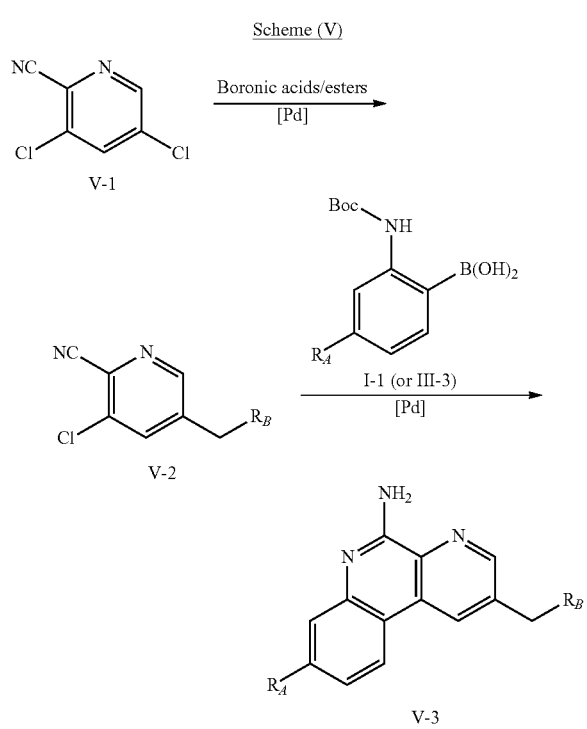

In scheme (V), a 3,5-dihalopicolinonitrile, such as, by way of example only, 3,5-dichloropicolinonitrile (V-1), is first mono-substituted using one equivalent of boronic acid/ester thereby giving the corresponding picolinonitrile (V-2). Using more vigorous palladium-mediated conditions as in scheme (I), derivatives of nitrile (V-2) are coupled with boronic acids (I-1) (or boronate esters (III-3) to give the benzonaphthyridine (V-3) having carbon-linked substituents at the 2-position. In certain embodiments the carbon-linked substituent is an alkene, while in other embodiments such alkenes are further modified by hydrogenation to give benzonaphthyridines with alkyl groups at the 2-position.

In other embodiments, certain compounds of Formula (I) having various substituents, including benzonaphthyridines with various substituents at the 2-position, were synthesized using the methodologies described in scheme (VI).

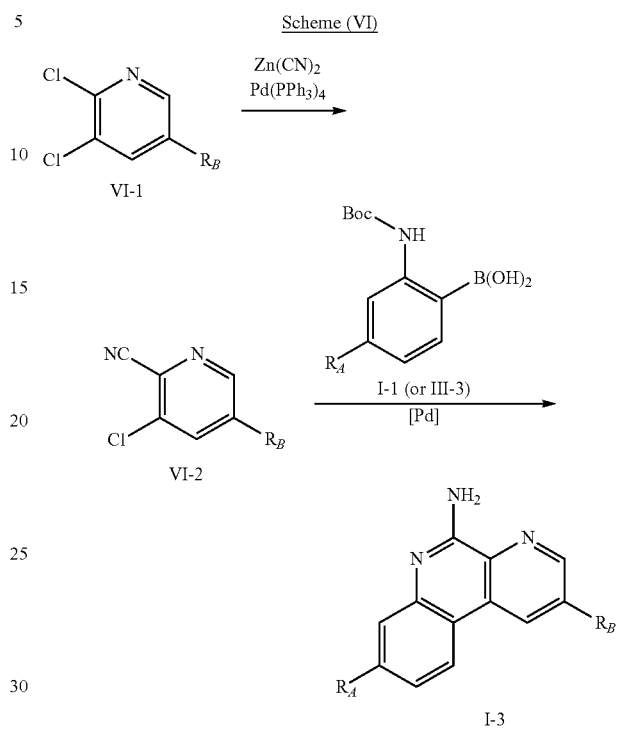

In scheme (VI), a 2,3-dihalopyridines substituted at the 5 position (VI-1), such as, by way of example only, (5,6-dichloropyridin-3-yl)methanol, is first converted to the corresponding nitrile (VI-2). Using palladium-mediated conditions as in scheme (I), derivatives of nitrile (VI-2) are coupled with boronic acids (I-1) (or boronate esters (III-3) to give the benzonaphthyridine (I-3).

In other embodiments, certain compounds of Formula (I) were synthesized using the methodologies described in scheme (VII).

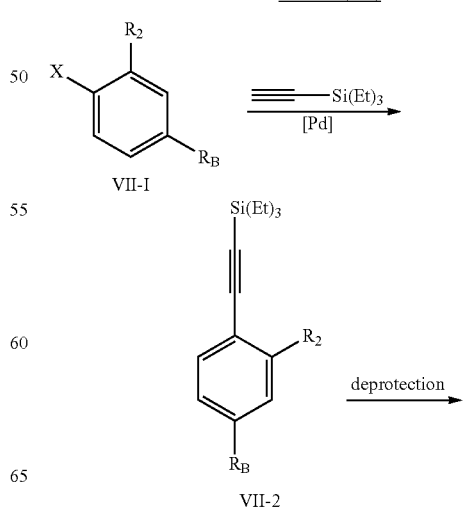

-continued

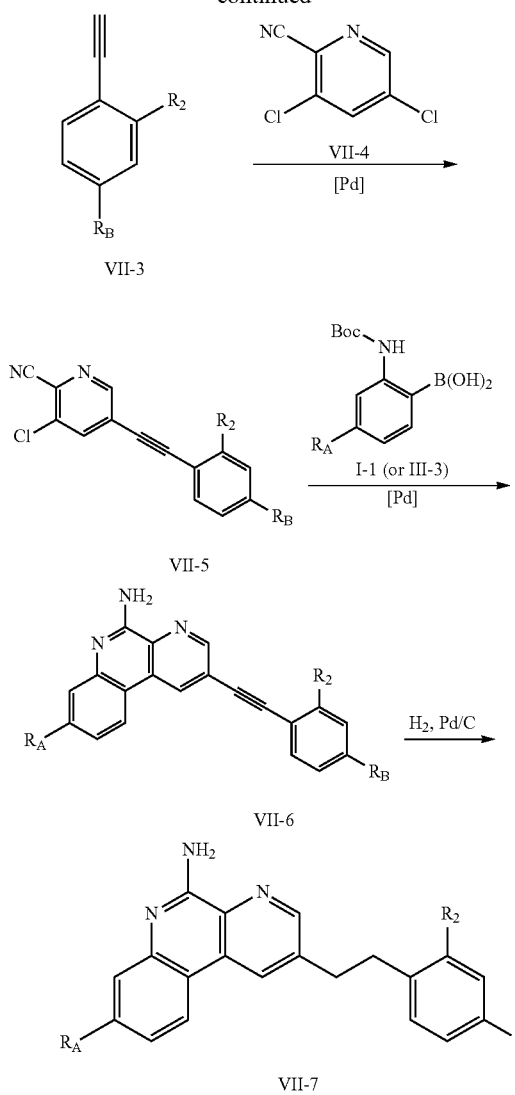

X = Br or I

In scheme (VII), aryl bromides or aryl iodides (VII-1) are coupled with triethyl(ethynyl)silane (or its equivalents) using palladium-mediated conditions to afford (VII-2). After deprotection of the silyl protection group, acetylene derivatives (VII-3) are coupled with 3,5-dichloropicolinonitrile (VII-4) using palladium-mediated conditions to afford 3-chloro-2-cyanopyridines (VII-5). Derivatives of (VII-5) such as, by way of example only, 3-chloro-5-(phenylethynyl) picolinonitrile are coupled with boronic acids (I-1) (or boronate esters (III-3) to give the benzonaphthyridine (VII-6). Compound (VII-6) is then subjected under hydrogenation conditions to give benzonaphthyridines (VII-7). $R_2$ is as described herein and the $R_A$ and $R_B$ groups on benzonaphthyridines (VII-7) are as described herein for substituents of Formula (I) at the respective positions, or $R_A$ and $R_B$ are groups that are further modified to obtain the respective substituents of Formula (I), as described herein.

In other embodiments, certain compounds of Formula (I) were synthesized using the methodologies described in scheme (VIII).

Scheme (VIII)

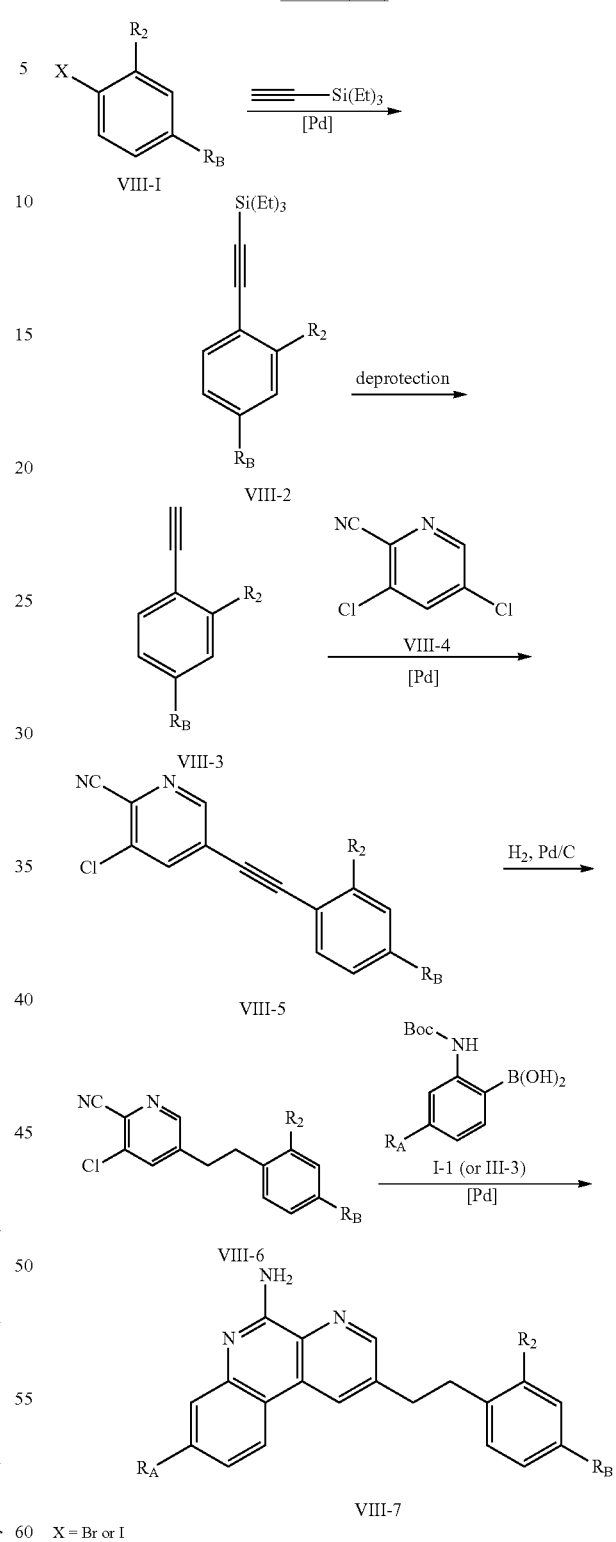

X = Br or I

In scheme (VIII), aryl bromides or aryl iodides (VIII-1) are coupled with triethyl(ethynyl)silane (or its equivalents) using palladium-mediated conditions to afford (VIII-2). After deprotection of the silyl protection group, acetylene derivatives (VIII-3) are coupled with 3,5-dichloropicolinonitrile (VIII-4) using palladium-mediated conditions to afford 3-chloro-2-cyanopyridines (VIII-5). Derivatives of (VIII-5) such as, by way of example only, 3-chloro-5-(phenylethynyl) picolinonitrile are reduced to the corresponding 3-chloro-5-phenethylpicolinonitrile (VIII-6) under hydrogenation conditions. Compound (VIII-6) is coupled with boronic acids (I-1) (or boronate esters (III-3) to give benzonaphthyridines (VIII-7). $R_2$ is as described herein and the $R_A$ and $R_B$ groups on benzonaphthyridines (VII-7) are as described herein for substituents of Formula (I) at the respective positions, or $R_A$ and $R_B$ are groups that are further modified to obtain the respective substituents of Formula (I), as described herein.

In other embodiments, certain compounds of Formula (I) were synthesized using the methodologies described in scheme (IX).

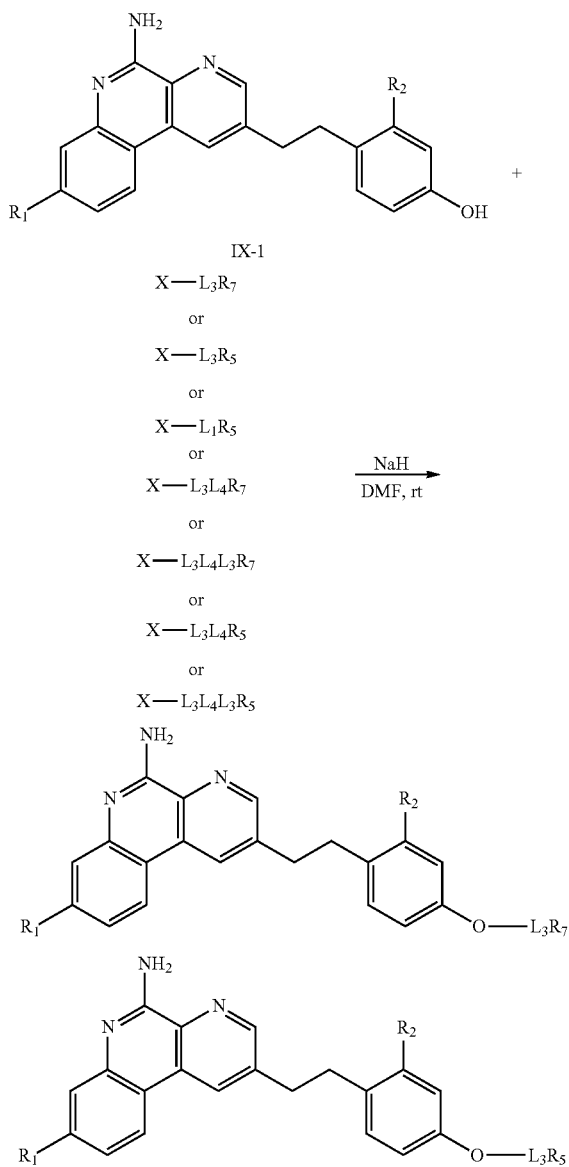

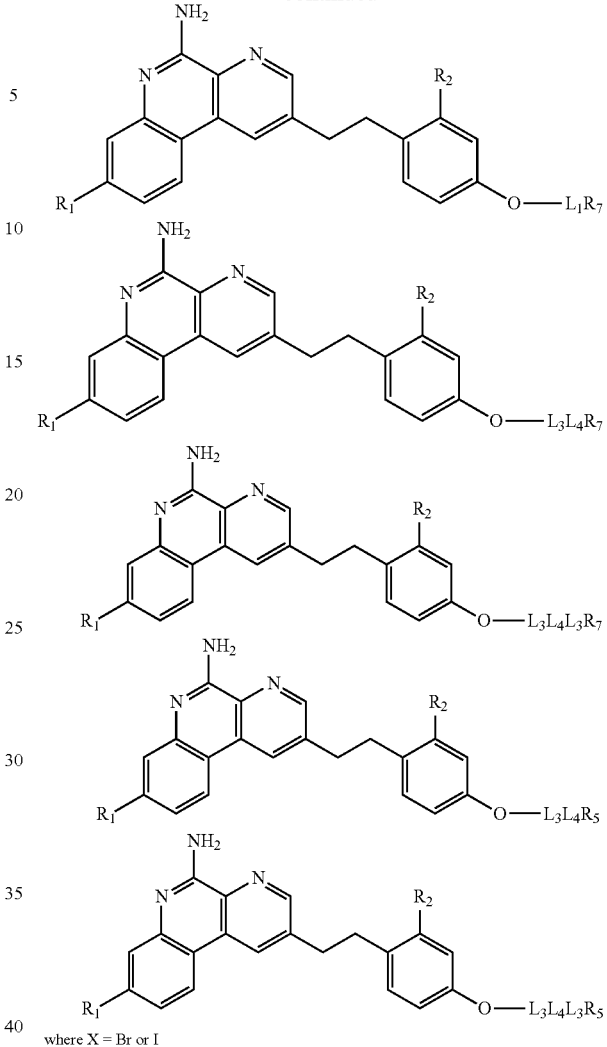

where X = Br or I

In scheme (IX) compound (IX-1) bearing a phenol group is alkylated with various electrophiles, where $R^1, R^2, L^1, L^3, L^4$, $R^5$ and $R^7$ are as defined herein. In certain examples, analogs containing alkoxy appendages at the phenol position were prepared as exemplified in Scheme 1, wherein a compound bearing a phenol group, was alkylated with a phosphonate-containing electrophile to give a protected phosphonate, which was treated with a suitable deprotecting agent to afford the phosphonic acid.

The examples provided herein are offered to illustrate, but not to limit, the compounds of Formula (I) provided herein, and the preparation of such compounds. By way of example only, certain compounds of Formula (I) containing carboxylic acid appendages at the C-8 position were prepared as exemplified in Scheme 2.

By way of example only, certain compounds of Formula (I) containing α,α'-difluororo phosphonic acid appendages at the C-8 position were prepared as exemplified in Scheme 3, wherein a primary alcohol was oxidized to an aldehyde and alkylation of this aldehyde with the appropriate phosphonate reagent yielded a phosphonate. Additionally, oxidation of the benzylic alcoholgave the keto moiety and final hydrolysis gave the final phosphonic acid derivative.

By way of example only, certain compounds of Formula (I) containing phosphonic acid appendages at the C-8 position were prepared as shown in Scheme 4, wherein an aldehyde was treated with a Wittig reagent to provide a vinyl phosphonates. Hydrolysis of phosphonate with, by way of example only, trimethylsilyl bromide delivers a phosphonic acid. Allternatively, hydrogenation of the vinyl moiety provided an alkyl linked phosphonate which was hydrolyzed to give an alkyl linked phosphonic acid.

By way of example only, certain compounds of Formula (I) containing aryl phosphate groups were prepared according to Scheme 5, wherein a compound bearing a phenol group was treated with 1-(bromomethyl)-3-iodobenzene and cesium carbonate resulting in an intermediate which was palladium catalyzed cross-coupling with triethyl phosphoate, followed by hydrolysis with trimethylsilyl bromide giving a compound bearing a phosphonic acid.

By way of example only, certain compounds of Formula (I) containing α-keto phosphonic acid appendages at the C-8 position are prepared as exemplified in Scheme 6, wherein treatment of an aldehyde with tris(trimethylsilyl) phosphite followed by oxidation with IBX resulted in the phosphonic acid.

Pharmacology and Utility

When a foreign antigen challenges the immune system it responds by launching a protective response that is characterized by the coordinated interaction of both the innate and acquired immune systems. These two interdependent systems fulfill two mutually exclusive requirements: speed (contributed by the innate system) and specificity (contributed by the adaptive system).

The innate immune system serves as the first line of defense against invading pathogens, holding the pathogen in check while the adaptive responses are matured. It is triggered within minutes of infection in an antigen-independent fashion, responding to broadly conserved patterns in the pathogens (though it is not non-specific, and can distinguish between self and pathogens). Crucially, it also generates the inflammatory and co-stimulatory milieu (sometimes referred to as the danger signal) that potentiates the adaptive immune system and steers (or polarizes it) towards the cellular or humoral responses most appropriate for combating the infectious agent. The development of TLR modulators for therapeutic targeting of innate immunity has been reviewed (see *Nature Medicine,* 2007, 13, 552-559; *Drug Discovery Today: Therapeutic Stategies,* 2006, 3, 343-352 and *Journal of Immunology,* 2005, 174, 1259-1268).

The adaptive response becomes effective over days or weeks, but ultimately provides the fine antigenic specificity required for complete elimination of the pathogen and the generation of immunologic memory. It is mediated principally by T and B cells that have undergone germline gene rearrangement and are characterized by specificity and long-lasting memory. However, it also involves the recruitment of elements of the innate immune system, including professional phagocytes (macrophages, neutrophils etc.) and granulocytes (basophils, eosinophils etc.) that engulf bacteria and even relatively large protozoal parasites. Once an adaptive immune response has matured, subsequent exposure to the pathogen results in its rapid elimination due to highly specific memory cells have been generated that are rapidly activated upon subsequent exposure to their cognate antigen.

Autoimmune diseases, are defined by (i) humoral or autoantibody response to a self antigen (by way of example only, Graves' primary hyperthyroidism with antibodies to the TSH receptor), or (ii) cellular response wherein immune cells destroy nonimmune cells from which the self-antigen is derived (by way of example only, the thyrocyte (Hashimoto's thyroiditis) or pancreatic β-islet cell (Type 1 diabetes). Many autoimmune diseases are a combination of both phenomena, for instance, Hashimoto's and Type 1 diabetes also have auto-antibodies, anti-thyroid peroxidase (TPO) or anti-glutamic acid decarboxylase (GAD)/Islet Cell. Autoimmune diseases often have an inflammatory component including, but not limited to, increases in adhesion molecules (by way of example only, vascular cell adhesion molecule-1 (VCAM-1), and altered leukocyte adhesion to the vasculature such as, by way of example only, colitis, systemic lupus, systemic sclerosis, and the vascular complications of diabetes.

Toll-like receptors (TLRs) are type-I transmembrane proteins characterized by an extracellular N-terminal leucine-rich repeat (LRR) domain, followed by a cysteine-rich region, a TM domain, and an intracellular (cytoplasmic) tail that contains a conserved region named the Toll/IL-1 receptor (TIR) domain. TLRs are pattern recognition receptors (PRR) that are expressed predominantly on immune cells including, but not limited to, dendritic cells, T lymphocytes, macrophages, monocytes and natural killer cells. The LLR domain is important for ligand binding and associated signaling and is a common feature of PRRs. The TIR domain is important in protein-protein interactions and is associated with innate immunity. The TIR domain also unites a larger IL-1 R/TLR superfamily that is composed of three subgroups. Members of the first group possess immunoglobin domains in their extracellular regions and include IL-1 and IL-18 receptors and accessory proteins as well as ST2. The second group encompasses the TLRs. The third group includes intracellular adaptor proteins important for signaling.

TLRs are a group of pattern recognition receptors which bind to pathogen-associated molecular patterns (PAMPS) from bacteria, fungi, protozoa and viruses, and act as a first line of defense against invading pathogens. TLRs are essential to induce expression of genes involved in inflammatory responses, and TLRs and the innate immune system are a critical step in the development of antigen-specific acquired immunity.

Adaptive (humoral or cell-mediated) immunity is associated with the TLR signal mechanism of innate immunity. Innate immunity is a protective immune cell response that functions rapidly to fight environmental insults including, but not limited to, bacterial or viral agents. Adaptive immunity is a slower response, which involves differentiation and activation of naive T lymphocytes into T helper 1 (Th1) or T helper 2 (Th2) cell types. Th1 cells mainly promote cellular immunity, whereas Th2 cells mainly promote humoral immunity. Though primarily a host protective system, pathologic expression of the innate immunity signals emanating from the TLR pathway are implicated in initiating autoimmune-inflammatory diseases.

All TLRs appear to function as either a homodimer or heterodimer in the recognition of a specific, or set of specific, molecular determinants present on pathogenic organisms including bacterial cell-surface lipopolysaccharides, lipoproteins, bacterial flagellin, DNA from both bacteria and viruses and viral RNA. The cellular response to TLR activation involves activation of one or more transcription factors, leading to the production and secretion of cytokines and co-stimulatory molecules such as interferons, TNF-, interleukins, MIP-1 and MCP-1 which contribute to the killing and clearance of the pathogenic invasion.

TLR spatial expression is coincident with the host's environmental interface. While only a few other Toll-like proteins have been cloned in *Drosophila,* the human TLR family is composed of at least 11 members, TLR1 through TLR11, that elicit overlapping yet distinct biological responses due to differences in cellular expression and signaling pathways they initiate. Each of the TLRs is expressed on a different subset of leukocytes and each of the TLRs is specific in its expression patterns and PAMP sensitivities and detects different subsets of pathogens allowing vigilant surveillance by the immune system.

Toll-Like Receptor 1 (TLR1)

TLR1 maps to chromosome 4p14 and its sequence encodes a putative 786 amino acid (aa) protein with 18 N-terminal LRRs and a calculated molecular weight of 84 kDa. TLR1 is most closely related to TLR6 and TLR10 with 68% and 48% overall (aa) sequence identity, respectively.

TLR1 mRNA is ubiquitously expressed and found at higher levels than the other TLRs. Of the major leukocyte populations, TLR1 is most highly expressed by monocytes, but is also expressed by macrophages, dendritic cells, polymorphonuclear leukocytes, B, T, and NK cells. In vivo, two different sized transcripts for TLR1 are observed suggesting that the mRNA is alternatively spliced to generate two different forms of the protein. In vitro, TLR1 mRNA and protein expression is upregulated in monocytic leukemic (THP-1) cells upon PMA-induced differentiation. TLR1 expression is upregulated by autocrine IL-6, and is also elevated by IFN-γβ, IL-10, and TNF-α. However, TLR1 level is unaffected by exposure to both Gram-positive and Gram-negative bacteria. Ex vivo, both monocyte and granulocyte TLR1 expression is downregulated after exposure to Gram-negative bacteria. TLR1 forms a heterodimer with TLR2. TLR1 also heterodimerizes with TLR4, which inhibits TLR4 activity.

Toll-Like Receptor 2 (TLR2)

TLR2 maps to chromosome 4q31-32 and encodes a putative 784 (aa) protein with 19 N-terminal LLRs and a calculated molecular weight of 84 kDa. TLR2 is most closely related to TLR6 with 31% overall (aa) sequence identity.

TLR2 mRNA expression is observed in brain, heart, lung, and spleen tissues and is highest in PBLs, specifically those of myelomonocytic origin. In vivo, two different sized transcripts for TLR2 are observed suggesting that the mRNA is alternatively spliced. In vitro, TLR2 mRNA and protein expression is upregulated in monocytic leukemic (THP-1) cells upon PMA-induced differentiation. TLR2 is upregulated by autocrine IL-6 and TNF-α, IL-1β, and IL-10. TLR2 mRNA expression is elevated after exposure to both Gram-positive and Gram-negative bacteria. TLR2 forms heterodimers with TLR1, TLR6, and possibly TLR10, where each complex is particularly sensitive to subsets of TLR2-associated PAMPs. TLR2 complexes recognize a wide range of PAMPs, mostly from bacteria. These include, but are not limited to, lipoarabinomannan (LAM), lipopolysaccharide (LPS), lipoteichoic acid (LTA), peptidoglycan (PGN), and other glycolipids, glycoproteins, and lipoproteins. TLR2 complexes are also capable of detecting viruses, including but not limited to, measles virus (MV), human cytomegalovirus (HCMV), and hepatitis C virus (HCV) and fungal PAMPs, including but not limited to, zymosan. TLR2 recognizes a variety of lipoproteins/lipopeptides from various pathogens such as, by way of example only, Gram-positive bacteria, mycobacteria, *Trypanosoma cruzi*, fungi and *Treponema*. In addition, TLR2 recognizes LPS preparations from non-enterobacteria such as, by way of example only, *Leptospira interrogans*, *Porphyromonas gingivalis* and *Helicobacter pylori*. TLR2 complexes are capable of both detection of non-self patterns and detecting altered self patterns, such as those displayed by necrotic cells. TLR2 is recruited to phagosomes and is involved in the internalization of microbial products by cells.

Toll-like Receptor 3 (TLR3)

TLR3 maps to chromosome 4q35 and its sequence encodes a putative 904 (aa) protein with 24 N-terminal LRRs and a calculated molecular weight of 97 kDa. TLR3 is most closely related to TLR5, TLR7, and TLR8, each with 26% overall (aa) sequence identity.

TLR3 mRNA is expressed at highest levels in the placenta and pancreas. TLR3 is expressed by dendritic cells, T and NK cells. In vivo, two different sized transcripts for TLR3 are observed suggesting that the mRNA is alternatively spliced to generate two different forms of the protein. In vitro, PMA-differentiated THP-1 TLR3 is moderately upregulated by autocrine IFN-γ, IL-1β, IL-6, IL-10, and TNF-α. TLR3 mRNA is elevated after exposure to Gram-negative bacteria and to an even greater extent in response to Gram-positive bacteria. Ex vivo, TLR3 expression is elevated in both monocytes and granulocytes upon exposure to Gram-negative bacteria. TLR3 forms a homodimer and recognizes viral double stranded RNA (dsRNA). While it is generally assumed that TLRs are expressed on the cell surface, however those TLRs sensitive to internal PAMPs, such as dsRNA in the case of TLR3, are localized intracellularly in the lysosomal compartment.

Toll-Like Receptor 4 (TLR4)

TLR4 maps to chromosome 9q32-33, and shows a high degree of similarity to dToll over the entire (aa) sequence. The TLR4 sequence encodes an 839 (aa) protein with 22 N-terminal LRR regions and a calculated molecular weight of 90 kDa. TLR4 is most closely related to TLR1 and TLR6 each with 25% overall (aa) sequence identity.

In vivo, TLR4 mRNA is expressed as a single transcript, and found at highest levels in spleen and PBLs. Of the PBL populations, TLR4 is expressed by B cells, dendritic cells, monocytes, macrophages, granulocytes, and T cells. TLR4 is also expressed in myelomonocytic cells and is highest in mononuclear cells. In vitro, TLR4 mRNA and protein expression is upregulated in THP-1 cells upon PMA-induced differentiation. TLR4 is moderately upregulated by autocrine IFN-γ, IL-1β. TLR4 mRNA expression in THP-1 cells is unaffected by exposure to both Gram-positive and Gram-negative bacteria. Ex vivo, granulocyte, and monocyte, TLR4 expression is upregulated upon exposure to Gram-negative bacteria.

TLR4 forms a homodimer and requires the extracellular association of an additional component, MD-2. Although TLR2 complexes are capable of recognizing lipopolysaccharide (LPS), TLR4 is generally considered the LPS receptor. MD-2-associated TLR4 homodimers do not bind LPS directly, however. LPS must first be bound by the soluble LPS binding protein (LBP). LBP is then bound by either soluble or GPI-linked CD14. Additional cell type-dependent components required for LPS detection by TLR4 include CXCR4, GDF-5, CD55, various heat shock proteins (HSPs), and complement receptors (CRs). The TLR4 complex also recognizes a few other bacterial PAMPs including LTA. Further, the TLR4 complex recognizes viruses including respiratory syncytial virus (RSV), hepatitis C virus (HCV), and mouse mammary tumor virus (MMTV). The TLR4 complex can also recognize endogenous ligands, for example, heat shock proteins (HSP60 and HSP70), fibrinogen, domain A of fibronectin, oligosaccharides of hyaluronic acid, heparan sulfate, surfactant protein A (SP-A), and β-defensins. TLR4 also forms heterodimers both with TLR5, which enhances its activity, and also with TLR1, which inhibits its activity.

Toll-Like Receptor 5 (TLR5)

TLR5 maps to chromosome 1q41-42, and the gene encodes a putative 858 (aa) protein with a calculated molecular weight of 91 kDa. It is most closely related to TLR3 with 26% overall (aa) sequence identity.

In vivo, TLR5 mRNA is expressed as a single transcript in ovary, prostate, and PBLs. TLR5 is expressed by several PBL populations with the highest expression found in monocytes. TLR5 is also expressed on the basolateral side of intestinal epithelial cells and intestinal endothelial cells of the subepithelial compartment. In vitro, TLR5 is upregulated in PMA-differentiated THP-1 cells by autocrine IL-6, IL-10, and TNF-α, but is also elevated by IFN-γβ. TLR5 mRNA expression is elevated after exposure to both Gram-positive and Gram-negative bacteria. Ex vivo, granulocyte and monocyte TLR5 expression is downregulated upon exposure to Gram-negative bacteria. TLR5 forms a homodimer as well as a heterodimer with TLR4. Both complexes function to recognize the Flagellin protein of flagellated bacteria. Expression of human TLR5 in CHO cells confers response to flagellin, a monomeric constituent of bacterial flagella. Flagellin activates lung epithelial cells to induce inflammatory cytokine production. A stop codon polymorphism in TLR5 has been associated with susceptibility to pneumonia caused by the flagellated bacterium *Legionella pneumophila*.

Toll-Like Receptor 6 (TLR6)

TLR6 maps to chromosome 4p14, and the TLR6 sequence encodes a 796 (aa) protein containing 20 N-terminal LRR motifs with a calculated molecular weight of 91 kDa. TLR6 is most closely related to TLR1, TLR10, and TLR2 with 68%, 46%, and 31% overall (aa) sequence identity, respectively.

In vivo, TLR6 transcript is observed in thymus, spleen, and lung. TLR6 mRNA expression is highest in B cells and monocytes. In vitro, TLR6 mRNA expression is upregulated in THP-1 cells upon PMA-induced differentiation. TLR6 is moderately upregulated by autocrine IFN-γ, IL-1β. However, TLR6 mRNA expression in THP-1 cells is unaffected by exposure to both Gram-positive and Gram-negative bacteria. Ex vivo, monocyte andgranulocyte TLR6 expression is downregulated upon exposure to Gram-negative bacteria. TLR6 forms a heterodimer with TLR2. Like TLR1, TLR6 is thought to specify or enhance the PAMP sensitivity of TLR2 and contribute to its signaling capabilities through heterodimerization.

Toll-Like Receptor 7 (TLR7)

TLR7 maps to human chromosome Xp22, and the TLR7 sequence encodes a 1049 (aa) protein containing 27 N-terminal LRRs with a calculated molecular weight of 121 kDa. TLR7 is most closely related to TLR8 and TLR9 with 43% and 36% overall (aa) sequence identity, respectively.

In vivo, TLR7 mRNA is expressed in lung, placenta, spleen, lymph node, and tonsil. TLR7 mRNA expression is highest in monocytes, B cells, and plasmocytoid dendritic cells. In vitro, TLR7 mRNA expression is upregulated in THP-1 cells upon PMA-induced differentiation. TLR7 is highly upregulated by exposure to IL-6 and to a slightly lesser extent by autocrine IFN-γ, IL-1β. TLR7 mRNA expression in THP-1 cells is elevated after exposure to both Gram-positive and Gram-negative bacteria. Ex vivo, expression of TLR7 is elevated after exposure to both Gram-positive and Gram-negative bacteria in monocytes and to a greater degree in granulocytes. TLR7 is expressed in the endosome. The role of TLR7, is to detect the presence of "foreign" single-stranded RNA within a cell, as a means to respond to viral invasion. TLR7 is a structurally highly conserved protein which recognizes guanosine- or uridine-rich, single-stranded RNA (ss-RNA) from viruses such as human immunodeficiency virus, vesicular stomatitis virus and influenza virus Toll-Like Receptor 8 (TLR8)

TLR8 maps to chromosome Xp22, and the TLR8 sequence encodes a 1041 (aa) protein containing 26 N-terminal LRRs with a calculated molecular weight of 120 kDa. TLR8 is most closely related to TLR7 and TLR9 with 43% and 35% overall (aa) sequence identity, respectively.

In vivo, TLR8 mRNA is expressed in lung, placenta, spleen, lymph node, bone marrow, and PBLs, with highest expression found in cells of myeloid origin, such as monocytes, granulocytes and myeloid dendritic cells. In vitro, TLR8 mRNA expression is upregulated in THP-1 cells upon PMA-induced differentiation. TLR8 is highly upregulated by autocrine IL-1β, IL-6, IL-10, and TNF-α, and is even more enhanced by exposure to IFN-γ. TLR8 mRNA expression in THP-1 cells is elevated after exposure to both Gram-positive and Gram-negative bacteria. Ex vivo, monocyte TLR8 expression increases while granulocyte expression decreases on exposure to Gram-negative bacteria. TLR8 is expressed in the endosome. The role of TLR8 is to detect the presence of "foreign" single-stranded RNA within a cell, as a means to respond to viral invasion. TLR8 is a structurally highly conserved protein which recognizes guanosine- or uridine-rich, single-stranded RNA (ssRNA) from viruses such as human immunodeficiency virus, vesicular stomatitis virus and influenza virus.

Toll-Like Receptor 9 (TLR9)

TLR9 maps to chromosome 3p21, and the TLR9 sequence encodes a 1032 (aa) protein containing 27 N-terminal LRRs with a calculated molecular weight of 116 kDa. TLR9 is most closely related to TLR7 and TLR8 with 36% and 35% overall (aa) sequence identity, respectively.

In vivo, TLR9 mRNA is expressed in spleen, lymph node, bone marrow, and PBLs. Specifically, TLR9 mRNA is expressed at the highest levels in B cells and dendritic cells. In vitro, TLR9 is moderately upregulated by autocrine IFN-γ, IL-1β, IL-6, IL-10, and TNF-α in PMA-differentiated THP-1 cells. TLR9 mRNA expression in THP-1 cells is unaffected by exposure to both Gram-positive and Gram-negative bacteria. Ex vivo, TLR9 expression in monocytes and particularly in granulocytes is downregulated in response to Gram-negative bacteria. TLR9 forms a homodimer and recognizes unmethylated bacterial DNA. TLR9 is involved in the inflammatory response to bacterial DNA and oligonucleotides that contain unmethylated CpG DNA sequences. TLR9 is localized internally, perhaps in lysosomic or endocytic compartments where it would more likely encounter PAMPs including unmethylated CpG DNA sequences.

TLR9 is a receptor for CpG DNA, and recognizes bacterial and viral CpG DNA. Bacterial and viral DNA contains unmethylated CpG motifs, which confer its immunostimulatory activity. In vertebrates, the frequency of CpG motifs is severely reduced and the cytosine residues of CpG motifs are highly methylated, leading to abrogation of the immunostimulatory activity. Structurally, there are at least two types of CpG DNA: B/K-type CpG DNA is a potent inducer of inflammatory cytokines such as IL-12 and TNF-α; A/D-type CpG DNA has a greater ability to induce IFN-α production from plasmacytoid dendritic cells (PDC). TLR9 is also involved in pathogenesis of autoimmune disorders, and may be important in Graves' autoimmune hyperthyroidism and production of rheumatoid factor by auto-reactive B cells. Similarly, internalization by the Fc receptor can cause TLR9 mediated PDC induction of IFN-α by immune complexes containing IgG and chromatin, which are implicated in the pathogenesis of systemic lupus erythematosus (SLE). TLR9 is involved in the pathogenesis of several autoimmune diseases through recognition of the chromatin structure.

Toll-Like Receptor 10 (TLR10)

The TLR10 sequence encodes a putative 811 (aa) protein with molecular weight of 95 kDa. TLR10 is most closely related to TLR1 and TLR6 with 48% and 46% overall (aa) identity, respectively.

In vivo, TLR10 mRNA expression is highest in immune system-related tissues including spleen, lymph node, thymus, and tonsil. TLR10 mRNA is most highly expressed on B cells and plasmacytoid dendritic cells (PDCs). In vitro, TLR10 is moderately upregulated by autocrine IFN-γ, IL-1β, IL-6, IL-10, and TNF-α in PMA-differentiated THP-1 cells. TLR10 mRNA expression in THP-1 cells is elevated after exposure to both Gram-positive and Gram-negative bacteria. Ex vivo, monocyte TLR10 expression increases, while granulocyte expression decreases on exposure to Gram-negative bacteria.

Toll-Like Receptor 11 (TLR11)

TLR11 is expressed in bladder epithelial cells and mediate resistance to infection by uropathogenic bacteria in mouse.

As presented above, TLR2 and TLR4 recognize Gram-positive and Gram-negative bacterial cell wall products, respectively; TLR5 recognizes a structural epitope of bacterial flagellin; TLR3, TLR7, TLR8, and TLR9 recognize different forms of microbial-derived nucleic acid.

The TIR domains interact with several TIR domain-containing adaptor molecules (MyD88), TIR domain-containing adaptor protein (TRAP), TIR domain-containing adaptor-inducing IFN-β (TRIF), and TRIF-related adaptor molecule (TRAM) which activate a cascade of events resulting in transcription factor induction.

TLR Signaling Pathways.

TLRs are distributed throughout the cell. TLR1, TLR2, TLR3 and TLR4 are expressed on the cell surface, whereas, TLR3, TLR7, TLR8 and TLR9 are expressed in intracellular compartments such as endosomes. TLR3-, TLR7- or TLR9-mediated recognition of their ligands require endosomal maturation and processing. When macrophages, monocytes, dendritic cells or nonimmune cells that become antigen presenting cells engulf bacteria by phagocytosis, the bacteria degrade and CpG DNA is release into phagosomes-lysosomes or in endosomes-lysosomes wherein they can interact with TLR9 that has been recruited from the endoplasmic reticulum upon non-specific uptake of CpG DNA. Furthermore, when viruses invade cells by receptor-mediated endocytosis, the viral contents are exposed to the cytoplasm by fusion of the viral membrane with the endosomal membrane. This results in exposure of TLR ligands such as dsRNA, ssRNA and CpG DNA to TLR9 in the phagosomal/lysosomal or endosomal/lysosomal compartments.

In the signaling pathways downstream of the TIR domain, a TIR domain-containing adaptor, MyD88, is essential for induction of inflammatory cytokines such as TNF-α and IL-12 through all TLRs. Although TIR domain-containing adaptor molecules (MyD88) are common to all TLRs, individual TLR signaling pathways are divergent and activation of specific TLRs leads to slightly different patterns of gene expression profiles. By way of example only, activation of TLR3 and TLR4 signaling pathways results in induction of type I interferons (IFNs), while activation of TLR2- and TLR5-mediated pathways do not. However, activation of TLR7, TLR8 and TLR9 signaling pathways also leads to induction of Type I IFNs, although this occurs through mechanisms distinct from TLR3/4-mediated induction.

Once engaged, TLRs initiate a signal transduction cascade leading to activation of NFκB via the adapter protein myeloid differentiation primary response gene 88 (MyD88) and recruitment of the IL-1 receptor associated kinase (IRAK). The MyD88-dependent pathway is analogous to signaling by the IL-1 receptors, and it is regarded that MyD88, harboring a C-terminal TIR domain and an N-terminal death domain, associates with the TIR domain of TLRs. Upon stimulation, MyD88 recruits IRAK-4 to TLRs through interaction of the death domains of both molecules, and facilitates IRAK-4-mediated phosphorylation of IRAK-1. Phosphorylation of IRAK-1 then leads to recruitment of TNF-receptor associated factor 6 (TRAF6), leading to the activation of two distinct signaling pathways. One pathway leads to activation of AP-1 transcription factors through activation of MAP kinases. Another pathway activates the TAK1/TAB complex, which enhances activity of the IκB kinase (IKK) complex. Once activated, the IKK complex induces phosphorylation and subsequent degradation of the NFκB inhibitor IκB, which leads to nuclear translocation of transcription factor NFκB and the initiation of transcription of genes whose promoters contain NFκB binding sites, such as cytokines. The MyD88-dependent pathway plays a crucial role and is essential for inflammatory cytokine production through all TLRs.

Stimulation of TLR8-expressing cells, such as PBMCs results in production of high levels of IL-12, IFN-γ, IL-1, TNF-α, IL-6 and other inflammatory cytokines. Similarly, stimulation of TLR7-expressing cells, such as plasmacytoid dendritic cells, results in production of high levels of interferon-α (IFNα) and low levels of inflammatory cytokines. Thus, through activation of dendritic cells and other antigen-presenting cells, TLR7, TLR8 or TLR9 engagement and cytokine production is expected to activate diverse innate and acquired immune response mechanisms leading to the destruction of pathogens, infected cells or tumor cells.

Compounds of Formula (I), pharmaceutically acceptable salts, solvates, N-oxides, prodrugs and isomers thereof, pharmaceutical compositions, and/or combinations provided herein are agonists of toll-like receptor 7 activity, and are used in the treatment of diseases and/or disorders associated with such TLR7 receptors.

In certain embodiments, the compounds of Formula (I), pharmaceutically acceptable salts, solvates, N-oxides, prodrugs and isomers thereof, pharmaceutical compositions, and/or combinations provided herein are used in the treatment of respiratory diseases and/or disorders including, but not limited to, asthma, bronchial asthma, allergic asthma, intrinsic asthma, extrinsic asthma, exercise-induced asthma, drug-induced asthma (including aspirin and NSAID-induced) and dust-induced asthma, chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus.

In certain embodiments, the compounds of Formula (I), pharmaceutically acceptable salts, solvates, N-oxides, prodrugs and isomers thereof, pharmaceutical compositions, and/or combinations provided herein are used in the treatment of dermatological disorders including, but not limited to, psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, basal cell carcinoma, actinic keratosis, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions.

In certain embodiments, the compounds of Formula (I), pharmaceutically acceptable salts, solvates, N-oxides, prodrugs and isomers thereof, pharmaceutical compositions, and/or combinations provided herein are used in the treatment of ocular diseases and/or disorders including, but not limited to, blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial.

In certain embodiments, the compounds of Formula (I), pharmaceutically acceptable salts, solvates, N-oxides, prodrugs and isomers thereof, pharmaceutical compositions, and/or combinations provided herein are used in the treatment of genitourinary diseases and/or disorders including, but not limited to, nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female).

In certain embodiments, the compounds of Formula (I), pharmaceutically acceptable salts, solvates, N-oxides, prodrugs and isomers thereof, pharmaceutical compositions, and/or combinations provided herein are used in the treatment of allograft rejection including, but not limited to, acute and chronic following, for example, transplantation of kidney, heart, liver, lung, bone marrow, skin or cornea or following blood transfusion; or chronic graft versus host disease.

In certain embodiments, the compounds of Formula (I), pharmaceutically acceptable salts, solvates, N-oxides, prodrugs and isomers thereof, pharmaceutical compositions, and/or combinations provided herein are used in the treatment of other auto-immune and allergic disorders including, but not limited to, rheumatoid arthritis, irritable bowel syndrome, systemic lupus erythematosus, multiple sclerosis, Hashimoto's thyroiditis, Crohns disease, inflammatory bowel disease (IBD), Graves' disease, Addison's disease, diabetes mellitus, idiopathic thrombocytopaenic purpura, eosinophilic fasciitis, hyper-IgE syndrome, antiphospholipid syndrome and Sazary syndrome.

In certain embodiments, the compounds of Formula (I), pharmaceutically acceptable salts, solvates, N-oxides, prodrugs and isomers thereof, and pharmaceutical compositions provided herein are used in the treatment of cancer including, but not limited to, prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumor recurrences, and paraneoplastic syndromes. In certain embodiments, the compounds of Formula (I), pharmaceutically acceptable salts, solvates, N-oxides, prodrugs and isomers thereof, and pharmaceutical compositions provided herein are useful as modulators of toll-like receptor activity, and are used in the treatment of neoplasias including, but not limited to, basal cell carcinoma, squamous cell carcinoma, actinic keratosis, melanoma, carcinomas, sarcomas, leukemias, renal cell carcinoma, Kaposi's sarcoma, myelogeous leukemia, chronic lymphocytic leukemia and multiple myeloma.

In certain embodiments, the compounds of Formula (I), pharmaceutically acceptable salts, solvates, N-oxides, prodrugs and isomers thereof, pharmaceutical compositions, and/or combinations provided herein are used in the treatment of infectious diseases including, but not limited to, viral diseases such as genital warts, common warts, plantar warts, respiratory syncytial virus (RSV), hepatitis B, hepatitis C, Dengue virus, herpes simplex virus (by way of example only, HSV-I, HSV-II, CMV, or VZV), molluscum contagiosum, vaccinia, variola, lentivirus, human immunodeficiency virus (HIV), human papilloma virus (HPV), cytomegalovirus (CMV), varicella zoster virus (VZV), rhinovirus, enterovirus, adenovirus, coronavirus (e.g., SARS), influenza, para-influenza, mumps virus, measles virus, papovavirus, hepadnavirus, flavivirus, retrovirus, arenavirus (by way of example only, LCM, Junin virus, Machupo virus, Guanarito virus and Lassa Fever) and filovirus (by way of example only, ebola virus or marbug virus).

In certain embodiments, the compounds of Formula (I), pharmaceutically acceptable salts, solvates, N-oxides, prodrugs and isomers thereof, pharmaceutical compositions, and/or combinations provided herein are used in the treatment of bacterial, fungal, and protozoal infections including, but not limited to, tuberculosis and *mycobacterium avium*, leprosy; *pneumocystis carnii*, cryptosporidiosis, histoplasmosis, toxoplasmosis, trypanosome infection, leishmaniasis, infections caused by bacteria of the genus *Escherichia, Enterobacter, Salmonella, Staphylococcus, Klebsiella, Proteus, Pseudomonas, Streptococcus*, and *Chlamydia*, and fungal infections such as candidiasis, aspergillosis, histoplasmosis, cryptococcal meningitis.

In certain embodiments, the compounds of Formula (I), pharmaceutically acceptable salts, solvates, N-oxides, prodrugs and isomers thereof, are used as immune potentiators. In certain embodiments, the compounds provided herein are included in immunogenic compositions or are used in combination with immunogenic compositions. In certain embodiments, the immunogenic compositions are useful as vaccines, and the compound is present in an amount sufficient to enhance an immune response to the vaccine, or to an antigen admixed with the compound. The vaccine comprises at least one antigen, which may be a bacterial antigen or a cancer-associated antigen, or a viral antigen. In certain embodiments, the compounds of Formula (I), pharmaceutically acceptable salts, solvates, N-oxides, prodrugs and isomers thereof, and pharmaceutical compositions provided herein are included in therapeutic vaccines or are used in combination with therapeutic vaccines. In certain embodiments, the compounds of Formula (I), pharmaceutically acceptable salts, solvates, N-oxides, prodrugs and isomers thereof, and pharmaceutical compositions provided herein are included in prophylactic vaccines or used in combination with prophylactic vaccines. In certain embodiments, the compounds of Formula (I), pharmaceutically acceptable salts, solvates, N-oxides, prodrugs and isomers thereof, and pharmaceutical compositions provided herein are included in, or are used in combination with, therapeutic viral vaccines. In certain embodiments, the compounds of Formula (I), pharmaceutically acceptable salts, solvates, N-oxides, prodrugs and isomers thereof, and pharmaceutical compositions provided herein are included in, or are used in combination with, with cancer vaccines.

In other embodiments, the compounds of Formula (I), or a pharmaceutically acceptable salt or solvate thereof, described herein are useful for the treatment of damaged or ageing skin such as scarring and wrinkles.

Administration and Pharmaceutical Compositions

For the therapeutic uses of compounds of Formula (I), or pharmaceutically acceptable salts, solvates, N-oxides, prodrugs and isomers thereof, described herein, such compounds are administered in therapeutically effective amounts either alone or as part of a pharmaceutical composition. Accordingly, provided herein are pharmaceutical compositions, which comprise at least one compound of Formula (I) provided herein, pharmaceutically acceptable salts and/or solvates thereof, and one or more pharmaceutically acceptable carriers, diluents, or excipients. In addition, such compounds and compositions are administered singly or in combination with one or more additional therapeutic agents. The method of administration of such compounds and compositions include, but are not limited to, oral administration, rectal administration, parenteral, intravenous administration, intravitreal administration, intramuscular administration, inhalation, intranasal administration, topical administration, ophthalmic administration or otic administration.

The therapeutically effective amount will vary depending on, among others, the disease indicated, the severity of the disease, the age and relative health of the subject, the potency of the compound administered, the mode of administration and the treatment desired. In certain embodiments, the daily dosage of a compound of Formula (I), satisfactory results are indicated to be obtained systemically at daily dosages of from about 0.03 to 2.5 mg/kg per body weight. In certain embodiments, the daily dosage of a compound of Formula (I), administered by inhalation, is in the range from 0.05 micrograms per kilogram body weight ($\mu g/kg$) to 100 micrograms per kilogram body weight ($\mu g/kg$). In other embodiments, the daily dosage of a compound of Formula (I), administered orally, is in the range from 0.01 micrograms per kilogram body weight ($\mu g/kg$) to 100 milligrams per kilogram body weight (mg/kg). An indicated daily dosage in the larger mammal, e.g. humans, is in the range from about 0.5 mg to about 100 mg of a compound of Formula (I), conveniently administered, e.g. in divided doses up to four times a day or in controlled release form. In certain embodiment, unit dosage forms for oral administration comprise from about 1 to 50 mg of a compound of Formula (I).

Other aspects provided herein are processes for the preparation of pharmaceutical composition which comprise at least one compound of Formula (I) provided herein, or pharmaceutically acceptable salts and/or solvates thereof. In certain embodiments, such processes include admixing a compound of the Formula (I) provided herein, and pharmaceutically acceptable salts and solvates thereof, with one or more pharmaceutically acceptable carriers, diluents or excipients. In certain embodiments, the pharmaceutical compositions comprising a compound of Formula (I) in free form or in a pharmaceutically acceptable salt or solvate form, in association with at least one pharmaceutically acceptable carrier, diluent or excipient are manufactured by mixing, granulating and/or coating methods. In other embodiments, such compositions are optionally contain excipients, such as preserving, stabilizing, wetting or emulsifying agents, solution promoters, salts for regulating the osmotic pressure and/or buffers. In other embodiments, such compositions are sterilized.

Oral Dosage Forms

In certain embodiments, the pharmaceutical compositions containing at least one compound of Formula (I) are administered orally as discrete dosage forms, wherein such dosage forms include, but are not limited to, capsules, gelatin capsules, caplets, tablets, chewable tablets, powders, granules, syrups, flavored syrups, solutions or suspensions in aqueous or non-aqueous liquids, edible foams or whips, and oil-in-water liquid emulsions or water-in-oil liquid emulsions.

The capsules, gelatin capsules, caplets, tablets, chewable tablets, powders or granules, used for the oral administration of at least one compound of Formula (I) are prepared by admixing at least one compound of Formula (I) (active ingredient) together with at least one excipient using conventional pharmaceutical compounding techniques. Non-limiting examples of excipients used in oral dosage forms described herein include, but are not limited to, binders, fillers, disintegrants, lubricants, absorbents, colorants, flavors, preservatives and sweeteners.

Non-limiting examples of such binders include, but are not limited to, corn starch, potato starch, starch paste, pre-gelatinized starch, or other starches, sugars, gelatin, natural and synthetic gums such as acacia, sodium alginate, alginic acid, other alginates, tragacanth, guar gum, cellulose and its derivatives (by way of example only, ethyl cellulose, cellulose acetate, carboxymethyl cellulose calcium, sodium carboxymethylcellulose, methyl cellulose, hydroxypropyl methylcellulose and microcrystalline cellulose), magnesium aluminum silicate, polyvinyl pyrrolidone and combinations thereof.

Non-limiting examples of such fillers include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein are present in from about 50 to about 99 weight percent of the pharmaceutical composition or dosage form.

Non-limiting examples of such disintegrants include, but are not limited to, agar-agar, alginic acid, sodium alginate, calcium carbonate, sodium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and combinations thereof. In certain embodiments, the amount of disintegrant used in the pharmaceutical compositions provided herein is from about 0.5 to about 15 weight percent of disintegrant, while in other embodiments the amount is from about 1 to about 5 weight percent of disintegrant.

Non-limiting examples of such lubricants include, but are not limited to, sodium stearate, calcium stearate, magnesium stearate, stearic acid, mineral oil, light mineral oil, glycerin, sorbitol, mannitol, polyethylene glycol, other glycols, sodium lauryl sulfate, talc, hydrogenated vegetable oil (by way of example only, peanut oil, cottonseed oil, sunflower oil, sesame oil, olive oil, corn oil, and soybean oil), zinc stearate, sodium oleate, ethyl oleate, ethyl laureate, agar, silica, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.) and combinations thereof. In certain embodiments, the amount of lubricants used in the pharmaceutical compositions provided herein is in an amount of less than about 1 weight percent of the pharmaceutical compositions or dosage forms.

Non-limiting examples of such diluents include, but are not limited to, lactose, dextrose, sucrose, mannitol, sorbitol, cellulose, glycine or combinations thereof.

In certain embodiments, tablets and capsules are prepared by uniformly admixing at least one compound of Formula (I) (active ingredients) with liquid carriers, finely divided solid carriers, or both, and then shaping the product into the desired presentation if necessary. In certain embodiments, tablets are prepared by compression. In other embodiments, tablets are prepared by molding.

In certain embodiments, at least one compound of Formula (I) is orally administered as a controlled release dosage form. Such dosage forms are used to provide slow or controlled-release of one or more compounds of Formula (I). Controlled release is obtained using, for example, hydroxypropylmethyl cellulose, other polymer matrices, gels, permeable membranes, osmotic systems, multilayer coatings, microparticles, liposomes, microspheres, or a combination thereof. In certain embodiments, controlled-release dosage forms are used to extend activity of the compound of Formula (I), reduce dosage frequency, and increase patient compliance.

Administration of compounds of Formula (I) as oral fluids such as solution, syrups and elixirs are prepared in unit dosage forms such that a given quantity of solution, syrups or elixirs contains a predetermined amount of a compound of Formula (I). Syrups are prepared by dissolving the compound in a suitably flavored aqueous solution, while elixirs are prepared through the use of a non-toxic alcoholic vehicle. Suspensions are formulated by dispersing the compound in a non-toxic vehicle. Non-limiting examples of excipients used in as oral fluids for oral administration include, but are not limited to, solubilizers, emulsifiers, flavoring agents, preservatives, and coloring agents. Non-limiting examples of solubilizers and emulsifiers include, but are not limited to, water, glycols, oils, alcohols, ethoxylated isostearyl alcohols and polyoxy ethylene sorbitol ethers. Non-limiting examples of preservatives include, but are not limited to, sodium benzoate. Non-limiting examples of flavoring agents include, but are not limited to, peppermint oil or natural sweeteners or saccharin or other artificial sweeteners.

Parenteral Dosage Forms

In certain embodiments pharmaceutical compositions containing at least one compound of Formula (I) are administered parenterally by various routes including, but not limited to, subcutaneous, intravenous (including bolus injection), intramuscular, and intraarterial.

Such parenteral dosage forms are administered in the form of sterile or sterilizable injectable solutions, suspensions, dry and/or lyophylized products ready to be dissolved or suspended in a pharmaceutically acceptable vehicle for injection (reconstitutable powders) and emulsions. Vehicles used in such dosage forms include, but are not limited to, Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Transdermal Dosage Forms

In certain embodiments pharmaceutical compositions containing at least one compound of Formula (I) are administered transdermally. Such transdermal dosage forms include "reservoir type" or "matrix type" patches, which are applied to the skin and worn for a specific period of time to permit the penetration of a desired amount of a compound of Formula (I). By way of example only, such transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. In other embodiments, matrix transdermal formulations are used.

Formulations for transdermal delivery of a compound of Formula (I) include an effective amount of a compound of Formula (I), a carrier and an optional diluent. A carrier includes, but is not limited to, absorbable pharmacologically acceptable solvents to assist passage through the skin of the host, such as water, acetone, ethanol, ethylene glycol, propylene glycol, butane-1,3-diol, isopropyl myristate, isopropyl palmitate, mineral oil, and combinations thereof.

In certain embodiments, such transdermal delivery systems include penetration enhancers to assist in delivering one or more compounds of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In other embodiments, the pH of such a transdermal pharmaceutical composition or dosage form, or of the tissue to which the pharmaceutical composition or dosage form is applied, is adjusted to improve delivery of one or more compounds of Formula (I). In other embodiments, the polarity of a solvent carrier, its ionic strength, or tonicity are adjusted to improve delivery. In other embodiments, compounds such as stearates are added to advantageously alter the hydrophilicity or lipophilicity of one or more compounds of Formula (I) so as to improve delivery. In certain embodiments, such stearates serve as a lipid vehicle for the formulation, as an emulsifying agent or surfactant, and as a delivery-enhancing or penetration-enhancing agent. In other embodiments, different salts, hydrates or solvates of the compounds of Formula (I) are used to further adjust the properties of the resulting composition.

Topical Dosage Forms

In certain embodiments at least one compound of Formula (I) is administered by topical application of pharmaceutical composition containing at least one compound of Formula (I) in the form of lotions, gels, ointments solutions, emulsions, suspensions or creams. Suitable formulations for topical application to the skin are aqueous solutions, ointments, creams or gels, while formulations for ophthalmic administration are aqueous solutions. Such formulations optionally contain solubilizers, stabilizers, tonicity enhancing agents, buffers and preservatives.

Such topical formulations include at least one carrier, and optionally at least one diluent. Such carriers and diluents include, but are not limited to, water, acetone, ethanol, ethylene glycol, propylene glycol, butane-1,3-diol, isopropyl myristate, isopropyl palmitate, mineral oil, and combinations thereof.

In certain embodiments, such topical formulations include penetration enhancers to assist in delivering one or more compounds of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In certain embodiments pharmaceutical compositions containing at least one compound of Formula (I) are administered by inhalation. Dosage forms for inhaled administration are formulated as aerosols or dry powders. Aerosol formulations for inhalation administration comprise a solution or fine suspension of at least one compound of Formula (I) in a pharmaceutically acceptable aqueous or non-aqueous solvent. In addition, such pharmaceutical compositions optionally comprise a powder base such as lactose, glucose, trehalose, mannitol or starch, and optionally a performance modifier such as L-leucine or another amino acid, and/or metals salts of stearic acid such as magnesium or calcium stearate.

In certain embodiments, compounds of Formula (I) are be administered directly to the lung by inhalation using a Metered Dose Inhaler ("MDI"), which utilizes canisters that contain a suitable low boiling propellant, e.g., dichlorodifluoromethane, trichlorofluoromethane, dichlorotetrafluoroethane, carbon dioxide or other suitable gas, or a Dry Powder Inhaler (DPI) device which uses a burst of gas to create a cloud of dry powder inside a container, which is then be inhaled by the patient. In certain embodiments, capsules and cartridges of gelatin for use in an inhaler or insufflator are formulated containing a powder mixture of a compound of Formula (I) and a powder base such as lactose or starch. In certain embodiments, compounds of Formula (I) are delivered to the lung using a liquid spray device, wherein such devices use extremely small nozzle holes to aerosolize liquid drug formulations that can then be directly inhaled into the lung. In other embodiments, compounds of Formula (I) are delivered to the lung using a nebulizer device, wherein a nebulizers creates an aerosols of liquid drug formulations by using ultrasonic energy to form fine particles that can be readily inhaled. In other embodiments, compounds of Formula (I) are delivered to the lung using an electrohydrodynamic ("EHD") aerosol device wherein such EHD aerosol devices use electrical energy to aerosolize liquid drug solutions or suspensions.

In certain embodiments, the pharmaceutical composition containing at least one compound of Formula (I), or pharmaceutically acceptable salts and solvates thereof, described herein, also contain one or more absorption enhancers. In certain embodiments, such absorption enhancers include, but are not limited to, sodium glycocholate, sodium caprate, N-lauryl-β-D-maltopyranoside, EDTA, and mixed micelles.

In certain embodiments pharmaceutical compositions containing at least one compound of Formula (I) are administered nasally. The dosage forms for nasal administration are formulated as aerosols, solutions, drops, gels or dry powders.

In certain embodiments pharmaceutical compositions containing at least one compound of Formula (I) are administered rectally in the form of suppositories, enemas, ointment, creams rectal foams or rectal gels. In certain embodiments such suppositories are prepared from fatty emulsions or suspensions, cocoa butter or other glycerides.

In certain embodiments pharmaceutical compositions containing at least one compound of Formula (I) are administered opthamically as eye drops. Such formulations are aqueous solutions that optionally contain solubilizers, stabilizers, tonicity enhancing agents, buffers and preservatives.

In certain embodiments pharmaceutical compositions containing at least one compound of Formula (I) are administered otically as ear drops. Such formulations are aqueous solutions that optionally contain solubilizers, stabilizers, tonicity enhancing agents, buffers and preservatives.

In certain embodiments pharmaceutical compositions containing at least one compound of Formula (I) are formulated as a depot preparation. Such formulations are administered by implantation (for example subcutaneously or intramuscularly) or by intramuscular injection. In certain embodiments, such formulations include polymeric or hydrophobic materials (for example, as an emulsion in an acceptable oil) or ion exchange resins, or as sparingly soluble derivatives, for example, as a sparingly soluble salt.

In a further embodiment, the pharmaceutical compositions comprising at least one compound of Formula (I) are adapted for oral administration for the treatment of viral diseases and/or disorders associated with TLR7 activity.

In a further embodiment, the pharmaceutical compositions comprising at least one compound of Formula (I) are adapted for oral administration for the treatment of infectious diseases and/or disorders associated with TLR7.

In a further embodiment, the pharmaceutical compositions comprising at least one compound of Formula (I) are adapted for oral administration for the treatment of bacterial diseases and/or disorders associated with TLR7.

In a further embodiment, the pharmaceutical compositions comprising at least one compound of Formula (I) are adapted for oral administration for the treatment of fungal diseases and/or disorders associated with TLR7.

In a further embodiment, the pharmaceutical compositions comprising at least one compound of Formula (I) are adapted for oral administration for the treatment of cancer associated with TLR7.

In a further embodiment, the pharmaceutical compositions comprising at least one compound of Formula (I) are adapted for intravenous administration for the treatment of cancer associated with TLR7.

In a further embodiment, the pharmaceutical compositions comprising at least one compound of Formula (I) are adapted for oral administration for the treatment of allograft rejection diseases and/or disorders associated with TLR7.

In a further embodiment, the pharmaceutical compositions comprising at least one compound of Formula (I) are adapted for oral administration for the treatment of genitourinary diseases and/or disorders associated with TLR7.

In a further embodiment, the pharmaceutical compositions comprising at least one compound of Formula (I) are adapted for administration as eye drops for the treatment of ophthalmic diseases and/or disorders associated with TLR7.

In a further embodiment, the pharmaceutical compositions comprising at least one compound of Formula (I) are adapted for topical administration for the treatment of dermatological diseases and/or disorders associated with TLR7.

In a further embodiment, the pharmaceutical compositions comprising at least one compound of Formula (I) are adapted for topical administration for the treatment of actinic keratosis. In a further embodiment, the pharmaceutical compositions comprising at least one compound of Formula (I) are adapted for topical administration as a cream for the treatment of actinic keratosis.

In a further embodiment, the pharmaceutical compositions comprising at least one compound of Formula (I) are adapted for topical administration for the treatment of basal cell carcinoma. In a further embodiment, the pharmaceutical compositions comprising at least one compound of Formula (I)

are adapted for topical administration as a cream for the treatment of basal cell carcinoma.

In a further embodiment, the pharmaceutical compositions comprising at least one compound of Formula (I) are adapted for administration by inhalation for the treatment of respiratory diseases and/or disorders associated with TLR7. In certain embodiments, the respiratory disease is allergic asthma.

Provided herein are compounds of Formula (I), pharmaceutically acceptable salts and solvates thereof, and pharmaceutical compositions containing at least one compound of Formula (I) and/or pharmaceutically acceptable salts and solvates thereof, for use in activating TLR7 activity, and thereby are used to in the prevention or treatment of diseases and/or disorders associated with TLR7 activity. Such compounds of Formula (I), pharmaceutically acceptable salts and solvates thereof, and pharmaceutical compositions are agonists of TLR7.

Also provided herein are methods for the treatment of a subject suffering from a disease and/or disorder associated with TLR7 activity, wherein the methods include administering to the subject an effective amount of a compound of Formula (I) or a pharmaceutically acceptable salt, solvate, either alone or as part of a pharmaceutical composition as described herein.

Provided herein is the use of a compound of Formula (I), or a pharmaceutically acceptable salt or solvate thereof, in the preparation of a medicament for the treatment of a disease or disorder associated with TLR7 activity.

Combination Treatment

In certain embodiments, a compound of Formula (I) provided herein, or a pharmaceutically acceptable salt or solvate thereof, or a pharmaceutical composition containing at least one compound of Formula (I) provided herein, is administered alone (without an additional therapeutic agent) for the treatment of one or more of the disease and/or disorders associated with TLR activity described herein.

In other embodiments, a compound of Formula (I) provided herein, or a pharmaceutically acceptable salt or solvate thereof, or a pharmaceutical composition containing at least one compound of Formula (I) provided herein, is administered in combination with one or more additional therapeutic agents, for the treatment of one or more of the disease and/or disorders associated with TLR7 activity described herein.

In other embodiments, a compound of Formula (I) provided herein, or a pharmaceutically acceptable salt or solvate thereof, or a pharmaceutical composition containing at least one compound of Formula (I) provided herein, is formulated in combination with one or more additional therapeutic agents and administered for the treatment of one or more of the disease and/or disorders associated with TLR7 activity described herein.

In a compound of Formula (I) provided herein, or a pharmaceutically acceptable salt or solvate thereof, or a pharmaceutical composition containing at least one compound of Formula (I) provided herein, is administered sequentially with one or more additional therapeutic agents, for the treatment of one or more of the disease and/or disorders associated with TLR7 activity described herein.

In other embodiments, the combination treatments provided herein include administration of a compound of Formula (I) provided herein, or a pharmaceutically acceptable salt or solvate thereof, or a pharmaceutical composition containing a compound of Formula (I), prior to administration of one or more additional therapeutic agents, for the treatment of one or more of the disease and/or disorders associated with TLR7 activity described herein.

In other embodiments, the combination treatments provided herein include administration of a compound of Formula (I) provided herein, or a pharmaceutically acceptable salt or solvate thereof, or a pharmaceutical composition containing a compound of Formula (I), subsequent to administration of one or more additional therapeutic agents, for the treatment of one or more of the disease and/or disorders associated with TLR7 activity described herein.

In certain embodiments, the combination treatments provided herein include administration of a compound of Formula (I) provided herein, or a pharmaceutically acceptable salt or solvate thereof, or a pharmaceutical composition containing a compound of Formula (I), concurrently with one or more additional therapeutic agents, for the treatment of one or more of the disease and/or disorders associated with TLR7 activity described herein.

In certain embodiments, the combination treatments provided herein include administration of a compound of Formula (I) provided herein, or a pharmaceutically acceptable salt or solvate thereof, or a pharmaceutical composition containing a compound of Formula (I) formulated with one or more additional therapeutic agents, for the treatment of one or more of the disease and/or disorders associated with TLR7 activity described herein.

In certain embodiments of the combination treatments described herein the compounds of Formula (I), or a pharmaceutically acceptable salts or solvates thereof, are agonists of TLR7 activity.

In certain embodiments of the combination therapies described herein, the compounds of Formula (I) provided herein, or a pharmaceutically acceptable salts or solvates thereof, and the additional therapeutics agent(s) act additively. In certain embodiments of the combination therapies described herein, the compounds of Formula (I) provided herein, or a pharmaceutically acceptable salts or solvates thereof, and the additional therapeutics agent(s) act synergistically.

In other embodiments, a compound of Formula (I) provided herein, or a pharmaceutically acceptable salts or solvates thereof, or a pharmaceutical composition containing a compound of Formula (I), is administered to a patient who has not previously undergone or is not currently undergoing treatment with another therapeutic agent.

The additional therapeutic agents used in combination with at least one compound of Formula (I) provided herein, or a pharmaceutically acceptable salt or solvate thereof, include, but are not limited to antibiotics or antibacterial agents, antiemetic agents, antifungal agents, anti-inflammatory agents, antiviral agents, immunomodulatory agents, cytokines, antidepressants, hormones, alkylating agents, antimetabolites, antitumour antibiotics, antimitotic agents, topoisomerase inhibitors, cytostatic agents, anti-invasion agents, antiangiogenic agents, inhibitors of growth factor function inhibitors of viral replication, viral enzyme inhibitors, anticancer agents, α-interferons, β-interferons, ribavirin, hormones, cytokines, and other toll-like receptor modulators.

The antibiotics or antibacterial agents used in combination with at least one compound of Formula (I) provided herein, or a pharmaceutically acceptable salt or solvate thereof, include, but are not limited to, valganciclovir hydrochloride, metronidazole, a beta-lactam, macrolides (such as, by way of example only, azithromycin, tobramycin (TOBI™)), cephalosporins (such as, by way of example only, cefaclor, cefadroxil, cephalexin, cephradine, cefamandole, cefatrizine, cefazedone, cefixime, cefozopran, cefpimizole, cefuroxime, cefpiramide, cefprozil, cefpirome, KEFLEX™, VELOSEF™, CEFTIN™, CEFZIL™, CECLOR™, SUPRAX™ and DURICEF™), a clarithromycin (such as, by way of example only, clarithromycin and BIAXIN™), an erythromycin (such as, by way of example only, erythromycin and EMYCIN™), ciprofloxacin, CIPRO™, a norfloxacin (such as, by way of example only, NOROXIN™), aminoglycoside antibiotics (such as, by way of example only, apramycin, arbekacin, bambermycins, butirosin, dibekacin, neomycin, neomycin, undecylenate, netilmicin, paromomycin, ribostamycin, sisomicin, and spectinomycin), amphenicol antibiotics (such as, by way of example only, azidamfenicol, chloramphenicol, florfenicol, and thiamphenicol), ansamycin antibiotics (such as, by way of example only, rifamide and rifampin), carbacephems (such as, by way of example only, loracarbef), carbapenems (such as, by way of example only, biapenem and imipenem), cephamycins (such as, by way of example only, cefbuperazone, cefinetazole, and cefminox), monobactams (such as, by way of example only, aztreonam, carumonam, and tigemonam), oxacephems (such as, by way of example only, flomoxef, and moxalactam), penicillins (such as, by way of example only, amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, phencihicillin potassium, V-CILLIN K™ and PEN VEE K™), lincosamides (such as, by way of example only, clindamycin, and lincomycin), amphomycin, bacitracin, capreomycin, colistin, enduracidin, enviomycin, tetracyclines (such as, by way of example only, apicycline, chlortetracycline, clomocycline, and demeclocycline), 2,4-diaminopyrimidines (such as, by way of example only, brodimoprim), nitrofurans (such as, by way of example only, furaltadone, and furazolium chloride), quinolones and analogs thereof (such as, by way of example only, a fluoroquinolone, ofloxacin, cinoxacin, clinafloxacin, flumequine, grepagloxacin and FLOXIN™), sulfonamides (such as, by way of example only, acetyl sulfamethoxypyrazine, benzylsulfamide, noprylsulfamide, phthalylsulfacetamide, sulfachrysoidine, and sulfacytine), sulfones (such as, by way of example only, diathymosulfone, glucosulfone sodium, and solasulfone), cycloserine, mupirocin, tuberin and combinations thereof.

The antiemetic agents used in combination with at least one compound of Formula (I) provided herein, or a pharmaceutically acceptable salt or solvate thereof, include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and combinations thereof.

The antifungal agents used in combination with at least one compound of Formula (I) provided herein, or a pharmaceutically acceptable salt or solvate thereof, include, but are not limited to, amphotericin B, itraconazole, ketoconazole, fluconazole, fosfluconazole, intrathecal, flucytosine, miconazole, butoconazole, itraconazole, clotrimazole, nystatin, terconazole, tioconazole, voriconazole, ciclopirox, econazole, haloprogrin, naftifine, terbinafine, undecylenate, and griseofulvin.

The anti-inflammatory agents used in combination with at least one compound of Formula (I) provided herein, or a pharmaceutically acceptable salt or solvate thereof, include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide, leukotriene antagonists including, but not limited to, zileuton, aurothioglucose, gold sodium thiomalate and auranofin, steroids including, but not limited to, alclometasone diprionate, amcinonide, beclomethasone dipropionate, betametasone, betamethasone benzoate, betamethasone diprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide and other anti-inflammatory agents including, but not limited to, methotrexate, colchicine, allopurinol, probenecid, thalidomide or a derivative thereof, 5-aminosalicylic acid, retinoid, dithranol or calcipotriol, sulfinpyrazone and benzbromarone.

The antiviral agents used in combination with at least one compound of Formula (I) provided herein, or a pharmaceutically acceptable salt or solvate thereof, include, but are not limited to, protease inhibitors, nucleoside/nucleotide reverse transcriptase inhibitors (NRTIs), non-nucleoside reverse transcriptase inhibitors (NNRTIs), CCR1 antagonist, CCR5 antagonists, and nucleoside analogs. The antiviral agents include but are not limited to fomivirsen, didanosine, lamivudine, stavudine, zalcitabine, zidovudine, acyclovir, famciclovir, valaciclovir, ganciclovir, gangcyclovir, cidofovir, zanamivir, oseltamavir, vidarabine, idoxuridine, trifluridine, levovirin, viramidine and ribavirin, as well as foscarnet, amantadine, rimantadine, saquinavir, indinavir, nelfinavir, amprenavir, lopinavir, ritonavir, the α-interferons; β-interferons; adefovir, clevadine, entecavir, pleconaril, HCV-086, EMZ702, emtricitabine, celgosivir, valopicitabine, inhibitors of HCV protease, such as BILN 2061, SCH-503034, ITMN-191 or VX-950, inhibitors of NS5B polymerase such as NM107 (and its prodrug NM283), R1626, R7078, BILN1941, GSK625433, GILD9128 or HCV-796, efavirenz, HBY-097, nevirapine, TMC-120 (dapivirine), TMC-125, BX-471, etravirine, delavirdine, DPC-083, DPC-961, capravirine, rilpivirine, 5-{[3,5-diethyl-1-(2-hydroxyethyl)-1H-pyrazol-4-yl]oxy}isophthalonitrile, GW-678248, GW-695634, MW-150, calanolide, TAK-779, SC-351125, ancriviroc, vicriviroc, maraviroc, PRO-140, aplaviroc 40, Ono-4128, AK-602), AMD-887 CMPD-167, methyl 1-endo-{8-[(3S)-3-(acetylamino)-3-(3-fluorophenyl)propyl]-8-azabicyclo[3.-2.1]oct-3-yl}-2-methyl-4,5,6,7-tetrahydro-1H-imidazo[4,5-c]pyridine-5-carboxylate, methyl 3-endo-{8-[(3S)-3-(acetamido)-3-(3-fluorophenyl)propyl]-8-azabicyclo[3.2.-1]oct-3-yl}-2-methyl-4,5,6,7-tetrahydro-3H-imidazo[4,5-c]pyridine-5-carboxylate, ethyl 1-endo-{8-[(3S)-3-(acetylamino)-3-(3-fluorophenyl)propyl]-8-azabicyclo[3.-2.1]oct-3-yl}-2-methyl-4,5,6,7-tetrahydro-1H-imidazo[4,5-c]pyridine-5-carboxylate, and N-{(1S)-3-[3-endo-(5-Isobutyryl-2-methyl-4,5,6,7-tetrahydro-1H-imidazo[4,-5-c]pyridin-1-yl)-8-azabicyclo[3.2.1]oct-8-yl]-1-(3-fluorophenyl)propyl}acetamide), BMS-806, BMS- 488043, 5-{(1S)-2-[(2R)-4-benzoyl-2-methyl-piperazin-1-yl]-1-methyl-2-oxo-ethoxy}-4-methoxy-pyridine-2-carboxylic acid methylamide and 4-{(1S)-2-[(2R)-4-benzoyl-2-methyl-piperazin-1-yl]-1-methyl-2-oxo-ethoxy}-3-methoxy-N-methyl-benzamide, enfuvirtide (T-20), sifuvirtide SP-01A, T1249, PRO 542, AMD-3100, soluble CD4, HMG CoA reductase inhibitors, atorvastatin, 3-O-(3'3'-dimethylsuccinyl) betulic acid (otherwise known as PA-457) and αHGA.

The immunomodulatory agents used in combination with at least one compound of Formula (I) provided herein, or a pharmaceutically acceptable salt or solvate thereof, include, but are not limited to, azathioprine, tacrolimus, cyclosporin methothrexate, leflunomide, corticosteroids, cyclophosphamide, cyclosporine A, cyclosporin G, mycophenolate mofetil, ascomycin, rapamycin (sirolimus), FK-506, mizoribine, deoxyspergualin, brequinar, mycophenolic acid, malononitriloamindes (such as, by way of example only, leflunamide), T cell receptor modulators, and cytokine receptor modulators, peptide mimetics, and antibodies (such as, by way of example only, human, humanized, chimeric, monoclonal, polyclonal, Fvs, ScFvs, Fab or F(ab)₂ fragments or epitope binding fragments), nucleic acid molecules (such as, by way of example only, antisense nucleic acid molecules and triple helices), small molecules, organic compounds, and inorganic compounds. Examples of T cell receptor modulators include, but are not limited to, anti-T cell receptor antibodies (such as, by way of example only, anti-CD4 antibodies (such as, by way of example only, cM-T412 (Boehringer), IDEC-CE9.1™ (IDEC and SKB), mAB 4162W94, Orthoclone and OKTcdr4a (Janssen-Cilag)), anti-CD3 antibodies (such as, by way of example only, Nuvion (Product Design Labs), OKT3 (Johnson & Johnson), or Rituxan (IDEC)), anti-CD5 antibodies (such as, by way of example only, an anti-CD5 ricin-linked immunoconjugate), anti-CD7 antibodies (such as, by way of example only, CHH-380 (Novartis)), anti-CD8 antibodies, anti-CD40 ligand monoclonal antibodies (such as, by way of example only, IDEC-131 (IDEC)), anti-CD52 antibodies (such as, by way of example only, CAMPATH 1H (Ilex)), anti-CD2 antibodies, anti-CD11a antibodies (such as, by way of example only, Xanelim (Genentech)), anti-B7 antibodies (such as, by way of example only, IDEC-114 (IDEC)), CTLA4-immunoglobulin, and other toll receptor-like (TLR) modulators. Examples of cytokine receptor modulators include, but are not limited to, soluble cytokine receptors (such as, by way of example only, the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (such as, by way of example only, interleukin (IL)-2, IL-3, IL-4, IL-5, IL-6, IL-7, IL-8, IL-9, IL-10, IL-11, IL-12, IL-15, TNF-.alpha., interferon (IFN)-α, IFN-β, IFN-γ, and GM-CSF), anti-cytokine receptor antibodies (such as, by way of example only, anti-IFN receptor antibodies, anti-IL-2 receptor antibodies (such as, by way of example only, Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (such as, by way of example only, anti-IFN antibodies, anti-TNF-α antibodies, anti-IL-1β antibodies, anti-IL-6 antibodies, anti-IL-8 antibodies (such as, by way of example only, ABX-IL-8 (Abgenix)), and anti-IL-12 antibodies).

The cytokines or modulator of cytokine function used in combination with at least one compound of Formula (I) provided herein, or a pharmaceutically acceptable salt or solvate thereof, include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, alpha-, beta-, and gamma-interferon, interferon β-1a, interferon β-1b, interferon α-1, interferon α-2a (roferon), interferon α-2b, pegylated interferons (by way of example only, peginterferon α-2a and peginterferon α-2b), intron, Peg-Intron, Pegasys, consensus interferon (infergen), albumin-interferon cc and albuferon.

The antidepressants used in combination with at least one compound of Formula (I) provided herein, or a pharmaceutically acceptable salt or solvate thereof, include, but are not limited to, binedaline, caroxazone, citalopram, dimethazan, fencamine, indalpine, indeloxazine indocholoride, nefopam, nomifensine, oxitriptan, oxypertine, paroxetine, sertraline, thiazesim, trazodone, benmoxine, echinopsidine iodide, etryptamine, iproclozide, iproniazid, isocarboxazid, mebanazine, metfendrazine, nialamide, pargyline, octamoxin, phenelzine, pheniprazine, phenoxypropazine, pivhydrazine, safrazine, selegiline, 1-deprenyl, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

In certain embodiments, the antidepressants used in combination with at least one compound of Formula (I) provided herein, or a pharmaceutically acceptable salt or solvate thereof, are MAO-inhibitors including, but not limited to, benmoxin, echinopsidine iodide, etryptamine, iproclozide, iproniazid, isocarboxazid, mebanazine, metfendrazine, moclobamide, nialamide, pargyline, phenelzine, pheniprazine, phenoxypropazine, pivhydrazine, safrazine, selegiline, 1-deprenyl, toloxatone and tranylcypromine.

The hormones used in combination with at least one compound of Formula (I) provided herein, or a pharmaceutically acceptable salt or solvate thereof, include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, thymostimulin, synthetic and natural opioids, insulin thyroid stimulating hormones, and endorphins.

The alkylating agents used in combination with at least one compound of Formula (I) provided herein, or a pharmaceutically acceptable salt or solvate thereof, include, but are not limited to, nitrogen mustards, ethylenimines, methylmelamines, alkyl sulfonates, nitrosoureas, carmustine, lomustine, triazenes, melphalan, mechlorethamine, cis-platin, oxaliplatin, carboplatin, cyclophosphamide, ifosfamide, melphalan, chlorambucil, hexamethylmelaine, thiotepa, busulfan, carmustine, streptozocin, dacarbazine and temozolomide.

The antimetabolites used in combination with at least one compound of Formula (I) provided herein, or a pharmaceutically acceptable salt or solvate thereof, include, but are not limited to, cytarabile, gemcitabine and antifolates such as, by way of example only, fluoropyrimidines (by way of example only, 5-fluorouracil and tegafur), raltitrexed, methotrexate, cytosine arabinoside, and hydroxyurea.

The antitumour antibiotics in combination with at least one compound of Formula (I) provided herein, or a pharmaceutically acceptable salt or solvate thereof, include, but are not limited to, anthracyclines, bleomycin, doxorubicin, daunomycin, epirubicin, idarubicin, mitomycin-C, dactinomycin and mithramycin.

The antimitotic agents used in combination with at least one compound of Formula (I) provided herein, or a pharmaceutically acceptable salt or solvate thereof, include, but are not limited to, vinca alkaloids (by way of example only, vincristine, vinblastine, vindesine and vinorelbine), taxoids (by way of example only, taxol, paclitaxel and taxotere) and polokinase inhibitors.

The topoisomerase inhibitors used in combination with at least one compound of Formula (I) provided herein, or a pharmaceutically acceptable salt or solvate thereof, include, but are not limited to, epipodophyllotoxins by way of example only, etoposide and teniposide, amsacrine, topotecan, irinotecan and camptothecin.

The cytostatic agents used in combination with at least one compound of Formula (I) provided herein, or a pharmaceutically acceptable salt or solvate thereof, include, but are not limited to, antioestrogens (such as, by way of example only, tamoxifen, fulvestrant, toremifene, raloxifene, droloxifene and iodoxyfene), antiandrogens (such as, by way of example only, bicalutamide, flutamide, nilutamide and cyproterone acetate), LHRH antagonists or LHRH agonists (such as, by way of example only, goserelin, leuprorelin, leuprolide and buserelin), progestogens (such as, by way of example only, megestrol acetate), aromatase inhibitors (such as, by way of example only, as anastrozole, letrozole, vorazole and exemestane) and inhibitors of 5α-reductase (such as, by way of example only, finasteride).

The anti-invasion agents used in combination with at least one compound of Formula (I) provided herein, or a pharmaceutically acceptable salt or solvate thereof, include, but are not limited to, c-Src kinase family inhibitors (such as, by way of example only, 4-(6-chloro-2,3-methylenedioxyanilino)-7-[2-(4-methylpiperazin-1-yl)ethoxy]-5-tetrahydropyran-4-yloxyquinazoline (AZD0530) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825)), and metalloproteinase inhibitors (such as, by way of example only, marimastat, inhibitors of urokinase plasminogen activator receptor function andantibodies to Heparanase).

The antiangiogenic agents used in combination with at least one compound of Formula (I) provided herein, or a pharmaceutically acceptable salt or solvate thereof, include, but are not limited to, those which inhibit the effects of vascular endothelial growth factor such as, by way of example only, anti-vascular endothelial cell growth factor antibody bevacizumab (AVASTIN™) and VEGF receptor tyrosine kinase inhibitors such as 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787) and SU1 1248 (sunitinib), linomide, and inhibitors of integrin αvβ3 function and angiostatin.

The inhibitors of growth factor function used in combination with at least one compound of Formula (I) provided herein, or a pharmaceutically acceptable salt or solvate thereof, include, but are not limited to, growth factor antibodies and growth factor receptor antibodies (such as, by way of example only, the anti-erbB2 antibody trastuzumab (HERCEPTIN™), the anti-EGFR antibody panitumumab, the anti-erbB1 antibody cetuximab (Erbitux, C225), tyrosine kinase inhibitors, such as, by way of example only, inhibitors of the epidermal growth factor family (for example EGFR family tyrosine kinase inhibitors such as, by way of example only, N-(3-chloro-4-fluorophenyl)-7-methoxy-6-(3-orpholinopropoxy)quinazolin-4-amine (gefitinib, ZD1 839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as, by way of example only, lapatinib, inhibitors of the hepatocyte growth factor family, inhibitors of the platelet-derived growth factor family such as imatinib, GLEEVEC™ inhibitors of serine/threonine kinases (such as, by way of example only, Ras/Raf signaling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1 152, PH739358, VX-680, MLv8054, R763, MP235, MP529, VX-528 AND AX39459) and cyclin dependent kinase inhibitors such as CDK2 and/or CDK4 inhibitors.

In other embodiments, at least one compound of Formula (I) provided herein, or a pharmaceutically acceptable salt or solvate thereof, is used in combination with vascular damaging agents such as, by way of example only, Combretastatin A4.

In other embodiments, at least one compound of Formula (I) provided herein, or a pharmaceutically acceptable salt or solvate thereof, is used in combination with antisense therapies, such as, by way of example only, ISIS 2503, an anti-ras antisense.

In other embodiments, at least one compound of Formula (I) provided herein, or a pharmaceutically acceptable salt or solvate thereof, is used in combination with gene therapy approaches, including for example approaches to replace aberrant genes such as aberrant p53 or aberrant BRCA1 or BRCA2, GDEPT (gene-directed enzyme pro-drug s therapy) approaches such as those using cytosine deaminase, thymidine kinase or a bacterial nitroreductase enzyme and approaches to increase patient tolerance to chemotherapy or radiotherapy such as multi-drug resistance gene therapy.

In other embodiments, at least one compound of Formula (I) provided herein, or a pharmaceutically acceptable salt or solvate thereof, is used in combination with immunotherapy approaches, including for example ex-vivo and in-vivo approaches to increase the immunogenicity of patient tumor cells, such as transfection with cytokines such o as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies.

In other embodiments, at least one compound of Formula (I) provided herein, or a pharmaceutically acceptable salt or solvate thereof, is used in combination with other treatment methods including, but not limited to, surgery and radiotherapy (γ-radiation, neutron beam radiotherapy, electron beam radiotherapy, proton therapy, brachytherapy, and systemic radioactive isotopes).

In certain embodiments, the compounds of Formula (I) provided herein, or pharmaceutically acceptable salts and solvates thereof, are administered or formulated in combination with an absorption enhancer, including, but not limited to, sodium glycocholate, sodium caprate, N-lauryl-β-D-maltopyranoside, EDTA, and mixed micelles. In certain embodiments, such absorption enhancers target the lymphatic system.

In certain embodiments, the additional therapeutic agent(s) used in the combination therapies described herein include, but are not limited to, agents such as tumor necrosis factor alpha (TNF-α) inhibitors (such as anti-TNF monoclonal antibodies (by way of example only, Remicade, CDP-870 and adalimumab) and TNF receptor immunoglobulin molecules (by way of example only, Enbrel)); non-selective cyclo-oxygenase COX-1/COX-2 inhibitors (by way of example only, piroxicam, diclofenac, propionic acids such as naproxen, flubiprofen, fenoprofen, ketoprofen and ibuprofen, fenamates such as mefenamic acid, indomethacin, sulindac, azapropazone, pyrazolones such as phenylbutazone, salicylates such as aspirin), COX-2 inhibitors (by way of example only, meloxicam, celecoxib, rofecoxib, valdecoxib, lumarocoxib, parecoxib and etoricoxib); glucocorticosteroids; methotrexate, lefunomide; hydroxychloroquine, d-penicillamine, auranofin or other parenteral or oral gold preparations.

In other embodiments, the combinations described herein include combination of a compound of Formula (I) provided herein, or a pharmaceutically acceptable salt or solvate thereof, with a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAYx1005.

In other embodiments, the combinations described herein include combination of a compound of Formula (I) provided herein, or a pharmaceutically acceptable salt or solvate thereof, with a receptor antagonist for leukotrienes (LT B4, LTC4, LTD4, and LTE4) selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, SINGULAIR™, pranlukast, verlukast (MK-679), RG-12525, Ro-245913, iralukast (CGP 45715A), and BAYx7195.

In other embodiments, the combinations described herein include combination of a compound of Formula (I) provided herein, or a pharmaceutically acceptable salt or solvate thereof, with a phosphodiesterase (PDE) inhibitor such as a methylxanthanine including theophylline and aminophylline; a selective PDE isoenzyme inhibitor including a PDE4 inhibitor, including, but not limited to, cilomilast or roflumilast, an inhibitor of the isoform PDE4D, or an inhibitor of PDE5.

In other embodiments, the combinations described herein include combination of a compound of Formula (I) provided herein, or a pharmaceutically acceptable salt or solvate thereof, with a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine.

In other embodiments, the combinations described herein include combination of a compound of Formula (I) provided herein, or a pharmaceutically acceptable salt or solvate thereof, with a gastroprotective histamine type 2 receptor antagonist. In other embodiments, the combinations described herein include combination of a compound of Formula (I), or a pharmaceutically acceptable salt or solvate thereof, described herein, with an antagonist of the histamine type 4 receptor.

In other embodiments, the combinations described herein include combination of a compound of Formula (I) provided herein, or a pharmaceutically acceptable salt or solvate thereof, with an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

In other embodiments, the combinations described herein include combination of a compound of Formula (I) provided herein, or a pharmaceutically acceptable salt or solvate thereof, with an anticholinergic agent including muscarinic receptor (M1, M2, and M3) antagonists such as atropine, hyoscine, glycopyrrrolate, ipratropium bromide, tiotropium bromide, oxitropium bromide, pirenzepine or telenzepine.

In other embodiments, the combinations described herein include combination of a compound of Formula (I) provided herein, or a pharmaceutically acceptable salt or solvate thereof, with a beta-adrenoceptor agonist (including beta receptor subtypes 1-4) such as isoprenaline, salbutamol, albuterol, formoterol, salmeterol, terbutaline, orciprenaline, bitolterol mesylate, and pirbuterol.

In other embodiments, the combinations described herein include combination of a compound of Formula (I) provided herein, or a pharmaceutically acceptable salt or solvate thereof, with a chromone, such as sodium cromoglycate or nedocromil sodium.

In other embodiments, the combinations described herein include combination of a compound of Formula (I) provided herein, or a pharmaceutically acceptable salt or solvate thereof, with an insulin-like growth factor type I (IGF-I) mimetic.

In other embodiments, the combinations described herein include combination of a compound of Formula (I) provided herein, or a pharmaceutically acceptable salt or solvate thereof, with a glucocorticoid, such as flunisolide, triamcinolone acetonide, beclomethasone dipropionate, budesonide, fluticasone propionate, ciclesonide or mometasone furoate.

In other embodiments, the combinations described herein include combination of a compound of Formula (I) provided herein, or a pharmaceutically acceptable salt or solvate thereof, with an inhibitor of matrix metalloproteases (MMPs), i.e., the stromelysins, the collagenases, and the gelatinases, as well as aggrecanase; especially collagenase-1 (MMP-I), collagenase-2 (MMP-8), collagenase-3 (MMP-13), stromelysin-1 (MMP-3), stromelysin-2 (MMP-IO), and stromelysin-3 (MMP-II) and MMP-9 and MMP-12.

In other embodiments, the combinations described herein include combination of a compound of Formula (I) provided herein, or a pharmaceutically acceptable salt or solvate thereof, with modulators of chemokine receptor function such as antagonists of CCR1, CCR2, CCR2A, CCR2B, CCR3, CCR4, CCR5, CCR6, CCR7, CCR8, CCR9, CCR10 and CCR11 (for the C-C family); CXCR1, CXCR2, CXCR3, CXCR4 and CXCR5 (for the C-X-C family) and CX3CR1 for the C-X3-C family.

In other embodiments, the combinations described herein include combination of a compound of Formula (I) provided herein, or a pharmaceutically acceptable salt or solvate thereof, with an immunoglobulin (Ig), gamma globulin, Ig preparation or an antagonist or antibody modulating Ig function such as anti-IgE (omalizumab).

Compounds of Formula (I) as Immune Potentiators

In certain embodiments, pharmaceutical compositions containing at least one compound of Formula (I) provided herein, or a pharmaceutically acceptable salt or solvate thereof, are immunogenic compositions. In certain embodiments, such immunogenic compositions are useful as vaccines. In certain embodiments, such vaccines are prophylactic (i.e. to prevent infection), while in other embodiments, such vaccines are therapeutic (i.e. to treat infection).

In other embodiments, the compound(s) of Formula (I) provided herein, or a pharmaceutically acceptable salt or solvate thereof, are immune potentiators and impart an immunostimulatory effect upon administration when compared to immunogenic formulations that do not contain compound(s) of Formula (I). In certain embodiments, compounds of Formula (I) impart an immunostimulatory effect upon administration when included in an immunogenic composition having one or more immunoregulatory agents, while in other embodiments, compounds of Formula (I) impart an immunostimulatory effect upon administration when included in an immunogenic composition without the presence of other immunoregulatory agents.

The immunostimulatory effect referred to herein is often an enhancement of the immunogenic composition's effect. In certain embodiments the enhancement of the efficacy of the immunogenic composition is by at least 10% relative to the effect of the immunogenic composition in the absence of the immune potentiator. In certain embodiments the enhancement of the efficacy of the immunogenic composition is by at least 20% relative to the effect of the immunogenic composition in the absence of the immune potentiator. In certain embodiments the enhancement of the efficacy of the immunogenic composition is by at least 30% relative to the effect of the immunogenic composition in the absence of the immune potentiator. In certain embodiments the enhancement of the efficacy of the immunogenic composition is by at least 40% relative to the effect of the immunogenic composition in the absence of the immune potentiator. In certain embodiments the enhancement of the efficacy of the immunogenic composition is by at least 50% relative to the effect of the immunogenic composition in the absence of the immune potentiator. In certain embodiments the enhancement of the efficacy of the immunogenic composition is by at least 60% relative to the effect of the immunogenic composition in the absence of the immune potentiator. In certain embodiments the enhancement of the efficacy of the immunogenic composition is by at least 70% relative to the effect of the immunogenic composition in the absence of the immune potentiator. In certain embodiments the enhancement of the efficacy of the immunogenic composition is by at least 80% relative to the effect of the immunogenic composition in the absence of the immune potentiator. In certain embodiments the enhancement of the efficacy of the immunogenic composition is by at least 90% relative to the effect of the immunogenic composition in the absence of the immune potentiator. In certain embodiments the enhancement of the efficacy of the immunogenic composition is by at least 100% relative to the effect of the immunogenic composition in the absence of the immune potentiator.

In certain embodiments, the enhancement of the immunogenic composition's effect is measured by the increased effectiveness of the immunogenic composition for achieving its protective effects. In certain embodiments, this increased effectiveness is measured as a decreased probability that a subject receiving the immunogenic composition will experience a condition for which the immunogenic composition is considered protective, or a decrease in duration or severity of the effects of such condition. In other embodiments, this increased effectiveness is measured as an increase in a titer of an antibody elicited by the immunogenic composition in a treated subject.

Along with one or more compounds of Formula (I) provided herein, or a pharmaceutically acceptable salt or solvate thereof, such immunogenic compositions include an effective amount of one or more antigens, and a pharmaceutically acceptable carrier. Such carriers are include, but are not limited to, proteins, polysaccharides, polylactic acids, polyglycolic acids, polymeric amino acids, amino acid copolymers, sucrose, trehalose, lactose, lipid aggregates (such as oil droplets or liposomes), and inactive virus particles. The immunogenic compositions typically also contain diluents, such as water, saline, and glycerol, and optionally contain other excipients, such as wetting or emulsifying agents, and pH buffering substances.

In certain embodiments, immunogenic compositions optionally include one or more immunoregulatory agents. In certain embodiments, one or more of the immunoregulatory agents include one or more adjuvants. Such adjuvants include, but are not limited to, a TH1 adjuvant and/or a TH2 adjuvant, further discussed below. In certain embodiments, the adjuvants used in immunogenic compositions provide herein include, but are not limited to:

A. Mineral-Containing Compositions;
B. Oil Emulsions;
C. Saponin Formulations;
D. Virosomes and Virus-Like Particles;
E. Bacterial or Microbial Derivatives;
F. Human Immunomodulators;
G. Bioadhesives and Mucoadhesives;
H. Microparticles;
I. Liposomes;
J. Polyoxyethylene Ether and Polyoxyethylene Ester Formulations;
K. Polyphosphazene (PCPP);
L. Muramyl Peptides, and
M. Imidazoquinolone Compounds.

Mineral-containing compositions suitable for use as adjuvants include, but are not limited to, mineral salts, such as aluminium salts and calcium salts. By way of example only, such mineral salts include, hydroxides (e.g. oxyhydroxides, including aluminium hydroxides and aluminium oxyhydroxides), phosphates (e.g. hydroxyphosphates and orthophosphates, including aluminium phosphates, aluminium hydroxyphosphates, aluminium orthophosphates and calcium phosphate), sulfates (e.g. aluminium sulfate), or mixtures of different mineral compounds. Such mineral salts are in any suitable form, such as, by way of example only, gel, crystalline, and amorphous forms. In certain embodiments, such mineral containing compositions are formulated as a particle of the metal salt. In certain embodiments, components of the immunogenic compositions described herein are adsorbed to such mineral salts. In certain embodiments, an aluminium hydroxide and/or aluminium phosphate adjuvant is used in the immunogenic compositions described herein. In other embodiments, antigens used in an immunogenic composition described herein are adsorbed to such aluminium hydroxide and/or aluminium phosphate adjuvants. In certain embodiments, a calcium phosphate adjuvant is used in the immunogenic compositions described herein. In other embodiments, antigens used in an immunogenic composition described herein are adsorbed to such calcium phosphate adjuvants.

In certain embodiments, aluminum phosphates are used as an adjuvant in the immunogenic compositions described herein. In other embodiments, aluminum phosphates are used as an adjuvant in the immunogenic compositions described herein, wherein such compositions include a H. influenzae saccharide antigen. In certain embodiments, the adjuvant is amorphous aluminium hydroxyphosphate with a $PO_4/Al$ molar ratio between 0.84 and 0.92, included at 0.6 mg $Al^{3+}$/ml. In other embodiments, adsorption with a low dose of aluminium phosphate is used, by way of example only, between 50 and 100 μg $Al^{3+}$ per conjugate per dose. Where there is more than one conjugate in a composition, not all conjugates need to be adsorbed.

Oil emulsions suitable for use as adjuvants include, but are not limited to, squalene-water emulsions (such as MF59 (5% Squalene, 0.5% Tween 80, and 0.5% Span 85, formulated into submicron particles using a microfluidizer), Complete Freund's adjuvant (CFA) and incomplete Freund's adjuvant (IFA).

Saponins are a heterologous group of sterol glycosides and triterpenoid glycosides that are found in the bark, leaves, stems, roots and even flowers of a wide range of plant species. Saponin formulations suitable for use as adjuvants include, but are not limited to, saponins from the bark of the *Quillaia saponaria* Molina tree, from *Smilax ornata* (sarsaprilla), *Gypsophilla paniculata* (brides veil), and *Saponaria officinalis* (soap root). In certain embodiments, saponin formulations suitable for use as adjuvants include, but are not limited to, purified formulations including, but not limited to, QS7, QS17, QS18, QS21, QH-A, QH-B and QH-C. QS21 is marketed as STIMULOM™. In other embodiments, saponin formulations include sterols, cholesterols and lipid formulations, such as unique particles formed by the combinations of saponins and cholesterols called immunostimulating complexes (ISCOMs). In certain embodiments, the ISCOMs also include a phospholipid such as phosphatidylethanolamine or phosphatidylcholine. Any known saponin can be used in ISCOMs. In certain embodiments, the ISCOM includes one or more of QuilA, QHA & QHC. In other embodiments, the ISCOMS are optionally devoid of an additional detergent.

Virosomes and virus-like particles (VLPs) suitable for use as adjuvants include, but are not limited to, one or more proteins from a virus optionally combined or formulated with a phospholipid. Such virosomes and VLPs are generally non-pathogenic, non-replicating and generally do not contain any of the native viral genome. In certain embodiments, the viral proteins are recombinantly produced, while in other embodiments the viral proteins are isolated from whole viruses.

The viral proteins suitable for use in virosomes or VLPs include, but are not limited to, proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1).

Bacterial or microbial derivatives suitable for use as adjuvants include, but are not limited to, bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof. Such non-toxic derivatives of LPS include, but are not limited to, monophosphoryl lipid A (MPL) and 3-O-deacylated MPL (3dMPL). 3dMPL is a mixture of 3 de-O-acylated monophosphoryl lipid A with 4, 5 or 6 acylated chains. Other non-toxic LPS derivatives include monophosphoryl lipid A mimics, such as aminoalkyl glucosaminide phosphate derivatives (e.g. RC-529). Lipid A derivatives include, but are not limited to, derivatives of lipid A from *Escherichia coli* (e.g. OM-174).

Immunostimulatory oligonucleotides used as adjuvants include, but are not limited to, nucleotide sequences containing a CpG motif (a dinucleotide sequence containing an unmethylated cytosine linked by a phosphate bond to a guanosine). Such CpG sequences can be double-stranded or single-stranded. In certain embodiments, such nucleotide sequences are double-stranded RNAs or oligonucleotides containing palindromic or poly(dG) sequences. In other embodiments, the CpG's include nucleotide modifications/analogs such as phosphorothioate modifications.

In certain embodiments the CpG sequence are directed to TLR9, and in certain embodiments the motif is GTCGTT or TTCGTT. In certain embodiments the CpG sequence is specific for inducing a Th1 immune response, such as, by way of example only, a CpG-A ODN, or in other embodiments the CpG sequence is more specific for inducing a B cell response, such as, by way of example only, a CpG-B ODN. In certain embodiments the CpG is a CpG-A ODN.

In certain embodiments the CpG oligonucleotide is constructed so that the 5' end is accessible for receptor recognition. In other embodiments two CpG oligonucleotide sequences are optionally attached at their 3' ends to form "immunomers".

A particularly useful adjuvant based around immunostimulatory oligonucleotides is known as IC-31™. In certain embodiments, an adjuvant used with immunogenic compositions described herein, includes a mixture of (i) an oligonucleotide (such as, by way of example only, between 15-40 nucleotides) including at least one (and preferably multiple) CpI motifs (such as, by way of example only, a cytosine linked to an inosine to form a dinucleotide), and (ii) a polycationic polymer, such as, by way of example only, an oligopeptide (such as, by way of example only, between 5-20 amino acids) including at least one (and preferably multiple) Lys-Arg-Lys tripeptide sequence(s). In certain embodiments, the oligonucleotide is a deoxynucleotide comprising 26-mer sequence 5'-$(IC)_{13}$-3'. In other embodiments, the polycationic polymer is a peptide comprising 11-mer amino acid sequence KLKLLLLLKLK.

In certain embodiments, bacterial ADP-ribosylating toxins and detoxified derivatives thereof are used as adjuvants in the immunogenic compositions described herein. In certain embodiments, such proteins are derived from *E. coli* (*E. coli* heat labile enterotoxin "LT"), cholera ("CT"), or pertussis ("PT"). In other embodiments, the toxin or toxoid is in the form of a holotoxin, comprising both A and B subunits. In other embodiments, the A subunit contains a detoxifying mutation; whereas the B subunit is not mutated. In other embodiments, the adjuvant is a detoxified LT mutant such as LT-K63, LT-R72, and LT-G192.

The human immunomodulators suitable for use as adjuvants include, but are not limited to, cytokines, such as, by way of example only, interleukins (IL-1, IL-2, IL-4, IL-5, IL-6, IL-7, IL-12), interferons (such as, by way of example only, interferon-γ), macrophage colony stimulating factor, and tumor necrosis factor.

The bioadhesives and mucoadhesives used as adjuvants in the immunogenic compositions described herein include, but are not limited to, esterified hyaluronic acid microspheres, and cross-linked derivatives of poly(acrylic acid), polyvinyl alcohol, polyvinyl pyrollidone, polysaccharides and carboxymethylcellulose. In certain embodiments, chitosan and derivatives thereof are used as in the vaccine compositions described herein adjuvants.

The microparticles suitable for use as adjuvants include, but are not limited to, microparticles formed from materials that are biodegradable and non-toxic (e.g. a poly(.alpha.-hydroxy acid), a polyhydroxybutyric acid, a polyorthoester, a polyanhydride, a polycaprolactone, etc.), with poly(lactide-co-glycolide). In certain embodiments, such microparticles are treated to have a negatively-charged surface (e.g. with SDS) or a positively-charged surface (e.g. with a cationic detergent, such as CTAB). The microparticles suitable for use as adjuvants have a particle diameter of about 100 nm to about 150 μm in diameter. In certain embodiments, the particle diameter is about 200 nm to about 30 μm, and in other embodiments the particle diameter is about 500 nm to 10 μm.

The polyoxyethylene ether and polyoxyethylene ester formulations suitable for use as adjuvants include, but are not limited to, polyoxyethylene sorbitan ester surfactants in combination with an octoxynol, and polyoxyethylene alkyl ethers or ester surfactants in combination with at least one additional non-ionic surfactant such as an octoxynol. In certain embodiments, the polyoxyethylene ethers are selected from polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

The muramyl peptides suitable for use as adjuvants include, but are not limited to, N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-s-n-glycero-3-hydroxyphosphoryloxy)-ethylamine MTP-PE).

In certain embodiments, one or more compounds of Formula (I) used as an immune potentiator are included in compositions having combinations of one or more of the adjuvants identified above. Such combinations include, but are not limited to, (1) a saponin and an oil-in-water emulsion;
(2) a saponin (e.g. QS21)+a non-toxic LPS derivative (e.g. 3dMPL);
(3) a saponin (e.g. QS21)+a non-toxic LPS derivative (e.g. 3dMPL)+a cholesterol;
(4) a saponin (e.g. QS21)+3dMPTL+IL-12 (optionally including a sterol);
(5) combinations of 3dMPL with, for example, QS21 and/or oil-in-water emulsions;
(6) SAF, containing 10% squalane, 0.4% Tween 80™, 5% pluronic-block polymer L121, and thr-MDP, either microfluidized into a submicron emulsion or vortexed to generate a larger particle size emulsion.
(7) RIBI™ adjuvant system (RAS), (Ribi Immunochem) containing 2% squalene, 0.2% Tween 80, and one or more bacterial cell wall components from the group consisting of monophospholipid A (MPL), trehalose dimycolate (TDM), and cell wall skeleton (CWS), preferably MPL+CWS (Detox™) and
(8) one or more mineral salts (such as an aluminum salt)+a non-toxic derivative of LPS (such as 3dMPL).

In other embodiments, the adjuvant combinations used in the immunogenic combinations provided herein include combinations of Th1 and Th2 adjuvants such as, by way of example only, CpG and alum or resiquimod and alum.

In certain embodiments, the immunogenic compositions provided herein elicit both a cell mediated immune response as well as a humoral immune response. In other embodiments, the immune response induces long lasting (e.g. neutralising) antibodies and a cell mediated immunity that quickly responds upon exposure to the infectious agent.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class 1 molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-γ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

A TH1 immune response may include one or more of an increase in CTLs, an increase in one or more of the cytokines associated with a TH1 immune response (such as IL-2, IFN-γ, and TNF-β), an increase in activated macrophages, an increase in NK activity, or an increase in the production of IgG2a. Preferably, the enhanced TH1 immune response will include an increase in IgG2a production.

TH1 adjuvants can be used to elicit a TH1 immune response. A TH1 adjuvant will generally elicit increased levels of IgG2a production relative to immunization of the antigen without adjuvant. TH1 adjuvants suitable for use in immunogenic compositions provided herein include, but are not limited to, saponin formulations, virosomes and virus like particles, non-toxic derivatives of enterobacterial lipopolysaccharide (LPS), immunostimulatory oligonucleotides. In certain embodiments, the immunostimulatory oligonucleotides used as TH1 adjuvants in the immunogenic compositions provided herein contain a CpG motif.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

TH2 adjuvants can be used to elicit a TH2 immune response. A TH2 adjuvant will generally elicit increased levels of IgG1 production relative to immunization of the antigen without adjuvant. TH2 adjuvants suitable for use in immunogenic compositions provided herein include, but are not limited to, mineral containing compositions, oil-emulsions, and ADP-ribosylating toxins and detoxified derivatives thereof. In certain embodiments, the mineral containing compositions used as TH2 adjuvants in the immunogenic compositions provided herein are aluminium salts.

In certain embodiments, the immunogenic compositions provided herein include a TH1 adjuvant and a TH2 adjuvant. In other embodiments, such compositions elicit an enhanced TH1 and an enhanced TH2 response, such as, an increase in the production of both IgG1 and IgG2a production relative to immunization without an adjuvant. In still other embodiments, such compositions comprising a combination of a TH1 and a TH2 adjuvant elicit an increased TH1 and/or an increased TH2 immune response relative to immunization with a single adjuvant (i.e., relative to immunization with a TH1 adjuvant alone or immunization with a TH2 adjuvant alone).

In certain embodiments, the immune response is one or both of a TH1 immune response and a TH2 response. In other embodiments, the immune response provides for one or both of an enhanced TH1 response and an enhanced TH2 response.

In certain embodiments, the enhanced immune response is one or both of a systemic and a mucosal immune response. In other embodiments, the immune response provides for one or both of an enhanced systemic and an enhanced mucosal immune response. In certain embodiments, the mucosal immune response is a TH2 immune response. In certain embodiments, the mucosal immune response includes an increase in the production of IgA.

In certain embodiments the immunogenic compositions provided herein are used as vaccines, wherein such compositions include an immunologically effective amount of one or more antigen).

Antigens for use in the immunogenic compositions provided herein may be provided in an effective amount (e.g., an amount effective for use in therapeutic, prophylactic or diagnostic methods). For example, immunogenic compositions of the invention may be used to treat or prevent infections caused by any of the below-listed pathogens.

Antigens for use in the immunogenic compositions provided herein are typically macromolecules (e.g., polypeptides, polysaccharides, polynucleotides) that are foreign to the host, and include, but are not limited to, one or more of the antigens set forth below, or antigens derived from one or more of the pathogens set forth below.

Bacterial Antigens

Bacterial antigens suitable for use in immunogenic compositions provided herein include, but are not limited to, proteins, polysaccharides, lipopolysaccharides, polynucleotides, and outer membrane vesicles which are isolated, purified or derived from a bacteria. In certain embodiments, the bacterial antigens include bacterial lysates and inactivated bacteria formulations. In certain embodiments, the bacterial antigens are produced by recombinant expression. In certain embodiments, the bacterial antigens include epitopes which are exposed on the surface of the bacteria during at least one stage of its life cycle. Bacterial antigens are preferably conserved across multiple serotypes. In certain embodiments, the bacterial antigens include antigens derived from one or more of the bacteria set forth below as well as the specific antigens examples identified below:

*Neisseria meningitidis*: Meningitidis antigens include, but are not limited to, proteins, saccharides (including a polysaccharide, oligosaccharide, lipooligosaccharide or lipopolysaccharide), or outer-membrane vesicles purified or derived from *N. meningitides* serogroup such as A, C, W135, Y, X and/or B. In certain embodiments meningitides protein antigens are be selected from adhesions, autotransporters, toxins, Fe acquisition proteins, and membrane associated proteins (preferably integral outer membrane protein).

*Streptococcus pneumoniae*: *Streptococcus pneumoniae* antigens include, but are not limited to, a saccharide (including a polysaccharide or an oligosaccharide) and/or protein from *Streptococcus pneumoniae*. The saccharide may be a polysaccharide having the size that arises during purification of the saccharide from bacteria, or it may be an oligosaccharide achieved by fragmentation of such a polysaccharide. In the 7-valent PREVNAR™ product, for instance, 6 of the saccharides are presented as intact polysaccharides while one (the 18C serotype) is presented as an oligosaccharide. In certain embodiments saccharide antigens are selected from one or more of the following pneumococcal serotypes 1, 2, 3, 4, 5, 6A, 6B, 7F, 8, 9N, 9V, 10A, 11A, 12F, 14, 15B, 17F, 18C, 19A, 19F, 20, 22F, 23F, and/or 33F. An immunogenic composition may include multiple serotypes e.g. 2, 3, 4, 5, 6, 7, 8, 9, 10, 11, 12, 13, 14, 15, 16, 17, 18, 19, 20, 21, 22, 23 or more serotypes. 7-valent, 9-valent, 10-valent, 11-valent and 13-valent conjugate combinations are already known in the art, as is a 23-valent unconjugated combination. For example, an 10-valent combination may include saccharide from serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; r 22F and 15B; A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F. etc. In certain embodiments, protein antigens may be selected from a protein identified in WO98/18931, WO98/18930, U.S. Pat. No. 6,699,703, U.S. Pat. No. 6,800,744, WO97/43303, WO97/37026, WO 02/079241, WO 02/34773, WO 00/06737, WO 00/06738, WO 00/58475, WO 2003/082183, WO 00/37105, WO 02/22167, WO 02/22168, WO 2003/104272, WO 02/08426, WO 01/12219, WO 99/53940, WO 01/81380, WO 2004/092209, WO 00/76540, WO 2007/116322, LeMieux et al., Infect. 1 mm. (2006) 74:2453-2456, Hoskins et al., J. Bacteriol. (2001) 183: 5709-5717, Adamou et al., Infect. Immun. (2001) 69(2): 949-958, Briles et al., J. Infect. Dis. (2000) 182:1694-1701, Talkington et al., Microb. Pathog. (1996) 21(1): 17-22, Bethe et al., FEMS Microbiol. Lett. (2001) 205 (1):99-104, Brown et al., Infect. Immun. (2001) 69:6702-6706, Whalen et al., FEMS Immunol. Med. Microbiol. (2005) 43:73-80, Jomaa et al., Vaccine (2006) 24(24):5133-5139. In other embodiments, *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, SpIO1, Sp130, Sp125, Sp133, pneumococcal pilus subunits.

*Streptococcus pyogenes* (Group A *Streptococcus*): Group A *Streptococcus* antigens include, but are not limited to, a protein identified in WO 02/34771 or WO 2005/032582 (including GAS 40), fusions of fragments of GAS M proteins (including those described in WO 02/094851, and Dale, Vaccine (1999) 17:193-200, and Dale, Vaccine 14(10): 944-948), fibronectin binding protein (Sfb1), Streptococcal heme-associated protein (Shp), and Streptolysin S (SagA).

*Moraxella catarrhalis*: *Moraxella* antigens include, but are not limited to, antigens identified in WO 02/18595 and WO 99/58562, outer membrane protein antigens (HMW-OMP), C-antigen, and/or LPS.

*Bordetella pertussis*: Pertussis antigens include, but are not limited to, pertussis holotoxin (PT) and filamentous haemagglutinin (FHA) from *B. pertussis*, optionally also combination with pertactin and/or agglutinogens 2 and 3.

*Burkholderia*: *Burkholderia* antigens include, but are not limited to *Burkholderia mallei*, *Burkholderia pseudomallei* and *Burkholderia cepacia*.

*Staphylococcus aureus*: Staph aureus antigens include, but are not limited to, a polysaccharide and/or protein from *S. aureus*. *S. aureus* polysaccharides include, but are not limited to, type 5 and type 8 capsular polysaccharides (CP5 and CP8) optionally conjugated to nontoxic recombinant *Pseudomonas aeruginosa* exotoxin A, such as StaphVAX™, type 336 polysaccharides (336PS), polysaccharide intercellular adhesions (PIA, also known as PNAG). *S. aureus* proteins include, but are not limited to, antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin). In certain embodiments, *S. aureus* antigens may be selected from a protein identified in WO 02/094868, WO 2008/019162, WO 02/059148, WO 02/102829, WO 03/011899, WO 2005/079315, WO 02/077183, WO 99/27109, WO 01/70955, WO 00/12689, WO 00/12131, WO 2006/032475, WO 2006/032472, WO 2006/032500, WO 2007/113222, WO 2007/113223, WO 2007/113224. In other embodiments, *S. aureus* antigens may be selected from IsdA, IsdB, IsdC, SdrC, SdrD, SdrE, ClfA, ClfB, SasF, SasD, SasH (AdsA), Spa, EsaC, EsxA, EsxB, Emp, H1aH35L, CP5, CP8, PNAG, 336PS.

*Staphylococcus epidermis*: *S. epidermidis* antigens include, but are not limited to, slime-associated antigen (SAA).

*Clostridium tetani* (Tetanus): Tetanus antigens include, but are not limited to, tetanus toxoid (TT). In certain embodiments such antigens are used as a carrier protein in conjunction/conjugated with the immunogenic compositions provided herein.

*Clostridium perfringens*: Antigens include, but are not limited to, Epsilon toxin from *Clostridium perfringen*.

*Clostridium botulinums* (Botulism): Botulism antigens include, but are not limited to, those derived from *C. botulinum*.

*Cornynebacterium diphtheriae* (Diphtheria): Diphtheria antigens include, but are not limited to, diphtheria toxin, preferably detoxified, such as $CRM_{197}$. Additionally antigens capable of modulating, inhibiting or associated with ADP ribosylation are contemplated for combination/co-administration/conjugation with the immunogenic compositions provided herein. In certain embodiments, the diphtheria toxoids are used as carrier proteins.

*Haemophilus influenzae* B (Hib): Hib antigens include, but are not limited to, a Hib saccharide antigen.

*Pseudomonas aeruginosa*: *Pseudomonas* antigens include, but are not limited to, endotoxin A, Wzz protein, *P. aeruginosa* LPS, LPS isolated from PAO1 (O5 serotype), and/or Outer Membrane Proteins, including Outer Membrane Proteins F (OprF).

*Legionella pneumophila*. Bacterial antigens derived from *Legionella pneumophila*.

Coxiella burnetii. Bacterial antigens derived from *Coxiella burnetii*.

*Brucella*. Bacterial antigens derived from *Brucella*, including but not limited to, *B. abortus*, *B. canis*, *B. melitensis*, *B. neotomae*, *B. ovis*, *B. suis* and *B. pinnipediae*.

*Francisella*. Bacterial antigens derived from *Francisella*, including but not limited to, *F. novicida*, *F. philomiragia* and *F. tularensis*.

*Streptococcus agalactiae* (Group B *Streptococcus*): Group B *Streptococcus* antigens include, but are not limited to, a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes Ia, Ib, Ia/c, II, III, IV, V, VI, VII and VIII).

*Neisserria gonorrhoeae*: Gonorrhoeae antigens include, but are not limited to, Por (or porin) protein, such as PorB (see Zhu et al., *Vaccine* (2004) 22:660-669), a transferring binding protein, such as TbpA and TbpB (See Price et al., Infection and Immunity (2004) 71(1):277-283), a opacity protein (such as Opa), a reduction-modifiable protein (Rmp), and outer membrane vesicle (OMV) preparations (see Plante et al, J Infectious Disease (2000) 182:848-855), also see, e.g., WO99/24578, WO99/36544, WO99/57280, WO02/079243).

*Chlamydia trachomatis*: *Chlamydia trachomatis* antigens include, but are not limited to, antigens derived from serotypes A, B, Ba and C (agents of trachoma, a cause of blindness), serotypes $L_1, L_2$ & $L_3$ (associated with Lymphogranuloma venereum), and serotypes, D-K. In certain embodiments, chlamydia trachomas antigens include, but are not limited to, an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include, but are not limited to, TmpA antigen.

*Haemophilus ducreyi* (causing chancroid): Ducreyi antigens include, but are not limited to, outer membrane protein (DsrA).

*Enterococcus faecalis* or *Enterococcus faecium*: Antigens include, but are not limited to, a trisaccharide repeat or other *Enterococcus* derived antigens.

*Helicobacter pylori*: H pylori antigens include, but are not limited to, Cag, Vac, Nap, HopX, HopY and/or urease antigen.

*Staphylococcus saprophyticus*: Antigens include, but are not limited to, the 160 kDa hemagglutinin of *S. saprophyticus* antigen.

*Yersinia enterocolitica* Antigens include, but are not limited to, LPS.

*E. coli*: *E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC antigens include, but are not limited to, accessory colonization factor (orf3526), orf353, bacterial Ig-like domain (group 1) protein (orf405), orf1364, NodT-family outer-membrane-factor-lipoprotein efflux transporter (orf1767), gspK (orf3515), gspJ (orf3516), tonB-dependent siderophore receptor (orf3597), fimbrial protein (orf3613), upec-948, upec-1232, A chain precursor of the type-1 fimbrial protein (upec-1875), yap H homolog (upec-2820), and hemolysin A (recp-3768).

*Bacillus anthracis* (anthrax): *B. anthracis* antigens include, but are not limited to, A-components (lethal factor (LF) and edema factor (EF)), both of which can share a common B-component known as protective antigen (PA). In certain embodiments, *B. anthracis* antigens are optionally detoxified.

*Yersinia pestis* (plague): Plague antigens include, but are not limited to, F1 capsular antigen, LPS, *Yersinia pestis* V antigen.

*Mycobacterium tuberculosis*: Tuberculosis antigens include, but are not limited to, lipoproteins, LPS, BCG antigens, a fusion protein of antigen 85B (Ag85B), ESAT-6 optionally formulated in cationic lipid vesicles, *Mycobacterium tuberculosis* (Mtb) isocitrate dehydrogenase associated antigens, and MPT51 antigens.

*Rickettsia*: Antigens include, but are not limited to, outer membrane proteins, including the outer membrane protein A and/or B (OmpB), LPS, and surface protein antigen (SPA).

*Listeria monocytogenes*: Bacterial antigens include, but are not limited to, those derived from *Listeria monocytogenes*.

*Chlamydia pneumoniae*: Antigens include, but are not limited to, those identified in WO 02/02606.

*Vibrio cholerae*: Antigens include, but are not limited to, proteinase antigens, LPS, particularly lipopolysaccharides of *Vibrio cholerae* II, O1 Inaba O-specific polysaccharides, *V. cholera* 0139, antigens of IEM108 vaccine and Zonula occludens toxin (Zot).

*Salmonella typhi* (typhoid fever): Antigens include, but are not limited to, capsular polysaccharides preferably conjugates (Vi, i.e. vax-TyVi).

*Borrelia burgdorferi* (Lyme disease): Antigens include, but are not limited to, lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein, V1sE Antigenic Variation Protein.

*Porphyromonas gingivalis*: Antigens include, but are not limited to, *P. gingivalis* outer membrane protein (OMP).

*Klebsiella*: Antigens include, but are not limited to, an OMP, including OMP A, or a polysaccharide optionally conjugated to tetanus toxoid.

Other bacterial antigens used in the immunogenic compositions provided herein include, but are not limited to, capsular antigens, polysaccharide antigens, protein antigens or polynucleotide antigens of any of the above. Other bacterial antigens used in the immunogenic compositions provided herein include, but are not limited to, an outer membrane vesicle (OMV) preparation. Additionally, other bacterial antigens used in the immunogenic compositions provided herein include, but are not limited to, live, attenuated, and/or purified versions of any of the aforementioned bacteria. In certain embodiments, the bacterial antigens used in the immunogenic compositions provided herein are derived from gram-negative bacteria, while in other embodiments they are derived from gram-positive bacteria. In certain embodiments, the bacterial antigens used in the immunogenic compositions provided herein are derived from aerobic bacteria, while in other embodiments they are derived from anaerobic bacteria.

In certain embodiments, any of the above bacterial-derived saccharides (polysaccharides, LPS, LOS or oligosaccharides) are conjugated to another agent or antigen, such as a carrier protein (for example $CRM_{197}$). In certain embodiments, such conjugations are direct conjugations effected by reductive amination of carbonyl moieties on the saccharide to amino groups on the protein. In other embodiments, the saccharides are conjugated through a linker, such as, with succinamide or other linkages provided in *Bioconjugate Techniques*, 1996 and *CRC, Chemistry of Protein Conjugation and Cross-Linking*, 1993.

In certain embodiments useful for the treatment or prevention of *Neisseria* infection and related diseases and disorders, recombinant proteins from *N. meningitidis* for use in the immunogenic compositions provided herein may be found in WO99/24578, WO99/36544, WO99/57280, WO00/22430, WO96/29412, WO01/64920, WO03/020756, WO2004/048404, and WO2004/032958. Such antigens may be used alone or in combinations. Where multiple purified proteins are combined then it is helpful to use a mixture of 10 or fewer (e.g. 9, 8, 7, 6, 5, 4, 3, 2) purified antigens.

A particularly useful combination of antigens for use in the immunogenic compositions provided herein is disclosed in Giuliani et al. (2006) *Proc Natl Acad Sci USA* 103(29):10834-9 and WO2004/032958, and so an immunogenic composition may include 1, 2, 3, 4 or 5 of: (1) a 'NadA' protein (aka GNA1994 and NMB1994); (2) a 'fHBP' protein (aka '741', LP2086, GNA1870, and NMB1870); (3) a '936' protein (aka GNA2091 and NMB2091); (4) a '953' protein (aka GNA1030 and NMB1030); and (5) a '287' protein (aka GNA2132 and NMB2132). Other possible antigen combinations may comprise a transferrin binding protein (e.g. TbpA and/or TbpB) and an Hsf antigen. Other possible purified antigens for use in the immunogenic compositions provided herein include proteins comprising one of the following amino acid sequences: SEQ ID NO:650 from WO99/24578; SEQ ID NO:878 from WO99/24578; SEQ ID NO:884 from WO99/24578; SEQ ID NO:4 from WO99/36544; SEQ ID NO:598 from WO99/57280; SEQ ID NO:818 from WO99/57280; SEQ ID NO:864 from WO99/57280; SEQ ID NO:866 from WO99/57280; SEQ ID NO:1196 from WO99/57280; SEQ ID NO:1272 from WO99/57280; SEQ ID NO:1274 from WO99/57280; SEQ ID NO:1640 from WO99/57280; SEQ ID NO:1788 from WO99/57280; SEQ ID NO:2288 from WO99/57280; SEQ ID NO:2466 from WO99/57280; SEQ ID NO:2554 from WO99/57280; SEQ ID NO:2576 from WO99/57280; SEQ ID NO:2606 from WO99/57280; SEQ ID NO:2608 from WO99/57280; SEQ ID NO:2616 from WO99/57280; SEQ ID NO:2668 from WO99/57280; SEQ ID NO:2780 from WO99/57280; SEQ ID NO:2932 from WO99/57280; SEQ ID NO:2958 from WO99/57280; SEQ ID NO:2970 from WO99/57280; SEQ ID NO:2988 from WO99/57280 (each of the forgoing amino acid sequences is hereby incorporated by reference from the cited document), or a polypeptide comprising an amino acid sequence which: (a) has 50% or more identity (e.g., 60%, 70%, 80%, 90%, 95%, 99% or more) to said sequences; and/or (b) comprises a fragment of at least n consecutive amino acids from said sequences, wherein n is 7 or more (e.g., 8, 10, 12, 14, 16, 18, 20, 25, 30, 35, 40, 50, 60, 70, 80, 90, 100, 150, 200, 250 or more). Preferred fragments for (b) comprise an epitope from the relevant sequence. More than one (e.g., 2, 3, 4, 5, 6) of these polypeptides may be included in the immunogenic compositions.

The fHBP antigen falls into three distinct variants (WO2004/048404). An *N. meningitidis* serogroup vaccine based upon the immunogenic compositions disclosed herein utilizing one of the compounds disclosed herein may include a single fHBP variant, but is will usefully include an fHBP from each of two or all three variants. Thus the immunogenic composition may include a combination of two or three different purified fHBPs, selected from: (a) a first protein, comprising an amino acid sequence having at least a % sequence identity to SEQ ID NO: 1 and/or comprising an amino acid sequence consisting of a fragment of at least x contiguous amino acids from SEQ ID NO: 1; (b) a second protein, comprising an amino acid sequence having at least b % sequence identity to SEQ ID NO: 2 and/or comprising an amino acid sequence consisting of a fragment of at least y contiguous amino acids from SEQ ID NO: 2; and/or (c) a third protein, comprising an amino acid sequence having at least c % sequence identity to SEQ ID NO: 3 and/or comprising an amino acid sequence consisting of a fragment of at least z contiguous amino acids from SEQ ID NO: 3

SEQ ID NO: 1
VAADIGAGLADALTAPLDHKDKGLQSLTLDQSVRKNEKLKLAAQGAEKTY
GNGDSLNTGKLKNDKVSRFDFIRQIEVDGQLITLESGEFQVYKQSHSALT
AFQTEQIQDSEHSGKMVAKRQFRIGDIAGEHTSFDKLPEGGRATYRGTAF
GSDDAGGKLTYTIDFAAKQGNGKIEHLKSPELNVDLAAADIKPDGKRHAV
ISGSVLYNQAEKGSYSLGIFGGKAQEVAGSAEVKTVNGIRHIGLAAKQ

SEQ ID NO: 2
VAADIGAGLADALTAPLDHKDKSLQSLTLDQSVRKNEKLKLAAQGAEKTY
GNGDSLNTGKLKNDKVSRFDFIRQIEVDGQLITLESGEFQIYKQDHSAVV
ALQIEKINNPDKIDSLINQRSFLVSGLGGEHTAFNQLPDGKAEYHGKAFS
SDDAGGKLTYTIDFAAKQGHGKIEHLKTPEQNVELAAAELKADEKSHAVI
LGDTRYGSEEKGTYHLALFGDRAQEIAGSATVKIGEKVHEIGIAGKQ

SEQ ID NO: 3
VAADIGTGLADALTAPLDHKDKGLKSLTLEDSIPQNGTLTLSAQGAEKTF
KAGDKDNSLNTGKLKNDKISRFDFVQKIEVDGQTITLASGEFQIYKQNHS
AVVALQIEKINNPDKTDSLINQRSFLVSGLGGEHTAFNQLPGGKAEYHGK
AFSSDDPNGRLHYSIDFTKKQGYGRIEHLKTLEQNVELAAAELKADEKSH
AVILGDTRYGSEEKGTYHLALFGDRAQEIAGSATVKIGEKVHEIGIAGK
Q.

The value of a is at least 85, e.g., 86, 87, 88, 89, 90, 91, 92, 93, 94, 95, 96, 97, 98, 99, 99.5, or more. The value of b is at least 85, e.g., 86, 87, 88, 89, 90, 91, 92, 93, 94, 95, 96, 97, 98, 99, 99.5, or more. The value of c is at least 85, e.g., 86, 87, 88, 89, 90, 91, 92, 93, 94, 95, 96, 97, 98, 99, 99.5, or more. The values of a, b and c are not intrinsically related to each other.

The value of x is at least 7, e.g., 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of y is at least 7, e.g., 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of z is at least 7, e.g., 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The values of x, y and z are not intrinsically related to each other.

In some embodiments, the immunogenic compositions as disclosed herein will include fHBP protein(s) that are lipidated, e.g., at a N-terminal cysteine. In other embodiments they will not be lipidated A useful immunogenic composition as disclosed herein includes purified proteins comprises a mixture of: (i) a first polypeptide having amino acid sequence SEQ ID NO: 4; (ii) a second polypeptide having amino acid sequence SEQ ID NO: 5; and (iii) a third polypeptide having amino acid sequence SEQ ID NO: 6. See Giuliani et al. (2006) *Proc Natl Acad Sci USA* 103(29):10834-9 and WO2004/032958. A useful immunogenic composition as disclosed herein includes purified proteins comprises a mixture of: (i) a first polypeptide having at least a % sequence identity to amino acid sequence SEQ ID NO: 4; (ii) a second polypeptide having at least b % sequence identity to amino acid sequence SEQ ID NO: 5; and (iii) a third polypeptide having at least a % sequence identity to amino acid sequence SEQ ID NO: 6.

SEQ ID NO: 4
MASPDVKSADTLSKPAAPVVSEKETEAKEDAPQAGSQGQGAPSAQGGQDM
AAVSEENTGNGGAAATDKPKNEDEGAQNDMPQNAADTDSLTPNHTPASNM
PAGNMENQAPDAGESEQPANQPDMANTADGMQGDDPSAGGENAGNTAAQG
TNQAENNQTAGSQNPASSTNPSATNSGGDFGRTNVGNSVVIDGPSQNITL
THCKGDSCSGNNFLDEEVQLKSEFEKLSDADKISNYKKDGKNDGKNDKFV
GLVADSVQMKGINQYIIFYKPKPTSFARFRRSARSRRSLPAEMPLIPVNQ
ADTLIVDGEAVSLTGHSGNIFAPEGNYRYLTYGAEKLPGGSYALRVQGEP
SKGEMLAGTAVYNGEVLHFHTENGRPSPSRGRFAAKVDFGSKSVDGIIDS
GDGLHMGTQKFKAAIDGNGFKGTWTENGGGDVSGKFYGPAGEEVAGKYSY
RPTDAEKGGFGVFAGKKEQDGSGGGATYKVDEYHANARFAIDHFNTSTN
VGGFYGLTGSVEFDQAKRDGKIDITIPVANLQSGSQHFTDHLKSADIFDA
AQYPDIRFVSTKFNFNGKKLVSVDGNLTMHGKTAPVKLKAEKFNCYQSPM
AKTEVCGGDFSTTIDRTKWGVDYLVNVGMTKSVRIDIQIEAAKQ

SEQ ID NO: 5
MVSAVIGSAAVGAKSAVDRRTTGAQTDDNVMALRIETTARSYLRQNNQTK
GYTPQISVVGYNRHLLLLGQVATEGEKQFVGQIARSEQAAEGVYNYITVA
SLPRTAGDIAGDTWNTSKVRATLLGISPATQARVKIVTYGNVTYVMGILT
PEEQAQITQKVSTTVGVQKVITLYQNYVQRGSGGGVAADIGAGLADALT
APLDHKDKGLQSLTLDQSVRKNEKLKLAAQGAEKTYGNGDSLNTGKLKND
KVSRFDFIRQIEVDGQLITLESGEFQVYKQSHSALTAFQTEQIQDSEHSG
KMVAKRQFRIGDIAGEHTSFDKLPEGGRATYRGTAFGSDDAGGKLTYTID
FAAKQGNGKIEHLKSPELNVDLAAADIKPDGKRHAVISGSVLYNQAEKGS
YSLGIFGGKAQEVAGSAEVKTVNGIRHIGLAAKQ

```
                                                SEQ ID NO: 6
ATNDDDVKKAATVAIAAAYNNGQEINGFKAGETIYDIDEDGTITKKDATA

ADVEADDFKGLGLKKVVTNLTKTVNENKQNVDAKVKAAESEIEKLTTKLA

DTDAALADTDAALDATTNALNKLGENITTFAEETKTNIVKIDEKLEAVAD

TVDKHAEAFNDIADSLDETNTKADEAVKTANEAKQTAEETKQNVDAKVKA

AETAAGKAEAAAGTANTAADKAEAVAAKVTDIKADIATNKDNIAKKANSA

DVYTREESDSKFVRIDGLNATTEKLDTRLASAEKSIADHDTRLNGLDKTV

SDLRKETRQGLAEQAALSGLFQPYNVG.
```

Bacterial Vesicle Antigens

The immunogenic compositions as disclosed herein may include outer membrane vesicles. Such outer membrane vesicles may be obtained from a wide array of pathogenic bacteria and used as antigenic components of the immunogenic compositions as disclosed herein. Vesicles for use as antigenic components of such immunogenic compositions include any proteoliposomic vesicle obtained by disrupting a bacterial outer membrane to form vesicles therefrom that include protein components of the outer membrane. Thus the term includes OMVs (sometimes referred to as 'blebs'), microvesicles (MVs, see, e.g., WO02/09643) and 'native OMVs' ('NOMVs' see, e.g., Katial et al. (2002) *Infect. Immun.* 70:702-707). Immunogenic compositions as disclosed herein that include vesicles from one or more pathogenic bacteria can be used in the treatment or prevention of infection by such pathogenic bacteria and related diseases and disorders.

MVs and NOMVs are naturally-occurring membrane vesicles that form spontaneously during bacterial growth and are released into culture medium. MVs can be obtained by culturing bacteria such as *Neisseria* in broth culture medium, separating whole cells from the smaller MVs in the broth culture medium (e.g., by filtration or by low-speed centrifugation to pellet only the cells and not the smaller vesicles), and then collecting the MVs from the cell-depleted medium (e.g., by filtration, by differential precipitation or aggregation of MVs, by high-speed centrifugation to pellet the MVs). Strains for use in production of MVs can generally be selected on the basis of the amount of MVs produced in culture (see, e.g., U.S. Pat. No. 6,180,111 and WO01/34642 describing *Neisseria* with high MV production).

OMVs are prepared artificially from bacteria, and may be prepared using detergent treatment (e.g., with deoxycholate), or by non detergent means (see, e.g., WO04/019977). Methods for obtaining suitable OMV preparations are well known in the art. Techniques for forming OMVs include treating bacteria with a bile acid salt detergent (e.g., salts of lithocholic acid, chenodeoxycholic acid, ursodeoxycholic acid, deoxycholic acid, cholic acid, ursocholic acid, etc., with sodium deoxycholate (EP0011243 and Fredriksen et al. (1991) *NIPH Ann.* 14(2):67-80) being preferred for treating *Neisseria*) at a pH sufficiently high not to precipitate the detergent (see, e.g., WO01/91788). Other techniques may be performed substantially in the absence of detergent (see, e.g., WO04/019977) using techniques such as sonication, homogenisation, microfluidisation, cavitation, osmotic shock, grinding, French press, blending, etc. Methods using no or low detergent can retain useful antigens such as NspA in Neisserial OMVs. Thus a method may use an OMV extraction buffer with about 0.5% deoxycholate or lower, e.g., about 0.2%, about 0.1%, <0.05% or zero.

A useful process for OMV preparation is described in WO05/004908 and involves ultrafiltration on crude OMVs, rather than instead of high speed centrifugation. The process may involve a step of ultracentrifugation after the ultrafiltration takes place.

Vesicles can be prepared from any pathogenic strain such as *Neisseria minigtidis* for use with the invention. Vessicles from Neisserial meningitidis serogroup B may be of any serotype (e.g., 1, 2a, 2b, 4, 14, 15, 16, etc.), any serosubtype, and any immunotype (e.g., L1; L2; L3; L3,3,7; L10; etc.). The meningococci may be from any suitable lineage, including hyperinvasive and hypervirulent lineages, e.g., any of the following seven hypervirulent lineages: subgroup I; subgroup III; subgroup IV 1; ET 5 complex; ET 37 complex; A4 cluster; lineage 3. These lineages have been defined by multilocus enzyme electrophoresis (MLEE), but multilocus sequence typing (MLST) has also been used to classify meningococci, e.g., the ET 37 complex is the ST 11 complex by MLST, the ET 5 complex is ST-32 (ET-5), lineage 3 is ST 41/44, etc. Vesicles can be prepared from strains having one of the following subtypes: P1.2; P1.2,5; P1.4; P1.5; P1.5,2; P1.5,c; P1.5c,10; P1.7,16; P1.7,16b; P1.7h,4; P1.9; P1.15; P1.9,15; P1.12,13; P1.13; P1.14; P1.21,16; P1.22,14.

Vesicles included in the immunogenic compositions disclosed herein may be prepared from wild type pathogenic strains such as *N. meningitidis* strains or from mutant strains. By way of example, WO98/56901 discloses preparations of vesicles obtained from *N. meningitidis* with a modified fur gene. WO02/09746 teaches that nspA expression should be up regulated with concomitant porA and cps knockout. Further knockout mutants of *N. meningitidis* for OMV production are disclosed in WO02/0974, WO02/062378, and WO04/014417. WO06/081259 discloses vesicles in which fHBP is upregulated. Claassen et al. (1996) 14(10):1001-8, disclose the construction of vesicles from strains modified to express six different PorA subtypes. Mutant *Neisseria* with low endotoxin levels, achieved by knockout of enzymes involved in LPS biosynthesis, may also be used (see, e.g., WO99/10497 and Steeghs et al. (2001) i20:6937-6945). These or others mutants can all be used with the invention.

Thus *N. meningitidis* serogroup B strains included in the immunogenic compositions disclosed herein may in some embodiments express more than one PorA subtype. Six valent and nine valent PorA strains have previously been constructed. The strain may express 2, 3, 4, 5, 6, 7, 8 or 9 of PorA subtypes: P1.7,16; P1.5-1, 2-2; P1,19,15-1; P1.5-2,10; P1.12 1,13; P1.7-2,4; P1.22,14; P1.7-1,1 and/or P1.18-1,3,6. In other embodiments a strain may have been down regulated for PorA expression, e.g., in which the amount of PorA has been reduced by at least 20% (e.g., >30%, >40%, >50%, >60%, >70%, >80%, >90%, >95%, etc.), or even knocked out, relative to wild type levels (e.g., relative to strain H44/76, as disclosed in WO03/105890).

In some embodiments *N. meningitidis* serogroup B strains may over express (relative to the corresponding wild-type strain) certain proteins. For instance, strains may over express NspA, protein 287 (WO01/52885—also referred to as NMB2132 and GNA2132), one or more fHBP (WO06/081259 and U.S. Pat. Pub. 2008/0248065—also referred to as protein 741, NMB1870 and GNA1870), TbpA and/or TbpB (WO00/25811), Cu,Zn-superoxide dismutase (WO00/25811), etc.

In some embodiments *N. meningitidis* serogroup B strains may include one or more of the knockout and/or over expression mutations. Preferred genes for down regulation and/or knockout include: (a) Cps, CtrA, CtrB, CtrC, CtrD, FrpB, GalE, HtrB/MsbB, LbpA, LbpB, LpxK, Opa, Opc, PilC, PorB, SiaA, SiaB, SiaC, SiaD, TbpA, and/or TbpB (WO01/09350); (b) CtrA, CtrB, CtrC, CtrD, FrpB, GalE, HtrB/MsbB, LbpA, LbpB, LpxK, Opa, Opc, PhoP, PilC, PmrE, PmrF, SiaA, SiaB, SiaC, SiaD, TbpA, and/or TbpB (WO02/09746); (c) ExbB, ExbD, rmpM, CtrA, CtrB, CtrD, GalE, LbpA, LpbB, Opa, Opc, PilC, PorB, SiaA, SiaB, SiaC, SiaD, TbpA, and/or TbpB (WO02/062378); and (d) CtrA, CtrB, CtrD, FrpB, OpA, OpC, PilC, PorB, SiaD, SynA, SynB, and/or SynC (WO04/014417).

Where a mutant strain is used, in some embodiments it may have one or more, or all, of the following characteristics: (i) down regulated or knocked-out LgtB and/or GalE to truncate the meningococcal LOS; (ii) up regulated TbpA; (iii) up regulated Hsf; (iv) up regulated Omp85; (v) up regulated LbpA; (vi) up regulated NspA; (vii) knocked-out PorA; (viii) down regulated or knocked-out FrpB; (ix) down regulated or knocked-out Opa; (x) down regulated or knocked-out Opc; (xii) deleted cps gene complex. A truncated LOS can be one that does not include a sialyl-lacto-N-neotetraose epitope, e.g., it might be a galactose-deficient LOS. The LOS may have no a chain.

If LOS is present in a vesicle then it is possible to treat the vesicle so as to link its LOS and protein components ("intra-bleb" conjugation (WO04/014417)).

The immunogenic compositions as disclosed herein may include mixtures of vesicles from different strains. By way of example, WO03/105890 discloses vaccine comprising multivalent meningococcal vesicle compositions, comprising a first vesicle derived from a meningococcal strain with a serosubtype prevalent in a country of use, and a second vesicle derived from a strain that need not have a serosubtype prevent in a country of use. WO06/024946 discloses useful combinations of different vesicles. A combination of vesicles from strains in each of the L2 and L3 immunotypes may be used in some embodiments.

Vesicle-based antigens can be prepared from *N. meningitidis* serogroups other than serogroup B (e.g., WO01/91788 discloses a process for serogroup A). The immunogenic compositions disclosed herein accordingly can include vesicles prepared serogroups other than B (e.g. A, C, W135 and/or Y) and from bacterial pathogens other than *Neisseria*.

Viral Antigens

Viral antigens suitable for use in the immunogenic compositions provided herein include, but are not limited to, inactivated (or killed) virus, attenuated virus, split virus formulations, purified subunit formulations, viral proteins which may be isolated, purified or derived from a virus, Virus Like Particles (VLPs) and polynucleotide antigens which may be isolated, purified or derived from a virus or recombinantly synthesized. In certain embodiments, viral antigens are derived from viruses propagated on cell culture or other substrate. In other embodiments, viral antigens are expressed recombinantly. In certain embodiments, viral antigens preferably include epitopes which are exposed on the surface of the virus during at least one stage of its life cycle. Viral antigens are preferably conserved across multiple serotypes or isolates. Viral antigens suitable for use in the immunogenic compositions provided herein include, but are not limited to, antigens derived from one or more of the viruses set forth below as well as the specific antigens examples identified below.

Orthomyxovirus: Viral antigens include, but are not limited to, those derived from an Orthomyxovirus, such as Influenza A, B and C. In certain embodiments, orthomyxovirus antigens are selected from one or more of the viral proteins, including hemagglutinin (HA), neuraminidase (NA), nucleoprotein (NP), matrix protein (M1), membrane protein (M2), one or more of the transcriptase components (PB1, PB2 and PA). In certain embodiments the viral antigen include HA and NA. In certain embodiments, the influenza antigens are derived from interpandemic (annual) flu strains, while in other embodiments, the influenza antigens are derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens include, but are not limited to, those derived from Paramyxoviridae viruses, such as Pneumoviruses (RSV), Paramyxoviruses (PIV), Metapneumovirus and Morbilliviruses (Measles).

Pneumovirus: Viral antigens include, but are not limited to, those derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. In certain embodiments, pneumovirus antigens are selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. In other embodiments, pneumovirus antigens include F, G and M. In certain embodiments, pneumovirus antigens are also formulated in or derived from chimeric viruses, such as, by way of example only, chimeric RSV/PIV viruses comprising components of both RSV and PIV.

Paramyxovirus: Viral antigens include, but are not limited to, those derived from a Paramyxovirus, such as Parainfluenza virus types 1-4 (PIV), Mumps, Sendai viruses, Simian virus 5, Bovine parainfluenza virus, Nipahvirus, Henipavirus and Newcastle disease virus. In certain embodiments, the Paramyxovirus is PIV or Mumps. In certain embodiments, paramyxovirus antigens are selected from one or more of the following proteins: Hemagglutinin-Neuraminidase (HN), Fusion proteins F1 and F2, Nucleoprotein (NP), Phosphoprotein (P), Large protein (L), and Matrix protein (M). In other embodiments, paramyxovirus proteins include HN, F1 and F2. In certain embodiments, paramyxovirus antigens are also formulated in or derived from chimeric viruses, such as, by way of example only, chimeric RSV/PIV viruses comprising components of both RSV and PIV. Commercially available mumps vaccines include live attenuated mumps virus, in either a monovalent form or in combination with measles and rubella vaccines (MMR). In other embodiments, the Paramyxovirus is Nipahvirus or Henipavirus and the anitgens are selected from one or more of the following proteins: Fusion (F) protein, Glycoprotein (G) protein, Matrix (M) protein, Nucleocapsid (N) protein, Large (L) protein and Phosphoprotein (P).

Poxyiridae: Viral antigens include, but are not limited to, those derived from Orthopoxvirus such as Variola vera, including but not limited to, Variola major and Variola minor.

Metapneumovirus: Viral antigens include, but are not limited to, Metapneumovirus, such as human metapneumovirus (hMPV) and avian metapneumoviruses (aMPV). In certain embodiments, metapneumovirus antigens are selected from one or more of the following proteins, including surface proteins Fusion (F), Glycoprotein (G) and Small Hydrophobic protein (SH), matrix proteins M and M2, nucleocapsid proteins N, P and L. In other embodiments, metapneumovirus antigens include F, G and M. In certain embodiments, metapneumovirus antigens are also formulated in or derived from chimeric viruses.

Morbillivirus: Viral antigens include, but are not limited to, those derived from a Morbillivirus, such as Measles. In certain embodiments, morbillivirus antigens are selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens include, but are not limited to, those derived from Picornaviruses, such as Enteroviruses, Rhinoviruses, Heparnavirus, Cardioviruses and Aphthoviruses. In certain embodiments, the antigens are derived from Enteroviruses, while in other embodiments the enterovirus is Poliovirus. In still other embodiments, the antigens are derived from Rhinoviruses. In certain embodiments, the antigens are formulated into virus-like particles (VLPs).

Enterovirus: Viral antigens include, but are not limited to, those derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. In certain embodiments, the antigens are derived from Enteroviruses, while in other embodiments the enterovirus is Poliovirus. In certain embodiments, the enterovirus antigens are selected from one or more of the following Capsid proteins VP0, VP1, VP2, VP3 and VP4. Commercially available polio vaccines include Inactivated Polio Vaccine (IPV) and Oral poliovirus vaccine (OPV). In certain embodiments, the antigens are formulated into virus-like particles.

Bunyavirus: Viral antigens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Rhinovirus: Viral antigens include, but are not limited to, those derived from rhinovirus. In certain embodiments, the rhinovirus antigens are selected from one or more of the following Capsid proteins: VP0, VP1, VP2, VP2 and VP4. In certain embodiments, the antigens are formulated into virus-like particles (VLPs).

Heparnavirus: Viral antigens include, but are not limited to, those derived from a Heparnavirus, such as, by way of example only, Hepatitis A virus (HAV). Commercially available HAV vaccines include inactivated HAV vaccine.

Togavirus: Viral antigens include, but are not limited to, those derived from a Togavirus, such as a Rubivirus, an Alphavirus, or an Arterivirus. In certain embodiments, the antigens are derived from Rubivirus, such as by way of example only, Rubella virus. In certain embodiments, the togavirus antigens are selected from E1, E2, E3, C, NSP-1, NSPO-2, NSP-3 or NSP-4. In certain embodiments, the togavirus antigens are selected from E1, E2 or E3. Commercially available Rubella vaccines include a live cold-adapted virus, typically in combination with mumps and measles vaccines (MMR).

Flavivirus: Viral antigens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus. In certain embodiments, the flavivirus antigens are selected from PrM, M, C, E, NS-1, NS-2a, NS2b, NS3, NS4a, NS4b, and NS5. In certain embodiments, the flavivirus antigens are selected from PrM, M and E. Commercially available TBE vaccine includes inactivated virus vaccines. In certain embodiments, the antigens are formulated into virus-like particles (VLPs).

Pestivirus: Viral antigens include, but are not limited to, those derived from a Pestivirus, such as Bovine viral diarrhea (BVDV), Classical swine fever (CSFV) or Border disease (BDV).

Hepadnavirus: Viral antigens include, but are not limited to, those derived from a Hepadnavirus, such as Hepatitis B virus. In certain embodiments, the hepadnavirus antigens are selected from surface antigens (L, M and S), core antigens (HBc, HBe). Commercially available HBV vaccines include subunit vaccines comprising the surface antigen S protein.

Hepatitis C virus: Viral antigens include, but are not limited to, those derived from a Hepatitis C virus (HCV). In certain embodiments, the HCV antigens are selected from one or more of E1, E2, E1/E2, NS345 polyprotein, NS 345-core polyprotein, core, and/or peptides from the nonstructural regions. In certain embodiments, the Hepatitis C virus antigens include one or more of the following: HCV E1 and or E2 proteins, E1/E2 heterodimer complexes, core proteins and non-structural proteins, or fragments of these antigens, wherein the non-structural proteins can optionally be modified to remove enzymatic activity but retain immunogenicity. In certain embodiments, the antigens are formulated into virus-like particles (VLPs).

Rhabdovirus: Viral antigens include, but are not limited to, those derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS). Commercially available Rabies virus vaccine comprise killed virus grown on human diploid cells or fetal rhesus lung cells.

Caliciviridae; Viral antigens include, but are not limited to, those derived from Calciviridae, such as Norwalk virus, and Norwalk-like Viruses, such as Hawaii Virus and Snow Mountain Virus. In certain embodiments, the antigens are formulated into virus-like particles (VLPs).

Coronavirus: Viral antigens include, but are not limited to, those derived from a Coronavirus, SARS, Human respiratory coronavirus, Avian infectious bronchitis (IBV), Mouse hepatitis virus (MHV), and Porcine transmissible gastroenteritis virus (TGEV). In certain embodiments, the coronavirus antigens are selected from spike (S), envelope (E), matrix (M), nucleocapsid (N), and Hemagglutinin-esterase glycoprotein (HE). In certain embodiments, the coronavirus antigen is derived from a SARS virus. In certain embodiments, the coronavirus is derived from a SARS viral antigen as described in WO 04/92360.

Retrovirus: Viral antigens include, but are not limited to, those derived from a Retrovirus, such as an Oncovirus, a Lentivirus or a Spumavirus. In certain embodiments, the oncovirus antigens are derived from HTLV-1, HTLV-2 or HTLV-5. In certain embodiments, the lentivirus antigens are derived from HIV-1 or HIV-2. In certain embodiments, the antigens are derived from HIV-1 subtypes (or clades), including, but not limited to, HIV-1 subtypes (or clades) A, B, C, D, F, G, H, J, K, O. In other embodiments, the antigens are derived from HIV-1 circulating recombinant forms (CRFs), including, but not limited to, A/B, A/E, A/G, A/G/I, etc. In certain embodiments, the retrovirus antigens are selected from gag, pol, env, tax, tat, rex, rev, nef, vif, vpu, and vpr. In certain embodiments, the HIV antigens are selected from gag (p24gag and p55gag), env (gp160 and gp41), pol, tat, nef, rev vpu, miniproteins, (preferably p55 gag and gp140v delete). In certain embodiments, the HIV antigens are derived from one or more of the following strains: $HIV_{IIIb}$, $HIV_{SF2}$, $HIV_{LAV}$, $HIV_{LAI}$, $HIV_{MN}$, $HIV-1_{CM235}$, $HIV-1_{US4}$, $HIV-1_{SF162}$, $HIV-1_{TV1}$, $HIV-1_{MJ4}$. In certain embodiments, the antigens are derived from endogenous human retroviruses, including, but not limited to, HERV-K ("old" HERV-K and "new" HERV-K).

Reovirus: Viral antigens include, but are not limited to, those derived from a Reovirus, such as an Orthoreovirus, a Rotavirus, an Orbivirus, or a Coltivirus. In certain embodiments, the reovirus antigens are selected from structural proteins $\lambda 1, \lambda 2, \lambda 3, \mu 1, \mu 2, \sigma 1, \sigma 2$, or $\sigma 3$, or nonstructural proteins $\sigma NS$, $\mu NS$, or $\sigma 1s$. In certain embodiments, the reovirus antigens are derived from a Rotavirus. In certain embodiments, the rotavirus antigens are selected from VP1, VP2, VP3, VP4 (or the cleaved product VP5 and VP8), NSP 1, VP6, NSP3, NSP2, VP7, NSP4, or NSP5. In certain embodiments, the rotavirus antigens include VP4 (or the cleaved product VP5 and VP8), and VP7.

Parvovirus: Viral antigens include, but are not limited to, those derived from a Parvovirus, such as Parvovirus B19. In certain embodiments, the Parvovirus antigens are selected from VP-1, VP-2, VP-3, NS-1 and NS-2. In certain embodiments, the Parvovirus antigen is capsid protein VP1 or VP-2. In certain embodiments, the antigens are formulated into virus-like particles (VLPs).

Delta hepatitis virus (HDV): Viral antigens include, but are not limited to, those derived from HDV, particularly δ-antigen from HDV.

Hepatitis E virus (HEV): Viral antigens include, but are not limited to, those derived from HEV.

Hepatitis G virus (HGV): Viral antigens include, but are not limited to, those derived from HGV.

Human Herpesvirus Viral antigens include, but are not limited to, those derived from a Human Herpesvirus, such as, by way of example only, Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). In certain embodiments, the Human Herpesvirus antigens are selected from immediate early proteins (α), early proteins (β), and late proteins (γ). In certain embodiments, the HSV antigens are derived from HSV-1 or HSV-2 strains. In certain embodiments, the HSV antigens are selected from glycoproteins gB, gC, gD and gH, fusion protein (gB), or immune escape proteins (gC, gE, or gI). In certain embodiments, the VZV antigens are selected from core, nucleocapsid, tegument, or envelope proteins. A live attenuated VZV vaccine is commercially available. In certain embodiments, the EBV antigens are selected from early antigen (EA) proteins, viral capsid antigen (VCA), and glycoproteins of the membrane antigen (MA). In certain embodiments, the CMV antigens are selected from capsid proteins, envelope glycoproteins (such as gB and gH), and tegument proteins. In other embodiments, CMV antigens may be selected from one or more of the following proteins: pp65, IE1, gB, gD, gH, gL, gM, gN, gO, UL128, UL129, gUL130, UL150, UL131, UL33, UL78, US27, US28, RL5A, RL6, RL10, RL11, RL12, RL13, UL1, UL2, UL4, UL5, UL6, UL7, UL8, UL9, UL10, UL11, UL14, UL15A, UL16, UL17, UL18, UL22A, UL38, UL40, UL41A, UL42, UL116, UL119, UL120, UL121, UL124, UL132, UL147A, UL148, UL142, UL144, UL141, UL140, UL135, UL136, UL138, UL139, UL133, UL135, UL148A, UL148B, UL148C, UL148D, US2, US3, US6, US7, USB, US9, US10, US11, US12, US13, US14, US15, US16, US17, US18, US19, US20, US21, US29, US30 and US34A. CMV antigens may also be fusions of one or more CMV proteins, such as, by way of example only, pp65/IE1 (Reap et al., *Vaccine* (2007) 25:7441-7449). In certain embodiments, the antigens are formulated into virus-like particles (VLPs).

Papovaviruses: Antigens include, but are not limited to, those derived from Papovaviruses, such as Papillomaviruses and Polyomaviruses. In certain embodiments, the Papillomaviruses include HPV serotypes 1, 2, 4, 5, 6, 8, 11, 13, 16, 18, 31, 33, 35, 39, 41, 42, 47, 51, 57, 58, 63 and 65. In certain embodiments, the HPV antigens are derived from serotypes 6, 11, 16 or 18. In certain embodiments, the HPV antigens are selected from capsid proteins (L1) and (L2), or E1-E7, or fusions thereof. In certain embodiments, the HPV antigens are formulated into virus-like particles (VLPs). In certain embodiments, the Polyomyavirus viruses include BK virus and JK virus. In certain embodiments, the Polyomavirus antigens are selected from VP1, VP2 or VP3.

Adenovirus: Antigens include those derived from Adenovirus. In certain embodiments, the Adenovirus antigens are derived from Adenovirus serotype 36 (Ad-36). In certain embodiments, the antigen is derived from a protein or peptide sequence encoding an Ad-36 coat protein or fragment thereof (WO 2007/120362).

Further provided are antigens, compositions, methods, and microbes included in *Vaccines*, 4$^{th}$ Edition (Plotkin and Orenstein ed. 2004); *Medical Microbiology* 4$^{th}$ Edition (Murray et al. ed. 2002); *Virology*, 3rd Edition (W. K. Joklik ed. 1988); *Fundamental Virology*, 2nd Edition (B. N. Fields and D. M. Knipe, eds. 1991), which are contemplated in conjunction with the immunogenic compositions provided herein.

Fungal Antigens

Fungal antigens for use in the immunogenic compositions provided herein include, but are not limited to, those derived from one or more of the fungi set forth below.

Fungal antigens are derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. album, var. discoides, var. ochraceum, *Trichophyton violaceum*, and/or *Trichophyton faviforme*; and Fungal pathogens are derived from *Aspergillus fumigatus, Aspergillus flavus, Aspergillus niger, Aspergillus nidu-* lans, *Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

In certain embodiments, the process for producing a fungal antigen includes a method wherein a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

Protazoan Antigens/Pathogens

Protazoan antigens/pathogens for use in the immunogenic compositions provided herein include, but are not limited to, those derived from one or more of the following protozoa: *Entamoeba histolytica, Giardia lambli, Cryptosporidium parvum, Cyclospora cayatanensis* and *Toxoplasma*.

Plant Antigens/Pathogens

Plant antigens/pathogens for use in the immunogenic compositions provided herein include, but are not limited to, those derived from *Ricinus communis*.

STD Antigens

In certain embodiments, the immunogenic compositions provided herein include one or more antigens derived from a sexually transmitted disease (STD). In certain embodiments, such antigens provide for prophylactis for STD's such as chlamydia, genital herpes, hepatitis (such as HCV), genital warts, gonorrhea, syphilis and/or chancroid. In other embodiments, such antigens provide for therapy for STD's such as chlamydia, genital herpes, hepatitis (such as HCV), genital warts, gonorrhea, syphilis and/or chancroid. Such antigens are derived from one or more viral or bacterial STD's. In certain embodiments, the viral STD antigens are derived from HIV, herpes simplex virus (HSV-1 and HSV-2), human papillomavirus (HPV), and hepatitis (HCV). In certain embodiments, the bacterial STD antigens are derived from *Neiserria gonorrhoeae, Chlamydia trachomatis, Treponema pallidum, Haemophilus ducreyi, E. coli,* and *Streptococcus agalactiae*. Examples of specific antigens derived from these pathogens are described above.

Respiratory Antigens

In certain embodiments, the immunogenic compositions provided herein include one or more antigens derived from a pathogen which causes respiratory disease. By way of example only, such respiratory antigens are derived from a respiratory virus such as Orthomyxoviruses (influenza), Pneumovirus (RSV), Paramyxovirus (PIV), Morbillivirus (measles), Togavirus (Rubella), VZV, and Coronavirus (SARS). In certain embodiments, the respiratory antigens are derived from a bacteria which causes respiratory disease, such as, by way of example only, *Streptococcus pneumoniae, Pseudomonas aeruginosa, Bordetella pertussis, Mycobacterium tuberculosis, Mycoplasma pneumoniae, Chlamydia pneumoniae, Bacillus anthracis,* and *Moraxella catarrhalis*. Examples of specific antigens derived from these pathogens are described above.

Pediatric Vaccine Antigens

In certain embodiments, the immunogenic compositions provided herein include one or more antigens suitable for use in pediatric subjects. Pediatric subjects are typically less than about 3 years old, or less than about 2 years old, or less than about 1 years old. Pediatric antigens are administered multiple times over the course of 6 months, 1, 2 or 3 years. Pediatric antigens are derived from a virus which may target pediatric populations and/or a virus from which pediatric populations are susceptible to infection. Pediatric viral antigens include, but are not limited to, antigens derived from one or more of Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), and Varicella-zoster virus (VZV), Epstein Barr virus (EBV). Pediatric bacterial antigens include antigens derived from one or more of *Streptococcus pneumoniae, Neisseria meningitides, Streptococcus pyogenes* (Group A *Streptococcus*), *Moraxella catarrhalis, Bordetella pertussis, Staphylococcus aureus, Clostridium tetani* (Tetanus), *Cornynebacterium diphtheriae* (Diphtheria), *Haemophilus influenzae* B (Hib), *Pseudomonas aeruginosa, Streptococcus agalactiae* (Group B *Streptococcus*), and *E. coli*. Examples of specific antigens derived from these pathogens are described above.

Antigens suitable for use in Elderly or Immunocompromised Individuals

In certain embodiments, the immunogenic compositions provided herein include one or more antigens suitable for use in elderly or immunocompromised individuals. Such individuals may need to be vaccinated more frequently, with higher doses or with adjuvanted formulations to improve their immune response to the targeted antigens. Antigens which are targeted for use in Elderly or Immunocompromised individuals include antigens derived from one or more of the following pathogens: *Neisseria meningitides, Streptococcus pneumoniae, Streptococcus pyogenes* (Group A *Streptococcus*), *Moraxella catarrhalis, Bordetella pertussis, Staphylococcus aureus, Staphylococcus epidermis, Clostridium tetani* (Tetanus), *Cornynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Chlamydia pneumoniae,* Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), Varicella-zoster virus (VZV), Epstein Barr virus (EBV), Cytomegalovirus (CMV). Examples of specific antigens derived from these pathogens are described above.

Antigens Suitable for Use in Adolescent Vaccines

In certain embodiments, the immunogenic compositions provided herein include one or more antigens suitable for use in adolescent subjects. Adolescents are in need of a boost of a previously administered pediatric antigen. Pediatric antigens which are suitable for use in adolescents are described above. In addition, adolescents are targeted to receive antigens derived from an STD pathogen in order to ensure protective or therapeutic immunity before the beginning of sexual activity. STD antigens which are suitable for use in adolescents are described above.

Tumor Antigens

In certain embodiments, a tumor antigen or cancer antigen is used in conjunction with the immunogenic compositions provided herein. In certain embodiments, the tumor antigens is a peptide-containing tumor antigens, such as a polypeptide tumor antigen or glycoprotein tumor antigens. In certain embodiments, the tumor antigen is a saccharide-containing tumor antigen, such as a glycolipid tumor antigen or a ganglioside tumor antigen. In certain embodiments, the tumor antigen is a polynucleotide-containing tumor antigen that expresses a polypeptide-containing tumor antigen, for instance, an RNA vector construct or a DNA vector construct, such as plasmid DNA.

Tumor antigens appropriate for the use in conjunction with the immunogenic compositions provided herein encompass a wide variety of molecules, such as (a) polypeptide-containing tumor antigens, including polypeptides (which can range, for example, from 8-20 amino acids in length, although lengths outside this range are also common), lipopolypeptides and glycoproteins, (b) saccharide-containing tumor antigens, including poly-saccharides, mucins, gangliosides, glycolipids and glycoproteins, and (c) polynucleotides that express antigenic polypeptides.

In certain embodiments, the tumor antigens are, for example, (a) full length molecules associated with cancer cells, (b) homologs and modified forms of the same, including molecules with deleted, added and/or substituted portions, and (c) fragments of the same. In certain embodiments, the tumor antigens are provided in recombinant form. In certain embodiments, the tumor antigens include, for example, class I-restricted antigens recognized by CD8+ lymphocytes or class II-restricted antigens recognized by CD4+ lymphocytes.

In certain embodiments, the tumor antigens include, but are not limited to, (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, $MC^1R$, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl $Le^x$ (associated with, e.g., breast and colorectal cancer) as well as various mucins; glycoproteins are coupled to a carrier protein (e.g., MUC-1 are coupled to KLH); (ii) lipopolypeptides (e.g., MUC-1 linked to a lipid moiety); (iii) polysaccharides (e.g., Globo H synthetic hexasaccharide), which are coupled to a carrier proteins (e.g., to KLH), (iv) gangliosides such as GM2, GM12, GD2, GD3 (associated with, e.g., brain, lung cancer, melanoma), which also are coupled to carrier proteins (e.g., KLH).

In certain embodiments, the tumor antigens include, but are not limited to, p15, Hom/Me1-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

Polynucleotide-containing antigens used in conjunction with the immunogenic compositions provided herein include polynucleotides that encode polypeptide cancer antigens such as those listed above. In certain embodiments, the polynucleotide-containing antigens include, but are not limited to, DNA or RNA vector constructs, such as plasmid vectors (e.g., pCMV), which are capable of expressing polypeptide cancer antigens in vivo.

In certain embodiments, the tumor antigens are derived from mutated or altered cellular components. After alteration, the cellular components no longer perform their regulatory functions, and hence the cell may experience uncontrolled growth. Representative examples of altered cellular components include, but are not limited to ras, p53, Rb, altered protein encoded by the Wilms' tumor gene, ubiquitin, mucin, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor.

Additionally, bacterial and viral antigens, are used in conjunction with the immunogenic compositions provided herein for the treatment of cancer. In certain embodiments, the, carrier proteins, such as $CRM_{197}$, tetanus toxoid, or *Salmonella typhimurium* antigen are used in conjunction/conjugation with compounds provided herein for treatment of cancer. The cancer antigen combination therapies will show increased efficacy and bioavailability as compared with existing therapies.

In certain embodiments, the immunogenic compositions containing at least one compound of Formula (I) include capsular saccharides from at least two of serogroups A, C, W135 and Y of *Neisseria meningitides*. In other embodiments, such vaccines further comprise an antigen from one or more of the following: (a) serogroup B *N. meningitidis*; (b) *Haemophilus influenzae* type B; and/or (c) *Streptococcus pneumoniae*.

In certain embodiments the immunogenic compositions containing at least one compound of Formula (I) include serogroups C, W135 & Y of *N. meningitides*. In certain embodiments the immunogenic compositions containing at least one compound of Formula (I) include serogroups A, C, W135 & Y of *N. meningitides*. In certain embodiments the immunogenic compositions containing at least one compound of Formula (I) include serogroups B, C, W135 & Y of *N. meningitides*. In certain embodiments the immunogenic compositions containing at least one compound of Formula (I) include serogroups A, B, C, W135 & Y of *N. meningitides*. In certain embodiments the immunogenic compositions containing at least one compound of Formula (I) include *H. influenzae* type B and serogroups C, W135 & Y of *N. meningitides*. In certain embodiments the immunogenic compositions containing at least one compound of Formula (I) include *H. influenzae* type B and serogroups A, C, W135 & Y of *N. meningitides*. In certain embodiments the immunogenic compositions containing at least one compound of Formula (I) include *H. influenzae* type B and serogroups B, C, W135 & Y of *N. meningitides*. In certain embodiments the immunogenic compositions containing at least one compound of Formula (I) include *H. influenzae* type B and serogroups A, B, C, W135 & Y of *N. meningitides*. In certain embodiments the immunogenic compositions containing at least one compound of Formula (I) include *S. pneumoniae* and serogroups C, W135 & Y of *N. meningitides*. In certain embodiments the immunogenic compositions containing at least one compound of Formula (I) include *S. pneumoniae* and serogroups A, C, W135 & Y of *N. meningitides*. In certain embodiments the immunogenic compositions containing at least one compound of Formula (I) include *S. pneumoniae* and serogroups B, C, W135 & Y of *N. meningitides*. In certain embodiments the immunogenic compositions containing at least one compound of Formula (I) include *S. pneumoniae* and serogroups A, B, C, W135 & Y of *N. meningitides*. In certain embodiments the immunogenic compositions containing at least one compound of Formula (I) include *H. influenzae* type B, *S. pneumoniae* and serogroups C, W135 & Y of *N. meningitides*. In certain embodiments the immunogenic compositions containing at least one compound of Formula (I) include *H. influenzae* type B, *S. pneumoniae* and serogroups A, C, W135 & Y of *N. meningitides*. In certain embodiments the immunogenic compositions containing at least one compound of Formula (I) include *H. influenzae* type B, *S. pneumoniae* and serogroups B, C, W135 & Y of *N. meningitides*. In certain embodiments the immunogenic compositions containing at least one compound of Formula (I) include *H. influenzae* type B, *S. pneumoniae* and serogroups A, B, C, W135 & Y of *N. meningitidis*.

Kits

Also provided herein are pharmaceutical packs or kits that include one or more containers containing a compound of Formula (I) useful for the treatment or prevention of a disease or disorder associated with toll-like receptors. In other embodiments, the such pharmaceutical packs or kits include one or more containers containing a compound of Formula (I) useful for the treatment or prevention of a disease or disorder associated with toll-like receptors and one or more containers containing an additional therapeutic agent, including but not limited to those listed above. In certain embodiments, such pharmaceutical packs or kits optionally include instructions for its administration of a compound of Formula (I) as disclosed herein. In some embodiments of such kits, the compound of Formula (I) is provided in the form of a vaccine composition as described herein, and optionally includes a syringe for injecting a subject with the vaccine composition Methods of Treatment, Prevention and Administration of Vaccines The immunogenic compositions as disclosed herein may be used in conjunction with vaccines to improve the immunogenicity of the vaccine or where the immunogenic composition includes one or more antigens, the immunogenic composition may be used as a vaccine. Therefore in certain embodiment, the immunogenic compositions disclosed herein may be used in a method for raising or enhancing an immune response in a mammal comprising the step of administering an effective amount of an immunogenic composition as disclosed herein. The immune response is preferably protective and preferably involves antibodies and/or cell-mediated immunity. The method may raise a booster response.

In certain embodiments, the immunogenic compositions disclosed herein may be used as a medicament, e.g., for use in raising or enhancing an immune response in a mammal.

In certain embodiments, the immunogenic compositions disclosed herein may be used in the manufacture of a medicament for raising an immune response in a mammal.

The invention also provides a delivery device pre-filled with an immunogenic composition disclosed herein.

By raising an immune response in the mammal by these uses and methods, the mammal can be infection by pathogens comprising the antigen included in the immunogenic composition or administered in conjunction with the immunogenic composition can be reduced or even prevented. The mammal is preferably a human, but may be, e.g., a cow, a pig, a chicken, a cat or a dog, as the pathogens covered herein may be problematic across a wide range of species. Where the vaccine is for prophylactic use, the human is preferably a child (e.g., a toddler or infant) or a teenager; where the vaccine is for therapeutic use, the human is preferably a teenager or an adult. A vaccine intended for children may also be administered to adults, e.g., to assess safety, dosage, immunogenicity, etc.

One way of checking efficacy of therapeutic treatment involves monitoring pathogen infection after administration of the immunogenic compositions disclosed herein. One way of checking efficacy of prophylactic treatment involves monitoring immune responses, systemically (such as monitoring the level of IgG1 and IgG2a production) and/or mucosally (such as monitoring the level of IgA production), against the antigens included in or administered in conjunction with the immunogenic compositions disclosed herein after administration of the immunogenic composition (and the antigen if administered separately). Typically, antigen-specific serum antibody responses are determined post-immunisation but pre-challenge whereas antigen-specific mucosal antibody responses are determined post-immunisation and post-challenge.

Another way of assessing the immunogenicity of the immunogenic compositions disclosed herein where the antigen is a protein is to express the proteins recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within protein antigens.

The efficacy of the immunogenic compositions can also be determined in vivo by challenging appropriate animal models of the pathogen of interest infection.

The immunogenic compositions disclosed herein will generally be administered directly to a subject. Direct delivery may be accomplished by parenteral injection (e.g., subcutaneously, intraperitoneally, intravenously, intramuscularly, or to the interstitial space of a tissue), or mucosally, such as by rectal, oral (e.g., tablet, spray), vaginal, topical, transdermal or transcutaneous, intranasal, ocular, aural, pulmonary or other mucosal administration.

The immunogenic compositions may be used to elicit systemic and/or mucosal immunity, preferably to elicit an enhanced systemic and/or mucosal immunity.

Preferably the enhanced systemic and/or mucosal immunity is reflected in an enhanced TH1 and/or TH2 immune response. Preferably, the enhanced immune response includes an increase in the production of IgG1 and/or IgG2a and/or IgA.

Dosage can be by a single dose schedule or a multiple dose schedule. Multiple doses may be used in a primary immunisation schedule and/or in a booster immunisation schedule. In a multiple dose schedule the various doses may be given by the same or different routes, e.g., a parenteral prime and mucosal boost, a mucosal prime and parenteral boost, etc. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.).

The immunogenic compositions disclosed herein that include one or more antigens or are used in conjunction with one or more antigens may be used to treat both children and adults. Thus a human subject may be less than 1 year old, 1-5 years old, 5-15 years old, 15-55 years old, or at least 55 years old. Preferred subjects for receiving such immunogenic compositions are the elderly (e.g., >50 years old, >60 years old, and preferably >65 years), the young (e.g., <5 years old), hospitalised patients, healthcare workers, armed service and military personnel, pregnant women, the chronically ill, or immunodeficient patients. The immunogenic compositions are not suitable solely for these groups, however, and may be used more generally in a population.

The immunogenic compositions disclosed herein that include one or more antigens or are used in conjunction with one or more antigens may be administered to patients at substantially the same time as (e.g., during the same medical consultation or visit to a healthcare professional or vaccination centre) other vaccines, e.g., at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated H. influenzae type b vaccine, an inactivated poliovirus vaccine, a hepatitis B virus vaccine, a meningococcal conjugate vaccine (such as a tetravalent A C W135 Y vaccine), a respiratory syncytial virus vaccine, etc.

Compounds of Formula (I) Formulated with Aluminum-Containing Adjuvants

In certain embodiments, at least one compound of Formula (I) provided herein, or a pharmaceutically acceptable salt or solvate thereof, is combined with an aluminum-containing adjuvant and an effective amount of one or more antigens, resulting in an immunogenic composition. In such immunogenic compositions the compound of Formula (I) is bound to the aluminum-containing adjuvant. In such immunogenic compositions the antigen is any antigen provided herein. In such immunogenic compositions, the antigen and the compound of Formula (I), a TLR7 agonist, are co-delivered to a desired site.

In such immunogenic composition, the binding of a compound of Formula (I) to an aluminum-containing adjuvant does not interfere with the binding of the antigen to the aluminum-containing adjuvant. By way of example only, FIG. 1 demonstrates that the adsorption of antigens of Neisseria meningitis to aluminum hydroxide is not affected by the binding of a compound of Formula (I) to the aluminum hydroxide adjuvant.

In certain embodiments, such immunogenic compositions are useful as vaccines. In certain embodiments, such vaccines are prophylactic (i.e. to prevent infection), while in other embodiments, such vaccines are therapeutic (i.e. to treat infection).

The compound(s) of Formula (I) provided herein, or a pharmaceutically acceptable salt or solvate thereof, are TLR7 agonists and are immune potentiators that impart an immunostimulatory effect upon administration when compared to immunogenic formulations that do not contain compound(s) of Formula (I). In certain embodiments, compounds of Formula (I) impart an immunostimulatory effect upon administration when included in an immunogenic composition having one or more immunoregulatory agents, while in other embodiments, compounds of Formula (I) impart an immunostimulatory effect upon administration when included in an immunogenic composition without the presence of other immunoregulatory agents.

In certain embodiments, such immunogenic compositions enhance immune response through the retention of the compound of Formula (I) at the site of injection. Rather than binding a TLR agonist to alum, an alternative strategy for increasing the residence time of TRL agonists at the site of injection is to modify the hydrophilicity, hydrophobicity and/or solubility properties of the TLR agonist. Nononpolar (hydrophobic, or insoluble) compounds can have increased residence time at a site of injection when administered intramuscularly, thereby decreasing systemic exposure levels compared to polar (hydrophilic, or soluble) compounds with similar potency which show faster injection site clearance and higher systemic exposure. Similarly, nonpolar compounds of Formula (I) can display these useful properties.

In certain embodiments, such immunogenic compositions include a pharmaceutically acceptable carrier such as, but are not limited to, proteins, polysaccharides, polylactic acids, polyglycolic acids, polymeric amino acids, amino acid copolymers, sucrose, trehalose, lactose, lipid aggregates (such as oil droplets or liposomes), and inactive virus particles. The immunogenic compositions typically also contain diluents, such as water, saline, and glycerol, and optionally contain other excipients, such as wetting or emulsifying agents, and pH buffering substances. In certain embodiments, such immunogenic compositions include one or more additional adjuvants provided herein.

EXAMPLES

The following examples were offered to illustrate, but not to limit, the compounds of Formula (I) provided herein, and the preparation of such compounds.

SYNTHESIS of STARTING COMPOUNDS

Preparation of tert-butyl 5-methyl-2-(4,4,5,5-tetramethyl-1,3,2-dioxaborolan-2-yl)phenylcarbamate (A-1)

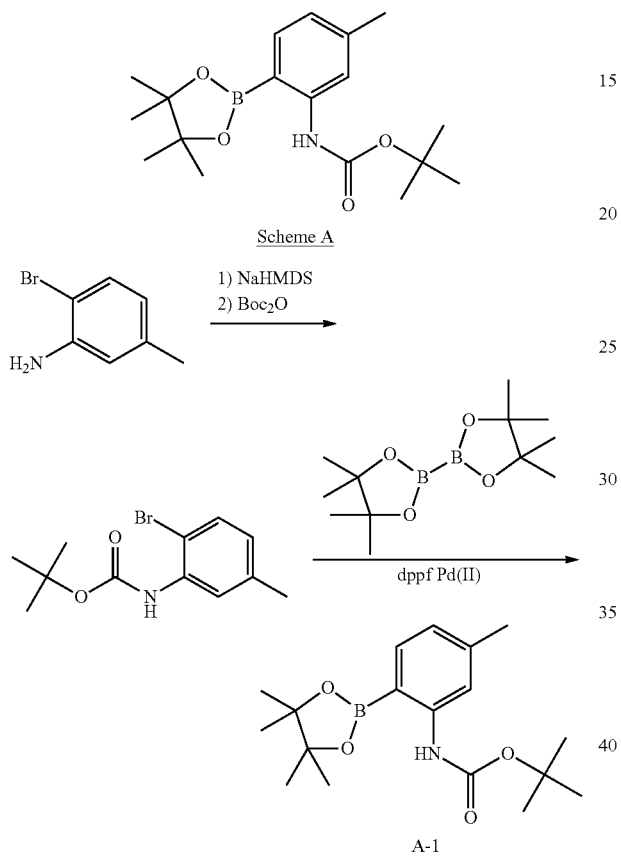

Step 1: tert-butyl 2-bromo-5-methylphenylcarbamate

To a solution of 2-bromo-5-methylaniline (1.0 eq.) in tetrahydrofuran (0.2 M) at 0° C. under $N_2$ atmosphere was added dropwise 1M NaHMDS (2.5 eq.). The reaction was stirred for 15 minutes at 0° C., and a solution of di-tert-butyl dicarbonate in tetrahydrofuran was added. The reaction was warmed to room temperature overnight. The solvent was evaporated, and the resulting residue was quenched with 0.1N HCl aqueous solution. The aqueous suspension was extracted twice with ethyl acetate. The combined organic layers were washed with brine, dried over anhydrous $MgSO_4$, and concentrated en vacuo. The crude material was purified by flash chromatography on a COMBIFLASH® system (ISCO) using 0-5% ethyl acetate in hexane to give tert-butyl 2-bromo-5-methylphenylcarbamate as a light yellow oil.

Step 2: tert-butyl 5-methyl-2-(4,4,5,5-tetramethyl-1,3,2-dioxaborolan-2-yl)phenylcarbamate Tert-butyl 2-bromo-5-methylphenylcarbamate (from previous step) (1.0 eq.), 4,4,4',4',5,5,5',5'-octamethyl-2,2'-bi(1,3,2-dioxaborolane) (1.5 eq.), dichloro[1,1'-bis(diphenylphosphino)ferrocene]palladium (II) (5%), and sodium acetate (4.5 eq.) were mixed in dioxane (0.2 M) under $N_2$ atmosphere. The reaction was heated to 100° C. and stirred overnight. The resulting suspension was cooled to ambient temperature, diluted with ether, filtered through celite, and the filtrate was concentrated en vacuo. The crude material was purified by flash chromatography on a COMBIFLASH® system (ISCO) using 0-8% ether in hexane to give tert-butyl 5-methyl-2-(4,4,5,5-tetramethyl-1,3,2-dioxaborolan-2-yl) phenylcarbamate (A-1).

Preparation of 4-(2-(5-amino-8-methylbenzo[f][1,7]naphthyridin-2-yl)ethyl)-3-methylphenol (B-4)

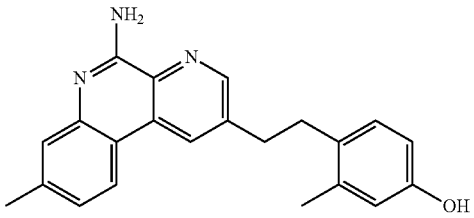 [SMILES: Cc1ccc2c(c1)nc(N)c1ncc(CCc3ccc(O)cc3C)cc12]

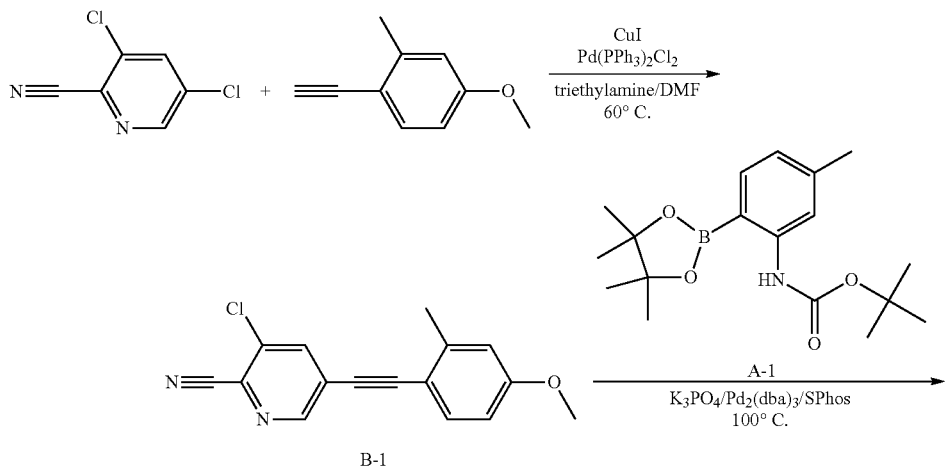

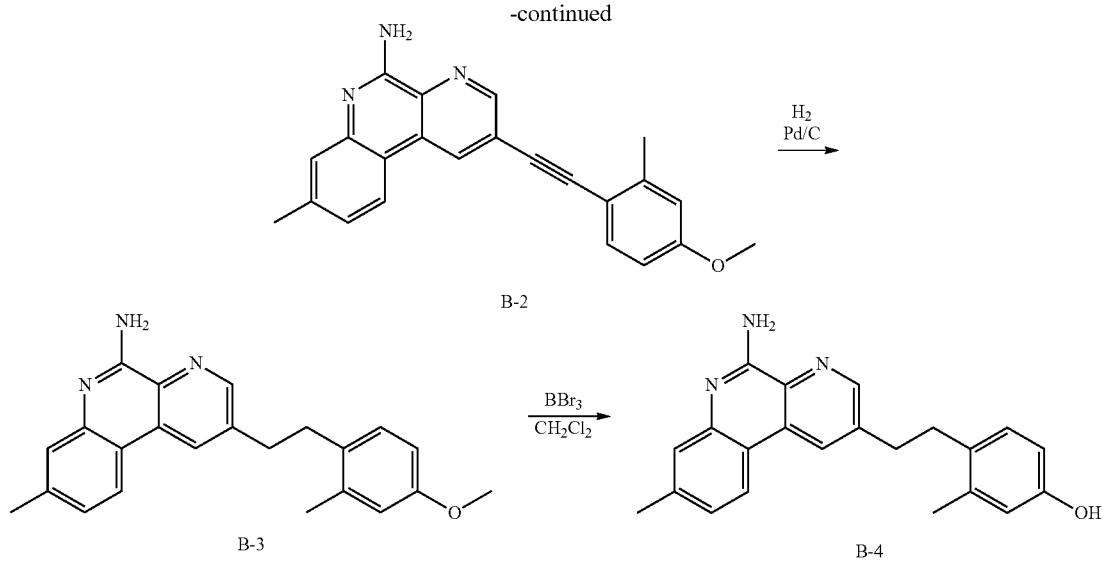

B-2

B-3

B-4

Step B-1: 3-chloro-5-((4-methoxy-2-methylphenyl) ethynyl)picolinonitrile (B-1)

To a round bottom flask capped with septa was added 1-ethynyl-4-methoxy-2-methylbenzene (1.1 eq), 3,5-dichloropicolinonitrile (1 eq.), triethylamine (5 eq.), and anhydrous DMF (0.2 M). The mixture was degassed (vacuum) and nitrogen flushed three times. CuI (0.05 eq.) and bis(triphenylphosphine)dichloro-palladium(II) (0.05 eq) were added and the septum was replaced with a refluxing condenser and the flask was heated at 60° C. overnight under nitrogen atmosphere. Upon completion of the reaction as monitored by TLC, the content of the flask was loaded onto a large silica gel column pretreated with hexanes. Flash chromatography (silica gel, hexanes:EtOAc (1:4%)) afforded the product 3-chloro-5-((4-methoxy-2-methylphenyl)ethynyl)picolinonitrile (B-1).

Step B-2: 2-((4-methoxy-2-methylphenyl)ethynyl)-8-methylbenzo[f][1,7]naphthyridin-5-amine (B-2)

To a round bottom flask with refluxing condenser were added 3-chloro-5-((4-methoxy-2-methylphenyl)ethynyl)picolinonitrile (B-1) (1 eq.), tert-butyl 5-methyl-2-(4,4,5,5-tetramethyl-1,3,2-dioxaborolan-2-yl)phenylcarbamate (A-1) (1.25 eq.), $K_3PO_4$ (2 eq.), tris(dibenzylideneacetone)dipalladium(0) (0.05 eq.), and 2-dicyclohexylphosphino-2',6'-dimethoxybiphenyl (Sphos) (0.1 eq.). n-butanol and water (5:2, 0.2 M) were added, and the content was degassed (vacuum followed by nitrogen flush) for three times. The reaction mixture was stirred vigorously under nitrogen at 100° C. overnight in an oil bath. The content was cooled and taken up in 200 mL of water followed by extraction with methylene chloride. Combined organic layers were dried ($Na_2SO_4$) and concentrated. Flash chromatography (silica gel, 0-50% EtOAc in $CH_2Cl_2$) afforded the product 2-((4-methoxy-2-methylphenyl)ethynyl)-8-methylbenzo[f][1,7]naphthyridin-5-amine (B-2).

Step B-3: 2-(4-methoxy-2-methylphenethyl)-8-methylbenzo[f][1,7]naphthyridin-5-amine (B-3)

2-(4-methoxy-2-methylphenethyl)-8-methylbenzo[f][1,7]naphthyridin-5-amine was prepared from 2-((4-methoxy-2-methylphenyl)ethynyl)-8-methylbenzo[f][1,7]naphthyridin-5-amine (from the previous step). To a round bottom flask was added 2-((4-methoxy-2-methylphenyl)ethynyl)-8-methylbenzo[f][1,7]naphthyridin-5-amine (1 eq.) with a stirring bar. Ethanol and methylene chloride (1:2, 0.2 M) were added, followed by palladium in carbon (activated powder, wet, 10% on carbon, 0.1 eq.). The content was degassed (vacuum) followed by hydrogen flush (three times). The reaction mixture was stirred vigorously at room temperature overnight, under a hydrogen balloon. Afterwards the reaction mixture was filtered through a celite pad, and the celite pad was washed subsequently with methylene chloride and EtOAc until the filtrate had no UV absorption. Combined organic washes were concentrated. Flash chromatography (silica gel, 0-50% EtOAc in $CH_2Cl_2$) afforded the product 2-(4-methoxy-2-methylphenethyl)-8-methylbenzo[f][1,7]naphthyridin-5-amine. $^1$H NMR (CDCl$_3$): δ 8.53 (d, 1H), 8.29 (d, 1H), 8.01 (d, 1H), 7.44 (s, 1H), 7.12 (dd, 1H), 6.93 (d, 1H), 6.67 (d, 1H), 6.60 (dd, 1H), 5.93 (bs, 2H), 3.70 (s, 3H), 3.05-3.00 (dd, 2H), 2.93-2.88 (dd, 2H), 2.44 (s, 3H), 2.19 (s, 3H). LRMS [M+H]=358.2

Step B-4: 4-(2-(5-amino-8-methylbenzo[f][1,7]naphthyridin-2-yl)ethyl)-3-methylphenol (B-4)

To a stirred solution of 2-(4-methoxy-2-methylphenethyl)-8-methylbenzo[f][1,7]naphthyridin-5-amine (from the previous step) in methylene chloride (0.2 M) in an ice-water bath was added 1 N solution of $BBr_3$ (2 eq) in $CH_2Cl_2$ in a dropwise fashion. In 30 minutes the reaction was quenched with methanol and was concentrated en vaccuo to obtain a crude residue. The crude material was purified by flash chromatography on a COMBIFLASH® system (ISCO) using 0-20% methanol in dichloromethane to give 4-(2-(5-amino-8-methylbenzo[f][1,7]naphthyridin-2-yl)ethyl)-3-methylphenol (B-4) as a white solid. $^1$H NMR (DMSO-d$_6$): δ 8.99 (s, 1H), 8.75 (d, 1H), 8.60 (d, 1H), 8.27 (d, 1H), 7.28 (s, 1H), 7.09 (dd, 1H), 6.99 (bs, 2H), 6.88 (d, 1H), 6.49 (d, 1H), 6.42 (dd, 1H), 3.02-2.96 (dd, 2H), 2.86-2.81 (dd, 2H), 2.38 (s, 3H), 2.13 (s, 3H). LRMS [M+H]=344.2.

Preparation of (5-amino-2-(4-methoxy-2-methylphenethyl) benzo[f][1,7]naphthyridin-8-yl)methanol (2-1: see scheme 2)

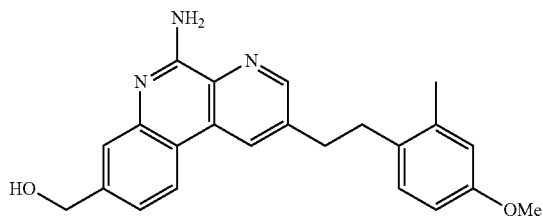 [SMILES: COc1ccc(CCc2cnc3c(N)nc4cc(CO)ccc4c3c2)c(C)c1]

Step 1: tert-butyl 5-((tert-butyldimethylsilyloxy)methyl)-2-chlorophenylcarbamate To a solution of 5-((tert-butyldimethylsilyloxy)methyl)-2-chloroaniline (commercially available) (1.0 equiv.) in THF (0.2 M) at 0° C. under $N_2$ atmosphere is added dropwise 1M NaHMDS (2.5 equiv.). The reaction is stirred for 15 minutes at 0° C., and a solution of di-tert-butyl dicarbonate in THF is added. The reaction is warmed to ambient temperature overnight. The solvent is evaporated, and the resulting residue is quenched with 0.1 N HCl aqueous solution. The aqueous suspension is extracted twice with EtOAc. The combined organic layers are washed with brine, dried over anhydrous $MgSO_4$, and concentrated in vacuo. The crude material is purified by flash chromatography on a COMBIFLASH® system (ISCO) using 0-30% EtOAc/Hexanes to give tert-butyl 5-((tert-butyldimethylsilyloxy)methyl)-2-chlorophenylcarbamate as a colorless oil.

Step 2: tert-butyl 5-((tert-butyldimethylsilyloxy)methyl)-2-(4,4,5,5-tetramethyl-1,3,2-dioxaborolan-2-yl)phenylcarbamate Tert-butyl 5-((tert-butyldimethylsilyloxy)methyl)-2-chlorophenylcarbamate (from the step 1) (1.0 equiv.), 4,4,4',4',5,5,5',5'-octamethyl-2,2'-bi(1,3,2-dioxaborolane) (3.0 equiv.), $Pd_2$ $dba_3$ (2.5%), XPhos (10%), and KOAc (3 equiv.) are mixed in dioxane (0.2 M) under $N_2$ atmosphere. The reaction is heated to 110° C. and stirred overnight. The resulting suspension is cooled to ambient temperature, diluted with ether, filtered through celite, and the filtrate is concentrated in vacuo. The combined organic layers are washed with brine, dried over anhydrous $MgSO_4$, and concentrated in vacuo. The crude material is purified by flash chromatography on a COMBIFLASH® system (ISCO) using 0-20% EtOAc/Hexanes to give tert-butyl 5-((tert-butyldimethylsilyloxy)methyl)-2-(4,4,5,5-tetramethyl-1,3,2-dioxaborolan-2-yl)phenylcarbamate as a white foam.

Step 3: 3-Chloro-5-((4-methoxy-2-methylphenyl)ethynyl)picolinonitrile

To a round bottom flask capped with septa was added 1-ethynyl-4-methoxy-2-methylbenzene (commercially available, 1.1 equiv.), 3,5-dichloropicolinonitrile (commercially available, 1 equiv.), triethylamine (5 equiv.), and anhydrous DMF (0.2 M). Vacuumed and nitrogen flushed for three times. CuI (0.05 equiv.) and bis(triphenylphosphine) dichloro-palladium(II) (0.05 equiv.) were added. The septum was replaced with a refluxing condenser and the flask was heated at 60° C. overnight under nitrogen atmosphere. Upon completion of the reaction as monitored by TLC, the content of the flask was loaded onto a large silica gel column pretreated with hexanes. Flash chromatography (silica gel, hexanes:EtOAc (1:4%)) afforded 3-chloro-5-((4-methoxy-2-methylphenyl)ethynyl)picolinonitrile.

Step 4: 8-((tert-butyldimethylsilyloxy)methyl)-2-((4-methoxy-2-methylphenyl)ethynyl)benzo[f][1,7]naphthyridin-5-amine To a round bottom flask with refluxing condenser were added 3-chloro-5-((4-methoxy-2-methylphenyl)ethynyl)picolinonitrile (from the step 3) (1 equiv.), tert-butyl 5-((tert-butyldimethylsilyloxy)methyl)-2-(4,4,5,5-tetramethyl-1,3,2-dioxaborolan-2-yl)phenylcarbamate (from step 2) (1.25 equiv.), $K_3PO_4$ (2 equiv.), tris(dibenzylideneacetone)dipalladium(0) (0.05 equiv.), and 2-Dicyclohexylphosphino-2',6'-dimethoxybiphenyl (0.1 equiv.). n-Butanol and water (5:2, 0.2 M) were added, and the content were degassed (vacuum followed by nitrogen flush) for three times. The reaction mixture was stirred vigorously under nitrogen at 100° C. overnight in an oil bath. The contents were cooled down and were taken up in water followed by extraction with methylene chloride. Combined organic layers were dried ($Na_2SO_4$) and concentrated. Flash chromatography (silica gel, 0-50% EtOAc in $CH_2Cl_2$) afforded 8-((tert-butyldimethylsilyloxy)methyl)-2-((4-methoxy-2-methylphenyl)ethynyl)benzo[f][1,7]naphthyridin-5-amine as a solid.

Step 5: 8-((tert-butyldimethylsilyloxy)methyl)-2-(4-methoxy-2-methylphenethyl)benzo[f][1,7]naphthyridin-5-amine To a round bottom flask was added 8-((tert-butyldimethylsilyloxy)methyl)-2-(4-methoxy-2-methylphenyl)ethynyl)benzo[f][1,7]naphthyridin-5-amine (from step 4) (1 equiv.) with a stirring bar. Ethanol and methylene chloride (1:2, 0.2 M) were added, followed by palladium in carbon (activated powder, wet, 10% on carbon, 0.1 equiv.). The contents were vacuumed followed by hydrogen flush for three times. The reaction mixture was stirred vigorously under hydrogen balloon at room temperature overnight. Afterwards the reaction mixture was filtered through a celite pad, and the celite pad was washed subsequently with methylene chloride and EtOAc until filtrate has no UV absorption. Combined organic washes were concentrated. Flash chromatography (silica gel, 0-50% EtOAc in $CH_2Cl_2$) afforded 8-((tert-butyldimethylsilyloxy)methyl)-2-(4-methoxy-2-methylphenethyl)benzo[f][1,7]naphthyridin-5-amine as a yellow solid.

Step 6: 5-amino-2-(4-methoxy-2-methylphenethyl)benzo[f][1,7]naphthyridin-8-yl)methanol (2-1)

(Tert-butyldimethylsilyloxy)methyl)-2-(4-methoxy-2-methylphenethyl)benzo[f][1,7]naphthyridin-5-amine (from step 5) (1.0 equiv.) and TBAF (1.1 equiv.) in THF is stirred at ambient temperature overnight. The reaction is quenched with saturated $NaHCO_3$. The two phases are separated, and the aqueous layer is extracted twice with $Et_2O$. The combined organic layers are washed with brine, dried over anhydrous $MgSO_4$, and concentrated in vacuo. The crude material is purified by flash chromatography on a COMBIFLASH® system (ISCO) using 0-5% MeOH/DCM to give 5-amino-2-(4-methoxy-2-methylphenethyl)benzo[f][1,7]naphthyridin-8-yl)methanol (2-1) as a white solid. $^1$H NMR (acetone-$d_6$): δ 8.79 (s, 1H), 8.73 (s, 1H), 8.35 (d, 1H), 7.61 (s, 1H), 7.33 (d, 1H), 7.09 (d, 1H), 6.75 (d, 1H), 6.68 (dd, 1H), 6.57 (br s, 2H), 4.47 (d, 2H), 4.32 (t, 1H), 3.58 (s, 3H), 3.17 (t, 2H), 3.04 (t, 2H), 2.30 (s, 3H). LRMS [M+H]=374.2.

Synthesis of Exemplary Compounds

Example 1

Table 1: Compound 6

Synthesis of 3 (2 (2 (4 (2 (5 amino-8-methylbenzo[f][1,7]naphthyridin-2-yl)ethyl)-3-methylphenoxy)ethoxy)ethoxy)-1,1-difluoropropylphosphonic acid (6)

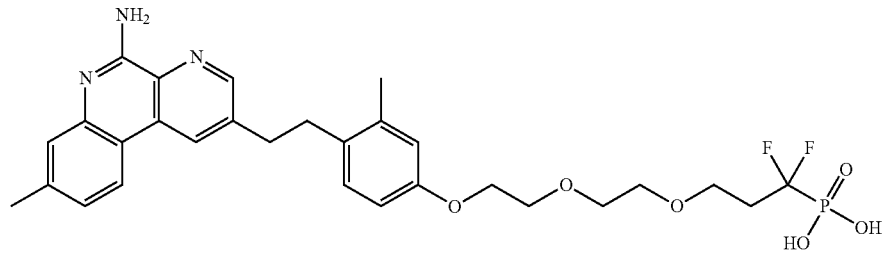 [SMILES: Cc1ccc2c(c1)nc(N)c1ncc(CCc3ccc(OCCOCCOCCC(F)(F)P(=O)(O)O)cc3C)cc12]

Scheme 1

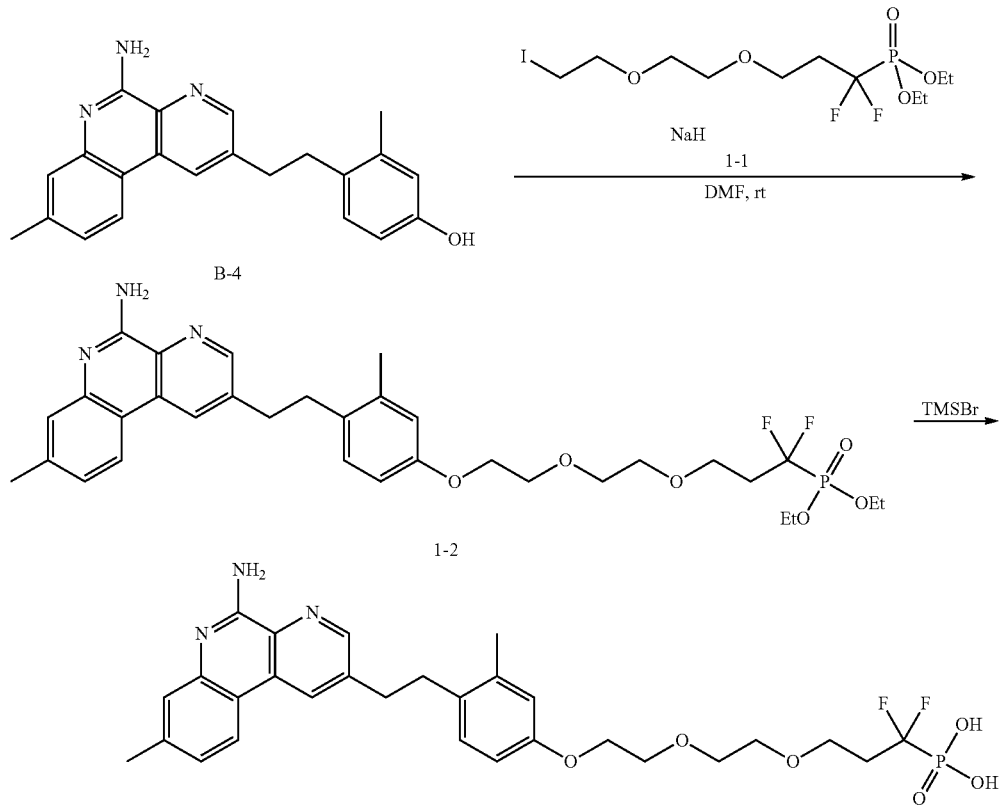

Step 1: diethyl 1,1-difluoro-3-(2-(2-iodoethoxy)ethoxy)propylphosphonate (I-1)

To a solution of diethyl difluoromethylphosphonate (1.0 equiv.) in THF (0.8 M) at −78° C. was slowly added a solution of LDA (2 M, 1.1 equiv.) in heptane/THF/ethylbenzene, and the mixture was vigorously stirred for 30 minutes. In a separate reaction flask, a solution of 1,2-bis(2-iodoethoxy)ethane (1.0 equiv.) in THF (0.8M) was cooled to −78° C. To this solution was transferred, by cannula, the freshly prepared alkyl lithium solution and the reaction mixture was allowed to stir for 1 hour at −78° C. At this point, the cooling bath was removed and the reaction mixture was allowed to warm to room temperature. The reaction mixture was then quenched with a 1 M aqueous solution of HCl. The resulting mixture was transferred to a separatory funnel and washed with $CH_2Cl_2$ three times. The combined organic layers were dried over anhydrous $Na_2SO_4$ and the volatiles were removed in vacuo. The resulting residue was purified by a COMBI-FLASH® system (ISCO) using $CH_2Cl_2$ to provide diethyl 1,1-difluoro-3-(2-(2-iodoethoxy)ethoxy)propylphosphonate (I-1) as a yellow oil. ¹H NMR (CDCl₃): δ 4.23-4.31 (m, 4H), 3.75-3.80 (m, 4H), 3.60-3.67 (m, 4H), 3.26 (t, 2H), 2.33-2.50 (m, 2H), 1.38 (t, 6H).

Step 2: Synthesis of diethyl 2-(2-(2-(4-(2-(5-amino-8-methylbenzo[f][1,7]naphthyridin-2-yl)ethyl)-3-methylphenoxy)ethoxy)ethoxy)-1,1-difluoroethylphosphonate (1-2)

To a solution of 4-(2-(5-amino-8-methylbenzo[f][1,7]naphthyridin-2-yl)ethyl)-3-methylphenol (B-4) (1.0 equiv.) in dimethylformamide (0.10 M) at 22° C. was added 60% dispersion of sodium hydride in mineral oil (1.5 equiv.) and the resulting mixture was allowed to stir for 30 minutes. At this point, diethyl 1,1-difluoro-3-(2-(2-iodoethoxy)ethoxy)propylphosphonate (1.2 equiv.) was added to this mixture. The reaction mixture was then allowed to stir for 18 hours, after which it was diluted with ethyl acetate and water. The biphasic layers were separated and the organic layer was washed twice with water. The organic layer was dried over anhydrous Na₂SO₄ and the volatiles were removed in vacuo. The resulting residue was purified by a COMBIFLASH® system (ISCO) using 0-50% ethyl acetate in hexanes gradient to provide diethyl 3-(2-(2-(4-(2-(5-amino-8-methylbenzo[f][1,7]naphthyridin-2-yl)ethyl)-3-methylphenoxy)ethoxy)ethoxy)-1,1-difluoropropylphosphonate (1-2) as a solid.

Step 3: Synthesis of 3-(2-(2-(4-(2-(5-amino-8-methylbenzo[f][1,7]naphthyridin-2-yl)ethyl)-3-methylphenoxy)ethoxy)ethoxy)-1,1-difluoroethylphosphonic acid (6)

To a solution of diethyl 3-(2-(2-(4-(2-(5-amino-8-methylbenzo[f][1,7]naphthyridin-2-yl)ethyl)-3-methylphenoxy)ethoxy)ethoxy)-1,1-difluoropropylphosphonate (1-2) (1.0 equiv.) in CH₂Cl₂ (0.10 M) at 0° C. was slowly added trimethylsilyl bromide (10 equiv.). After 1 hour the ice-bath was removed and the reaction mixture was allowed to stir at 22° C. for 18 hours. At this point, the volatiles were removed in vacuo and the resulting residue was purified by Reverse Phase-HPLC using a 20-90% 0.5 mM NH₄OAc (in MeCN) to 10 mM NH₄OAc (in water) gradient to deliver 3-(2-(2-(4-(2-(5-amino-8-methylbenzo[f][1,7]naphthyridin-2-yl)ethyl)-3-methylphenoxy)ethoxy)ethoxy)-1,1-difluoropropylphosphonic acid (6) as a solid. ¹H NMR (Dimethylsulfoxide-d₆): δ 8.83 (s, 1H), 8.68 (s, 1H), 8.32 (s, 1H), 7.34 (s, 1H), 7.14 (d, 1H), 7.09 (br, 2H), 7.08 (d, 1H), 6.74 (s, 1H), 6.68 (d, 1H), 4.01 (t, 2H), 3.70 (t, 2H), 3.61 (t, 2H), 3.54-3.59 (m, 2H), 3.48-3.50 (m, 2H), 3.07 (t, 2H), 2.94 (t, 2H), 2.43 (s, 3H), 2.25 (s, 3H), 2.06-2.21 (m, 2H). LRMS [M+H]=590.2

Example 2

Table 1: Compound 1

Synthesis of 3-(4-(2-(5-amino-8-methylbenzo[f][1,7]naphthyridin-2-yl)ethyl)-3-methylphenoxy)propylphosphonic acid (1)

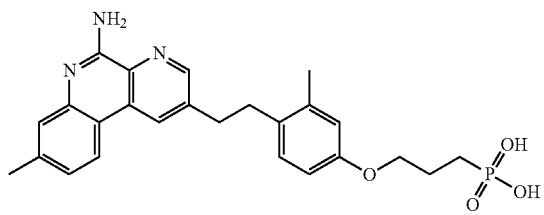

Step 1: Diethyl 3-(4-(2-(5-amino-8-methylbenzo[f][1,7]naphthyridin-2-yl)ethyl)-3-methylphenoxy)propylphosphonate Diethyl 3-(4-(2-(5-amino-8-methylbenzo[f][1,7]naphthyridin-2-yl)ethyl)-3-methylphenoxy)propylphosphonate was prepared according to the procedure described in Example 1—Step 2, but using commercially available diethyl 3-bromopropylphosphonate as the reagent.

Step 2: 3-(4-(2-(5-amino-8-methylbenzo[f][1,7]naphthyridin-2-yl)ethyl)-3-methylphenoxy)propylphosphonic acid 3-(4-(2-(5-amino-8-methylbenzo[f][1,7]naphthyridin-2-yl)ethyl)-3-methylphenoxy)propylphosphonic acid (1) was prepared according to the procedure described in Example 1—Step 3, but using diethyl 3-(4-(2-(5-amino-8-methylbenzo[f][1,7]naphthyridin-2-yl)ethyl)-3-methylphenoxy)propylphosphonate from the previous step. TFA was added to the ¹H NMR sample to solubilize the compound for analysis. The ¹H NMR (Dimethylsulfoxide-d₆) obtained for 3-(4-(2-(5-amino-8-methylbenzo[f][1,7]naphthyridin-2-yl)ethyl)-3-methylphenoxy)propylphosphonic acid (1) was: δ 9.72 (br, 1H), 9.01 (s, 1H), 8.96 (br, 1H), 8.85 (s, 1H), 8.54 (d, 1H, J=8.4 Hz), 7.54 (s, 1H), 7.42 (d, 1H, J=8.2 Hz), 7.08 (d, 1H, J=8.4 Hz), 6.74 (s, 1H), 6.66 (d, 1H, J=8.3 Hz), 3.95 (t, 2H, J=6.4 Hz), 3.14 (t, 2H, J=8.6 Hz), 2.97 (t, 2H, J=8.6 Hz), 2.50 (s, 3H), 2.27 (s, 3H), 1.91-1.81 (m, 2H), 1.67-1.56 (m, 2H). LRMS [M+H]=466.2

Example 3

Table 1: Compound 2

Synthesis of 4-(2-(5-amino-8-methylbenzo[f][1,7]naphthyridin-2-yl)ethyl)-3-methylphenyl dihydrogen phosphate (2)

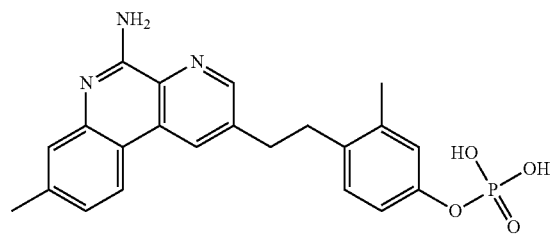 [SMILES: Cc1ccc2c(c1)nc(N)c1ncc(CCc3ccc(OP(=O)(O)O)cc3C)cc12]

Step 1: 4-(2-(5-amino-8-methylbenzo[f][1,7]naphthyridin-2-yl)ethyl)-3-methylphenyl dibenzyl phosphate 4-(2-(5-amino-8-methylbenzo[f][1,7]naphthyridin-2-yl)ethyl)-3-methylphenyl dibenzyl phosphate was prepared according to the procedure described in Example 1—Step 2, but using commercially available dibenzyl phosphorochloridate as the reagent.

Step 2: 4-(2-(5-amino-8-methylbenzo[f][1,7]naph-thyridin-2-yl)ethyl)-3-methylphenyl dihydrogen phosphate 4-(2-(5-amino-8-methylbenzo[f][1,7]naphthyridin-2-yl)ethyl)-3-methylphenyl dibenzyl phosphate (1.0 equiv.) and 10% Pd/C (20% equiv. by weight) in MeOH (0.66 M) was allowed to stir for 18 hours under a balloon of $H_2$. At this point the reaction mixture was passed through a pad of Celite, washing with a 2:1 mixture of $CHCl_3$:MeOH. The combined organic layers were dried over anhydrous $Na_2SO_4$ and the volatiles were removed in vacuo. The resulting residue was purified by Reverse Phase-HPLC using a 20-90% 0.5 mM $NH_4OAc$ (in MeCN) to 10 mM $NH_4OAc$ (in water) gradient to give 4-(2-(5-amino-8-methylbenzo[f][1,7]naphthyridin-2-yl)ethyl)-3-methylphenyl dihydrogen phosphate (2) as a solid. TFA was added to the $^1H$ NMR sample to solubilize the compound for analysis. $^1H$ NMR (Dimethylsulfoxide-$d_6$): δ 9.69 (br, 1H), 9.33 (s, 1H), 9.03 (s, 1H), 8.87 (s, 1H), 8.54 (d, 1H, J=8.4 Hz), 7.51 (s, 1H), 7.42 (d, 1H, J=9.4 Hz), 7.22 (s, 1H), 7.17 (d, 1H, J=8.3 Hz), 7.10 (s, 1H), 6.97 (s, 1H), 6.92 (d, 1H, J=6.1 Hz), 3.15 (t, 2H, J=6.8 Hz), 3.00 (t, 2H, J=6.8 Hz), 2.50 (s, 3H), 2.29 (s, 3H). LRMS [M+H]=424.1

Example 4

Table 1: Compound 3

Synthesis of (4-(2-(5-amino-8-methylbenzo[f][1,7]naphthyridin-2-yl)ethyl)-3-methylphenoxy)methylphosphonic acid (3)

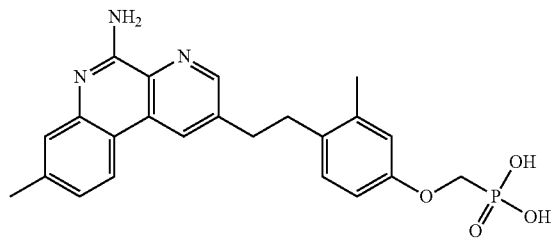 [SMILES: Cc1ccc2c(c1)nc(N)c1ncc(CCc3ccc(OCP(=O)(O)O)cc3C)cc12]

Step 1: diethyl (4-(2-(5-amino-8-methylbenzo[f][1,7]naphthyridin-2-yl)ethyl)-3-methylphenoxy)methylphosphonate Diethyl (4-(2-(5-amino-8-methylbenzo[f][1,7]naphthyridin-2-yl)ethyl)-3-methylphenoxy)methylphosphonate was prepared according to the procedure described in Example 1—Step 2, but using commercially available (diethoxyphosphoryl)methyl 4-methylbenzenesulfonate as the reagent.

Step 2: (4-(2-(5-amino-8-methylbenzo[f][1,7]naphthyridin-2-yl)ethyl)-3-methylphenoxy)methylphosphonic acid (4-(2-(5-amino-8-methylbenzo[f][1,7]naphthyridin-2-yl)ethyl)-3-methylphenoxy)methylphosphonic acid (3) was prepared according to the procedure described in Example 1—Step 3, but using diethyl (4-(2-(5-amino-8-methylbenzo[f][1,7]naphthyridin-2-yl)ethyl)-3-methylphenoxy)methylphosphonate from the previous step. The $^1H$ NMR (Dimethylsulfoxide-$d_6$) obtained for (4-(2-(5-amino-8-methylbenzo[f][1,7]naphthyridin-2-yl)ethyl)-3-methylphenoxy)methylphosphonic acid (3) was: δ 8.86 (br, 1H), 8.67 (br, 1H), 8.34 (d, 1H, J=10.4 Hz), 7.37 (s, 1H), 7.35 (s, 1H), 7.14 (d, 1H, J=8.4 Hz), 7.05 (d, 1H, J=8.2 Hz), 6.73 (s, 1H), 6.69 (d, 1H, J=8.6 Hz), 6.60 (s, 1H), 3.70-3.61 (m, 2H), 3.10 (t, 2H, J=8.8 Hz), 2.94 (t, 2H, J=8.8 Hz), 2.45 (s, 3H), 2.25 (s, 3H). LRMS [M+H]=438.2

Example 5

Table 1: Compound 4

Synthesis of 5-(4-(2-(5-amino-8-methylbenzo[f][1,7]naphthyridin-2-yl)ethyl)-3-methylphenoxy)-1,1-difluoropentylphosphonic acid (4)

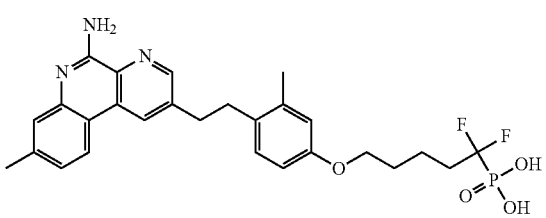 [SMILES: Cc1ccc2c(c1)nc(N)c1ncc(CCc3ccc(OCCCCC(F)(F)P(=O)(O)O)cc3C)cc12]

Step 1: diethyl 5-bromo-1,1-difluoropentylphosphonate

Diethyl 5-bromo-1,1-difluoropentylphosphonate was prepared according to the procedure described in Example 1—Step 1, but using commercially available 1,4-dibromobutane as the reagent.

Step 2: diethyl 5-(4-(2-(5-amino-8-methylbenzo[f][1,7]naphthyridin-2-yl)ethyl)-3-methylphenoxy)-1,1-difluoropentylphosphonate Diethyl 5-(4-(2-(5-amino-8-methylbenzo[f][1,7]naphthyridin-2-yl)ethyl)-3-methylphenoxy)-1,1-difluoropentylphosphonate was prepared according to the procedure described in Example 1—Step 2, but using diethyl 5-bromo-1,1-difluoropentylphosphonate from the previous step as the reagent.

Step 3: 5-(4-(2-(5-amino-8-methylbenzo[f][1,7]naphthyridin-2-yl)ethyl)-3-methylphenoxy)-1,1-difluoropentylphosphonic acid (4)

5-(4-(2-(5-amino-8-methylbenzo[f][1,7]naphthyridin-2-yl)ethyl)-3-methylphenoxy)-1,1-difluoropentylphosphonic acid (4) was prepared according to the procedure described in Example 1—Step 3, but using diethyl 5-(4-(2-(5-amino-8-methylbenzo[f][1,7]naphthyridin-2-yl)ethyl)-3-methylphenoxy)-1,1-difluoropentylphosphonate from step 2. TFA was added to the $^1H$ NMR sample to solubilize the compound for analysis. The $^1H$ NMR (Dimethylsulfoxide-$d_6$) obtained for 5-(4-(2-(5-amino-8-methylbenzo[f][1,7]naphthyridin-2-yl)ethyl)-3-methylphenoxy)-1,1-difluoropentylphosphonic acid (4) was: δ 9.70 (br, 1H), 9.33 (br, 1H), 8.98 (s, 1H), 8.84 (s, 1H), 8.50 (d, 1H, J=8.4 Hz), 7.52 (s, 1H), 7.40 (d, 1H, J=8.4 Hz), 7.06 (d, 1H, J=8.4 Hz), 6.74 (s, 1H), 6.68 (d, 1H, J=10.8 Hz), 3.91 (t, 2H, J=6.2 Hz), 3.14 (t, 2H, J=8.4 Hz), 2.97 (t, 2H, J=8.4 Hz), 2.50 (s, 3H), 2.27 (s, 3H), 2.13-1.94 (m, 2H), 1.78-1.70 (m, 2H), 1.66-1.59 (m, 2H). LRMS [M+H]=530.2

Example 6

Table 1: Compound 5

Synthesis of 4-(4-(2-(5-amino-8-methylbenzo[f][1,7]naphthyridin-2-yl)ethyl)-3-methylphenoxy)-1,1-difluorobutylphosphonic acid (5)

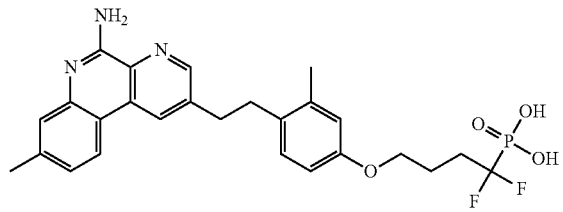 [SMILES: Cc1ccc2c(c1)nc(N)c1ncc(CCc3ccc(OCCCC(F)(F)P(=O)(O)O)cc3C)cc12]

Step 1: diethyl 4-bromo-1,1-difluorobutylphosphonate

Diethyl 4-bromo-1,1-difluorobutylphosphonate was prepared according to the procedure described in Example 1—Step 1, but using commercially available 1,3-dibromopropane as the reagent.

Step 2: diethyl 4-(4-(2-(5-amino-8-methylbenzo[f][1,7]naphthyridin-2-yl)ethyl)-3-methylphenoxy)-1,1-difluorobutylphosphonate Diethyl 4-(4-(2-(5-amino-8-methylbenzo[f][1,7]naphthyridin-2-yl)ethyl)-3-methylphenoxy)-1,1-difluorobutylphosphonate was prepared according to the procedure described in Example 1—Step 2, but using diethyl 4-bromo-1,1-difluorobutylphosphonate from the previous step as the reagent.

Step 3: 4-(4-(2-(5-amino-8-methylbenzo[f][1,7]naphthyridin-2-yl)ethyl)-3-methylphenoxy)-1,1-difluorobutylphosphonic acid (5)

4-(4-(2-(5-amino-8-methylbenzo[f][1,7]naphthyridin-2-yl)ethyl)-3-methylphenoxy)-1,1-difluorobutylphosphonic acid (5) was prepared according to the procedure described in Example 1—Step 3, but using diethyl 4-(4-(2-(5-amino-8-methylbenzo[f][1,7]naphthyridin-2-yl)ethyl)-3-methylphenoxy)-1,1-difluorobutylphosphonate from step 2. TFA was added to the $^1$H NMR sample to solubilize the compound for analysis. The $^1$H NMR (Dimethylsulfoxide-$d_6$) obtained for 4-(4-(2-(5-amino-8-methylbenzo[f][1,7]naphthyridin-2-yl)ethyl)-3-methylphenoxy)-1,1-difluorobutylphosphonic acid (5) was: δ 9.71 (br, 1H), 9.33 (br, 1H), 9.00 (s, 1H), 8.85 (s, 1H), 8.54 (d, 1H, J=8.4 Hz), 7.53 (s, 1H), 7.42 (d, 1H, J=8.3 Hz), 7.08 (d, 1H, J=8.4 Hz), 6.76 (s, 1H), 6.70 (d, 1H, J=8.3 Hz), 3.97 (t, 2H, J=6.2 Hz), 3.15 (t, 2H, J=8.5 Hz), 2.98 (t, 2H, J=8.5 Hz), 2.50 (s, 3H), 2.28 (s, 3H), 2.21-2.06 (m, 2H), 1.97-1.87 (m, 2H). LRMS [M+H]=516.2

Example 7

Table 1: Compound 7

Synthesis of 3 (2 (4 (2 (5 amino-8-methylbenzo[f][1,7]naphthyridin-2-yl)ethyl)-3-methylphenoxy)ethoxy)-1,1-difluoropropylphosphonic acid (7)

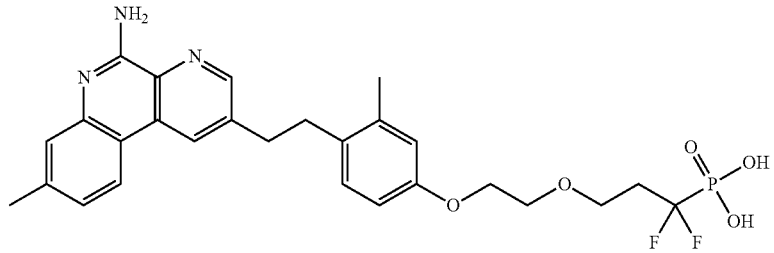 [SMILES: Cc1ccc2c(c1)nc(N)c1ncc(CCc3ccc(OCCOCCC(F)(F)P(=O)(O)O)cc3C)cc12]

Step 1: diethyl 3-(2-bromoethoxy)-1,1-difluoropropylphosphonate

An oven dried round-bottom flask was charged with dry THF (1.07 M) and diisopropylamine (2.0 equiv.). The flask was cooled in an acetone-dry ice bath, and was treated with n-butyllithium (1.6 equiv.) solution in cyclohexane (1.52 M) in dropwised fashion via syringe. The flask was transferred to an ice-water bath upon completion of the addition, and stirred for 30 minutes. The flask was then cooled back down to the dry ice-acetone bath, and was treated with a solution of diethyl difluoromethylphosphonate (1.0 equiv.) in HMPA (1:1 v/v) via syringe. The stirring was allowed to proceed for an hour. To the above reaction mixture, a cooled solution of 1-bromo-2-(2-bromoethoxy)ethane (3.0 equiv.) in THF (3 M) was added quickly through a syringe, and the reaction was allowed to stir for another 3 hours before quenching with 1 N HCl. The flask was warmed to room temperature, and the pH was adjusted to <4 with 1 N HCl. The mixture was extracted with EtOAc (3×). The combined organic extracts were dried over anhydrous $Na_2SO_4$, and concentrated in vacuo. The crude material was purified by Combiflash using 0-75% EtOAc in hexanes, followed by RP-HPLC (0.035% TFA in ACN:0.05% TFA in H₂O, C18 column), to afford diethyl 3-(2-bromoethoxy)-1,1-difluoropropylphosphonate as a pale yellow oil.

Step 2: diethyl 3-(2-(4-(2-(5-amino-8-methylbenzo [f][1,7]naphthyridin-2-yl)ethyl)-3-methylphenoxy) ethoxy)-1,1-difluoropropylphosphonate Diethyl 3-(2-(4-(2-(5-amino-8-methylbenzo[f][1,7]naphthyridin-2-yl)ethyl)-3-methylphenoxy)ethoxy)-1,1-difluoropropylphosphonate was prepared according to the procedure described in Example 1—Step 2, but using diethyl 3-(2-bromoethoxy)-1,1-difluoropropylphosphonate from the previous step as the reagent.

Step 3: 3-(2-(4-(2-(5-amino-8-methylbenzo[f][1,7] naphthyridin-2-yl)ethyl)-3-methylphenoxy)ethoxy)-1,1-difluoropropylphosphonic acid 3-(2-(4-(2-(5-amino-8-methylbenzo[f][1,7]naphthyridin-2-yl)ethyl)-3-methylphenoxy)ethoxy)-1,1-difluoropropylphosphonic acid (7) was prepared according to the procedure described in Example 1—Step 3, but using Diethyl 3-(2-(4-(2-(5-amino-8-methylbenzo[f][1,7]naphthyridin-2-yl)ethyl)-3-methylphenoxy)ethoxy)-1,1-difluoropropylphosphonate from the previous step 2. The ¹H NMR (Dimethylsulfoxide-d₆) obtained for 3-(2-(4-(2-(5-amino-8-methylbenzo[f][1,7]naphthyridin-2-yl)ethyl)-3-methylphenoxy)ethoxy)-1,1-difluoropropylphosphonic acid (7) was: δ 8.83 (s, 1H), 8.69 (s, 1H), 8.35 (d, 1H, J=8.3 Hz), 7.36 (s, 1H), 7.26 (br, 2H), 7.16 (d, 1H, J=8.3 Hz), 7.07 (d, 1H, J=8.4 Hz), 6.75 (s, 1H), 6.66 (d, 1H, 8.3 J=Hz), 4.00 (t, 2H, J=4.4 Hz), 3.67 (t, 2H, J=6.7 Hz), 3.08 (t, 2H, J=6.8 Hz), 2.94 (t, 2H, J=6.8 Hz), 2.44 (s, 3H), 2.25 (s, 3H), 2.22-2.09 (m, 2H). LRMS [M+H]=546.2

Example 8

Table 1: Compound 8

Synthesis of 2-(4-((4-(2-(5-amino-8-methylbenzo[f] [1,7]naphthyridin-2-yl)ethyl)-3-methylphenoxy) methyl)phenyl)-1,1-difluoroethylphosphonic acid (8)

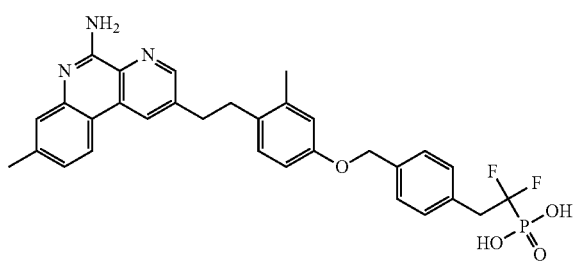 [SMILES: Cc1ccc2c(c1)nc(N)c1ncc(CCc3ccc(OCc4ccc(CC(F)(F)P(=O)(O)O)cc4)cc3C)cc12]

Step 1: diethyl 2-(4-(bromomethyl)phenyl)-1,1-difluoroethylphosphonate

Diethyl 2-(4-(bromomethyl)phenyl)-1,1-difluoroethylphosphonate was prepared according to the procedure described in Example 1—Step 1, but using commercially available 1,4-bis(bromomethyl)benzene as the reagent.

Step 2: diethyl 2-(4-((4-(2-(5-amino-8-methylbenzo [f][1,7]naphthyridin-2-yl)ethyl)-3-methylphenoxy) methyl)phenyl)-1,1-difluoroethylphosphonate Diethyl 2-(4-((4-(2-(5-amino-8-methylbenzo[f][1,7]naphthyridin-2-yl)ethyl)-3-methylphenoxy)methyl)phenyl)-1,1-difluoroethylphosphonate was prepared according to the procedure described in Example 1—Step 2, but using diethyl 2-(4-(bromomethyl)phenyl)-1,1-difluoroethylphosphonate from the previous step as the reagent.

Step 3: 2-(4-((4-(2-(5-amino-8-methylbenzo[f][1,7] naphthyridin-2-yl)ethyl)-3-methylphenoxy)methyl) phenyl)-1,1-difluoroethylphosphonic acid 2-(4-((4-(2-(5-amino-8-methylbenzo[f][1,7]naphthyridin-2-yl)ethyl)-3-methylphenoxy)methyl)phenyl)-1,1-difluoroethylphosphonic acid (8) was prepared according to the procedure described in Example 1—Step 3, but using diethyl 2-(4-((4-(2-(5-amino-8-methylbenzo[f][1,7]naphthyridin-2-yl)ethyl)-3-methylphenoxy)methyl)phenyl)-1,1-difluoroethylphosphonate from the previous step 3. TFA was added to the ¹H NMR sample to solubilize the compound for analysis. The ¹H NMR (Dimethylsulfoxide-d₆) obtained for 2-(4-((4-(2-(5-amino-8-methylbenzo[f][1,7]naphthyridin-2-yl)ethyl)-3-methylphenoxy)methyl)phenyl)-1,1-difluoroethylphosphonic acid (8) was: δ 9.71 (br, 1H), 9.35 (br, 1H), 9.01 (s, 1H), 8.86 (s, 1H), 8.54 (d, 1H, J=8.4 Hz), 7.53 (s, 1H), 7.44 (d, 1H), 7.40 (s, 1H), 7.38 (s, 1H), 7.29 (d, 1H, J=8.0 Hz), 7.24 (s, 1H), 7.11 (s, 1H), 7.09 (s, 1H), 6.99 (s, 1H), 6.85 (s, 1H), 6.76 (d, 1H, J=8.3 Hz), 5.04 (s, 2H), 3.84-3.73 (m, 2H), 3.15 (t, 2H, J=8.5 Hz), 2.99 (t, 2H, J=8.5 Hz), 2.50 (s, 3H), 2.29 (s, 3H). LRMS [M+H]=578.2

Example 9

Table 1: Compound 9

Synthesis of 2-(5-amino-2-(4-methoxy-2-methylphenethyl)benzo[f][1,7]naphthyridin-8-yl)-1,1-difluoro-2-oxoethylphosphonic acid (9)

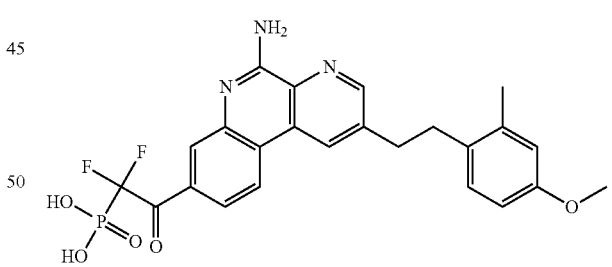

Scheme 2

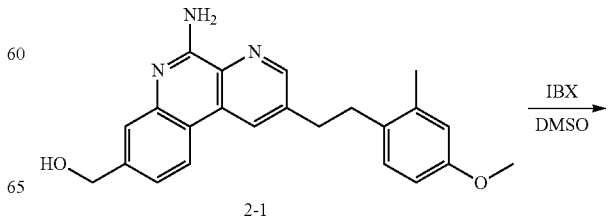

2-1

-continued

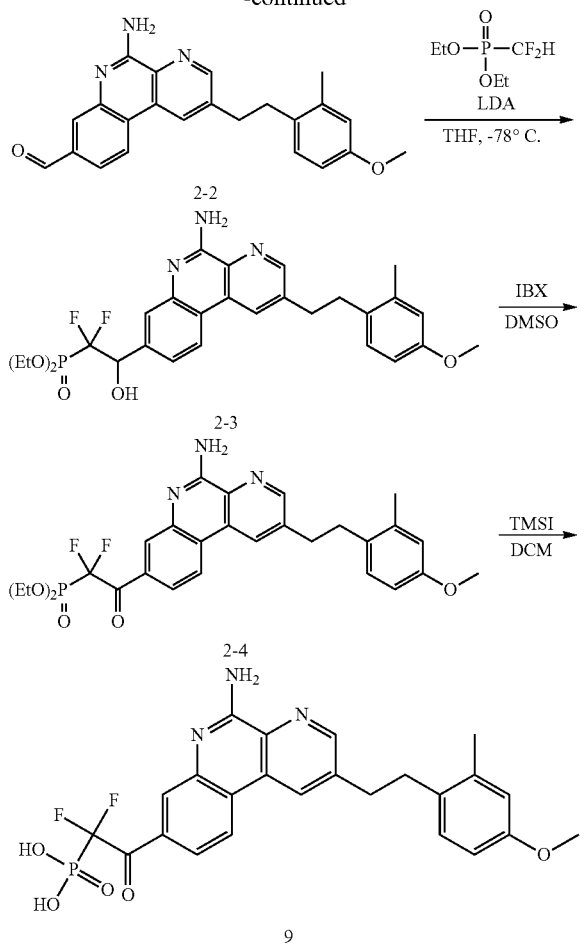

Step 1: 5-amino-2-(4-methoxy-2-methylphenethyl)benzo[f][1,7]naphthyridine-8-carbaldehyde (2-2)

To a solution of (5-amino-2-(4-methoxy-2-methylphenethyl)benzo[f][1,7]naphthyridin-8-yl)methanol (2-1), 1.0 equiv. in DMSO (0.15 M) at room temperature was added IBX (1.5 equiv.). The reaction was stirred for 2.5 hours and then diluted with water. The aqueous layer was extracted with 2% MeOH/DCM (4×). The combined organic layers were dried over anhydrous $MgSO_4$ and concentrated in vacuo. The resulting residue was purified by a COMBIFLASH® system (ISCO) using a gradient of 0-5% MeOH/DCM to provide 5-amino-2-(4-methoxy-2-methylphenethyl)benzo[f][1,7]naphthyridine-8-carbaldehyde (2-2) as a solid.

Step 2: diethyl 2-(5-amino-2-(4-methoxy-2-methylphenethyl)benzo[f][1,7]naphthyridin-8-yl)-1,1-difluoro-2-hydroxyethylphosphonate (2-3)

To a solution of diethyl difluoromethylphosphonate (3.0 equiv.) in THF (0.3 M) at −78° C. under nitrogen atmosphere was added dropwise 2M LDA (3.0 equiv., commercial grade). The reaction was stirred at −78° C. for 25 min, and a solution of 5-amino-2-(4-methoxy-2-methylphenethyl)benzo[f][1,7]naphthyridine-8-carbaldehyde (2-2) (1.0 equiv.) in THF (0.1 M) was added slowly. The reaction was stirred at −78° C. for 1 hour, 0° C. for 1 hour, and then warmed to room temperature over 30 minutes. The reaction was quenched with saturated aqueous ammonium chloride solution and extracted twice with ethyl acetate. The combined organic layers were washed with brine, dried over anhydrous $MgSO_4$, and concentrated in vacuo. The resulting residue was purified by a COMBIFLASH® system (ISCO) using a gradient of 0-5% MeOH/DCM to provide diethyl 2-(5-amino-2-(4-methoxy-2-methylphenethyl)benzo[f][1,7]naphthyridin-8-yl)-1,1-difluoro-2-hydroxyethylphosphonate (2-3) as a solid.

Step 3: diethyl 2-(5-amino-2-(4-methoxy-2-methylphenethyl)benzo[f][1,7]naphthyridin-8-yl)-1,1-difluoro-2-oxoethylphosphonate (2-4)

To a solution of diethyl 2-(5-amino-2-(4-methoxy-2-methylphenethyl)benzo[f][1,7]naphthyridin-8-yl)-1,1-difluoro-2-hydroxyethylphosphonate (2-3) (1.0 equiv.) in 1:1 DMSO/ethyl acetate (0.07 M) was added IBX (1.5 equiv.). The reaction was heated to 80° C. for 1 hour, and then cooled to room temperature. The mixture was diluted with ethyl acetate and filtered through celite. The filtrate was washed with water (2×), brine, dried over anhydrous $MgSO_4$, and concentrated in vacuo. The resulting residue was purified by a COMBIFLASH® system (ISCO) using a gradient of 0-5% MeOH/DCM to provide diethyl 2-(5-amino-2-(4-methoxy-2-methylphenethyl)benzo[f][1,7]naphthyridin-8-yl)-1,1-difluoro-2-oxoethylphosphonate (2-4) as a solid.

Step 4: 2-(5-amino-2-(4-methoxy-2-methylphenethyl)benzo[f][1,7]naphthyridin-8-yl)-1,1-difluoro-2-oxoethylphosphonic acid (9)

To a solution of diethyl 2-(5-amino-2-(4-methoxy-2-methylphenethyl)benzo[f][1,7]naphthyridin-8-yl)-1,1-difluoro-2-oxoethylphosphonate (2-4) (1.0 equiv.) in DCM (0.05 M) at 0° C. was added TMSI (5.0 equiv.). The reaction was warmed to room temperature over 2 hours, and more TMSI was added (2.5 equiv.). The reaction was stirred for another 30 minutes, and then quenched with small amounts of water. The DCM was removed by evaporation, and then added DMSO/water. The mixture was adjusted to pH 9 and directly purified on RP-HPLC using a C18 column, eluting with 10-40% 95:5 (MeCN/5 mM $NH_4OAc$) in 10 mM $NH_4OAc$ (pH 9) gradient. The fractions containing the product were combined and concentrated in vacuo to give 2-(5-amino-2-(4-methoxy-2-methylphenethyl)benzo[f][1,7]naphthyridin-8-yl)-1,1-difluoro-2-oxoethylphosphonic acid (9) as a solid. $^1$H NMR (Dimethylsulfoxide-$d_6$): δ 8.82 (s, 1H), 8.5 (br, 1H), 8.44 (s, 1H), 8.2 (br, 1H), 7.98 (d, 1H, J=8.2 Hz), 7.2 (br, 2H), 7.05 (d, 1H, J=8.3 Hz), 6.73 (s, 1H), 6.67 (d, 1H, J=8.3 Hz), 3.70 (s, 3H), 2.99-2.87 (m, 4H), 2.25 (s, 3H). LRMS [M+H]=502.2

Example 10

Table 1: Compound 10

Synthesis of (E)-2-(5-Amino-2-(4-methoxy-2-methylphenethyl)benzo[f][1,7]naphthyridin-8-yl)vinylphosphonic acid (10)

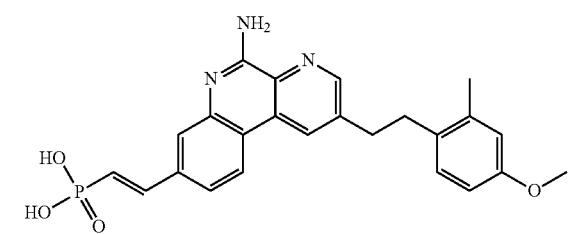 [SMILES: COc1ccc(CCc2cnc3c(N)nc4cc(/C=C/P(=O)(O)O)ccc4c3c2)c(C)c1]

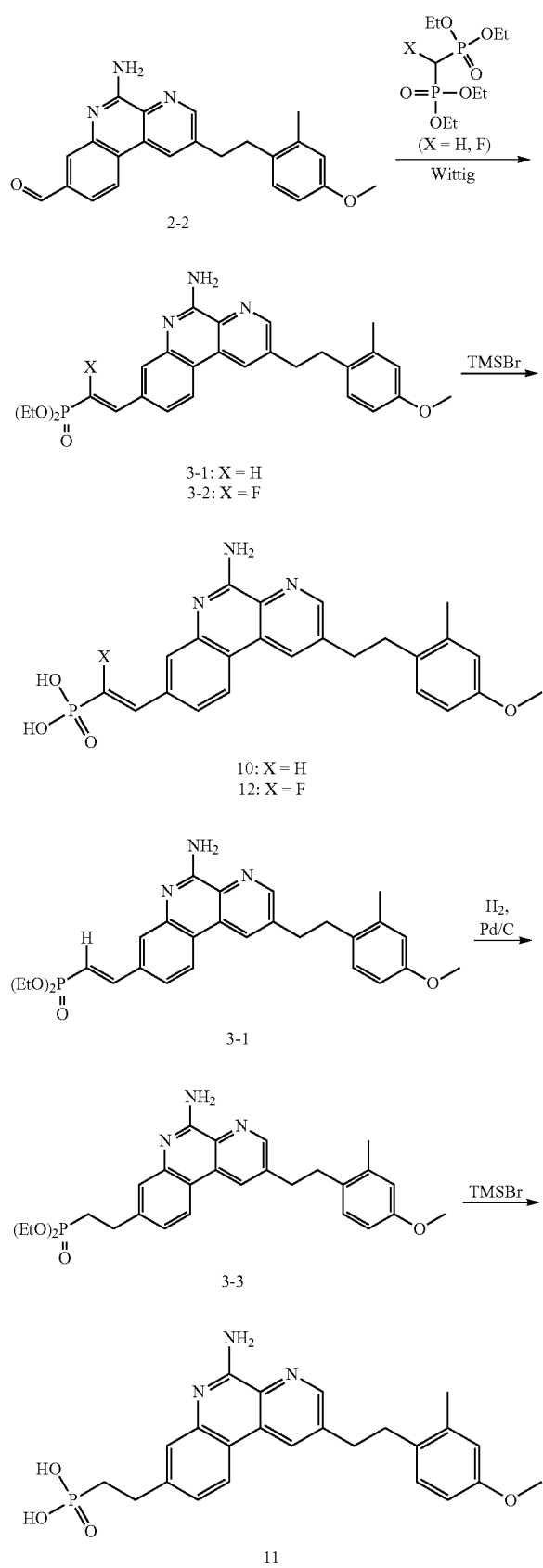

Scheme 3

Step 1: (E)-diethyl 2-(5-amino-2-(4-methoxy-2-methylphenethyl)benzo[f][1,7]naphthyridin-8-yl)vinylphosphonate (3-1)

To a stirred suspension of NaH (1.2 equiv.) in THF (0.1 M) cooled at 0° C. was added a solution of tetraethyl methylenediphosphonate (1.3 equiv.) in THF (0.21 M). To the resulting reaction mixture was added a solution of 5-amino-2-(4-methoxy-2-methylphenethyl)benzo[f][1,7]naphthyridine-8-carbaldehyde (2-2) (Example 9—Step 1) (1.0 equiv.) in THF (0.08 M). The reaction was stirred at room temperature for 30 minutes, then solvents were removed in vacuo, and the resulting residue was purified by a COMBIFLASH® system (ISCO) using a gradient of 0-5% MeOH/DCM to provide (E)-diethyl 2-(5-amino-2-(4-methoxy-2-methylphenethyl)benzo[f][1,7]naphthyridin-8-yl)vinylphosphonate (3-1) as a colorless solid.

Step 2: (E)-2-(5-amino-2-(4-methoxy-2-methylphenethyl)benzo[f][1,7]naphthyridin-8-yl)vinylphosphonic acid (10)

To a solution of (E)-diethyl 2-(5-amino-2-(4-methoxy-2-methylphenethyl)benzo[f][1,7]naphthyridin-8-yl)vinylphosphonate (3-1) (1.0 equiv.) in DCM (0.095 M) at 0° C. was added TMSBr (10 equiv.). The reaction was warmed to room temperature over 2 hours, and then quenched with small amounts of MeOH. The DCM was removed by evaporation, and then added DMSO/water. The mixture was adjusted to pH 9 and directly purified on RP-HPLC using a C18 column, eluting with 10-40% 95:5 (MeCN/5 mM $NH_4OAc$) in 10 mM $NH_4OAc$ (pH 9) gradient. The fractions containing the product were combined and concentrated in vacuo to give the (E)-2-(5-amino-2-(4-methoxy-2-methylphenethyl)benzo[f][1,7]naphthyridin-8-yl)vinylphosphonic acid (10) as a solid.
$^1$H NMR (Dimethylsulfoxide-$d_6$): δ 9.76 (s, 1H), 9.33 (s, 1H), 9.03 (s, 1H), 8.82 (s, 1H), 8.60 (d, 1H, J=8.4 Hz), 7.87 (d, 1H, J=8.4 Hz), 7.78 (s, 1H), 7.31 (dd, 1H, J=17.6, 21.6 Hz), 7.03 (d, 1H, J=8.4 Hz), 6.69 (m, 2H), 6.61 (dd, 1H, J=2.8, 8.4 Hz), 3.64 (s, 3H), 3.14-3.06 (m, 2H), 2.97-2.91 (m, 2H), 2.23 (s, 3H). LRMS [M+H]=450.2

Example 11

Table 1: Compound 11

Synthesis of 2-(5-amino-2-(4-methoxy-2-methylphenethyl)benzo[f][1,7]naphthyridin-8-yl)ethylphosphonic acid (11)

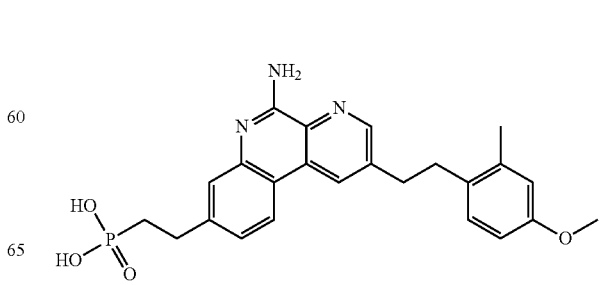

Step 1: diethyl 2-(5-amino-2-(4-methoxy-2-methylphenethyl)benzo[f][1,7]naphthyridin-8-yl)ethylphosphonate (3-3)

To a solution of (E)-diethyl 2-(5-amino-2-(4-methoxy-2-methylphenethyl)benzo[f][1,7]naphthyridin-8-yl)vinylphosphonate (3-1) (Example 10—Step 1) (1.0 equiv.) in DCM (0.05 M) and EtOH (0.08 M) was added 10% palladium on carbon (0.09 equiv.). A reaction vessel was charged with a hydrogen balloon and stirred at room temperature overnight. After the reaction was complete as monitored by LCMS, solvents were removed, and the resulting residue was purified by a COMBIFLASH® system (ISCO) using a gradient of 0-5% MeOH/DCM to provide diethyl 2-(5-amino-2-(4-methoxy-2-methylphenethyl)benzo[f][1,7]naphthyridin-8-yl)ethylphosphonate (3-3).

Step 2: 2-(5-amino-2-(4-methoxy-2-methylphenethyl)benzo[f][1,7]naphthyridin-8-yl)ethylphosphonic acid (11)

To a solution of diethyl 2-(5-amino-2-(4-methoxy-2-methylphenethyl)benzo[f][1,7]naphthyridin-8-yl)ethylphosphonate (3-3) (1.0 equiv.) in DCM (0.02 M) at 0° C. was added TMSBr (10 equiv.). The reaction was warmed to room temperature over 2 hours, and then quenched with small amounts of MeOH. The DCM was removed by evaporation, and then DMSO/water was added. The mixture was adjusted to pH 9 and directly purified on RP-HPLC using a C18 column, eluting with 10-40% 95:5 (MeCN/5 mM $NH_4OAc$) in 10 mM $NH_4OAc$ (pH 9) gradient. The fractions containing the product were combined and concentrated in vacuo to give 2-(5-amino-2-(4-methoxy-2-methylphenethyl)benzo[f][1,7]naphthyridin-8-yl)ethylphosphonic acid (11) as a solid. $^1$H NMR (Dimethylsulfoxide-$d_6$): δ 9.66 (s, 1H), 9.30 (s, 1H), 8.95 (s, 1H), 8.78 (s, 1H), 8.50 (d, 1H, J=8.4 Hz), 7.54 (s, 1H), 7.45 (d, 1H, J=8.4 Hz), 7.02 (d, 1H, J=8.4 Hz), 6.69 (d, 1H, J=2.8 Hz), 6.61 (dd, 1H, J=2.8, 8.4 Hz), 3.64 (s, 3H), 3.14-3.06 (m, 2H), 3.00-2.90 (m, 4H), 2.22 (s, 3H), 2.02-1.92 (m, 2H). LRMS [M+H]=452.2

Example 12

Table 1: Compound 12

Synthesis of (E)-2-(5-Amino-2-(4-methoxy-2-methylphenethyl)benzo[f][1,7]naphthyridin-8-yl)-1-fluorovinylphosphonic acid (12)

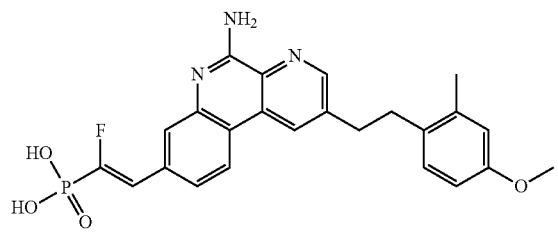 [SMILES: COc1ccc(CCc2cnc3c(N)nc4cc(/C=C(\F)P(=O)(O)O)ccc4c3c2)c(C)c1]

Step 1: (E)-Diethyl 2-(5-amino-2-(4-methoxy-2-methylphenethyl)benzo[f][1,7]naphthyridin-8-yl)-1-fluorovinylphosphonate (3-2)

To a stirred solution of tetraethyl fluoromethylenediphosphonate (2.5 equiv.) in THF (0.27 M) cooled at −78° C. was added LDA solution (1.8 M in ethylbenzene/pentane/hexane, 2.0 equiv.). The resulting reaction mixture was warmed up to room temperature and stirred for 30 minutes, before it was cooled back down to −78° C. A solution of 5-amino-2-(4-methoxy-2-methylphenethyl)benzo[f][1,7]naphthyridine-8-carbaldehyde (2-2) (Example 9–Step 1) (1.0 equiv.) in THF (0.18 M) was added, and the reaction mixture was allowed to warm up to room temperature slowly. The reaction was quenched with saturated $NH_4Cl$ solution. Aqueous phase was extracted with DCM (3×). The combined organic phases were combined and concentrated in vacuo. The residue was purified by a COMBIFLASH® system (ISCO) using a gradient of 0-5% MeOH/DCM to provide (E)-Diethyl 2-(5-amino-2-(4-methoxy-2-methylphenethyl)benzo[f][1,7]naphthyridin-8-yl)-1-fluorovinylphosphonate (3-2) as a colorless solid.

Step 2: (E)-2-(5-Amino-2-(4-methoxy-2-methylphenethyl)benzo[f][1,7]naphthyridin-8-yl)-1-fluorovinylphosphonic acid (12)

To a solution of (E)-diethyl 2-(5-amino-2-(4-methoxy-2-methylphenethyl)benzo[f][1,7]naphthyridin-8-yl)-1-fluorovinylphosphonate (3-2) (1.0 equiv.) in DCM (0.05 M) at 0° C. was added TMSBr (10 equiv.). The reaction was warmed to room temperature over 2 hours, and then quenched with small amounts of MeOH. The DCM was removed by evaporation, and then DMSO/water was added. The mixture was adjusted to pH 9 and directly purified on RP-HPLC using a C18 column, eluting with 10-40% 95:5 (MeCN/5 mM $NH_4OAc$) in 10 mM $NH_4OAc$ (pH 9) gradient. The fractions containing the product were combined and concentrated in vacuo to give (E)-2-(5-Amino-2-(4-methoxy-2-methylphenethyl)benzo[f][1,7]naphthyridin-8-yl)-1-fluorovinylphosphonic acid (12) as a solid. $^1$H NMR (Dimethylsulfoxide-$d_6$): δ 9.80 (s, 1H), 9.41 (s, 1H), 9.05 (s, 1H), 8.87 (s, 1H), 8.65 (d, 1H, J=8.8 Hz), 8.08 (s, 1H), 7.76 (d, 1H, J=8.4 Hz), 7.08 (d, 1H, J=8.4 Hz), 7.02 (d, 1H, J=8.4 Hz), 6.83-6.65 (m, 2H), 3.69 (s, 3H), 3.18-3.12 (m, 2H), 3.02-2.96 (m, 4H), 2.28 (s, 3H). LRMS [M+H]=468.1

Example 13

Table 1: Compound 13

Synthesis of 3-((4-(2-(5-amino-8-methylbenzo[f][1,7]naphthyridin-2-yl)ethyl)-3-methylphenoxy)methyl)phenylphosphonic acid (13)

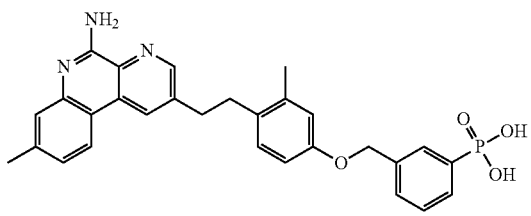 [SMILES: Cc1ccc2c(c1)nc(N)c1ncc(CCc3ccc(OCc4cccc(P(=O)(O)O)c4)cc3C)cc12]

Scheme 4

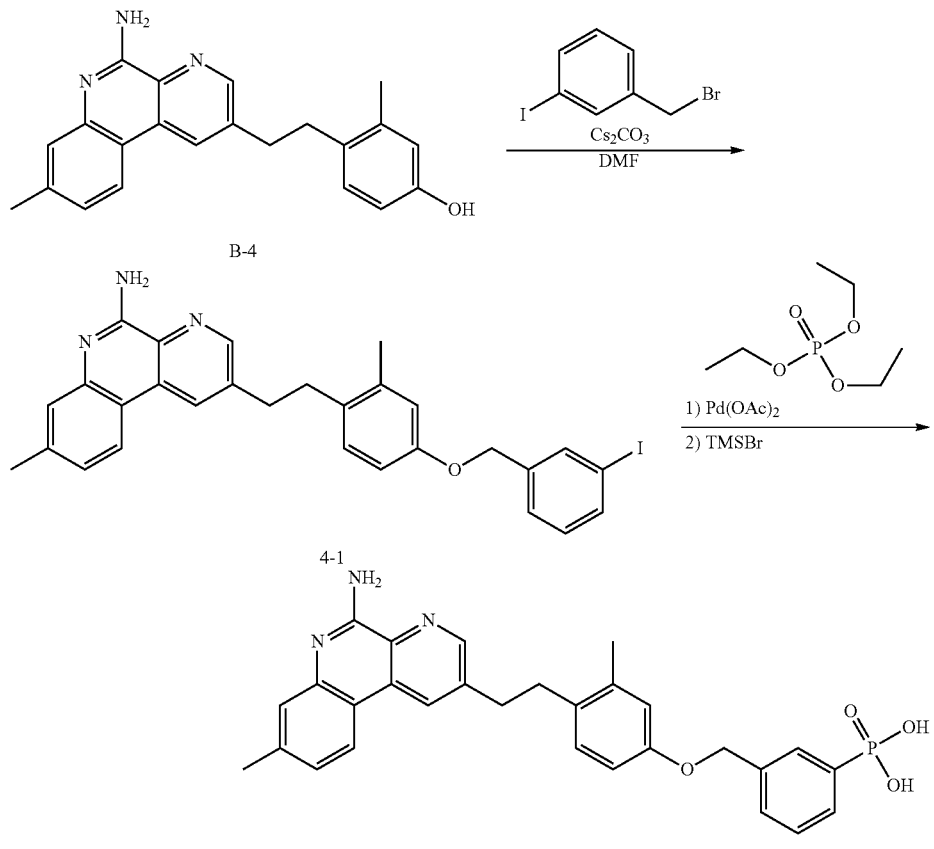

Step 1: 2-(4-(3-iodobenzyloxy)-2-methylphenethyl)-8-methylbenzo[f][1,7]naphthyridin-5-amine (4-1)

To a solution of 4-(2-(5-amino-8-methylbenzo[f][1,7] naphthyridin-2-yl)ethyl)-3-methylphenol (B-4), 1.0 equiv. in dimethylformamide (0.10 M) at 22° C. was added cesium carbonate (1.5 equiv.) and the resulting mixture was allowed to stir for 30 minutes. At this point, 1-(bromomethyl)-3-iodobenzene (1.5 equiv.) was added to this mixture. The reaction mixture was allowed to stir at 55° C. for 18 hours, after which it was diluted with ethyl acetate and water. The biphasic layers were separated and the organic layer was washed twice with water. The organic layer was dried over anhydrous $Na_2SO_4$ and the volatiles were removed in vacuo. The resulting residue was purified by a COMBIFLASH® system (ISCO) using 0-50% ethyl acetate in hexanes gradient to provide 2-(4-(3-iodobenzyloxy)-2-methylphenethyl)-8-methylbenzo[f][1,7]naphthyridin-5-amine (4-1) as a solid.

Step 2: 3-((4-(2-(5-amino-8-methylbenzo[f][1,7] naphthyridin-2-yl)ethyl)-3-methylphenoxy)methyl) phenylphosphonic acid (13)

To a stirred solution of 2-(4-(3-iodobenzyloxy)-2-methylphenethyl)-8-methylbenzo[f][1,7]naphthyridin-5-amine (1.0 equiv.) in triethyl phosphate (1.05 eq.) was added palladium acetate (0.08 eq.). The resulting reaction mixture was heated at 90° C. overnight. After the reaction was cooled down to room temperature, the residue was taken up in DCM (0.27 M) at 0° C., and was treated with TMSBr (11 equiv.). The reaction was warmed to room temperature over 2 hours, and then quenched with small amounts of MeOH. The DCM was removed by evaporation, and then added DMSO/water.

The mixture was adjusted to pH 9 and directly purified on RP-HPLC using a C18 column, eluting with 10-40% 95:5 (MeCN/5 mM $NH_4OAc$) in 10 mM $NH_4OAc$ (pH 9) gradient. The fractions containing the product were combined and concentrated in vacuo to give 3-((4-(2-(5-amino-8-methylbenzo[f][1,7]naphthyridin-2-yl)ethyl)-3-methylphenoxy) methyl)phenylphosphonic acid (13) as a solid. $^1H$ NMR (Dimethylsulfoxide-$d_6$): δ 8.84 (s, 1H), 8.72 (s, 1H), 8.35 (d, 1H, J=8.4 Hz), 7.67 (d, 1H, J=12 Hz), 7.60-7.54 (m, 1H), 7.30-7.20 (m, 2H), 7.15 (d, 1H, J=8.4 Hz), 7.11 (d, 1 H, J=8.4 Hz), 7.04 (s, 1H), 6.84 (s, 1H), 6.77 (m, 1H), 4.99 (s, 2H), 3.12-2.92 (m, 4H), 2.44 (s, 3 H), 2.27 (s, 3H). LRMS [M+H]= 514.2

Example 14

Table 1: Compound 14

Synthesis of 5-amino-2-(4-methoxy-2-methylphenethyl)benzo[f][1,7]naphthyridine-8-carbonylphosphonic acid (14)

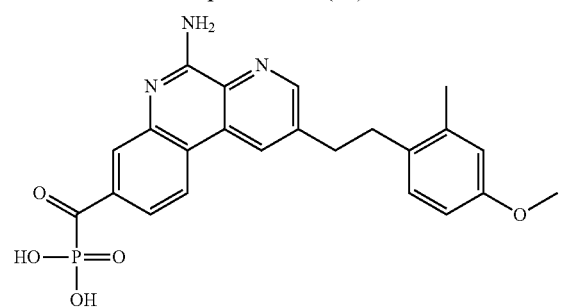

Scheme 5

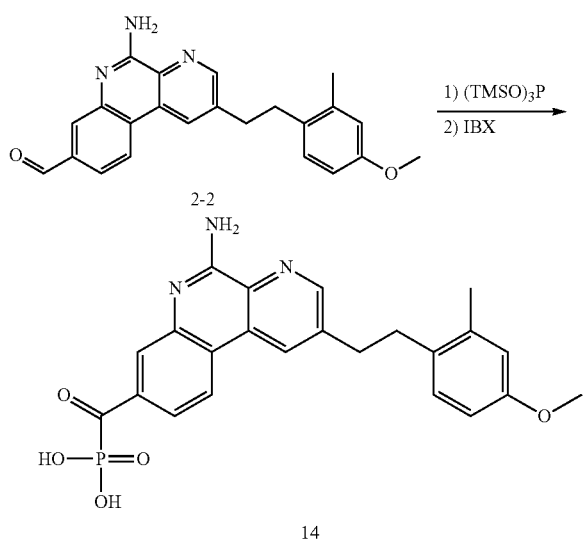

To a stirred suspension of 5-amino-2-(4-methoxy-2-methylphenethyl)benzo[f][1,7]naphthyridine-8-carbaldehyde (2-2) (Example 9—Step 1) (1.0 equiv.) in toluene (0.27 M) was added tris(trimethylsilyl) phosphite (1.0 equiv.). The reaction was stirred at 80° C. for 60 minutes, then solvents were removed, and the resulting residue was taken up in DMSO (0.27 M), and IBX (1.5 equiv.) was added. The reaction was stirred at room temperature for 2.5 hour, and was filtered and directly purified on RP-HPLC using a C18 column, eluting with 10-40% 95:5 (MeCN/5 mM NH$_4$OAc) in 10 mM NH$_4$OAc (pH 9) gradient. The fractions containing the product were combined and concentrated in vacuo to give 5-amino-2-(4-methoxy-2-methylphenethyl)benzo[f][1,7] naphthyridine-8-carbonylphosphonic acid (14) as a solid. $^1$H NMR (Dimethylsulfoxide-d$_6$): δ 9.84 (s, 1H), 9.35 (s, 1H), 9.09 (s, 1 H), 8.89 (s, 1H), 8.76 (d, 1H, J=8.4 Hz), 8.60 (s, 1H), 8.19 (d, 1H, J=8.8 Hz), 7.04 (d, J=8.8 Hz, 1H), 6.70 (d, 1H, J=2.8 Hz), 6.62 (dd, 1H, J=2.8, 8.4 Hz), 3.64 (s, 3H), 3.15-3.09 (m, 2H), 2.97-2.91 (m, 2H), 2.23 (s, 3H). LRMS [M+H]=452.1

Example 15

Table 1: Compound 15

Synthesis of 3-(5-amino-2-(2-methyl-4-(3-phosphonopropoxy)phenethyl)benzo[f][1,7]naphthyridin-8-yl)propanoic acid (15)

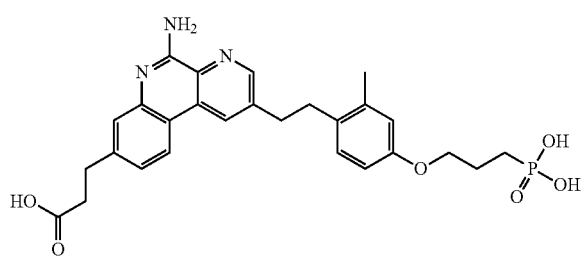 [SMILES: Cc1cc(OCCCP(=O)(O)O)ccc1CCc1cnc2c(N)nc3cc(CCC(=O)O)ccc3c2c1]

Step 1: 3-(5-amino-2-(4-(3-(diethoxyphosphoryl)propoxy)-2-methylphenethyl)benzo[f][1,7]naphthyridin-8-yl)propanoic acid 3-(5-amino-2-(4-(3-(diethoxyphosphoryl)propoxy)-2-methylphenethyl)benzo[f][1,7]naphthyridin-8-yl)propanoic acid was prepared according to the procedure described in Example 19—Step 11, but using commercially available diethyl 3-bromopropylphosphonate as the reagent.

Step 2: 3-(5-amino-2-(2-methyl-4-(3-phosphonopropoxy)phenethyl)benzo[f][1,7]naphthyridin-8-yl)propanoic acid (15)

3-(5-amino-2-(2-methyl-4-(3-phosphonopropoxy)phenethyl)benzo[f][1,7]naphthyridin-8-yl)propanoic acid (15) was prepared according to the procedure described in Example 19—Step 12, but using 3-(5-amino-2-(4-(3-(diethoxyphosphoryl)propoxy)-2-methylphenethyl)benzo[f][1,7]naphthyridin-8-yl)propanoic acid from the previous step. The $^1$H NMR (MeOD-d4) obtained for 3-(5-amino-2-(2-methyl-4-(3-phosphonopropoxy)phenethyl)benzo[f][1,7]naphthyridin-8-yl)propanoic acid (15) was: δ 8.60 (s, 1H), 8.27 (s, 1H), 8.07 (d, 1H, J=8.4 Hz), 7.52 (s, 1H), 7.30 (d, 1H, J=8.4 Hz), 6.87 (d, 1H, J=8.4 Hz), 6.67 (s, 1H), 6.60 (d, 1H, J=8.4 Hz), 3.93 (t, J=6.4 Hz, 2H), 3.49-3.47 (m, 2H), 3.14-3.09 (m, 2H), 2.99-2.95 (m, 2H), 2.69-2.64 (m, 2H), 2.17 (s, 3H), 2.02-2.00 (m, 2H), 1.74-0.66 (m, 2H). LRMS [M+H]=524.2

Example 16

Table 1: Compound 16

Synthesis of 3-(5-amino-2-(4-(4,4-difluoro-4-phosphonobutoxy)-2-methylphenethyl)benzo[f][1,7] naphthyridin-8-yl)propanoic acid (16)

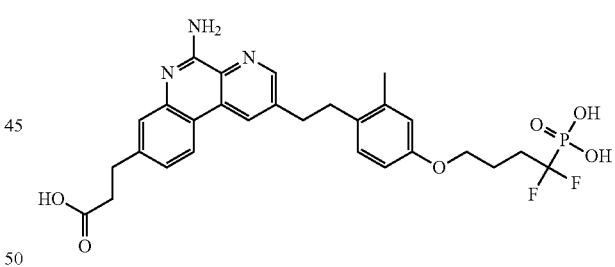

Step 1: diethyl 4-bromo-1,1-difluorobutylphosphonate

Diethyl 4-bromo-1,1-difluorobutylphosphonate was prepared according to the procedure described in Example 1—Step 1, but using commercially available 1,3-dibromopropane as the reagent.

Step 2: 3-(5-amino-2-(4-(4-(diethoxyphosphoryl)-4, 4-difluorobutoxy)-2-methylphenethyl)benzo[f][1,7] naphthyridin-8-yl)propanoic acid 3-(5-amino-2-(4-(4-(diethoxyphosphoryl)-4,4-difluorobutoxy)-2-methylphenethyl)benzo[f][1,7]naphthyridin-8-yl)propanoic acid was prepared according to the procedure described in Example 19—Step 11, but using diethyl 4-bromo-1,1-difluorobutylphosphonate from the previous step 1 as the reagent.

Step 3: 3-(5-amino-2-(4-(4,4-difluoro-4-phosphonobutoxy)-2-methylphenethyl)benzo[f][1,7]naphthyridin-8-yl)propanoic acid (16)

3-(5-amino-2-(4-(4,4-difluoro-4-phosphonobutoxy)-2-methylphenethyl)benzo[f][1,7]naphthyridin-8-yl)propanoic acid (16) was prepared according to the procedure described in Example 19—Step 12, but using 3-(5-amino-2-(4-(4-(diethoxyphosphoryl)-4,4-difluorobutoxy)-2-methylphenethyl) benzo[f][1,7]naphthyridin-8-yl)propanoic acid from the previous step 2. The $^1$H NMR (MeOD-d4) obtained for 3-(5-amino-2-(4-(4,4-difluoro-4-phosphonobutoxy)-2-methylphenethyl)benzo[f][1,7]naphthyridin-8-yl)propanoic acid (16) was: δ 8.69 (s, 1H), 8.45 (s, 1H), 8.22 (d, 1H, J=8.4 Hz), 7.53 (s, 1H), 7.45 (d, 1H, J=8.4 Hz), 6.89 (d, J=8.4 Hz, 1H), 6.69 (s, 1H), 6.60 (d, 1H, J=8.4 Hz), 3.95 (t, 2H, J=6.4 Hz), 3.92-3.90 (m, 2H), 3.49-3.47 (m, 2H), 3.20-3.16 (m, 2H), 3.14-3.10 (m, 2H), 3.03-2.99 (m, 2H), 2.74-2.70 (m, 2H), 2.22 (s, 3H). LRMS [M+H]=574.2

Example 17

Table 1: Compound 17

Synthesis of 3-(5-amino-2-(4-(2-(2-(3,3-difluoro-3-phosphonopropoxy)ethoxy)ethoxy)-2-methylphenethyl)benzo[f][1,7]naphthyridin-8-yl)propanoic acid (17)

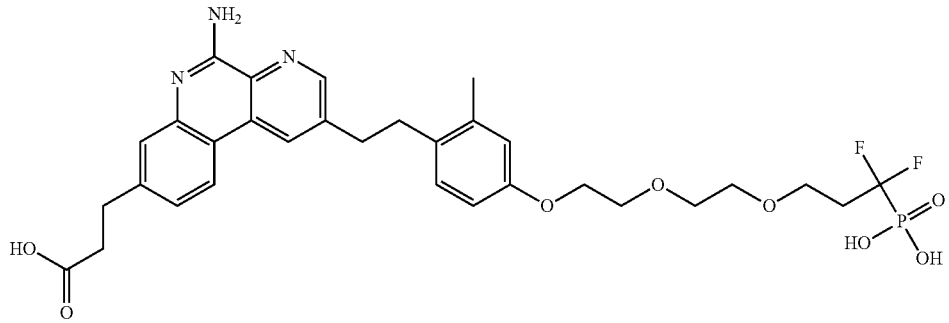 [SMILES: Cc1cc(OCCOCCOCCC(F)(F)P(=O)(O)O)ccc1CCc1cnc2c(N)nc3cc(CCC(=O)O)ccc3c2c1]

Step 1: ethyl 3-(5-amino-2-{2-[4-(2-{2-[3-(diethoxyphosphoryl)-3,3-difluoropropoxy]ethoxy}ethoxy)-2-methylphenyl]ethyl}benzo[f]1,7-naphthyridin-8-yl)propanoate Ethyl 3-(5-amino-2-{2-[4-(2-{2-[3-(diethoxyphosphoryl)-3,3-difluoropropoxy]ethoxy}ethoxy)-2-methylphenyl]ethyl}benzo[f]1,7-naphthyridin-8-yl)propanoate was prepared according to the procedure described in Example 19—Step 11, but using diethyl 1,1-difluoro-3-(2-(2-iodoethoxy)ethoxy)propylphosphonate (1-1) (described in Example 1—Step 1) as the reagent.

Step 2: 3-(5-amino-2-(4-(2-(2-(3,3-difluoro-3-phosphonopropoxy)ethoxy)ethoxy)-2-methylphenethyl)benzo[f][1,7]naphthyridin-8-yl)propanoic acid (17)

3-(5-amino-2-(4-(2-(2-(3,3-difluoro-3-phosphonopropoxy)ethoxy)ethoxy)-2-methylphenethyl)benzo[f][1,7]naphthyridin-8-yl)propanoic acid (17) was prepared according to the procedure described in Example 19—Step 12, but using ethyl 3-(5-amino-2-{2-[4-(2-{2-[3-(diethoxyphosphoryl)-3,3-difluoropropoxy]ethoxy}ethoxy)-2-methylphenyl]ethyl}benzo[f]1,7-naphthyridin-8-yl)propanoate from the previous step. The $^1$H NMR (DMSO-d$_6$) obtained for 3-(5-amino-2-(4-(2-(2-(3,3-difluoro-3-phosphonopropoxy)ethoxy)ethoxy)-2-methylphenethyl)benzo[f][1,7]naphthyridin-8-yl)propanoic acid (17) was: δ 9.02 (s, 1H), 8.82 (s, 1H), 8.55 (d, 1H, J=8.4 Hz), 7.58 (s, 1 H), 7.49 (d, 1H, J=8.4 Hz), 7.07 (d, 1H, J=8.4 Hz), 6.75 (s, 1H), 6.68 (d, 1H, J=8.0 Hz), 4.03-4.00 (m, 2H), 3.72-3.70 (m, 2H), 3.66-3.62 (m, 2H), 3.58-3.56 (m, 2H), 3.53-3.52 (m, 2H), 3.16-3.12 (m, 2H), 3.03-2.96 (m, 4H), 2.68-2.64 (m, 2H), 2.31-2.33 (m, 2H), 2.27 (s, 3H). LRMS [M+H]=648.2

Example 18

Table 1: Compound 18

Synthesis of 3-(5-amino-2-(2-methyl-4 (2 (2 (2 (2 phosphonoethoxy)ethoxy)ethoxy)ethoxy)phenethyl) benzo[f][1,7]naphthyridin-8-yl)propanoic acid (18)

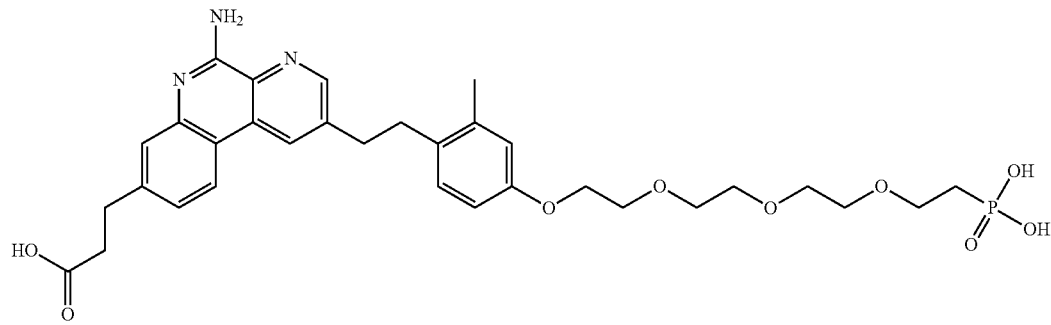 [SMILES: Cc1cc(OCCOCCOCCOCCP(=O)(O)O)ccc1CCc1cnc2c(N)nc3cc(CCC(=O)O)ccc3c2c1]

Step 1: diethyl 2-(2-(2-(2-iodoethoxy)ethoxy) ethoxy)ethylphosphonate

Diethyl 2-(2-(2-(2-iodoethoxy)ethoxy)ethoxy)ethylphosphonate was prepared according to the procedure described in Example 22—Step 1, but using commercially available 1-iodo-2-(2-(2-(2-iodoethoxy)ethoxy)ethoxy)ethane as the reagent.

Step 2: ethyl 3-[5-amino-2-(2-{4-[2-(2-{2-[2-(diethoxyphosphoryl)ethoxy]ethoxy}ethoxy)ethoxy]-2-methylphenyl}ethyl)benzo[f]1,7-naphthyridin-8-yl]propanoate Ethyl 3-[5-amino-2-(2-{4-[2-(2-{2-[2-(diethoxyphosphoryl)ethoxy]ethoxy}ethoxy)ethoxy]-2-methylphenyl}ethyl)benzo[f]1,7-naphthyridin-8-yl]propanoate was prepared according to the procedure described in Example 19—Step 11, but using diethyl 2-(2-(2-(2-iodoethoxy)ethoxy)ethoxy) ethylphosphonate from the previous step 1 as the reagent.

Step 3: 3-(5-amino-2-(2-methyl-4-(2-(2-(2-(2-phosphonoethoxy)ethoxy)ethoxy)ethoxy)phenethyl) benzo[f][1,7]naphthyridin-8-yl)propanoic acid 3-(5-amino-2-(2-methyl-4-(2-(2-(2-(2-phosphonoethoxy) ethoxy)ethoxy)ethoxy)phenethyl)benzo[f][1,7]naphthyridin-8-yl)propanoic acid (18) was prepared according to the procedure described in Example 19—Step 12, but using ethyl 3-[5-amino-2-(2-{4-[2-(2-{2-[2-(diethoxyphosphoryl) ethoxy]ethoxy}ethoxy)ethoxy]-2-methylphenyl}ethyl) benzo[f]1,7-naphthyridin-8-yl]propanoate from the previous step 2. The $^1$H NMR (Dimethylsulfoxide-$d_6$) obtained for 3-(5-amino-2-(2-methyl-4-(2-(2-(2-(2-phosphonoethoxy) ethoxy)ethoxy)ethoxy)phenethyl)benzo[f][1,7]naphthyridin-8-yl)propanoic acid (18) was: δ 9.02 (s, 1H), 8.82 (s, 1H), 8.56 (d, 1H, J=8.4 Hz), 7.57 (s, 1 H), 7.49 (d, 1H, J=8.4 Hz), 7.07 (d, 1H, J=8.4 Hz), 6.76 (s, 1 H), 6.68 (d, 1H, J=8.4 Hz), 4.03-4.01 (m, 2H), 3.72-3.69 (m, 2H), 3.59-3.47 (m, 10H), 3.16-3.13 (m, 2H), 3.03-2.96 (m, 4H), 2.68-2.64 (m, 2H), 1.87-1.82 (m, 2H), 2.27 (s, 3H). LRMS [M+H]=642.3

Example 19

Table 1: Compound 19

Synthesis of 3-(5-amino-2-(4-(2-(3,3-difluoro-3-phosphonopropoxy)ethoxy)-2-methylphenethyl) benzo[f][1,7]naphthyridin-8-yl)propanoic acid (19)

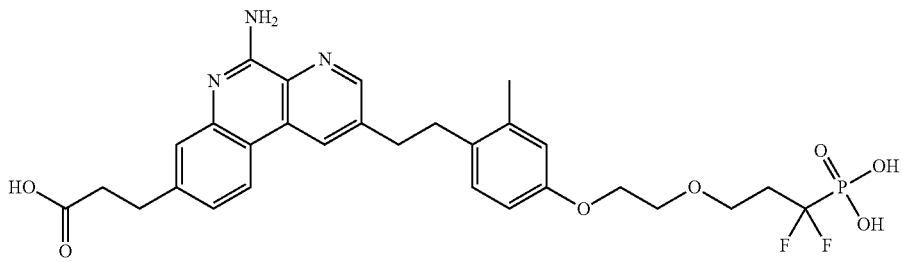 [SMILES: Cc1cc(OCCOCCC(F)(F)P(=O)(O)O)ccc1CCc1cnc2c(N)nc3cc(CCC(=O)O)ccc3c2c1]

Scheme 6
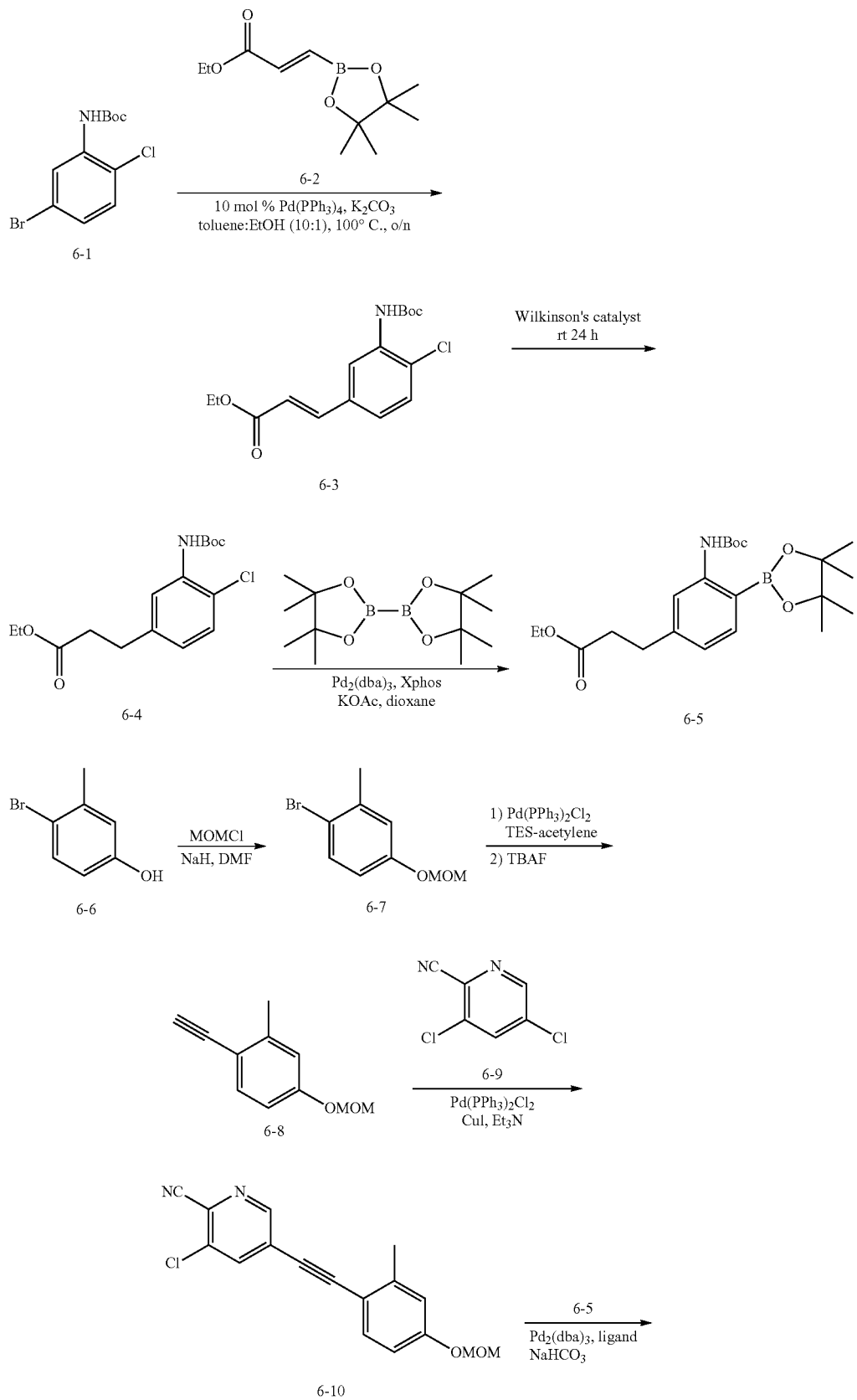

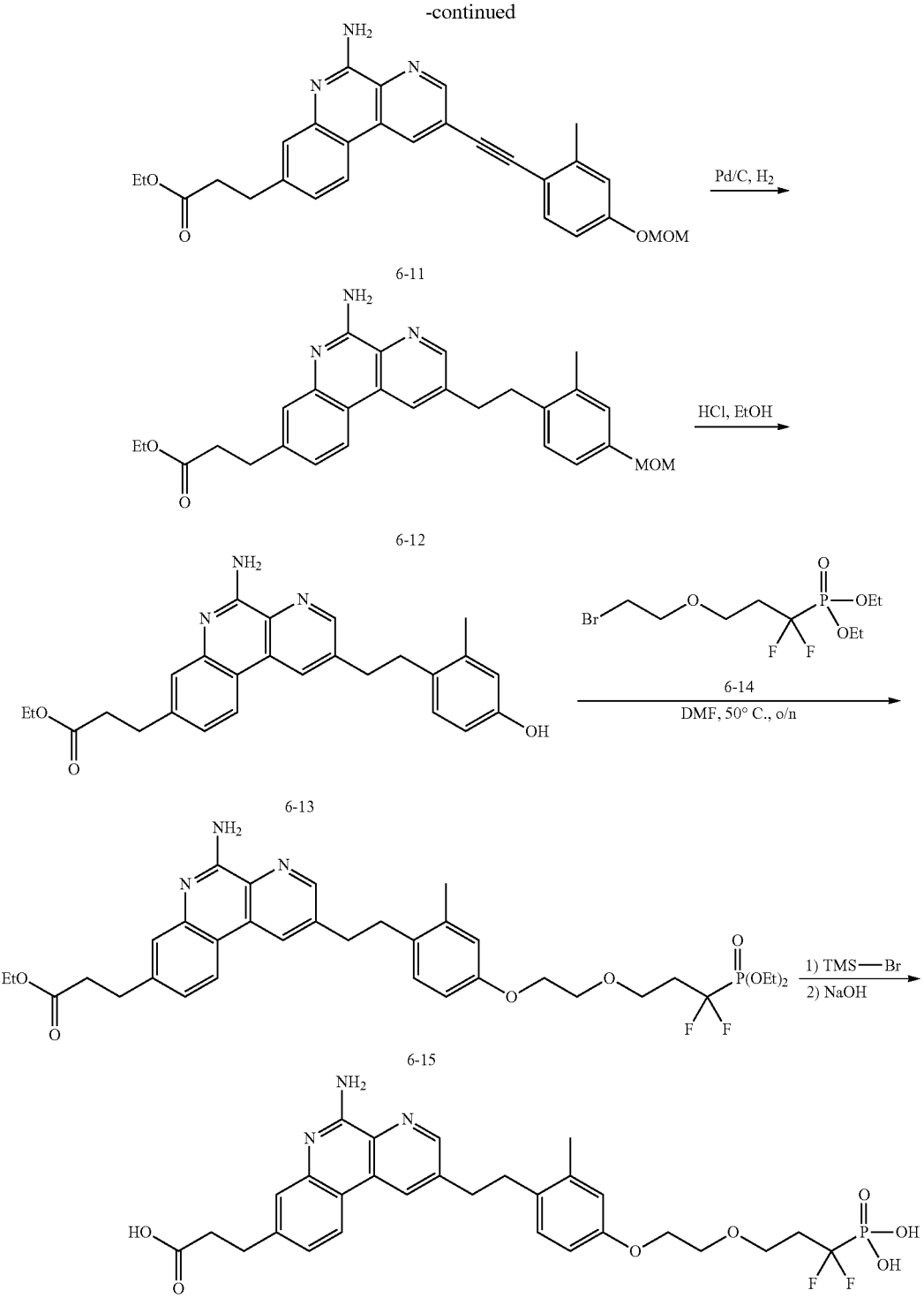

Step 1: (E)-ethyl 3-(3-(tert-butoxycarbonylamino)-4-chlorophenyl)acrylate (6-3)

To a solution of tert-butyl 5-bromo-2-chlorophenylcarbamate (6-1) (1.0 equiv.) in acetonitrile (0.3 M) and EtOH (0.5 M) was added $K_2CO_3$ (2.0 equiv.). The reaction was degassed and flushed with $N_2$, then added (E)-ethyl 3-(4,4,5,5-tetramethyl-1,3,2-dioxaborolan-2-yl)acrylate (6-2) (1.2 equiv.) and $Pd(PPh_3)_4$ (0.1 equiv.). The reaction was flushed again with $N_2$ and stirred at 100° C. overnight. After cooling to room temperature, hexane was added, and the mixture was filtered through a pad of silica, eluting with EA/Hex (1:1) until the product was completely eluted. The filtrate was concentrated and purified on Combiflash, eluting with 0-15% EA in Hex to give (E)-ethyl 3-(3-(tert-butoxycarbonylamino)-4-chlorophenyl)acrylate (6-3) as a white solid.

Step 2: ethyl 3-(3-(tert-butoxycarbonylamino)-4-chlorophenyl)propanoate (6-4)

To a solution of (E)-ethyl 3-(3-(tert-butoxycarbonylamino)-4-chlorophenyl)acrylate (6-3) (1.0 equiv.) in ethyl acetate/ethanol (1:1, 0.3 M) was added Wilkinson's catalyst (0.10 equiv.). Hydrogen gas was introduced via a ballon, and the reaction was stirred at room temperature for 24 hours. The mixture was filtered through a pad of celite, washing with dichloromethane. The filtrate was concentrated in vacuo and purified by Combiflash using 0-10% ethyl acetate in hexane to give ethyl 3-(3-(tert-butoxycarbonylamino)-4-chlorophenyl)propanoate (6-4) as a solid.

Step 3: ethyl 3-(3-(tert-butoxycarbonylamino)-4-(4,4,5,5-tetramethyl-1,3,2-dioxaborolan-2-yl)phenyl)propanoate (6-5)

A solution of ethyl 3-(3-(tert-butoxycarbonylamino)-4-chlorophenyl)propanoate (6-4) (1.0 equiv.), 4,4,4',4',5,5,5',5'-octamethyl-2,2'-bi(1,3,2-dioxaborolane) (2.0 equiv.), tris(dibenzylideneacetone)dipalladium(0) (0.05 equiv.), 2-dicyclohexylphosphino-2',4',6'-triisopropylbiphenyl (0.20 equiv.), and potassium acetate (2.0 equiv.) in 1,4-dioxane (0.2 M) was degassed and stirred at 100° C. overnight. After cooling to ambient temperature, the reaction content was concentrated in vacuo. The crude material was purified by Combiflash using 0-50% ethyl acetate in hexane to afford ethyl 3-(3-(tert-butoxycarbonylamino)-4-(4,4,5,5-tetramethyl-1,3,2-dioxaborolan-2-yl)phenyl)propanoate (6-5) as a brown oil. The product was stored at −20° C. and used within a month of synthesis.

Step 4: 1-bromo-4-(methoxymethoxy)-2-methylbenzene (6-7)

To a solution of 4-bromo-3-methylphenol (6-6) (1.0 equiv.) in DMF (0.5 M) at 0° C. was added portionwise 60% wt NaH (1.5 equiv.). The addition was controlled such that internal reaction temperature never went above 10° C. The reaction was stirred at room temperature for 45 minutes, then a solution of chloro(methoxy)methane (1.2 equiv.) in DMF (3 M) was added dropwise via additional funnel. The reaction was stirred at room temperature for 3.5 hours, and then quenched by pouring into ice. The resulting mixture was stirred at room temperature for 1 hour. Ether was added, and the two layers were separated. The aqueous layer was extracted (1×) with ether. The combined organic layers were washed with water (2×), brine, dried over $MgSO_4$, and concentrated to give 1-bromo-4-(methoxymethoxy)-2-methylbenzene (6-7) as a colorless oil. The crude material was used in the next step without further purification.

Step 5: triethyl((4-(methoxymethoxy)-2-methylphenyl)ethynyl)silane

A solution of 1-bromo-4-(methoxymethoxy)-2-methylbenzene (1.0 equiv.), triethylamine (5.0 equiv.) in DMF (0.5 M) was degassed and flushed with nitrogen. To the reaction was added TES-acetylene (1.05 equiv.), CuI (0.098 equiv.), and $Pd(PPh_3)_2Cl_2$ (0.098 equiv.). The reaction was heated to 60° C. and stirred overnight. After cooling to room temperature, water and ether were added. The layers were separated, and the organic layer was washed with water (2×). The organic layer was separated and passed through a pad of silica (packed with hexane). The silica was eluted with 10% EA in Hex. The fractions were combined and concentrated to give triethyl((4-(methoxymethoxy)-2-methylphenyl)ethynyl)silane as a black oil. The crude material was used in the next step without further purification.

Step 6: 1-ethynyl-4-(methoxymethoxy)-2-methylbenzene (6-8)

To a solution of triethyl((4-(methoxymethoxy)-2-methylphenyl)ethynyl)silane (1.0 equiv.) at 0° C. was slowly added tetrabutylammonium fluoride (1M solution in THF, 0.20 equiv.). At this point, the ice-bath was removed and the reaction mixture was allowed to stir at room temperature for 45 minutes. The reaction mixture was then passed through a pad of silica (packed with hexane) and eluted with 20% EtOAc in Hexanes to remove insoluble salts. The crude product was then purified by Combiflash using 0-10% EtOAc in Hexanes to give 1-ethynyl-4-(methoxymethoxy)-2-methylbenzene (6-8) as a slightly brown liquid.

Step 7: 3-chloro-5-((4-(methoxymethoxy)-2-methylphenyl)ethynyl)picolinonitrile (6-10)

A solution of 1-ethynyl-4-(methoxymethoxy)-2-methylbenzene (6-8) (1.0 equiv.), 3,5-dichloropicolinonitrile (6-9) (0.90 equiv.), CuI (0.10 equiv.), and $Pd(PPh_3)_2Cl_2$ (0.10 equiv.), and triethylamine (5.0 equiv.) in DMF (0.25 M) was degassed and flushed with nitrogen. The reaction mixture was then heated to 60° C. and stirred overnight. After cooling to room temperature, water was added. The mixture was extracted with EA (2×). The combined organic layers were washed with 10% aq $NH_4OH$ (2×), brine, and concentrated. The crude material was filtered through a pad of silica (wetted with hexane). The silica was eluted with 10% EA in Hex. The fractions were combined and concentrated. The resulting solids were washed in hot ether and filtered to give a yellow solid, which was used in the next step without further purification. The filtrate was concentrated and purified by Combiflash using 0-10% EtOAc in Hexanes to give 3-chloro-5-((4-(methoxymethoxy)-2-methylphenyl)ethynyl)picolinonitrile (6-10) as a yellow solid.

Step 8: ethyl 3-(5-amino-2-((4-(methoxymethoxy)-2-methylphenyl)ethynyl)-benzo[f][1,7]naphthyridin-8-yl)propanoate (6-11)

A solution of 3-chloro-5-((4-(methoxymethoxy)-2-methylphenyl)ethynyl)picolinonitrile (6-10) (1.0 equiv.), ethyl 3-(3-(tert-butoxycarbonylamino)-4-(4,4,5,5-tetramethyl-1,3,2-dioxaborolan-2-yl)phenyl)propanoate (6-5) (1.25 equiv.), tris(dibenzylideneacetone)dipalladium(0) (0.10 equiv.), dicyclohexyl(2',6'-dimethoxybiphenyl-2-yl)phosphine (0.20 equiv.), and sodium bicarbonate (3.0 equiv.) in n-butanol/$H_2O$ (5:1, 0.2 M) was degassed and stirred at 100° C. overnight. After cooling to ambient temperature, the reaction content was diluted with ethyl acetate and water. The two phases were separated, and the aqueous layer was extracted twice with ethyl acetate. The combined organic layers were washed with brine, dried over anhydrous $MgSO_4$, and concentrated in vacuo. The crude material was purified by flash chromatography on a COMBIFLASH® system (ISCO) using 0-40% ethyl acetate in DCM first to remove the impurity, then 0-4% MeOH in DCM to give ethyl 3-(5-amino-2-((4-(methoxymethoxy)-2-methylphenyl)ethynyl)-benzo[f][1,7]naphthyridin-8-yl)propanoate (6-11). Further purification was accomplished by precipitating and washing in hot ether.

Step 9: ethyl 3-(5-amino-2-(4-(methoxymethoxy)-2-methylphenethyl)benzo[f][1,7]naphthyridin-8-yl)propanoate (6-12)

A solution of ethyl 3-(5-amino-2-((4-(methoxymethoxy)-2-methylphenyl)ethynyl)-benzo[f][1,7]naphthyridin-8-yl)propanoate (6-11) (1.0 equiv.) in EtOH/THF (3:1, 0.16 M) was flushed with nitrogen. Then, 10% wt Pd/C (0.20 equiv. by weight) was added. The reaction was flushed with hydrogen (2×) and stirred under a hydrogen balloon. After 24 hours, the reaction was filtered through a pad of celite, washing with 5% MeOH in DCM. The filtrate was checked for the presence of starting material using LCMS. The hydrogenation reaction was repeated until no more of the alkyne starting material or alkene intermediate was detected. The crude product was purified by Combiflash using 0-4% MeOH in DCM to give ethyl 3-(5-amino-2-(4-(methoxymethoxy)-2-methylphenethyl)benzo[f][1,7]naphthyridin-8-yl)propanoate (6-12) as a white solid.

Step 10: ethyl 3-(5-amino-2-(4-hydroxy-2-methylphenethyl)benzo[f][1,7]naphthyridin-8-yl)propanoate (6-13)

Ethyl 3-(5-amino-2-(4-(methoxymethoxy)-2-methylphenethyl)benzo[f][1,7]naphthyridin-8-yl)propanoate (6-12) (1.0 equiv.) was dissolved in EtOH (0.2 M), then added a solution of 4M HCl in dioxane (0.2 M). The product precipitated out as a yellow salt. After stirring for 3 hours, the reaction was poured into a stirring solution of ether. The mixture was stirred for 10 minutes, then filtered and washed with ether. Ethyl 3-(5-amino-2-(4-hydroxy-2-methylphenethyl)benzo[f][1,7]naphthyridin-8-yl)propanoate (6-13) was obtained as a yellow solid which was dried on vacuum overnight (bis-HCl salt). Alternatively, the crude product was purified by Combiflash using 0-5% MeOH in DCM to give the free base.

Step 11: ethyl 3-(5-amino-2-(4-(2-(3-(diethoxyphosphoryl)-3,3-difluoropropoxy)ethoxy)-2-methylphenethyl)benzo[f][1,7]naphthyridin-8-yl)propanoate (6-15)

To a solution of ethyl 3-(5-amino-2-(4-hydroxy-2-methylphenethyl)benzo[f][1,7]naphthyridin-8-yl)propanoate (6-13) (1.0 equiv.) dissolved in DMF (0.14 M) was added a solution of diethyl 3-(2-bromoethoxy)-1,1-difluoropropylphosphonate (6-14: described in Example 7—Step 1) (1.3 equiv.) in DMF (0.7 M) and cesium carbonate (4 equiv.). The reaction was stirred at 60° C. After 1.5 hours (or until reaction is complete by LCMS), DCM (2 volume equivalent) was added to the reaction. The solids (inorganic) were filtered, and the filtrate was concentration. The crude product was purified by Combiflash using 0-5% MeOH in DCM to give ethyl 3-(5-amino-2-(4-(2-(3-(diethoxyphosphoryl)-3,3-difluoropropoxy)ethoxy)-2-methylphenethyl)benzo[f][1,7]naphthyridin-8-yl)propanoate (6-15) as an oil which upon standing became a white solid.

Step 12: 3-(5-amino-2-(4-(2-(3,3-difluoro-3-phosphonopropoxy)ethoxy)-2-methylphenethyl)benzo[f][1,7]naphthyridin-8-yl)propanoic acid (19)

To a solution of ethyl 3-(5-amino-2-(4-(2-(3-(diethoxyphosphoryl)-3,3-difluoropropoxy)ethoxy)-2-methylphenethyl)benzo[f][1,7]naphthyridin-8-yl)propanoate (6-15) (1.0 equiv.) in DCM (0.16 M) at 0° C. was added slowly TMSBr (10 equiv.). The reaction was stirred at room temperature overnight. Additional TMSBr (5.0 equiv.) was added at 0° C., and the reaction was again stirred at room temperature overnight. The solvent was removed by evaporation and the crude orange solids dried on hi-vac briefly. The solids were suspended in EtOH (0.5 M) and added 2.5 N NaOH (10.0 equiv.). The reaction was stirred at 80° C. for 3 hours. After cooling to room temperature, the mixture was adjusted to pH 9 to 10 and directly purified on RP-HPLC using a C18 column, eluting with 10-40% 95:5 (MeCN/5 mM $NH_4OAc$) in 10 mM $NH_4OAc$ (pH 9) gradient. The fractions containing the product were combined and concentrated in vacuo. The resulting white gel was dissolved in refluxing 1:1 EtOH/water (0.04 M) with the addition of a few drops of ammonium hydroxide. While hot, the mixture was slowly poured into a stirring hot solution of acetone (0.009 M) preheated at 50° C. The acetone suspension was slowly cooled to room temperature for 15 minutes with continued stirring, and then sat in an ice bath for 10 minutes. The solids were filtered and washed successively with acetone (2×) and ether (2×). The solids were dried on hi-vac overnight to give the 3-(5-amino-2-(4-(2-(3,3-difluoro-3-phosphonopropoxy)ethoxy)-2-methylphenethyl)benzo[f][1,7]naphthyridin-8-yl)propanoic acid (19) as a solid. $^1$H NMR (Dimethylsulfoxide-$d_6$): δ 9.02 (s, 1H), 8.82 (s, 1H), 8.55 (d, 1H, J=8.4 Hz), 7.58 (s, 1H), 7.48 (d, 1H, J=8.4 Hz), 7.07 (d, 1H, J=8.4 Hz), 6.75 (s, 1 H), 6.68 (d, 1H, J=8.4 Hz), 4.03-4.00 (m, 2H), 3.72-3.68 (m, 4H), 3.16-3.12 (m, 2H), 3.03-2.96 (m, 4H), 2.67-2.64 (m, 2H), 2.33-2.32 (m, 2H), 2.26 (s, 3H). LRMS [M+H]=604.2

Example 20

Table 1: Compound 20

Synthesis of 3-(5-amino-2-(2-methyl-4-(2-(2-(2-phosphonoethoxy)ethoxy)ethoxy)phenethyl)benzo[f][1,7]naphthyridin-8-yl)propanoic acid (20)

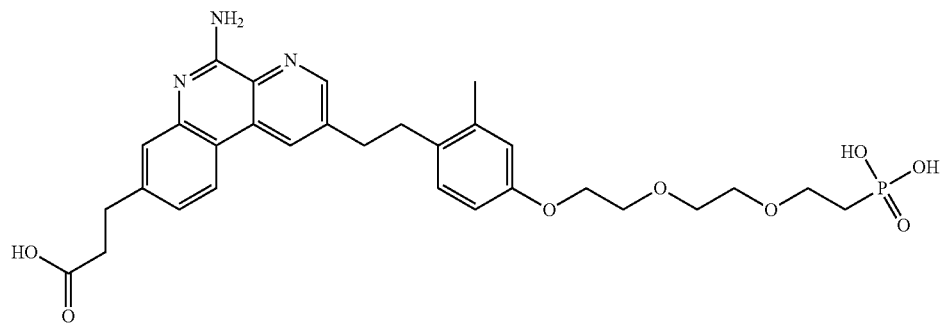 [SMILES: Cc1cc(OCCOCCOCCP(=O)(O)O)ccc1CCc1cnc2c(N)nc3cc(CCC(=O)O)ccc3c2c1]

Step 1: diethyl 2-(2-(2-iodoethoxy)ethoxy)ethylphosphonate

A microwave tube was charged with a stirring bar, commercially available 1,2-bis(2-iodoethoxy)ethane (1.0 equiv.) and triethylphosphite (1.0 equiv.). The microwave tube was capped and then irradiated at 160° C. for 40 minutes with stirring. The reaction mixture was cooled down to room temperature and was purified by Combiflash using 0-75% EtOAc in hexanes, or alternatively by RP-HPLC (0.035% TFA in ACN:0.05% TFA in $H_2O$, C18 column), to give diethyl 2-(2-(2-iodoethoxy)ethoxy)ethylphosphonate as pale yellow oil.

Step 2: ethyl 3-(5-amino-2-{2-[4-(2-{2-[2-(diethoxyphosphoryl)ethoxy]ethoxy}ethoxy)-2-methylphenyl]ethyl}benzo[f]1,7-naphthyridin-8-yl)propanoate Ethyl 3-(5-amino-2-{2-[4-(2-{2-[2-(diethoxyphosphoryl)ethoxy]ethoxy}ethoxy)-2-methylphenyl]ethyl}benzo[f]1,7-naphthyridin-8-yl)propanoate was prepared according to the procedure described in Example 19—Step 11, but using diethyl 2-(2-(2-iodoethoxy)ethoxy)ethylphosphonate from the previous step 1 as the reagent.

Step 3: 3-(5-amino-2-(2-methyl-4-(2-(2-(2-phosphonoethoxy)ethoxy)ethoxy)phenethyl)benzo[f][1,7]naphthyridin-8-yl)propanoic acid (20)

3-(5-amino-2-(2-methyl-4-(2-(2-(2-phosphonoethoxy)ethoxy)ethoxy)phenethyl)benzo[f][1,7]naphthyridin-8-yl)propanoic acid (20) was prepared according to the procedure described in Example 19—Step 12, but using ethyl 3-(5-amino-2-{2-[4-(2-{2-[2-(diethoxyphosphoryl)ethoxy]ethoxy}ethoxy)-2-methylphenyl]ethyl}benzo[f]1,7-naphthyridin-8-yl)propanoate from the previous step 2. The $^1$H NMR (Dimethylsulfoxide-d$_6$) obtained for 3-(5-amino-2-(2-methyl-4-(2-(2-(2-phosphonoethoxy)ethoxy)ethoxy)phenethyl)benzo[f][1,7]naphthyridin-8-yl)propanoic acid (20) was: δ 9.02 (s, 1H), 8.82 (s, 1H), 8.55 (d, 1H, J=8.0 Hz), 7.58 (s, 1 H), 7.49 (d, 1H, J=8.4 Hz), 7.06 (d, 1H, J=8.0 Hz), 6.76 (s, 1 H), 6.68 (d, 1H, J=8.0 Hz), 4.03-4.00 (m, 2H), 3.71-3.69 (m, 2H), 3.60-3.54 (m, 4H), 3.51-3.49 (m, 2H), 3.16-3.12 (m, 2H), 3.03-2.96 (m, 4H), 2.67-2.66 (m, 2H), 2.33-2.32 (m, 2H), 2.26 (s, 3H). LRMS [M+H]=598.2

Example 21

Table 1: Compound 21

Synthesis of 3-(5-amino-2-(2-methyl-4-(2-(2-phosphonoethoxy)ethoxy)phenethyl)benzo[f][1,7]naphthyridin-8-yl)propanoic acid 21

Step 1: diethyl 2-(2-bromoethoxy)ethylphosphonate

Diethyl 2-(2-bromoethoxy)ethylphosphonate was prepared according to the procedure described in Example 22—Step 1, but using commercially available 1-bromo-2-(2-bromoethoxy)ethane as the reagent.

Step 2: 3-(5-amino-2-(4-(2-(2-(diethoxyphosphoryl)ethoxy)ethoxy)-2-methylphenethyl)benzo[f][1,7]naphthyridin-8-yl)propanoic acid 3-(5-amino-2-(4-(2-(2-(diethoxyphosphoryl)ethoxy)ethoxy)-2-methylphenethyl)benzo[f][1,7]naphthyridin-8-yl)propanoic acid was prepared according to the procedure described in Example 19—Step 11, but using diethyl 2-(2-bromoethoxy)ethylphosphonate from the previous step 1 as the reagent.

Step 3: 3-(5-amino-2-(2-methyl-4-(2-(2-phosphonoethoxy)ethoxy)phenethyl)benzo[f][1,7]naphthyridin-8-yl)propanoic acid (21)

3-(5-amino-2-(2-methyl-4-(2-(2-phosphonoethoxy)ethoxy)phenethyl)benzo[f][1,7]naphthyridin-8-yl)propanoic acid (21) was prepared according to the procedure described in Example 19—Step 12, but using 3-(5-amino-2-(4-(2-(2-(diethoxyphosphoryl)ethoxy)ethoxy)-2-methylphenethyl)benzo[f][1,7]naphthyridin-8-yl)propanoic acid from the previous step 2. The $^1$H NMR (MeOD-d4) obtained for 3-(5-amino-2-(2-methyl-4-(2-(2-phosphonoethoxy)ethoxy)phenethyl)benzo[f][1,7]naphthyridin-8-yl)propanoic acid (21) was: δ 8.59 (s, 1H), 8.45 (s, 1H), 8.18 (d, 1H, J=8.4 Hz), 7.52 (s, 1 H), 7.31 (d, 1H, J=8.0 Hz), 6.93 (d, 1H, J=8.4 Hz), 6.72 (s, 1 H), 6.65 (d, 1H, J=8.4 Hz), 4.06-4.03 (m, 2H), 3.84-3.76 (m, 4H), 3.15-3.07 (m, 4H), 3.01-2.97 (m, 2H), 2.68-2.64 (m, 2H), 2.22 (s, 3H), 2.03-1.99 (m, 2H). LRMS [M+H]=554.2

Example 22

Table 1: Compound 22

Synthesis of 2-(4-(2-(5-amino-8-methylbenzo[f][1,7]naphthyridin-2-yl)ethyl)-3-methylphenoxy)ethylphosphonic acid (22)

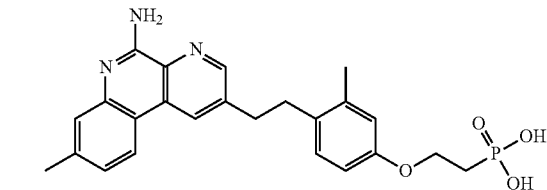

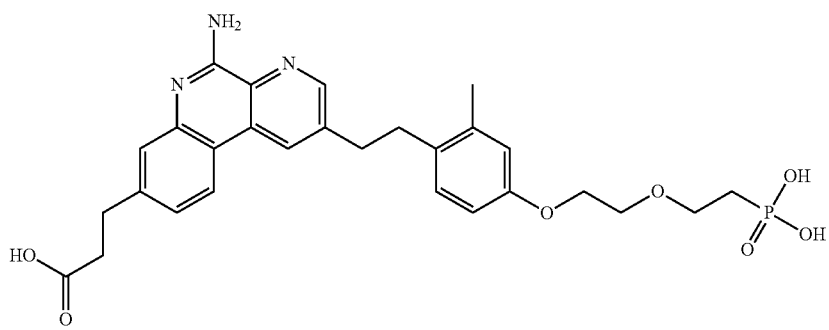 [SMILES: Cc1cc(OCCOCCP(=O)(O)O)ccc1CCc1cnc2c(N)nc3cc(CCC(=O)O)ccc3c2c1]

Step 1: diethyl 2-bromoethylphosphonate

Commercially available 1,2-dibromoethane (1.0 equiv.) and triethyl phosphite (1.0 equiv.) were heated with microwave irradiation at 160° C. for 20 minutes. The resulting residue was purified by reverse phase high performance liquid chromatography (HPLC) (0.035% TFA in ACN: 0.05% TFA in $H_2O$, C18 column) to give diethyl 2-bromoethylphosphonate as a colorless liquid.

Step 2: diethyl 2-(4-(2-(5-amino-8-methylbenzo[f][1,7]naphthyridin-2-yl)ethyl)-3-methylphenoxy)ethylphosphonate Diethyl 2-(4-(2-(5-amino-8-methylbenzo[f][1,7]naphthyridin-2-yl)ethyl)-3-methylphenoxy)ethylphosphonate was prepared according to the procedure described in Example 1—Step 2, but using diethyl 2-bromoethylphosphonate from the previous step 1 as the reagent.

Step 3: 2-(4-(2-(5-amino-8-methylbenzo[f][1,7]naphthyridin-2-yl)ethyl)-3-methylphenoxy)ethylphosphonic acid (22)

2-(4-(2-(5-amino-8-methylbenzo[f][1,7]naphthyridin-2-yl)ethyl)-3-methylphenoxy)ethylphosphonic acid (22) was prepared according to the procedure described in Example 1—Step 3, but using diethyl 2-(4-(2-(5-amino-8-methylbenzo[f][1,7]naphthyridin-2-yl)ethyl)-3-methylphenoxy)ethylphosphonate from the previous step 2. TFA was added to the $^1H$ NMR sample to solubilize the compound for analysis. The $^1H$ NMR (dimethyl sulfoxide) obtained for 2-(4-(2-(5-amino-8-methylbenzo[f][1,7]naphthyridin-2-yl)ethyl)-3-methylphenoxy)ethylphosphonic acid (22) was: δ 8.83 (s, 1H), 8.71 (s, 1H), 8.35 (d, 1H, J=8.3 Hz), 7.35 (s, 1H), 7.15 (d, 1H, J=9.6 Hz), 7.08 (d, 1H, J=8.4 Hz), 7.06-7.03 (br, 2H) 6.71 (s, 1H), 6.64 (d, 1H, J=8.1 Hz), 4.09-3.99 (m, 2H), 3.07 (t, 2H, J=6.9), 2.93 (t, 2H, J=6.7), 2.44 (s, 3 H), 2.26 (s, 3H), 1.72-1.62 (m, 2H). LRMS [M+H]=452.2

Example 23

Table 1: Compound 23

Synthesis of 6-(4-(2-(5-amino-8-methylbenzo[f][1,7]naphthyridin-2-yl)ethyl)-3-methylphenoxy)hexylphosphonic acid (23)

Step 1: diethyl 6-bromohexylphosphonate

Diethyl 6-bromohexylphosphonate was prepared according to the procedure described in Example 22—Step 1, but using commercially available 1,6-dibromohexane as the reagent.

Step 2: diethyl 6-(4-(2-(5-amino-8-methylbenzo[f][1,7]naphthyridin-2-yl)ethyl)-3-methylphenoxy)hexylphosphonate Diethyl 6-(4-(2-(5-amino-8-methylbenzo[f][1,7]naphthyridin-2-yl)ethyl)-3-methylphenoxy)hexylphosphonate was prepared according to the procedure described in Example 1—Step 2, but using diethyl 6-bromohexylphosphonate from the previous step 1 as the reagent.

Step 3: 6-(4-(2-(5-amino-8-methylbenzo[f][1,7]naphthyridin-2-yl)ethyl)-3-methylphenoxy)hexylphosphonic acid (23)

6-(4-(2-(5-amino-8-methylbenzo[f][1,7]naphthyridin-2-yl)ethyl)-3-methylphenoxy)hexylphosphonic acid (23) was prepared according to the procedure described in Example 1—Step 3, but using diethyl 6-(4-(2-(5-amino-8-methylbenzo[f][1,7]naphthyridin-2-yl)ethyl)-3-methylphenoxy)hexylphosphonate. TFA was added to the $^1H$ NMR sample to solubilize the compound for analysis. The $^1H$ NMR (dimethyl sulfoxide-$d_6$) obtained for 6-(4-(2-(5-amino-8-methylbenzo[f][1,7]naphthyridin-2-yl)ethyl)-3-methylphenoxy)hexylphosphonic acid (23) was: δ 8.95 (s, 1H), 8.81 (s, 1H), 8.50 (d, 1H, J=8.4 Hz), 7.52 (s, 1H), 7.40 (d, 1H, J=8.4 Hz), 7.01 (d, 1H, J=8.4 Hz), 6.71 (s, 1H), 6.64 (d, 1H, J=10.9 Hz), 3.87 (t, 2H, J=6.34 Hz), 3.13 (t, 2H, J=7.1 Hz), 2.96 (t, 2H, J=7.0 Hz), 2.69-2.66 (m, 1H), 2.35-2.32 (m, 1H), 2.25 (s, 2H), 1.72-1.62 (m, 2H), 1.62-1.51 (m, 2H), 1.51-1.40 (m, 2H). LRMS [M+H]=508.2

Example 24

Table 1: Compound 24

Synthesis of 6-(4-(2-(5-amino-8-methylbenzo[f][1,7]naphthyridin-2-yl)ethyl)-3-methylphenoxy)-1,1-difluorohexylphosphonic acid (24)

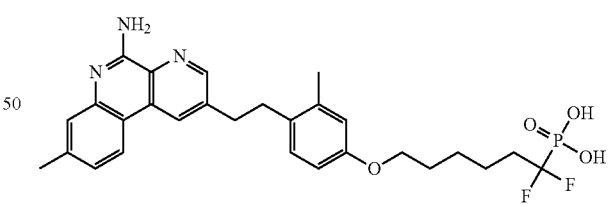

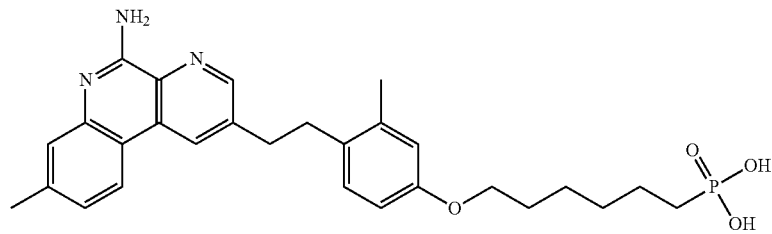 [SMILES: Cc1ccc2c(c1)nc(N)c1ncc(CCc3ccc(OCCCCCCP(=O)(O)O)cc3C)cc12]

Step 1: diethyl 6-bromo-1,1-difluorohexylphosphonate

Diethyl 6-bromo-1,1-difluorohexylphosphonate was prepared according to the procedure described in Example 1—Step 1, but using commercially available 1,5-dibromopentane as the reagent.

Step 2: diethyl 6-(4-(2-(5-amino-8-methylbenzo[f][1,7]naphthyridin-2-yl)ethyl)-3-methylphenoxy)-1,1-difluorohexylphosphonate Diethyl 6-(4-(2-(5-amino-8-methylbenzo[f][1,7]naphthyridin-2-yl)ethyl)-3-methylphenoxy)-1,1-difluorohexylphosphonate was prepared according to the procedure described in Example 1—Step 2, but using diethyl 6-bromo-1,1-difluorohexylphosphonate from the previous step 1 as the reagent.

Step 3: 6-(4-(2-(5-amino-8-methylbenzo[f][1,7]naphthyridin-2-yl)ethyl)-3-methylphenoxy)-1,1-difluorohexylphosphonic acid (24)

6-(4-(2-(5-amino-8-methylbenzo[f][1,7]naphthyridin-2-yl)ethyl)-3-methylphenoxy)-1,1-difluorohexylphosphonic acid (24) was prepared according to the procedure described in Example 1—Step 3, but using diethyl 6-(4-(2-(5-amino-8-methylbenzo[f][1,7]naphthyridin-2-yl)ethyl)-3-methylphenoxy)-1,1-difluorohexylphosphonate from the previous step 2. TFA was added to the $^1$H NMR sample to solubilize the compound for analysis. The $^1$H NMR (MeOD-d4) obtained for 6-(4-(2-(5-amino-8-methylbenzo[f][1,7]naphthyridin-2-yl)ethyl)-3-methylphenoxy)-1,1-difluorohexylphosphonic acid (24) was: δ 8.73 (s, 1H), 8.60 (s, 1H), 8.31 (d, 1H, J=8.4 Hz), 7.48 (s, 1H), 7.43 (d, 1H, J=8.3 Hz), 6.91 (d, 1H, J=8.4 Hz), 6.70 (s, 1H), 6.61 (d, 1H, J=11.0 Hz), 3.90 (t, 2H, J=6.3 Hz), 3.20 (t, 2H, J=7.3 Hz), 3.03 (t, 2H, J=7.5 Hz), 2.54 (s, 2H), 2.22 (s, 3H), 1.79-1.71 (m, 2H), 1.69-1.59 (m, 2H), 1.57-1.47 (m, 2H). LRMS [M+H]=544.2

Example 25

Table 1: Compound 25

Synthesis of 4-((4-(2-(5-amino-8-methylbenzo[f][1,7]naphthyridin-2-yl)ethyl)-3-methylphenoxy)methyl)benzylphosphonic acid (25)

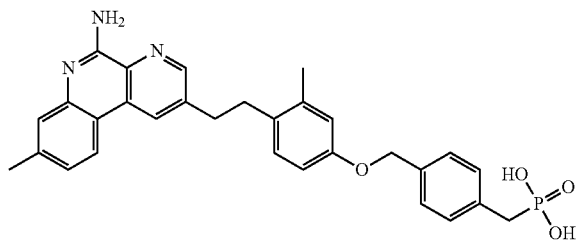 [SMILES: Cc1ccc2c(c1)nc(N)c1ncc(CCc3ccc(OCc4ccc(CP(=O)(O)O)cc4)cc3C)cc12]

Step 1: diethyl 4-(bromomethyl)benzylphosphonate

Diethyl 4-(bromomethyl)benzylphosphonate was prepared according to the procedure described in Example 22—Step 1, but using commercially available 1,4-bis(bromomethyl)benzene as the reagent.

Step 2: diethyl 4-((4-(2-(5-amino-8-methylbenzo[f][1,7]naphthyridin-2-yl)ethyl)-3-methylphenoxy)methyl)benzylphosphonate Diethyl 4-((4-(2-(5-amino-8-methylbenzo[f][1,7]naphthyridin-2-yl)ethyl)-3-methylphenoxy)methyl)benzylphosphonate was prepared according to the procedure described in Example 1—Step 2, but using diethyl 4-(bromomethyl)benzylphosphonate from the previous step 1 as the reagent.

Step 3: 4-((4-(2-(5-amino-8-methylbenzo[f][1,7]naphthyridin-2-yl)ethyl)-3-methylphenoxy)methyl)benzylphosphonic acid (25)

4-((4-(2-(5-amino-8-methylbenzo[f][1,7]naphthyridin-2-yl)ethyl)-3-methylphenoxy)methyl)benzylphosphonic acid (25) was prepared according to the procedure described in Example 1—Step 3, but using diethyl 4-((4-(2-(5-amino-8-methylbenzo[f][1,7]naphthyridin-2-yl)ethyl)-3-methylphenoxy)methyl)benzylphosphonate from the previous step 2. The $^1$H NMR (MeOD-d4) obtained for 4-((4-(2-(5-amino-8-methylbenzo[f][1,7]naphthyridin-2-yl)ethyl)-3-methylphenoxy)methyl)benzylphosphonic acid (25) was: δ 8.72 (s, 1H), 8.58 (s, 1H), 8.30 (d, 1H, J=8.4 Hz), 7.48 (s, 1H), 7.42 (d, 1H, J=9.5 Hz), 7.36-7.30 (m, 4H), 6.93 (d, 1H, J=8.4 Hz), 6.78 (s, 1H), 6.67 (d, 1H, J=8.4 Hz), 4.98 (s, 2H), 3.96 (s, 2H), 3.20 (t, 2H, J=7.2 Hz), 3.04 (t, 2H, J=7.2 Hz), 2.54 (s, 3H), 2.23 (s, 3H). LRMS [M+H]=528.2

Example 26

Table 1: Compound 26

Synthesis of 2 (2 (2 (4 (2 (5 amino-8-methylbenzo[f][1,7]naphthyridin-2-yl)ethyl)-3-methylphenoxy)ethoxy)ethoxy)ethylphosphonic acid (26)

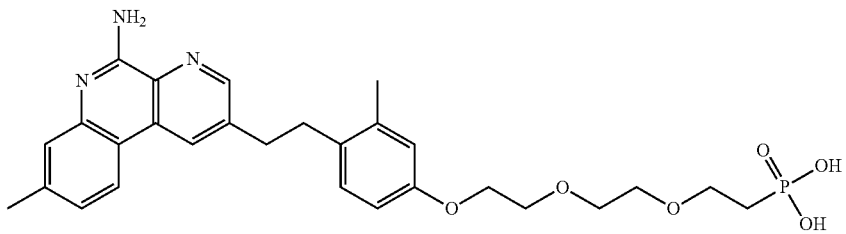 [SMILES: Cc1ccc2c(c1)nc(N)c1ncc(CCc3ccc(OCCOCCOCCP(=O)(O)O)cc3C)cc12]

Step 1: diethyl 2-(2-(2-iodoethoxy)ethoxy)ethylphosphonate

Diethyl 2-(2-(2-iodoethoxy)ethoxy)ethylphosphonate was prepared according to the procedure described in Example 20—Step 1.

Step 2: diethyl 2-(2-(2-(4-(2-(5-amino-8-methyl-benzo[f][1,7]naphthyridin-2-yl)ethyl)-3-methylphenoxy)ethoxy)ethoxy)ethylphosphonate Diethyl 2-(2-(2-(4-(2-(5-amino-8-methylbenzo[f][1,7]naphthyridin-2-yl)ethyl)-3-methylphenoxy)ethoxy)ethoxy)ethylphosphonate was prepared according to the procedure described in Example 1—Step 2, but using diethyl 2-(2-(2-iodoethoxy)ethoxy)ethylphosphonate from the previous step 1 as the reagent.

Step 3: 2-(2-(2-(4-(2-(5-amino-8-methylbenzo[f][1,7]naphthyridin-2-yl)ethyl)-3-methylphenoxy)ethoxy)ethoxy)ethylphosphonic acid (26)

2-(2-(2-(4-(2-(5-amino-8-methylbenzo[f][1,7]naphthyridin-2-yl)ethyl)-3-methylphenoxy)ethoxy)ethoxy)ethylphosphonic acid (26) was prepared according to the procedure described in Example 1—Step 3, but using diethyl 2-(2-(2-(4-(2-(5-amino-8-methylbenzo[f][1,7]naphthyridin-2-yl)ethyl)-3-methylphenoxy)ethoxy)ethoxy)ethylphosphonate from the previous step 2. The $^1$H NMR (MeOD-d4) obtained for 2-(2-(2-(4-(2-(5-amino-8-methylbenzo[f][1,7]naphthyridin-2-yl)ethyl)-3-methylphenoxy)ethoxy)ethoxy)ethylphosphonic acid (26) was: δ 8.73 (s, 1H), 8.66 (s, 1H), 8.38 (d, 1H, J=8.4 Hz), 7.52 (s, 1H), 7.47 (d, 1H, J=8.3 Hz), 7.36 (s, 1H), 6.93 (d, 1H, J=8.4 Hz), 6.75 (s, 2H), 6.64 (d, 1H, J=10.8 Hz), 4.09-4.06 (m, 2H), 3.80-3.76 (m, 2H), 3.69-3.64 (m, 2H), 3.64-3.59 (m, 2H), 3.53-3.49 (m, 2H), 3.25 (t, 2H, J=7.0 Hz), 3.09 (t, 2H, J=7.5 Hz), 2.58 (s, 3H), 2.28 (s, 3H), 2.13-2.01 (m, 2H). LRMS [M+H]=540.2

Example 27

Table 1: Compound 27

Synthesis of 5-(4-(2-(5-amino-8-methylbenzo[f][1,7]naphthyridin-2-yl)ethyl)-3-methylphenoxy)pentylphosphonic acid (27)

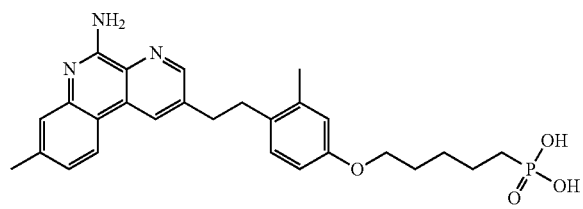 [SMILES: Cc1ccc2c(c1)nc(N)c1ncc(CCc3ccc(OCCCCCP(=O)(O)O)cc3C)cc12]

Step 1: diethyl 5-bromopentylphosphonate

Diethyl 5-bromopentylphosphonate was prepared according to the procedure described in Example 22—Step 1, but using commercially available 1,5-dibromopentane as the reagent.

Step 2: diethyl 5-(4-(2-(5-amino-8-methylbenzo[f][1,7]naphthyridin-2-yl)ethyl)-3-methylphenoxy)pentylphosphonate Diethyl 5-(4-(2-(5-amino-8-methylbenzo[f][1,7]naphthyridin-2-yl)ethyl)-3-methylphenoxy)pentylphosphonate was prepared according to the procedure described in Example 1—Step 2, but using diethyl 5-bromopentylphosphonate from the previous step 1 as the reagent.

Step 3: 5-(4-(2-(5-amino-8-methylbenzo[f][1,7]naphthyridin-2-yl)ethyl)-3-methylphenoxy)pentylphosphonic acid (27)

5-(4-(2-(5-amino-8-methylbenzo[f][1,7]naphthyridin-2-yl)ethyl)-3-methylphenoxy)pentylphosphonic acid (27) was prepared according to the procedure described in Example 1—Step 3, but using diethyl 5-(4-(2-(5-amino-8-methylbenzo[f][1,7]naphthyridin-2-yl)ethyl)-3-methylphenoxy)pentylphosphonate from the previous step 2. The $^1$H NMR (dimethyl sulfoxide-$d_6$) obtained for 5-(4-(2-(5-amino-8-methylbenzo[f][1,7]naphthyridin-2-yl)ethyl)-3-methylphenoxy)pentylphosphonic acid (27) was: δ 8.99 (s, 1H), 8.83 (s, 1H), 8.53 (d, 1H, J=8.4 Hz), 7.51 (s, 1H), 7.39 (d, 1H, J=8.4 Hz), 7.06 (d, 1H, J=8.4 Hz), 6.71 (s, 1H), 6.65 (d, 1H, J=8.3 Hz), 3.87 (t, 2H, J=6.3 Hz), 3.12 (t, 2H, J=7.0 Hz), 2.96 (t, 2H, J=7.0 Hz), 2.5 (s, 3H), 2.26 (s, 3H), 1.73-1.64 (m, 2H), 1.64-1.58 (m, 2H), 1.58-1.51 (m, 2H), 1.51-1.41 (m, 2H). LRMS [M+H]=494.2

Example 28

Table 1: Compound 28

Synthesis of 4-(4-(2-(5-amino-8-methylbenzo[f][1,7]naphthyridin-2-yl)ethyl)-3-methylphenoxy)butylphosphonic acid (28)

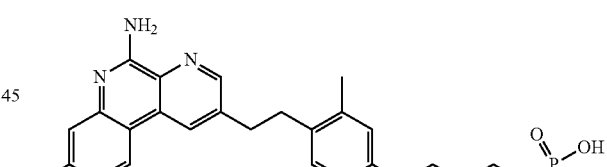

Step 1: diethyl 4-bromobutylphosphonate

Diethyl 4-bromobutylphosphonate was prepared according to the procedure described in Example 22—Step 1, but using commercially available 1,4-dibromobutane as the reagent.

Step 2: diethyl 4-(4-(2-(5-amino-8-methylbenzo[f][1,7]naphthyridin-2-yl)ethyl)-3-methylphenoxy)butylphosphonate Diethyl 4-(4-(2-(5-amino-8-methylbenzo[f][1,7]naphthyridin-2-yl)ethyl)-3-methylphenoxy)butylphosphonate was prepared according to the procedure described in Example 1—Step 2, but using diethyl 4-bromobutylphosphonate from the previous step 1 as the reagent.

Step 3: 4-(4-(2-(5-amino-8-methylbenzo[f][1,7]naphthyridin-2-yl)ethyl)-3-methylphenoxy)butylphosphonic acid (28)

4-(4-(2-(5-amino-8-methylbenzo[f][1,7]naphthyridin-2-yl)ethyl)-3-methylphenoxy)butylphosphonic acid (28) was prepared according to the procedure described in Example 1—Step 3, but using diethyl 4-(4-(2-(5-amino-8-methyl-benzo[f][1,7]naphthyridin-2-yl)ethyl)-3-methylphenoxy)butylphosphonate from the previous step 2. The $^1$H NMR (dimethyl sulfoxide-$d_6$) obtained for 4-(4-(2-(5-amino-8-methylbenzo[f][1,7]naphthyridin-2-yl)ethyl)-3-methylphenoxy)butylphosphonic acid (28) was: δ 8.93 (s, 1H), 8.79 (s, 1H), 8.48 (d, 1H, J=8.3 Hz), 7.51 (s, 1H), 7.37 (d, 1H, J=8.5 Hz), 7.04 (d, 1H, J=8.4 Hz), 6.71 (s, 1H), 6.63 (d, 1H, J=8.3 Hz), 3.89 (t, 2H, J=6.09 Hz), 3.12 (t, 2H, J=6.8 Hz), 2.96 (t, 2H, J=6.9 Hz), 2.47 (s, 3H), 2.34-2.31 (m, 2H), 2.24 (s, 3H), 1.80-1.67 (m, 4H), 1.67-1.61 (m, 2H). LRMS [M+H]=480.2

The compounds of Formula (I), prepared following the procedures described above, are set forth in Table 1 along with [M+H] data and Human TLR7 $EC_{50}$ (nM) data.

TABLE 1

| Compound Number | Structure | Physical Data MS (m/z) [M + H] | Human TLR7 $EC_{50}$ (nM) HEK293 |
|---|---|---|---|
| 1 | 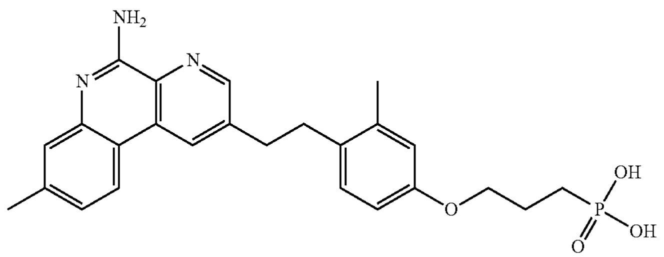 [SMILES: Cc1ccc2c(c1)nc(N)c1ncc(CCc3ccc(OCCCP(=O)(O)O)cc3C)cc12] | 466.2 | 226 |
| 2 | 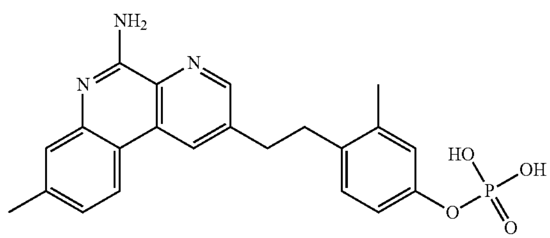 [SMILES: Cc1ccc2c(c1)nc(N)c1ncc(CCc3ccc(OP(=O)(O)O)cc3C)cc12] | 424.0 | 315 |
| 3 | 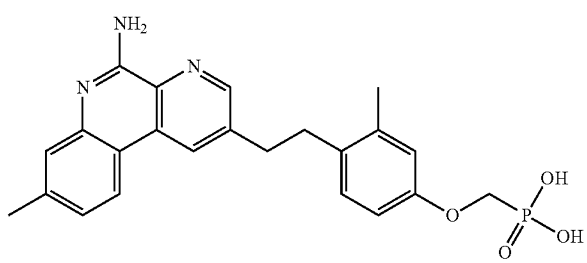 [SMILES: Cc1ccc2c(c1)nc(N)c1ncc(CCc3ccc(OCP(=O)(O)O)cc3C)cc12] | 438.0 | 3170 |
| 4 | 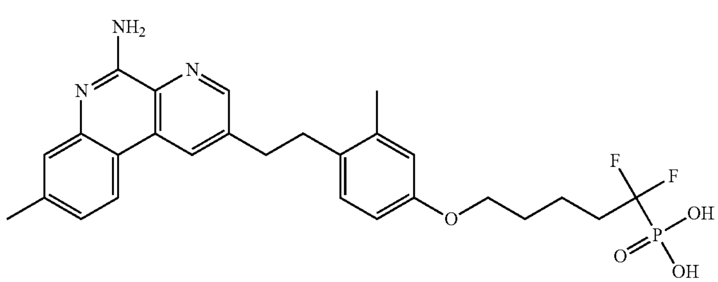 [SMILES: Cc1ccc2c(c1)nc(N)c1ncc(CCc3ccc(OCCCCC(F)(F)P(=O)(O)O)cc3C)cc12] | 530.2 | 559 |

TABLE 1-continued

| Compound Number | Structure | Physical Data MS (m/z) [M + H] | Human TLR7 EC$_{50}$ (nM) HEK293 |
|---|---|---|---|
| 5 | 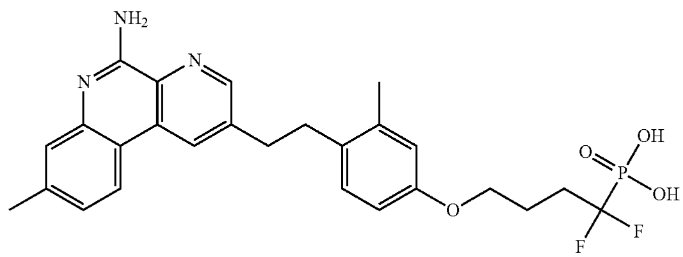 [SMILES: Cc1ccc2c(c1)nc(N)c1ncc(CCc3ccc(OCCCC(F)(F)P(=O)(O)O)cc3C)cc12] | 516.2 | 308 |
| 6 | 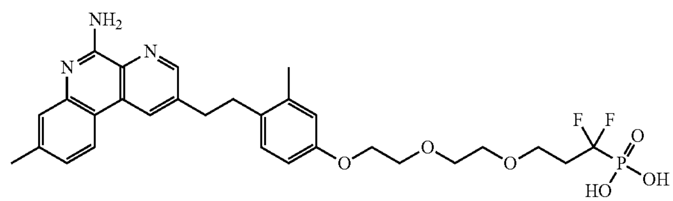 [SMILES: Cc1ccc2c(c1)nc(N)c1ncc(CCc3ccc(OCCOCCOCCC(F)(F)P(=O)(O)O)cc3C)cc12] | 590.2 | 1640 |
| 7 | 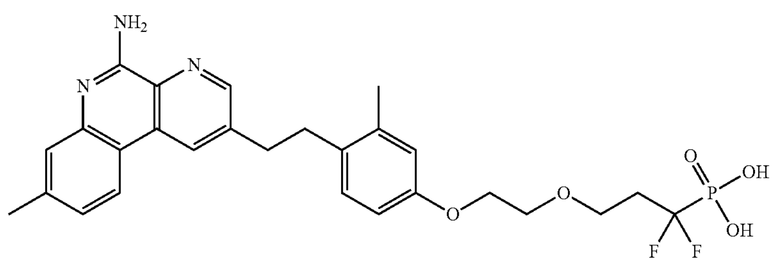 [SMILES: Cc1ccc2c(c1)nc(N)c1ncc(CCc3ccc(OCCOCCC(F)(F)P(=O)(O)O)cc3C)cc12] | 546.3 | 1010 |
| 8 | 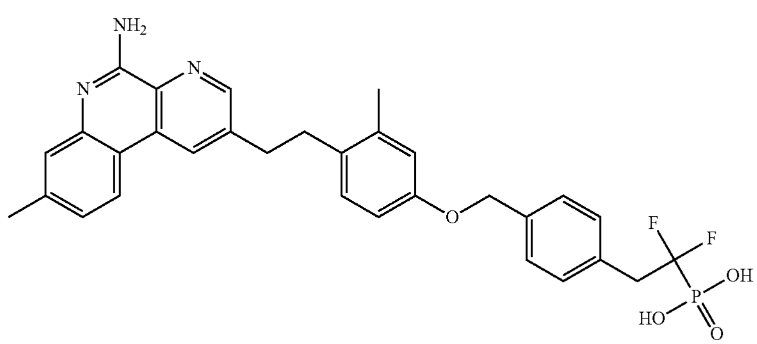 [SMILES: Cc1ccc2c(c1)nc(N)c1ncc(CCc3ccc(OCc4ccc(CC(F)(F)P(=O)(O)O)cc4)cc3C)cc12] | 578.2 | 375 |
| 9 | 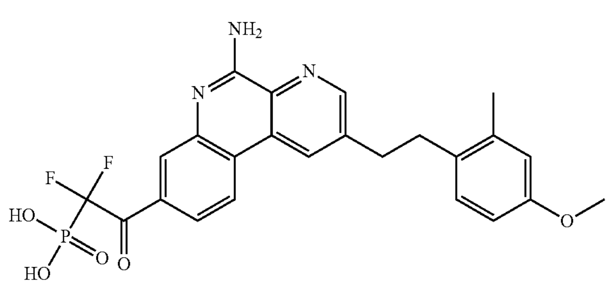 [SMILES: COc1ccc(CCc2cnc3c(N)nc4cc(C(=O)C(F)(F)P(=O)(O)O)ccc4c3c2)c(C)c1] | 502.6 | 390 |

TABLE 1-continued
| Compound Number | Structure | Physical Data MS (m/z) [M + H] | Human TLR7 EC$_{50}$ (nM) HEK293 |
|---|---|---|---|
| 10 | 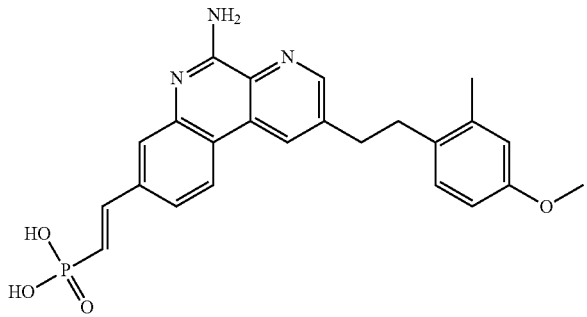 [SMILES: COc1ccc(CCc2cnc3c(N)nc4cc(/C=C/P(=O)(O)O)ccc4c3c2)c(C)c1] | 450.2 | 153 |
| 11 | 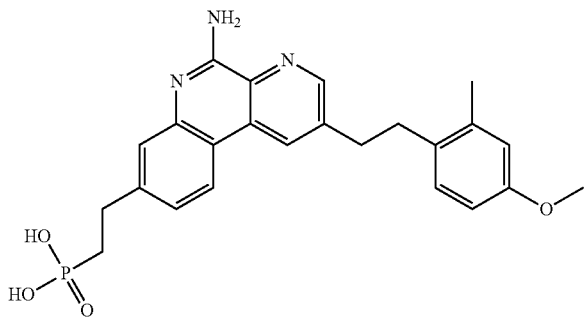 [SMILES: COc1ccc(CCc2cnc3c(N)nc4cc(CCP(=O)(O)O)ccc4c3c2)c(C)c1] | 452.2 | 90 |
| 12 | 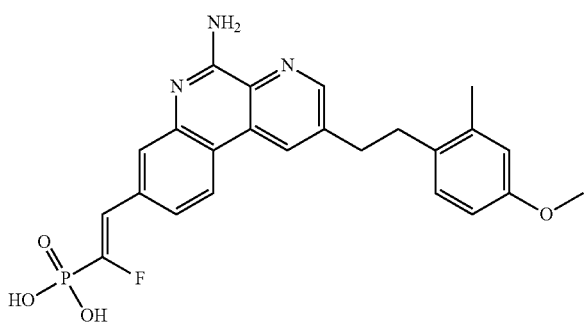 [SMILES: COc1ccc(CCc2cnc3c(N)nc4cc(/C=C(\F)P(=O)(O)O)ccc4c3c2)c(C)c1] | 468.1 | 201 |
| 13 | 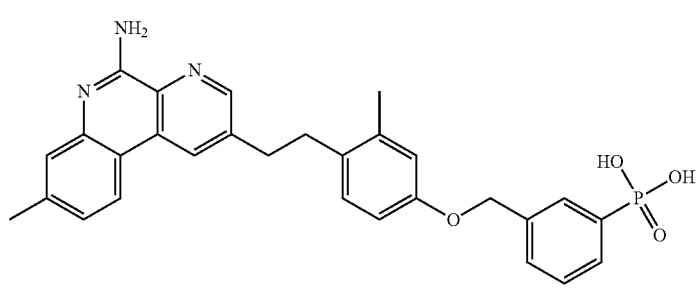 [SMILES: Cc1ccc2c(c1)nc(N)c1ncc(CCc3ccc(OCc4cccc(P(=O)(O)O)c4)cc3C)cc12] | 514.2 | 1051 |
| 14 | 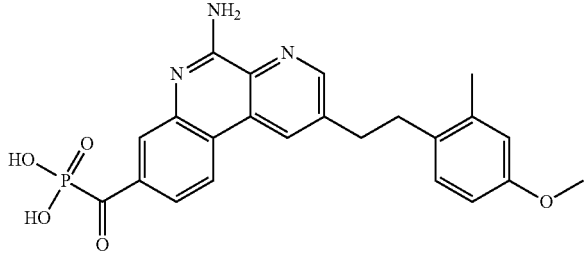 [SMILES: COc1ccc(CCc2cnc3c(N)nc4cc(C(=O)P(=O)(O)O)ccc4c3c2)c(C)c1] | 452.2 | 885 |

TABLE 1-continued
| Compound Number | Structure | Physical Data MS (m/z) [M + H] | Human TLR7 EC$_{50}$ (nM) HEK293 |
|---|---|---|---|
| 15 | 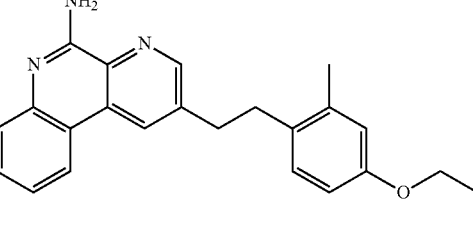 | 524.2 | 65 |
| 16 | 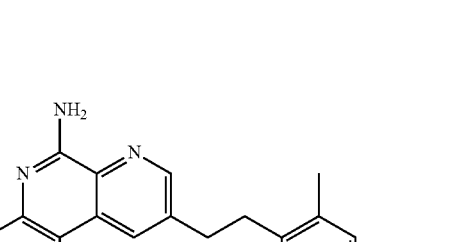 | 574.2 | 137 |
| 17 | 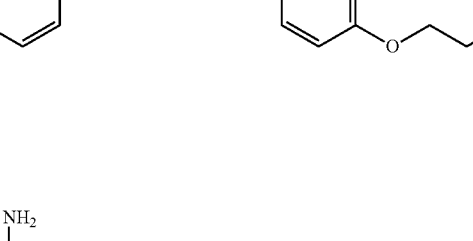 | 648.2 | 5 |
| 18 | 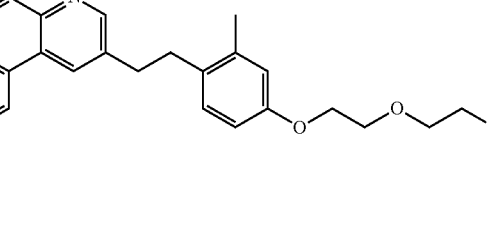 | 641.6 | 964 |
| 19 | 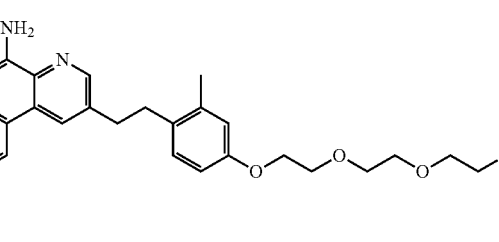 | 604.2 | 360 |

TABLE 1-continued

| Compound Number | Structure | Physical Data MS (m/z) [M + H] | Human TLR7 EC$_{50}$ (nM) HEK293 |
|---|---|---|---|
| 20 | 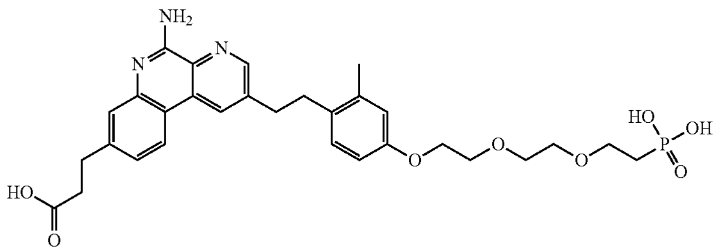 [SMILES: Cc1cc(OCCOCCOCCP(=O)(O)O)ccc1CCc1cnc2c(N)nc3cc(CCC(=O)O)ccc3c2c1] | 598.2 | 384 |
| 21 | 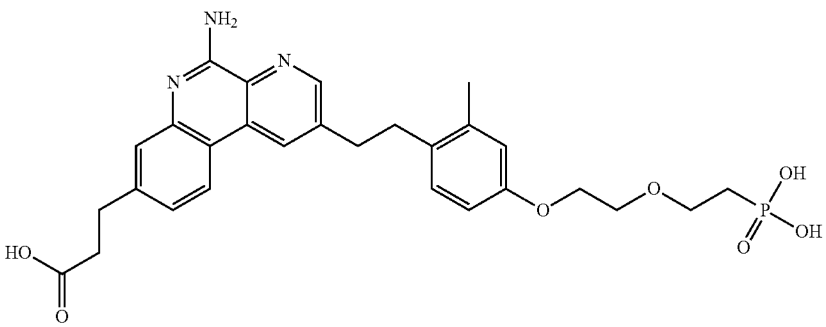 [SMILES: Cc1cc(OCCOCCP(=O)(O)O)ccc1CCc1cnc2c(N)nc3cc(CCC(=O)O)ccc3c2c1] | 554.2 | 204 |
| 22 | 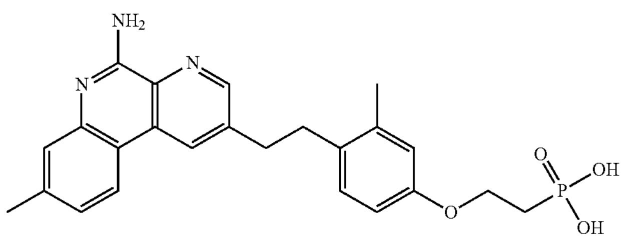 [SMILES: Cc1ccc2c(c1)nc(N)c1ncc(CCc3ccc(OCCP(=O)(O)O)cc3C)cc12] | 452.2 | 1160 |
| 23 | 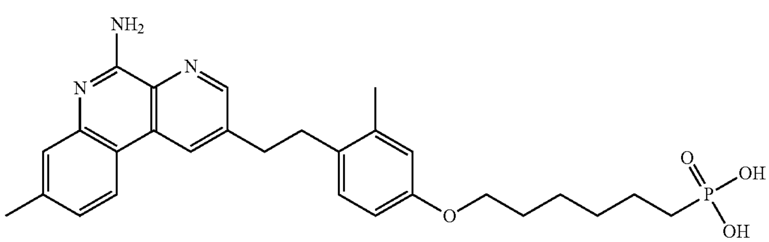 [SMILES: Cc1ccc2c(c1)nc(N)c1ncc(CCc3ccc(OCCCCCCP(=O)(O)O)cc3C)cc12] | 508.2 | 791 |
| 24 | 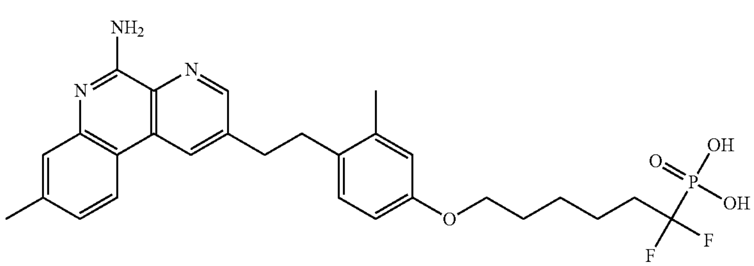 [SMILES: Cc1ccc2c(c1)nc(N)c1ncc(CCc3ccc(OCCCCCC(F)(F)P(=O)(O)O)cc3C)cc12] | 544.2 | 4260 |

TABLE 1-continued

| Compound Number | Structure | Physical Data MS (m/z) [M + H] | Human TLR7 EC$_{50}$ (nM) HEK293 |
| --- | --- | --- | --- |
| 25 | 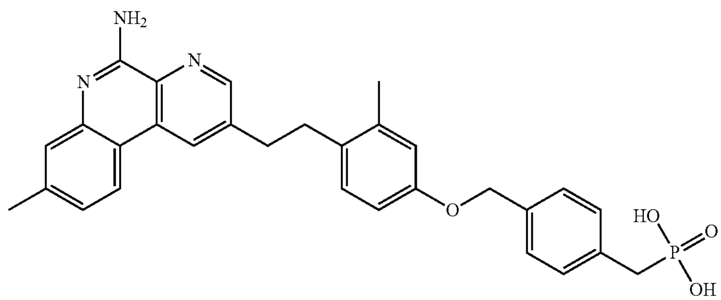 [SMILES: Cc1ccc2c(c1)nc(N)c1ncc(CCc3ccc(OCc4ccc(CP(=O)(O)O)cc4)cc3C)cc12] | 528.2 | 975 |
| 26 | 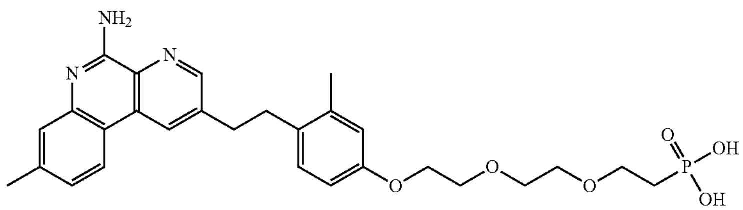 [SMILES: Cc1ccc2c(c1)nc(N)c1ncc(CCc3ccc(OCCOCCOCCP(=O)(O)O)cc3C)cc12] | 540.2 | 2592 |
| 27 | 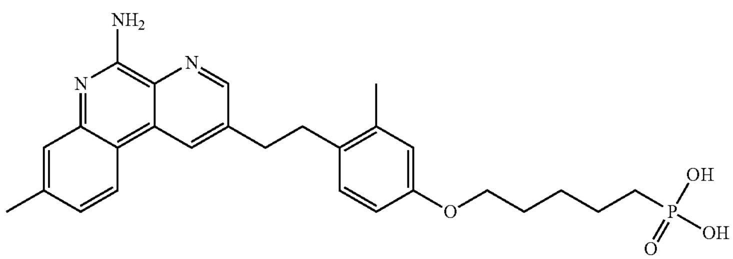 [SMILES: Cc1ccc2c(c1)nc(N)c1ncc(CCc3ccc(OCCCCCP(=O)(O)O)cc3C)cc12] | 494.2 | 921 |
| 28 | 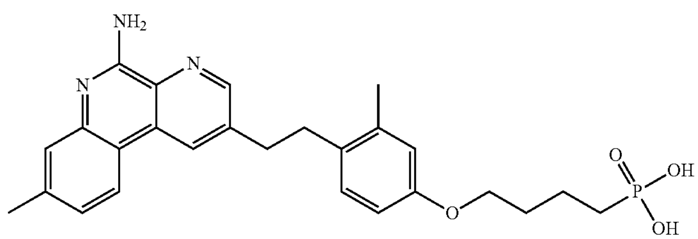 [SMILES: Cc1ccc2c(c1)nc(N)c1ncc(CCc3ccc(OCCCCP(=O)(O)O)cc3C)cc12] | 480.2 | 524 |

Assays

Compounds of Formula (I) provided herein were assayed to measure their capacity to modulate toll-like receptor 7.

Human Peripheral Blood Mononuclear Cell Assay

The bioactivity of the compounds of Formula (I) provided herein were tested in the human peripheral blood assay (human PBMC) using a panel of independent normal human donors according to approved guidelines by the institutional review committee. Human PBMC were isolated from freshly peripheral blood using a Ficoll density gradient (GE healthcare 17-1440-03). 30-35 mLs of peripheral human blood were layered onto 15 mLs of Ficoll in 50 ml conical tubes, followed by centrifugation at 1800 rpm (Eppendorf Centrifuge 5810R with biohazard caps over the tube buckets) at room temperature for 30 minutes with no acceleration and no brake. The buffy layers were then collected and transferred onto new 50 ml conical tubes and washed twice in complete media consisting of RPMI 1640 (11875085 from Invitrogen Corporation, Carlsbad, Calif.) supplemented with 10% heat inactivated fetal bovine serum (Gibco 10099-141), 1% Pen-Strep (Gibco#15140-122), 1 mM non essential amino acids (Gibco#11140-050), 1 mM sodium pyruvate (Gibco#11360-070), 2 mM L-Glutamine (Gibco#25030-081) and 1 mM HEPES (Gibco#15630-080). Viable cells were then counted using trypan blue staining, plated in 96 well flat bottom plates (Becton Dickinson #353070) at 2×10$^5$ cells per well in 200 µl total volume of complete media. Compounds were then added in a 10 point dose response format starting at 100 µM, 3 fold dilution. Negative controls wells received equal concentration of DMSO. Culture supernatants were collected after 18-24 hours incubation at 37° C., 5% CO$_2$, stored at −20° C. until further use.

IL-6 levels in the culture supernatants were measured using a Luminex kit (Biorad). Data analysis is performed using Prism software from GraphPad (San Diego, Calif.). Dose response curves are generated for each compound and EC$_{50}$ values were determined as the concentration that gives 50% of the maximal signal.

Reporter Gene Assay

Human embryonic kidney 293 (HEK 293) cells were stably transfected with human TLR7 and an NF-kB-driven luciferase reporter vector (pNifty-Luciferase). As a control assay, normal Hek293 transfected with pNifty-Luc were used. Cells were cultured in DMEM supplemented with 2 mM L-glutamine, 10% heart inactivated FBS, 1% penicillin and streptomycin, 2 µg/ml puromycin (InvivoGen #ant-pr-5) and 5 µg/ml of blasticidin (Invitrogen #46-1120). Bright-Glo™ Luciferase assay buffer and substrate were supplied by Promega #E263B and #E264B (assay substrate and buffer respectively). 384 well clear-bottom plates were supplied by Greiner bio-one (#789163-G) and were custom bar-coded plates.

Cells were plated at 25,000 cells/well in 384-well plates in a final volume of 50 µl of media. Cells were allowed to adhere to the plates after overnight (18 hours) culture at 37° C. and 5% $CO_2$. Serially diluted experimental and positive control compounds were then dispensed to each well and incubated for 7 hours at 37° C. and 5% $CO_2$. Cells stimulated with DMSO alone also serve as negative controls. After the incubation, 30 µl of the pre-mix assay buffer and substrate buffer were added to each well according to manufacturer's instructions. The luminescence signal was read on a CLIPR machine with an integration time of 20 seconds per plate.

Dose response curves are generated for each compound and $EC_{50}$ values were determined as the concentration that gives 50% of the maximal signal.

Certain Assay Results

Various compounds of Formula (I) in free form or in pharmaceutically acceptable salt form, exhibit pharmacological properties, for example, as indicated by the in vitro tests described in this application. The $EC_{50}$ value in those experiments is given as that concentration of the test compound in question that provoke a response halfway between the baseline and maximum responses. In certain examples compounds of Formula (I) have $EC_{50}$ values in the range from 1 nM to 100 µM. In other examples, compounds of Formula (I) have $EC_{50}$ values in the range from 1 nM to 50 µM. In other examples, compounds of Formula (I) have $EC_{50}$ values in the range from 1 nM to 25 µM. In other examples, compounds of Formula (I) have $EC_{50}$ values in the range from 1 nM to 20 µM. In other examples, compounds of Formula (I) have $EC_{50}$ values in the range from 1 nM to 15 µM. In other examples, compounds of Formula (I) have $EC_{50}$ values in the range from 1 nM to 10 µM. In other examples, compounds of Formula (I) have $EC_{50}$ values in the range from 1 nM to 5 µM. In other examples, compounds of Formula (I) have $EC_{50}$ values in the range from 1 nM to 2 µM. In other examples, compounds of Formula (I) have $EC_{50}$ values in the range from 1 nM to 1 µM. In other examples, compounds of Formula (I) have $EC_{50}$ values in the range from 1 nM to 500 nM. In other examples, compounds of Formula (I) have $EC_{50}$ values in the range from 1 nM to 250 nM. In other examples, compounds of Formula (I) have $EC_{50}$ values in the range from 1 nM to 100 nM. In other examples, compounds of Formula (I) have $EC_{50}$ values in the range from 1 nM to 50 nM. In other examples, compounds of Formula (I) have $EC_{50}$ values in the range from 1 nM to 25 nM. In other examples, compounds of Formula (I) have $EC_{50}$ values in the range from 1 nM to 10 nM. Such $EC_{50}$ values are obtained relative to the activity of resiquimod set to 100%.

By way of example only, the $EC_{50}$ for TLR-7 stimulation by certain compounds of Formula (I) are listed in Table 1.

Formulation with Aluminum-Containing Adjuvants

The binding of the compounds of Formula (I) provided herein to aluminum-containing adjuvants at pH 9 and pH 6.5 was evaluated using HPLC to monitor the presence of the compound of Formula (I) in the supernatant.

Evaluation of Binding at pH 9

Compound 1 (0.5 mg/mL) was dissolved in 10 mM NaOH and added to aluminum hydroxide adjuvant (2 mg/mL) resulting in a 100 µg/dose formulation. The supernatant was evaluated with HPLC using a ballistic gradient (from 10% $CH_3CN$-0.1% TFA to 100% $CH_3CN$-0.1% TFA in 2.5 minutes) on a C18 (50 cm×4.6 mm) ACE column at 45° C. To evaluate the effect of supernatant temperature and incubation time on binding, the supernatant was evaluated at a supernatant temperature of room temperature and at 37° C. after 1 hour, 5 hours and 24 hours. A control without aluminum hydroxide was also evaluated. The HPLC chromatograms for compound 1 formulations with and without aluminum hydroxide, at either temperature or incubation time, indicated that compound 1 was not present in the supernatant when aluminum hydroxide was included in the formulation. FIG. 1 shows the concentration of compound 1 in the supernatant, as measured via HPLC, for compound 1 with alum at room temperature and 37° C., and for compound 1 alone (control).

Compound 5 (1 mg/mL) was dissolved in 10 mM NaOH and added to aluminum hydroxide adjuvant (2 mg/mL) resulting in a 100 µg/dose formulation. The supernatant was evaluated with HPLC using a ballistic gradient (from 10% $CH_3CN$-0.1% TFA to 100% $CH_3CN$-0.1% TFA in 2.5 minutes) on a C18 (50 cm×4.6 mm) ACE column at 45° C. To evaluate the effect of supernatant temperature and incubation time on binding, the supernatant was evaluated at a supernatant temperature of room temperature and at 37° C. after 1 hour, 5 hours and 24 hours. A control without aluminum hydroxide was also evaluated. The HPLC chromatograms for compound 5 formulations with and without aluminum hydroxide, at either temperature or incubation time, indicated that compound 5 was not present in the supernatant when aluminum hydroxide was included in the formulation.

Evaluation of Binding at pH 6.5

Compound 1 (0.5 mg/mL) was dissolved in 10 mM NaOH and added to aluminum hydroxide adjuvant (2 mg/mL) resulting in a 100 µg/dose formulation. The pH of the solution was adjusted to pH 6.5 using HCl. The supernatant was evaluated with HPLC using a ballistic gradient (from 10% $CH_3CN$-0.1% TFA to 100% $CH_3CN$-0.1% TFA in 2.5 minutes) on a C18 (50 cm×4.6 mm) ACE column at 45° C. To evaluate the effect of supernatant temperature and incubation time on binding, the supernatant was evaluated at a supernatant temperature of room temperature and at 37° C. after 1 hour, 5 hours and 24 hours. A control without aluminum hydroxide was also evaluated. The HPLC chromatograms for compound 1 formulations with and without aluminum hydroxide, at either temperature or incubation time, indicated that compound 1 was not present in the supernatant when aluminum hydroxide was included in the formulation.

Evaluation of Binding at pH 6.7

Compound 5 (1 mg/mL) was dissolved in 10 mM histidine buffer (1 mg/mL) and added to aluminum hydroxide adjuvant (2 mg/mL) resulting in a 100 µg/dose formulation. The supernatant was evaluated with HPLC using a ballistic gradient (from 10% $CH_3CN$-0.1% TFA to 100% $CH_3CN$-0.1% TFA in 2.5 minutes) on a C18 (50 cm×4.6 mm) ACE column at 45° C. To evaluate the effect of supernatant temperature and incubation time on binding, the supernatant was evaluated at a supernatant temperature of room temperature and at 37° C. after 1 hour, 5 hours and 24 hours. A control without aluminum hydroxide was also evaluated. The HPLC chromatograms for compound 5 formulations with and without aluminum hydroxide, at either temperature or incubation time, indicated that compound 5 was not present in the supernatant when aluminum hydroxide was included in the formulation.

Evaluation of Binding at pH 9 (Histidine Buffer Adjusted to pH 9)

An organic solvent extraction method was used to evaluate whether compound 1 was covalently bound to aluminum hydroxide. The formulation was prepared as follows: 2 mg/ml aluminum hydroxide, 100 µg/dose compound 1, 10 mM histidine buffer) and the pH was adjusted to 9. A control formulation without aluminum hydroxide was also prepared.

One ml of the formulation containing Alum was mixed with 1 ml of $KH_2PO_4$ 1M pH 9 (0.5M final conc, pH 9) and was left in gentle agitation overnight at 37° C. to allow desorption of compound 1 (compound 5) from the aluminum hydroxide via ligand exchange with the phosphate anions. Organic extraction was then performed: 1 ml of each sample was mixed with 1 ml of n-butanol and vortexed. After the formation of 2 phases, the upper phase (butanol) was recovered, dried with $N_2$ and resuspended in MeOH/10 mM NaOH. HPLC analysis was run both for the formulation supernatants and for the butanol extracted samples (C18 column; 0-100% B in 2 min; A=0.1% TFA in $H_2O$; B=0.1% TFA in ACN). Increased quantities of compound 1 were observed in the supernatant of the formulation treated with $KH_2PO_4$, indicating desorption of compound 1 by the phosphate anions. The same trend was observed with the extracted samples. The data obtained is given in the table 2 below:

TABLE 2

|  | Retention Time (min) | Area | Concentration (mg/ml) |
|---|---|---|---|
| Compound 1 supernatent | 1.9 | 2687 | 0.005 +/− 0.001 |
| Compound 1 phosphate supernatent | 1.9 | 32303 | 0.059 +/− 0.001 |
| Compound 1 supernatant control | 1.9 | 180678 | 0.329 +/− 0.001 |
| Compound 1 extaract | 1.9 | 15008 | 0.027 +/− 0.001 |
| Compound 1 phosphate/extract | 1.9 | 65427 | 0.119 +/− 0.001 |
| Compound 1 control/extract | 1.9 | 119470 | 0.217 +/− 0.001 |

Effect on the Binding of MenB Antigens to Aluminum Hydroxide

SDS PAGE was used to evaluate the effect of the binding of compound 1 to aluminum hydroxide adjuvant on the ability of MenB antigens to bind to aluminum hydroxide adjuvant. Compound 1 was dissolved in 10 mM NaOH at 0.5 mg/ml final concentration. Alum and Compound 1 were combined at 1:6 (Compound 1:Alum) weight ratio in the presence of 10 mM Histidine final concentration. The pH was adjusted to 9.2 and the mixture was gently agitated for 3 hours at room temperature, allowing the reaction to occur. The mixture was centrifuged at 5000×g for 10 minutes and the supernatant discarded. The pellet (i.e. the compound 1-modified Alum) was resuspended in the initial Alum buffer to obtain the starting alum concentration. The pH was adjusted to 6.5. The modified Alum was then used for the formulation with the MenB antigens.

Figure 2:
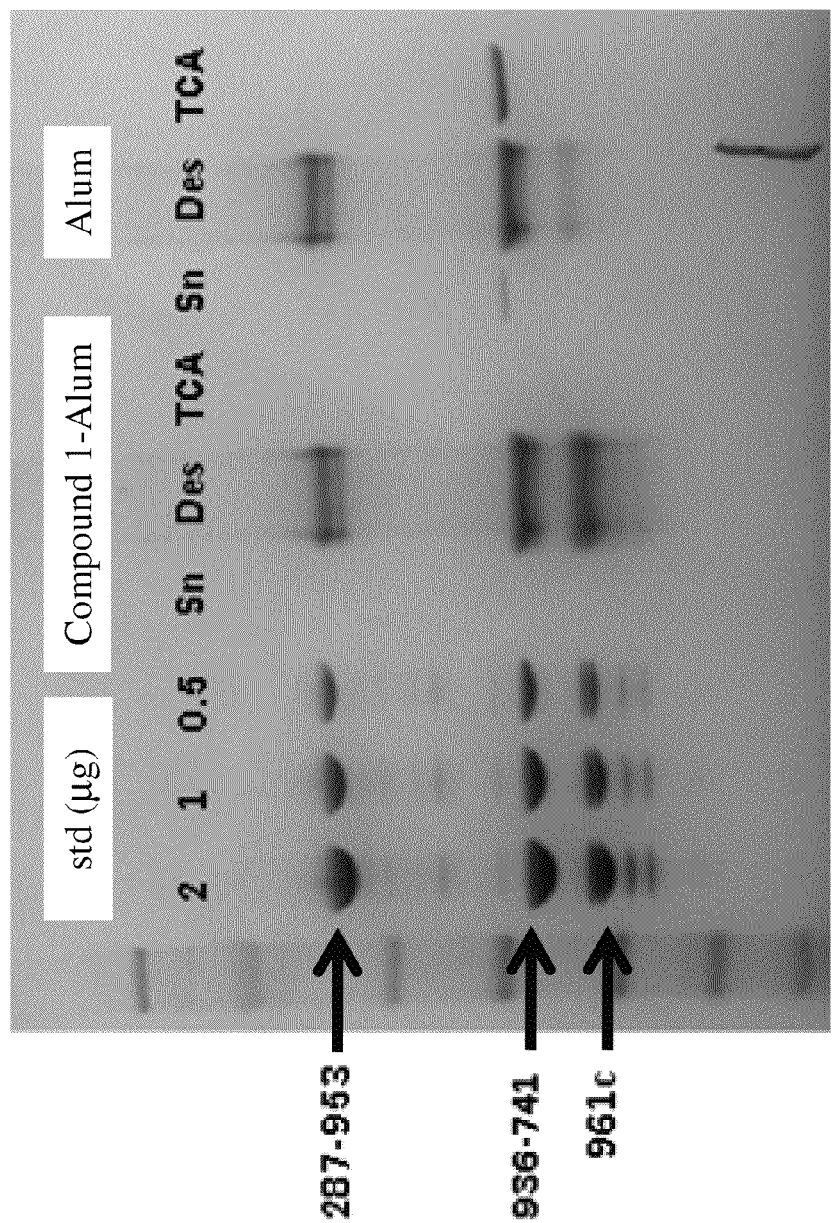
FIG. 2 shows the effect of the binding of compound 1 to aluminum hydroxide adjuvant on the binding of antigens of *Neisseria meningitis* (MenB) to aluminum hydroxide adjuvant.

SDS PAGE analysis of the supernatant of MenB antigens formulated with aluminum hydroxide adjuvant alone (Alum) or with aluminum hydroxide adjuvant together with compound 1 is shown in FIG. 1. The MenB antigens evaluated were 287-953, 936-741 and 961c, which antigens are described in WO2004/032958 and Giuliani et al. (2006) Proc. Natl. Acad. Sci. USA 103:10834-10839. Lanes labeled "Sn" and TCA" represent analysis of the formulations supernatants after centrifugation to pellet the aluminum hydroxide adjuvant. Lanes labeled "Des" represent analysis of antigens recovered after desorption from the aluminum hydroxide with 0.5 M phosphate buffer. FIG. 2 shows that the MenB antigens bind to aluminum hydroxide as effectively with compound 1 as obtained without compound 1.

The adsorption of compound 16 and compound 18 to aluminum hydroxide was also evaluated using the alum formulation described above for compound 1. HPLC analysis showed that, for both compounds, no compound was observed in the supernatant after addition of aluminum hydroxide. However, compound 16 and compound 18 were recovered after desorption with 0.5M $KH_2PO_4$. Note that organic solvent extraction was not required due to the water solubility of the two compounds. In addition, SDS PAGE analysis of antigen binding in the presence of compound 16 or compound 18 was carried out as described above. For both compounds all the 3 MenB antigens were completely adsorbed to the compound 16-modified alum and to the compound 18-modified alum.

Evaluation of Binding to Alum in 10 mM Histidine Buffer

The adsorption of compounds 6, 16, 17, 19 and 20 to aluminum hydroxide was evaluated as follows: to three volume equivalents of aqueous aluminum hydroxide (2 mg/mL) was added one volume equivalent of compound in 10 mM histidine buffer (4 mg/mL) at pH 6.8. The resulting solution was diluted 10-fold with blank histidine buffer to a final compound concentration of 0.1 mg/mL. Diluted solutions were incubated at 37° C. for 5 hours. The samples were centrifuged at 14,000 rpm for 10 minutes to pellet the insoluble. The supernatant (along with an internal standard) was then evaluated by LC-MS/MS using a ballistic gradient (from 5% $CH_3CN$-0.5% formic acid to 95% $CH_3CN$-1.0% formic acid in 3.5 minutes) on a Waters Atlantis dC18 (50 mm×2.1 mm) column at room temperature against a calibration curve prepared at known compound concentrations ranging from 0.005 to 50 µM. The concentration in the supernatant was calculated as % unbound to alum compared to control; the % bound to alum was calculated as 100% minus % unbound. Table 3 lists the % binding of the respective compounds tested.

TABLE 3

| Compound in Table 1 | % Alum bound in Histidine buffer |
|---|---|
| 6 | 98.2 |
| 16 | 94.5 |
| 17 | 96.2 |
| 19 | 96.0 |
| 20 | 97.0 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula (I), or pharmaceutically acceptable salt thereof:

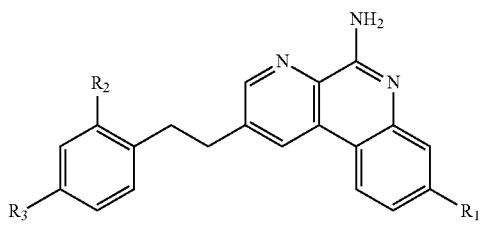

Formula (I)

wherein:
R$^1$ is -L$^2$R$^5$, -L$^2$R$^6$, —OL$^2$R$^5$, or —OL$^2$R$^6$
L$^2$ is C$_1$-C$_6$alkylene, C$_2$-C$_6$alkenylene, or —((CR$^4$R$^4$)$_p$O)$_q$(CH$_2$)$_p$—, wherein the C$_1$-C$_6$alkylene and C$_2$-C$_6$alkenylene of L$^2$ are optionally substituted with 1 to 4 fluoro groups;
each L$^3$ is independently selected from C$_1$-C$_6$alkylene and —((CR$^4$R$^4$)$_p$O)$_q$(CH$_2$)$_p$—, wherein the C$_1$-C$_6$alkylene of L$^3$ is optionally substituted with 1 to 4 fluoro groups;
R$^2$ is H or C$_1$-C$_4$alkyl;
R$^3$ is selected from -L$^3$R$^5$, -L$^3$R$^7$, —OL$^3$R$^7$;
each R$^4$ is independently selected from H and fluoro;
R$^5$ is —P(O)(OH)$_2$,
R$^6$ is —CF$_2$P(O)(OH)$_2$ or —C(O)OH;
R$^7$ is —CF$_2$P(O)(OH)$_2$ or —C(O)OH;
each p is independently selected from 1, 2, 3, 4, 5 and 6, and
q is 1, 2, 3 or 4.

2. A compound of Formula (I), or pharmaceutically acceptable salt thereof:

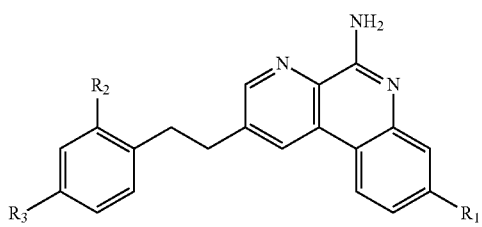

Formula (I)

wherein:
R$^1$ is -L$^2$R$^6$;
R$^2$ is C$_1$-C$_6$alkyl;
R$^3$ is —OL$^3$R$^5$ or —OL$^3$R$^7$;
R$^5$ is —P(O)(OH)$_2$;
R$^6$ is —C(O)OH;
R$^7$ is —CF$_2$P(O)(OH)$_2$;
L$^2$ is C$_1$-C$_6$alkylene, and
L$^3$ is C$_1$-C$_6$alkylene substituted with 1 to 4 fluoro groups.

3. The compound of claim 1, wherein:
R$^1$ is -L$^2$R$^6$;
R$^2$ is C$_1$-C$_6$alkyl;
R$^3$ is —OL$^3$R$^5$ or —OL$^3$R$^7$;
R$^5$ is —P(O)(OH)$_2$;
R$^6$ is —C(O)OH;
R$^7$ is —CF$_2$P(O)(OH)$_2$;
L$^2$ is C$_1$-C$_6$alkylene;
L$^3$ is —((CR$^4$R$^4$)$_p$O)$_q$(CH$_2$)$_p$—;
R$^4$ is H;
q is 1 or 2, and
p is 2.

4. The compound of claim 1, wherein R$^2$ is methyl.

5. The compound of claim 1, wherein the compound is selected from:
3-(5-amino-2-(4-(4,4-difluoro-4-phosphonobutoxy)-2-methylphenethyl)benzo[f][1,7]naphthyridin-8-yl)propanoic acid 3-(5-amino-2-(4-(2-(3,3-difluoro-3-phosphonopropoxy)ethoxy)-2-methylphenethyl)benzo[f][1,7]naphthyridin-8-yl)propanoic acid;

3-(5-amino-2-(2-methyl-4-(2-(2-(2-phosphonoethoxy)ethoxy)ethoxy)phenethyl)benzo[f][1,7]naphthyridin-8-yl)propanoic acid;

3-(5-amino-2-(2-methyl-4-(3-phosphonopropoxy)phenethyl)benzo[f][1,7]naphthyridin-8-yl)propanoic acid; and 3-(5-amino-2-(4-(2-(2-(3,3-difluoro-3-phosphonopropoxy)ethoxy)-2-methylphenethyl)benzo[f][1,7]naphthyridin-8-yl)propanoic acid.

6. A pharmaceutical composition comprising a therapeutically effective amount of a compound of claim 1 and a pharmaceutically acceptable carrier.

7. A method for activating a TLR7 receptor, wherein the method comprises administering to a system or a subject a therapeutically effective amount of a compound of Formula (I) of claim 1.

* * * * *

SEQUENCE LISTING

<160> NUMBER OF SEQ ID NOS: 6

<210> SEQ ID NO 1
<211> LENGTH: 248
<212> TYPE: PRT
<213> ORGANISM: Neisseria meningitidis

<400> SEQUENCE: 1

```
Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245
```

<210> SEQ ID NO 2
<211> LENGTH: 247
<212> TYPE: PRT
<213> ORGANISM: Neisseria meningitidis

<400> SEQUENCE: 2

```
Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60
```

```
Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Ile Tyr Lys Gln Asp His
                 85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Leu Val Ser Gly Leu Gly
            115                 120                 125

Gly Glu His Thr Ala Phe Asn Gln Leu Pro Asp Gly Lys Ala Glu Tyr
        130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
            195                 200                 205

Glu Glu Lys Gly Thr Tyr His Leu Ala Leu Phe Gly Asp Arg Ala Gln
        210                 215                 220

Glu Ile Ala Gly Ser Ala Thr Val Lys Ile Gly Glu Lys Val His Glu
225                 230                 235                 240

Ile Gly Ile Ala Gly Lys Gln
                245

<210> SEQ ID NO 3
<211> LENGTH: 250
<212> TYPE: PRT
<213> ORGANISM: Neisseria meningitidis

<400> SEQUENCE: 3

Val Ala Ala Asp Ile Gly Thr Gly Leu Ala Asp Ala Leu Thr Ala Pro
  1               5                  10                  15

Leu Asp His Lys Asp Lys Gly Leu Lys Ser Leu Thr Leu Glu Asp Ser
                 20                  25                  30

Ile Pro Gln Asn Gly Thr Leu Thr Leu Ser Ala Gln Gly Ala Glu Lys
             35                  40                  45

Thr Phe Lys Ala Gly Asp Lys Asp Asn Ser Leu Asn Thr Gly Lys Leu
         50                  55                  60

Lys Asn Asp Lys Ile Ser Arg Phe Asp Phe Val Gln Lys Ile Glu Val
 65                  70                  75                  80

Asp Gly Gln Thr Ile Thr Leu Ala Ser Gly Glu Phe Gln Ile Tyr Lys
                 85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Leu Val Ser
            115                 120                 125

Gly Leu Gly Gly Glu His Thr Ala Phe Asn Gln Leu Pro Gly Gly Lys
        130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190
```

```
Leu Lys Ala Asp Glu Lys Ser His Ala Val Ile Leu Gly Asp Thr Arg
            195                 200                 205

Tyr Gly Ser Glu Glu Lys Gly Thr Tyr His Leu Ala Leu Phe Gly Asp
        210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
            245                 250

<210> SEQ ID NO 4
<211> LENGTH: 644
<212> TYPE: PRT
<213> ORGANISM: Neisseria meningitidis

<400> SEQUENCE: 4

Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
        35                  40                  45

Asp Met Ala Ala Val Ser Glu Glu Asn Thr Gly Asn Gly Gly Ala Ala
    50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Asp Pro Ser Ala Gly Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
    290                 295                 300

Ile Val Asp Gly Glu Ala Val Ser Leu Thr Gly His Ser Gly Asn Ile
305                 310                 315                 320
```

```
Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Glu Val Leu His
        355                 360                 365

Phe His Thr Glu Asn Gly Arg Pro Ser Pro Ser Arg Gly Arg Phe Ala
    370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Asp Val
            420                 425                 430

Ser Gly Lys Phe Tyr Gly Pro Ala Gly Glu Val Ala Gly Lys Tyr
        435                 440                 445

Ser Tyr Arg Pro Thr Asp Ala Glu Lys Gly Gly Phe Gly Val Phe Ala
    450                 455                 460

Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
            500                 505                 510

Phe Asp Gln Ala Lys Arg Asp Gly Lys Ile Asp Ile Thr Ile Pro Val
        515                 520                 525

Ala Asn Leu Gln Ser Gly Ser Gln His Phe Thr Asp His Leu Lys Ser
    530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
            580                 585                 590

Phe Asn Cys Tyr Gln Ser Pro Met Ala Lys Thr Glu Val Cys Gly Gly
        595                 600                 605

Asp Phe Ser Thr Thr Ile Asp Arg Thr Lys Trp Gly Val Asp Tyr Leu
    610                 615                 620

Val Asn Val Gly Met Thr Lys Ser Val Arg Ile Asp Ile Gln Ile Glu
625                 630                 635                 640

Ala Ala Lys Gln

<210> SEQ ID NO 5
<211> LENGTH: 434
<212> TYPE: PRT
<213> ORGANISM: Neisseria meningitidis

<400> SEQUENCE: 5

Met Val Ser Ala Val Ile Gly Ser Ala Val Gly Ala Lys Ser Ala
1               5                   10                  15

Val Asp Arg Arg Thr Thr Gly Ala Gln Thr Asp Asp Asn Val Met Ala
                20                  25                  30

Leu Arg Ile Glu Thr Thr Ala Arg Ser Tyr Leu Arg Gln Asn Asn Gln
            35                  40                  45
```

Thr Lys Gly Tyr Thr Pro Gln Ile Ser Val Val Gly Tyr Asn Arg His
    50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
            115                 120                 125

Ala Thr Gln Ala Arg Val Lys Ile Val Thr Tyr Gly Asn Val Thr Tyr
    130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
            180                 185                 190

Ala Gly Leu Ala Asp Ala Leu Thr Ala Pro Leu Asp His Lys Asp Lys
            195                 200                 205

Gly Leu Gln Ser Leu Thr Leu Asp Gln Ser Val Arg Lys Asn Glu Lys
    210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
    275                 280                 285

Gln Thr Glu Gln Ile Gln Asp Ser Glu His Ser Gly Lys Met Val Ala
            290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
                325                 330                 335

Gly Ser Asp Asp Ala Gly Gly Lys Leu Thr Tyr Thr Ile Asp Phe Ala
            340                 345                 350

Ala Lys Gln Gly Asn Gly Lys Ile Glu His Leu Lys Ser Pro Glu Leu
    355                 360                 365

Asn Val Asp Leu Ala Ala Ala Asp Ile Lys Pro Asp Gly Lys Arg His
            370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
                405                 410                 415

Ala Glu Val Lys Thr Val Asn Gly Ile Arg His Ile Gly Leu Ala Ala
            420                 425                 430

Lys Gln

<210> SEQ ID NO 6
<211> LENGTH: 327
<212> TYPE: PRT
<213> ORGANISM: Neisseria meningitidis

```
<400> SEQUENCE: 6

Ala Thr Asn Asp Asp Val Lys Lys Ala Ala Thr Val Ala Ile Ala
1               5                   10                  15

Ala Ala Tyr Asn Asn Gly Gln Glu Ile Asn Gly Phe Lys Ala Gly Glu
            20                  25                  30

Thr Ile Tyr Asp Ile Asp Glu Asp Gly Thr Ile Thr Lys Lys Asp Ala
        35                  40                  45

Thr Ala Ala Asp Val Glu Ala Asp Asp Phe Lys Gly Leu Gly Leu Lys
    50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
            100                 105                 110

Leu Asp Ala Thr Thr Asn Ala Leu Asn Lys Leu Gly Glu Asn Ile Thr
            115                 120                 125

Thr Phe Ala Glu Glu Thr Lys Thr Asn Ile Val Lys Ile Asp Glu Lys
130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
            195                 200                 205

Glu Ala Ala Ala Gly Thr Ala Asn Thr Ala Ala Asp Lys Ala Glu Ala
210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
                245                 250                 255

Glu Ser Asp Ser Lys Phe Val Arg Ile Asp Gly Leu Asn Ala Thr Thr
            260                 265                 270

Glu Lys Leu Asp Thr Arg Leu Ala Ser Ala Glu Lys Ser Ile Ala Asp
            275                 280                 285

His Asp Thr Arg Leu Asn Gly Leu Asp Lys Thr Val Ser Asp Leu Arg
290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
                325
```